United States Patent
Church et al.

(10) Patent No.: US 11,981,917 B2
(45) Date of Patent: *May 14, 2024

(54) RNA-GUIDED TRANSCRIPTIONAL REGULATION

(71) Applicant: President and Fellows of Harvard College, Cambridge, MA (US)

(72) Inventors: George M. Church, Brookline, MA (US); Prashant G. Mali, La Jolla, CA (US); Kevin M. Esvelt, Auburndale, MA (US)

(73) Assignee: President and Fellows of Harvard College, Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/972,885

(22) Filed: Oct. 25, 2022

(65) Prior Publication Data

US 2023/0131972 A1 Apr. 27, 2023

Related U.S. Application Data

(63) Continuation of application No. 16/851,360, filed on Apr. 17, 2020, which is a continuation of application No. 16/441,209, filed on Jun. 14, 2019, now Pat. No. 10,767,194, which is a continuation of application No. 14/319,530, filed on Jun. 30, 2014, which is a continuation of application No. PCT/US2014/040868, filed on Jun. 4, 2014.

(60) Provisional application No. 61/830,787, filed on Jun. 4, 2013.

(51) Int. Cl.

| | |
|---|---|
| C12N 15/10 | (2006.01) |
| C12N 9/22 | (2006.01) |
| C12N 15/11 | (2006.01) |
| C12N 15/113 | (2010.01) |
| C12N 15/63 | (2006.01) |
| C12N 15/90 | (2006.01) |

(52) U.S. Cl.
CPC ............ *C12N 15/907* (2013.01); *C12N 9/22* (2013.01); *C12N 15/102* (2013.01); *C12N 15/11* (2013.01); *C12N 15/113* (2013.01); *C12N 15/635* (2013.01); *C12N 2310/20* (2017.05); *C12N 2310/3513* (2013.01); *C12Y 301/00* (2013.01)

(58) Field of Classification Search
CPC ...... C12N 15/907; C12N 9/22; C12N 15/102; C12N 15/11; C12N 15/113; C12N 15/635; C12N 2310/20; C12N 2310/3513; C12Y 301/00
See application file for complete search history.

(56) References Cited

U.S. PATENT DOCUMENTS

| | | |
|---|---|---|
| 4,123,610 A | 10/1978 | Summerton et al. |
| 4,844,617 A | 7/1989 | Kelderman et al. |
| 4,981,985 A | 1/1991 | Kaplan et al. |
| 5,151,189 A | 9/1992 | Hu et al. |
| 5,563,056 A | 10/1996 | Swan et al. |
| 5,594,235 A | 1/1997 | Lee |
| 5,695,940 A | 12/1997 | Drmanac et al. |
| 5,830,708 A | 11/1998 | Naughton |
| 5,834,758 A | 11/1998 | Trulson et al. |
| 5,871,921 A | 2/1999 | Landegren et al. |
| 6,083,726 A | 7/2000 | Mills, Jr. et al. |
| 6,306,597 B1 | 10/2001 | Macevicz |
| 6,534,266 B1 | 3/2003 | Singer |
| 6,632,655 B1 | 10/2003 | Mehta et al. |
| 7,255,994 B2 | 8/2007 | Lao |
| 7,323,305 B2 | 1/2008 | Leamon et al. |
| 7,427,479 B2 | 9/2008 | Karger et al. |
| 7,473,767 B2 | 1/2009 | Dimitrov |

(Continued)

FOREIGN PATENT DOCUMENTS

| | | |
|---|---|---|
| BR | 112015013784 A2 | 7/2017 |
| BR | 112015013785 A2 | 7/2017 |

(Continued)

OTHER PUBLICATIONS

Mali, P. et al. RNA-Guided Human Genome Engineering via Cas9. Science. Jan. 3, 2013, vol. 339; pp. 823-826; abstract; p. 823, second column, second to third paragraph; p. 823, third column, second paragraph to third paragraph; figure 1; Supplementary material, p. 4, first paragraph; p. 7, first paragraph; Supplementary figures S1, S3. DOI: 10.1126/science.1232033.

(Continued)

*Primary Examiner* — Samuel C Woolwine
*Assistant Examiner* — Tiffany Nicole Grooms

(57) ABSTRACT

Methods of modulating expression of a target nucleic acid in a cell are provided including introducing into the cell a first foreign nucleic acid encoding one or more RNAs complementary to DNA, wherein the DNA includes the target nucleic acid, introducing into the cell a second foreign nucleic acid encoding a nuclease-null Cas9 protein that binds to the DNA and is guided by the one or more RNAs, introducing into the cell a third foreign nucleic acid encoding a transcriptional regulator protein or domain, wherein the one or more RNAs, the nuclease-null Cas9 protein, and the transcriptional regulator protein or domain are expressed, wherein the one or more RNAs, the nuclease-null Cas9 protein and the transcriptional regulator protein or domain co-localize to the DNA and wherein the transcriptional regulator protein or domain regulates expression of the target nucleic acid.

20 Claims, 65 Drawing Sheets
(60 of 65 Drawing Sheet(s) Filed in Color)
Specification includes a Sequence Listing.

(56) References Cited

U.S. PATENT DOCUMENTS

| | | |
|---|---|---|
| 7,745,129 B1 | 6/2010 | Schatz |
| 7,906,285 B2 | 3/2011 | Drmanac |
| 8,124,751 B2 | 2/2012 | Pierce et al. |
| 8,268,554 B2 | 9/2012 | Schallmeiner |
| 8,460,865 B2 | 6/2013 | Chee et al. |
| 8,501,459 B2 | 8/2013 | Chen et al. |
| 8,551,710 B2 | 10/2013 | Bernitz et al. |
| 8,697,359 B1 | 4/2014 | Zhang |
| 8,871,445 B2 | 10/2014 | Cong et al. |
| 8,906,616 B2 | 12/2014 | Zhang et al. |
| 8,932,814 B2 | 1/2015 | Cong et al. |
| 8,993,233 B2 | 3/2015 | Zhang et al. |
| 8,999,641 B2 | 4/2015 | Zhang et al. |
| 9,201,063 B2 | 12/2015 | Sood et al. |
| 9,217,151 B2 | 12/2015 | Yin et al. |
| 9,257,135 B2 | 2/2016 | Ong et al. |
| 9,267,135 B2 | 2/2016 | Church et al. |
| 10,138,509 B2 | 11/2018 | Church et al. |
| 10,266,888 B2 | 4/2019 | Daugharthy et al. |
| 10,267,808 B2 | 4/2019 | Cai |
| 10,494,662 B2 | 12/2019 | Church et al. |
| 10,494,667 B2 | 12/2019 | Chee |
| 10,640,789 B2 * | 5/2020 | Church ............... C12N 15/635 |
| 2002/0015952 A1 | 2/2002 | Anderson et al. |
| 2002/0155989 A1 | 10/2002 | Efimov et al. |
| 2002/0172950 A1 | 11/2002 | Kenny et al. |
| 2003/0148335 A1 | 8/2003 | Shen et al. |
| 2004/0077014 A1 | 4/2004 | Becker |
| 2004/0248144 A1 | 12/2004 | Mir |
| 2004/0259190 A1 | 12/2004 | Naughton |
| 2005/0106629 A1 | 5/2005 | McGrath et al. |
| 2005/0147981 A1 | 7/2005 | Yamakawa et al. |
| 2005/0191687 A1 | 9/2005 | Wang et al. |
| 2005/0233318 A1 | 10/2005 | Chee et al. |
| 2006/0024711 A1 | 2/2006 | Lapidus et al. |
| 2006/0077536 A1 | 4/2006 | Bromage et al. |
| 2006/0177833 A1 | 8/2006 | Brenner |
| 2006/0183107 A1 | 8/2006 | Melkonyan et al. |
| 2006/0234261 A1 | 10/2006 | Pierce et al. |
| 2006/0248349 A1 | 11/2006 | Rathjen et al. |
| 2006/0292611 A1 | 12/2006 | Berka et al. |
| 2007/0020650 A1 | 1/2007 | Kahvejian |
| 2007/0087362 A1 | 4/2007 | Church et al. |
| 2007/0117109 A1 | 5/2007 | Rothemund |
| 2007/0117177 A1 | 5/2007 | Luo et al. |
| 2007/0206275 A1 | 9/2007 | Hemmer et al. |
| 2007/0231823 A1 | 10/2007 | McKernan et al. |
| 2007/0292877 A1 | 12/2007 | Dimitrov |
| 2008/0050718 A1 | 2/2008 | Gesteland et al. |
| 2008/0176769 A1 | 7/2008 | Rank et al. |
| 2008/0269068 A1 | 10/2008 | Church et al. |
| 2009/0005259 A1 | 1/2009 | Drmanac |
| 2009/0208965 A1 | 8/2009 | Tafas et al. |
| 2009/0220968 A1 | 9/2009 | Issadore et al. |
| 2009/0246879 A1 | 10/2009 | Drmanac et al. |
| 2010/0009868 A1 | 1/2010 | Yan et al. |
| 2010/0047924 A1 | 2/2010 | Webster et al. |
| 2010/0076057 A1 | 3/2010 | Sontheimer et al. |
| 2010/0087325 A1 | 4/2010 | Buermann |
| 2010/0151472 A1 | 6/2010 | Nolan et al. |
| 2010/0223276 A1 | 9/2010 | Al-Shameri et al. |
| 2010/0268478 A1 | 10/2010 | Andregg et al. |
| 2011/0020291 A1 | 1/2011 | Banerjee et al. |
| 2011/0033520 A1 | 2/2011 | Mather et al. |
| 2011/0086774 A1 | 4/2011 | Dunaway |
| 2011/0092376 A1 | 4/2011 | Colston, Jr. et al. |
| 2011/0104693 A1 | 5/2011 | Seligmann |
| 2011/0189776 A1 | 8/2011 | Terns et al. |
| 2011/0223585 A1 | 9/2011 | Gullberg et al. |
| 2011/0223638 A1 | 9/2011 | Wiedenheft et al. |
| 2011/0245111 A1 | 10/2011 | Chee |
| 2011/0257031 A1 | 10/2011 | Bodeau et al. |
| 2011/0294135 A1 | 12/2011 | Carlson |
| 2012/0040397 A1 | 2/2012 | Luo et al. |
| 2012/0122712 A1 | 5/2012 | Goldstein |
| 2012/0330636 A1 | 12/2012 | Albou |
| 2013/0017229 A1 | 1/2013 | Mooney et al. |
| 2013/0130248 A1 | 5/2013 | Haurwitz et al. |
| 2013/0245096 A1 | 9/2013 | Abitbol |
| 2013/0253040 A1 | 9/2013 | Miller et al. |
| 2014/0049632 A1 | 2/2014 | Hemmer |
| 2014/0068797 A1 | 3/2014 | Doudna et al. |
| 2014/0087378 A1 | 3/2014 | Chatre et al. |
| 2014/0087427 A1 | 3/2014 | Bujnicki et al. |
| 2014/0179006 A1 | 6/2014 | Zhang |
| 2014/0179770 A1 | 6/2014 | Zhang et al. |
| 2014/0200146 A1 | 7/2014 | Xie et al. |
| 2014/0220587 A1 | 8/2014 | Green, Jr. et al. |
| 2014/0270435 A1 | 9/2014 | Dunn |
| 2014/0273226 A1 | 9/2014 | Wu |
| 2014/0273233 A1 | 9/2014 | Chen et al. |
| 2014/0310830 A1 | 10/2014 | Zhang et al. |
| 2014/0315985 A1 | 10/2014 | May et al. |
| 2014/0342457 A1 | 11/2014 | Mali et al. |
| 2015/0133319 A1 | 5/2015 | Fu et al. |
| 2015/0247150 A1 | 9/2015 | Zhang et al. |
| 2016/0024524 A1 | 1/2016 | Joung et al. |
| 2016/0024555 A1 | 1/2016 | Church et al. |
| 2016/0153006 A1 | 6/2016 | Zhang et al. |
| 2016/0160210 A1 | 6/2016 | Mali et al. |
| 2016/0253584 A1 | 9/2016 | Fodor et al. |
| 2016/0265046 A1 | 9/2016 | Zhang et al. |
| 2016/0289740 A1 | 10/2016 | Fu et al. |
| 2016/0340662 A1 | 11/2016 | Zhang et al. |
| 2016/0355795 A1 | 12/2016 | Ran et al. |
| 2017/0176338 A1 | 6/2017 | Wu et al. |
| 2017/0191078 A1 | 7/2017 | Zhang et al. |
| 2017/0212983 A1 | 7/2017 | Cai et al. |
| 2018/0010166 A1 | 1/2018 | Pierce et al. |
| 2018/0051322 A1 | 2/2018 | Church et al. |
| 2018/0282787 A1 | 10/2018 | Walter et al. |

FOREIGN PATENT DOCUMENTS

| | | |
|---|---|---|
| BR | 112015008708 A2 | 9/2017 |
| BR | 112015012375 A2 | 9/2017 |
| BR | 112015014425 A2 | 10/2017 |
| BR | 112015022061 A2 | 11/2017 |
| CA | 2891347 A1 | 6/2014 |
| EA | 014097 B1 | 12/2007 |
| EP | 2878671 A1 | 6/2015 |
| JP | 2012-170337 A | 9/2012 |
| KR | 20080003402 A | 1/2008 |
| WO | 9746704 A1 | 12/1997 |
| WO | 98/56955 A1 | 12/1998 |
| WO | 0126708 A1 | 4/2001 |
| WO | 01/37266 A1 | 5/2001 |
| WO | 2003044229 A1 | 5/2003 |
| WO | 2004/104645 A2 | 12/2004 |
| WO | 2006/138257 A2 | 12/2006 |
| WO | 2007/001986 A2 | 1/2007 |
| WO | 2007076128 A2 | 7/2007 |
| WO | 2007086900 A2 | 8/2007 |
| WO | 2007121489 A2 | 10/2007 |
| WO | 2007/123744 A2 | 11/2007 |
| WO | 2007/149696 A1 | 12/2007 |
| WO | 2008069973 A2 | 6/2008 |
| WO | 2008/108989 A2 | 9/2008 |
| WO | 2008157696 A2 | 12/2008 |
| WO | 2009/046348 A1 | 4/2009 |
| WO | 2009046149 A1 | 4/2009 |
| WO | 2010/054108 A2 | 5/2010 |
| WO | 2010080134 A1 | 7/2010 |
| WO | 2010/087325 A1 | 8/2010 |
| WO | 2011/143124 A2 | 11/2011 |
| WO | 2011143583 A1 | 11/2011 |
| WO | 2012005595 A2 | 1/2012 |
| WO | 2012058638 A2 | 5/2012 |
| WO | 2012/110899 A2 | 8/2012 |
| WO | 2012150035 A1 | 11/2012 |
| WO | 2012/164565 A1 | 12/2012 |
| WO | 2013055995 A2 | 4/2013 |
| WO | 2013/098244 A1 | 7/2013 |
| WO | 2013/126794 A1 | 8/2013 |

(56) References Cited

FOREIGN PATENT DOCUMENTS

| WO | 2013/141680 A1 | 9/2013 |
|---|---|---|
| WO | 2013/142578 A1 | 9/2013 |
| WO | 2013176772 A1 | 11/2013 |
| WO | 2014/022702 A2 | 2/2014 |
| WO | 2014/048083 A1 | 4/2014 |
| WO | 2014/065596 A1 | 5/2014 |
| WO | 2014/089290 A1 | 6/2014 |
| WO | 2014/093595 A1 | 6/2014 |
| WO | 2014/093622 A2 | 6/2014 |
| WO | 2014/093661 A2 | 6/2014 |
| WO | 2014/093694 A1 | 6/2014 |
| WO | 2014099744 A1 | 6/2014 |
| WO | 2014/113493 A1 | 7/2014 |
| WO | 2014/144288 A1 | 9/2014 |
| WO | 2014/150624 A1 | 9/2014 |
| WO | 20140163886 A1 | 10/2014 |
| WO | 2014182528 A2 | 11/2014 |
| WO | 2014/191518 A1 | 12/2014 |
| WO | 2014/197568 A2 | 12/2014 |
| WO | 2015/127183 A2 | 8/2015 |
| WO | 2015118029 A1 | 8/2015 |
| WO | 2016081740 A1 | 5/2016 |
| WO | 2017/161251 A1 | 9/2017 |

OTHER PUBLICATIONS

Tiley, LS et al. The VP16 Transcription Activation Domain Is Functional When Targeted to a Promoter-Proximal RNA Sequence. Genes and Development. 1992. vol. 6; pp. 2077-2087; abstract; p. 2077, first column, first paragraph.

Trafton, A. Editing the Genome With High Precision [online]. MIT News office. Jan. 3, 2013 [retrieved on Dec. 4, 2014). Retrieved from the Internet: <URL:http:/lnewsoffice.Trafton.edut20 13/editing-the-genome-with-high-precision-01 03 >;pp. 1-3; p. 3, third paragraph.

Leman, AR et al. The Replication Forie Understanding the Eukaryotic Replication Machinery and the Challenges to Genome Duplication. Genes. Jan. 29, 2013. vol. 4; pp. 1-32; figure 1; DOI: 10.3390/genes4010001.

Qi, L et al. Repurposing CRISPR as an RNA-Guided Platform for Sequence-Specific Control of Gene Expression. Cell. Feb. 28, 2013. vol. 152; pp. 1173-1183; figures 2, 4. DOI: 10.1 016/j.cell.2013.02. 022.

Gasiunas, G et al Cas9-crRNA Ribonucleoprotein Complex Mediates Specific DNA Cleavage for Adaptive Immunity in Bacteria. PNAS. Sep. 4, 2012. vol 109, No. 39; pp. E2579-E2586; p. E2583, first column, first paragraph. DOI: 10.1073/pnas.1208507109.

Cong, Let al. Multiplex Genome Engineering Using CRISPR/Cas Systems. Science. Jan. 3, 2013, vol. 339; pp. 819-823; abstract; p. 821, third column; p. 822, first column, first paragraph; figure 4. DOI: 10.1126/science.1231143.

Jinek, M et al. A Programmable Dual-RNA-Guided DNA Endonuclease in Adaptive Bacterial Immunity. Science. Jun. 28, 2012. vol. 337; pp. 816-821; DOI: 10.1126/science.1225829.

CRISPR in the Lab: A Practical Guide [online]. Addgene. Sep. 4, 2014. Retrieved on Dec. 4, 2014. Retrieved from the Internet: <URL: https://www.addgene.org/CRISPR/guide/>.

Cheng, AW et al. Multiplexed Activation of Endogenous Genes by CRISP R-on, an RNA-Guided Transcriptional Activator System. Cell Research. Aug. 27, 2013. vol. 23; pp. 1163-1171. DOI: 10.1038/cr.2013.122.

Mali, P. et al. CAS9 Transcriptional Activators for Target Specificity Screening and Paired Nickases for Cooperative Genome Engineering. Nature Biotechnology. Aug. 1, 2013. vol. 31; pp. 833-838; entire document. DOI: 10.1038/nbt.2675.

Ran, FA et al. Double Nicking by RNA-Guided CRISPR Cas9 for Enhanced Genome Editing Specificity. Cell. Sep. 12, 2013. vol. 154; pp. 1380-1389. DOI: 10.1016/j.cell.2013.08.021.

International Search Report and Written Opinion issued in corresponding International Application No. PCT/US14/40868, dated Dec. 31, 2014.

Al-Attar et al., Clustered Regularly Interspaced Short Palindromic Repeats (CRISPRs ): The Hallmark of an Ingenious Antiviral Defense Mechanism in Prokaryotes, Bioi Chern. (20 11) vol. 392, Issue 4, pp. 277-289.

Carroll, "A CRISPR Approach to Gene Targeting" 20(9) Molecular Therapy 1658-1660 (Sep. 2012).

Jinek , et al. 'RNA-programmed genome editing in human cells.' eLite 2013;2:e00471 . [retrieved 1-3, 6, 7, 10-12 on Mar. 6, 2014). Retrieved from the Internet. <URL: http://elife .elifesciences.org/content/2/e00471 >. entire document.

Hale et al., Essential Features and Rational Design of CRISPR RNAs That Function With the Cas RAMP Module Complex to Cleave RNAs, Molecular Cell, (20 12) vol. 45, Issue 3, 292-302.

Hatoum-Aslan, et al. 'Mature clustered, regularly interspaced, short palindromic repeats RNA 5,9, 14 (crRNA) length is measured by a ruler mechanism anchored at the precursor processing site.' Proceedings of the National Academy of Sciences. vol. 108, No. 52. pp. 21218-21222. Dec. 2011. entire document.

Makarova et al., "Evolution and classification of the CRISPR-Cas systems" 9(6) Nature Reviews Microbiology 467-477 (1-23) (Jun. 2011).

Rho, Mina et al. 'Diverse CRISPRs Evolving in Human Microbiomes.' PLoS Genetics. vol. 8, No. 6. 1-14 pp. 1-12. Jun. 2012. entire document.

Sontheimer Erik, Project 7: Establishing RNA-Directed DNA Targeting in Eukaryotic Cells; Project dates: Nov. 16, 2011 to Dec. 31, 2012 (Feb. 4, 2012).

Wiedenheft eta!., "RNA-guided genetic silencing systems in bacteria and archaea" 482 Nature 331-338 (Feb. 16, 2012).

Liu et al, Cell-Penetrating Peptide-Mediated Delivery of TALEN Proteins via Bioconjugation for Genome Engineering, PLOS ONE, 2014, vol. 9(1), pp. 1-7.

Ramakrishna et al, Gene disruption by cell-penetrating peptide-mediated delivery of Cas9 protein and guide RNA, Genome Res. published online Apr. 2, 2014, pp. 1-20 plus figures.

The Delivery Problem, Nature Biotechnology, 2006, vol. 24(3), pp. 305-306.

Ansari et al, Rioboactivators: Transcription activation by non-coding RNA, Grit Rev Biochem Mol Bioi. 2009 ; 44(1 ): 50-61.

Sapranauskas et al (Nucleic Acids Research, 2011, 39:9275-9282).

U.S. Appl. No. 61/794,422, filed Mar. 15, 2013, Davis, G. et al.

U.S. Appl. No. 61/781,598, filed Mar. 14, 2013, Haurwitz, R.

Gilbert, Luke A., et al., "CRISPR-Mediated Modular RNA-Guided Regulation of Transcription in Eukaryotes," Cell, vol. 154, No. 2, Jul. 1, 2013 (Jul. 1, 2013), pp. 442-451.

Mali, P. et al., "Supplementary Materials for RNA-Guided Human Genome Engineering via Cas9," Science, vol. 339, No. 6121, Jan. 3, 2013 (Jan. 3, 2013), pp. 1-36.

Maeder, Morgan L., et al.,"Robust, synergistic regulation of human gene expression using TALE activators," HHS Public Access Author Manuscript, vol. 10, No. 3, Feb. 10, 2013 (Feb. 10, 2013), pp. 243-245.

Perez-Pinera, Pablo, et al., "Synergistic and tunable human gene activation by combinations of synthetic transcription factors," Nature Methods, vol. 10. No. 3, Feb. 3, 2013 (Feb. 3, 2013), pp. 239-242.

Preliminary Office Action issued by Brazilian Patent Office dated Apr. 7, 2020.

Official Notification dated May 24, 2020 for IL 242959.

Jun. 2, 2020—(JP) Notice of Reasons for Rejection for App. No. 2019-039027.

Jul. 3, 2020—(AU) Examination Report for App. No. 20202039777.

Aug. 19, 2020—(MX) Office Action—App. No. MX/a/2015/016798.

Sep. 10, 2020—(CA) Office Action—App. No. 2,914,638.

Sep. 21, 2020—(NZ) First Examination Report—App. No. 715280.

Office Action issued for corresponding European Patent Application No. 12780609.9, dated Sep. 23, 2015.

Seo, et al. Four-color DNA sequencing by synthesis on a chip using photocleavable fluorescent nucleotides. Proceeding of the National Academy of Sciences, Apr. 2005, 102 (17) 5926-5931.

(56) References Cited

OTHER PUBLICATIONS

Brenner, et al. "Gene expression analysis by massively parallel signature sequencing (MPSS) on microbead arrays". Nature Biotechnology vol. 18, pp. 630-634 (2000) doi:10.1038/76469.
Dec. 18, 2014 (PCT) International Preliminary Report—App PCT/US2013/044241.
Shendure Jay et al., "Accurate multiplex polony sequencing of an evolved bacterial genome," Science, American Association for the Advancement of Science, Washington, DC; US, vol. 309, No. 5741, Sep. 1, 2005, pp. 1728-1732, XP002427180, ISSN: 0036-8075, DOI: 10.1126/SCIENCE.1117839.
Extended European Seach Report issued in corresponding European Application No. 12860433.7, dated Aug. 13, 2015.
International Search Report and Written Opinion issued in corresponding International Application No. PCT/US2012/071398, dated Apr. 8, 2013.
Benner et al. "Gene Expression analysis by massively parallel signature sequencing (MPSS) on microbead arrays". Nature Biotechnology, vol. 18, pp. 630-634 (Jun. 31, 2000).
Han et al. "Quantum-dot-tagged microbeads for multiplexed optical coding of biomolecules". Nature Biotechnology, vol. 19, 99. 631-635 (Jul. 31, 2001).
Lee, JH et al. Highly Multiplexed Subcellular RNA Sequencing In Situ. Science. Mar. 21, 2014, vol. 343, No. 6177; pp. 1360-1363; abstract; p. 1360, second column, second paragraph to third column, first paragraph; p. 1361, first column, first paragraph; p. 1363, first column, second paragraph to second column, first paragraph; DOI: 10.1126/science.1250212.
Dewran et al., "Synthetic Transcription Factors and their Effects on Endogenous DNA Methylation in Human Cells", Thesis Degree of Master of Science, Jan. 1, 2013, XP055957948, Duke University.
Yan et al., "The CRISPR-Cas9 System: A Powerful Tool for Genome Engineering and Regulation", Advancements in Genetic Engineering, vol. 02, No. 03, Jan. 1, 2013, p. 1000e103.
Ascano, M et al. Identification of RNA-Protein Interaction Networks Using PAR-CLIP. Wiley Interdiscip Rev RNA. Mar. 2012, vol. 3, No. 2; pp. 159-177; p. 3, third paragraph; p. 16, figure 1; p. 25, figure 6; DOI: 10.1002/wrna. 1103.
Ginart, P et al. RNA Sequencing In Situ. Nat Biotechnol. Jun. 2014, vol. 32, No. 6; pp. 543-544; DOI: 10.1038/nbt.2921.
Saliba, AE et al. Single-Cell RNA-Seq: Advances and Future Challenges. Nucleic Acids Res. Jul. 22, 2014, vol. 42, No. 14; pp. 8845-8860; DOI: 10.1093/nar/gku555.
Eliscovich et al. mRNA on the move: The road to its biological destiny. Journal of Biological Chemistry, vol. 288, No. 28, pp. 20361-20368, Jul. 2013, in press May 2013 (Year: 2013).
Weis et al. Protein targeting to subcellular organelles via mRNA localization. Biochimica et Biophysica Acta, vol. 1833, pp. 260-273, 2013, available online Apr. 2012 (Year: 2012).
Jambhekar et al. Cis-acting determinants of asymmetric, cytoplasmic RNA transport. RNA, vol. 13, pp. 625-642, 2007 (Year: 2007).
Singer-Kruger et al. Here, there, everywhere. RNA Biology, vol. 11, No. 8, pp. 1031-1039, Aug. 2014. (Year: 2014).
Matlin et al. Spatial expression of the genome: the signal hypothesis at forty. Nature Reviews. Molecular Cell Biology, vol. 12, No. 5, pp. 333-340, May 2011, Epub Apr. 2011. (Year: 2011).
Polidoros et al. Rolling circle amplification-RACE: a method for simultaneous isolation of 5' and 3' cDNA ends from amplified cDNA templates. Bio Techniques, vol. 41, No. 1, pp. 35, 36, 38 and 40, Jul. 2006, including p. 1/1 of Supplementary Material. (Year: 2006).
Tsaftaris et al. Isolation of three homologous AP1-like MADS-box genes in crocus (*Crocus sativus* L.) and characterization of their expression. Plant Science, vol. 166, No. 5, pp. 1235-1243, May 2004. (Year: 2004).
Meeks et al. Characterization of genes encoding poly(A) polymerases in plants: Evidence for duplication and functional specialization. PLoS ONE, vol. 4, No. 11, e8082, Nov. 2009, printed as pp. 1/10-10/10. (Year: 2009).

Kalivas et al. famRCA-RACE: A rolling circle amplification RACE for isolating a family of homologous cDNAs in one reaction . . . Preparative Biochemistry and Biotechnology, vol. 40, No. 3, pp. 177-187, Jul. 2010. (Year: 2010).
Thisse et al. "High-Resolution in situ hybridization to whole-mount zebrafish embryos" 2008. Nature Protocols. vol. 3 No. 1 pp. 59-69. Doi:10.1038/nprot.2007.514.
Grompe (1993) Nature Genetics DOI: 10.1038/ng1093-111.
Thisse et al. 2008 Nature protocols vol. 3 No 1 pp. 59-69. Doi:10.1038/nprot.2007.514.
Doillon et al. "Actin Filaments in Normal Dermis and During Wound Healing" The American Journal of Pathology, vol. 126 Issue 1 (1987): pp. 164-170; p. 164 col. 1 para 1, p. 170 col. 1 para 2, fig. 4A-C.
International Search Report and Written Opinion based on PCT/US2018/027583 dated Jun. 29, 2018.
Soderberg, Ola et al.,"Direct observation of individual endogenous protein complexes in situ by proximity ligation," Nature Methods, Dec. 2006, pp. 995-1000, vol. 3, No. 12, Nature Publishing Group.
Schweitzer, Barry et al., "Immunoassays with rolling circle DNA amplification: A versatile platform for ultrasensitive antigen detection" PNAS, Aug. 29, 2000, pp. 10113-10119, vol. 97, No. 18.
Cao, Yi et al.,"In-situ immuno-PCR to detect antigens," The Lancet, Sep. 16, 2000, pp. 1002-1003, vol. 356.
Sano, Takeshi et al. "Immuno-PCR: Very Sensitive Antigen Detection by Means of Specific Antibody-DNA Conjugates," Science, Oct. 2, 1992, pp. 120-122, vol. 258.
Dasari, Vivek et al., "Platform for Spatial Molecular Data by Vivek Dasari 1-7 Sig nature redacted Thesis Supervisor", Aug. 20, 2015 (Aug. 20, 2015), XP055559164, Retreived from the Internet: URL:http://dspace.mit.edu/bitstream/handle/1721.1/107103/971494098-MIT.pdf?sequence=1 [retreived on Feb. 20, 2019].
Extended European Search Report dated May 13, 2019 for EP Application No. 16862929.3.
Lee, Je Hyuk et al., "Fluorescent in situ sequencing (FISSEQ) or RNA for gene expression profiling in intact cells and tissues", Nature Protocols, vol. 10, No. 3, Feb. 12, 2015 (Feb. 12, 2015), pp. 442-458. XP055272042, GB ISSN: 1754-2189, DOI: 10.1038/nprot.2014.191.
Extended European Search Report dated May 21, 2019 for European Application No. 16862945.9.
Choi, Harry M.T. et al., "Next-Generation in Situ Hybridization Chain Reaction: Higher Gain, Lower Cost, Greater Durability" ACS NANO, vol. 8, No. 5, May 27, 2014 (May 27, 2014), pp. 4284-4294, XP055409053, US.
Ravan, Hadi, et al. "Isothermal RNA detection through the formation of DNA concatemers contiaining HRP-mimicking DNAzymes on the surface of gold nanoparticles", Biosensors and Bioelectronics, Elsevier Science Ltd. UK, Amsterdam, NL, vol. 80, Jan. 18, 2016 (Jan. 18, 2016), pp. 67-73, XP029441324.
Extended European Search Report issued for EP Application No. 17790240.0 dated Sep. 4, 2019.
Brown et al., Review Article : In situ Hybridization with Riboprobes : An Overview for Veterinary Pathologists. Veterinary Pathology 35 : 159-167 (Year: 1998).
Choi et al.,Programmable in situ amplification for multiplexed imaging of mRNA expression. Nature Biotechnology 28 (11): 1208 (Year: 2010).
Choi & Love et al., Immuno-Hybridization Chain Reaction for Enhancing Detection of Individual Cytokine-Secreting Human Peripheral Mononuclear Cells. Analytical Chemistry 83 : 6890-6895 (Year: 2011).
Hansen et al., Sensitive ligand-based protein quantification using immuno-PCR: A critical review of single-probe and proximity ligation assays. Biotechniques 56:217-228 (Year: 2014).
Kuimelis et al., Cleavage properties of an oligonucleotide containing a bridged internucleotide 5-phosphorothioate RNA linkage. Nucleic Acids Research 23 (23) : 4753-4760 (Year: 1999).
Mag et al., Synthesis and selective cleavage of an oligodeoxynucleotide containing a bridged internucleotide 5'-phosphorothioate linkage. Nucleic Acids Research 19(7): 1437 (Year: 1991).

(56) References Cited

OTHER PUBLICATIONS

Richardson et al., Experimental and Theoretical Studies of Light-to-Heat Conversion and Collective Heating Effects in Metal Nanoparticle Solutions. Nano Letters 9(3) : 1139-1146 (Year: 2009).
Song et al., Hybridization chain reaction-based aptameric system for the highly selective and sensitive detection of protein. Analyst 137: 1396 (Year: 2012).
Xiao et al., Single-step electronic detection of femtomolar DNA by target-induced strand displacement in an electrode-bound duplex. PNAS 103(45): 16677-16680 (Year: 2006).
Zhang et al., Dynamic DNA nanotechnology using strand-displacement reactions. Nature Chemistry 3 : 103-113 (Year: 2011).
Zhao et al., An electrochemical aptasensor based on hybridization chain reaction with enzyme-signal amplification for interferon-gamma detection. Biosensors and Bioelectronics 36: 129-134 (Year: 2012).
Srinivas et al., On the biophysics and kinetics of toehold-mediated DNA strand displacement. Nucleic Acids Research 41 (22) : 10641-10658 (Year: 2013).
Weibrecht, Irene et al., "Simultaneous Visualization of Both Signaling Cascade Activity and End-Point Gene Expression in Single Cells", PLOS ONE, vol. 6, No. 5, May 25, 2011 (May 25, 2011).
Larsson, Chatarina; Grundberg, Ida; Sbderberg, Ola; Nilsson, Mats: 11 In situ detection and genotyping of individual MRNA molecules, Nature Methods, vol. 7, No. 5 Apr. 11, 2010 (Apr. 11, 2010), pp. 395-397, XP055035168, DOI: 10.1038/nmeth.1448 Retrieved from the Internet: URL:http://www.nature.com/nmeth/journal/v7/n5/pdf/nmeth.1448.pdf [retrieved on Aug. 9, 2012] the whole document.
Nuovo: "Co-labeling Using In Situ PCR: A Review" Journal of Histochemistry & Cytochemistry, vol. 49, No. 11, Nov. 1, 2001 (Nov. 1, 2001), pp. 1329-1339, XP055164942, ISSN: 0022-1554, DOI: 10.1177/002215540104901101 the whole document.
Mitra R. D. et al: 11 In situ localized amplification and contact replication of many individual DNA molecules 11 Nucleic Acids Research, Information Retrieval Ltd, GB, vol. 27, No. 24, Dec. 15, 1999 (Dec. 15, 1999), p. e34, XP002292358, ISSN: 0305-1048, DOI: 10.1093/NAR/27.24.E34 abstract.
Ke et al: 11 In situ sequencing for RNA analysis in preserved tissue and cells 11 Nature Methods, vol. 10, No. 9, Jul. 14, 2013 (Jul. 14, 2013), pp. 857-860, XP055163946, ISSN: 1548-7091, DOI: 10.1038/nmeth.2563 the whole document.
Lee et al: "Highly Multiplexed Subcellular RNA Sequencing in Situ", Science, vol. 343, No. 6177, Feb. 27, 2014 (Feb. 27, 2014), pp. 1360-1363, XP055305772, US ISSN: 0036-8075, DOI: 10.1126/science. 1250212.
Clausson et al: "Compaction of rolling circle amplification products increases signal integrity and signal-to-noise ratio", Scientific Reports, vol. 5, Jul. 23, 2015 (Jul. 23, 2015), p. 12317, XP055305777, DOI: 10.1038/srep12317.
Nadji et al.,"Photochemically and Photoenzymatically Cleavable DNA," J. Am. Chem. Soc. 1992, 114, 9266-9269.
Extended European Search Report and Written Opinion dated Dec. 17, 2019 for EP 19180827.8.
Supplementary European Search Report and Written Opinion dated Mar. 18, 2020.
Chen et al., "Expansion microscopy," Science, vol. 347, No. 6221, pp. 543-548 (Jan. 30, 2015).
Chozinski et al., "Expansion microscopy with conventional antibodies and fluorescent proteins," Nature Methods, vol. 13, No. 6, pp. 485-488 (Jun. 1, 2016).
Chen et al., "Nanoscale imaging of RNA with expansion microscopy," Nature Methods, vol. 133, No. 8, pp. 679-684 (Aug. 1, 2016).
Supplementary European Search Report dated Apr. 9, 2020 for EP 17847555.
Amasino, "Acceleration of nucleic acid hybridization rate by polyethylene glycol," Analytical Biochemistry, vol. 152, No. 2, pp. 304-307 (Feb. 1, 1986).
Bouché et al., "The effect of spermidine on endonuclease inhibition by agarose contaminants," Analytical Biochemistry, vol. 115, No. 1, pp. 42-45 (Jul. 15, 1981).

Kuznetsova et al., "What Macromolecular Crowding Can Do to a Protein," Int. J. Mol. Sci., vol. 15, No. 12, pp. 23090-23140 (Dec. 1, 2014).
Oupicky et al., "Laterally stabilized complexes of DNA with linear reducible polycations: Strategy for triggered intracellular actication of DNA delivery vectors," Journal of the American Chemical Society, vol. 124, No. 1, pp. 8-9 (Jan. 9, 2002).
Nguyen, Son C., "Strategies for Studying Chromatin Regulation and Organization," Doctoral Dissertation, Harvard University (May 1, 2018); retrieved from https://dash.harvard.edu/bitstream/handle/1/33493431/NGUYEN-DISSERTATION-2016.pdf?sequence=4&isAllowed=y on Apr. 8, 2020.
Zhou et al. "In Situ Detection of Messenger RNA Using Digoxigenin-Labeled Oligonucleotides and Rolling Circle Amplification" Experimental and Molecular Pathology 70, 281-288 (2001).
May 29, 2020—Examination Report issued for EP 18173059.9.
Jun. 1, 2020—Examination Report issued for GB 1809029.0.
Wright et al., "Dynamic closed-loop system for focus tracking using a spatial light modulator and a deformable membrane mirror," Optics Express, vol. 14, No. 1, pp. 222-228 (Jan. 9, 2006).
Wang et al., "The method of axial drift compensation of laser differential confocal microscopy based on zero-tracking," Proc. of SPIE, vol. 9618, 96180X (2015).
Ohata et al., "Confocal Imaging Analysis of Intracellular Ions in Mixed Cellular Systems or in Situ Using Two Types of Confocal Microscopic Systems," Methods in Enzymology, vol. 307, pp. 425-441 (1999), particularly p. 437.
Supplemental Material for Schweitzer et al. (PNAS 2000; 97(18):10113-10119) (Year: 2000).
Aug. 3, 2020—U.S. Non-Final Office Action—U.S. Appl. No. 16/157,243.
Aug. 3, 2020 U.S. Non-Final Office Action—U.S. Appl. No. 16/393,215.
Jul. 2, 2020—U.S. Non-Final Office Action—U.S. Appl. No. 16/255,920.
Aug. 10, 2020—(GB) Examination Report—GB App. No. 1809029.0.
Sep. 24, 2020—U.S. Final Office Action—U.S. Appl. No. 15/772,652.
Markaki et al. "Fluorescence In Situ Hybridization Applications for Super-Resolution 3D Structured Illumination Microscopy" Methods in Microbiology, Jan. 2013.
Achim et al. "High-throughput spatial mapping of single-cell RNA-seq data to tissue of origin" Nature Biotechnology, Apr. 13, 2015.
Sep. 25, 2020—U.S. Non-Final Office Action—U.S. Appl. No. 16/386,337.
Aug. 25, 2020—(JP) Notice of Reasons for Rejection—App. No. 2018-522985.
PI: Piezo Nano Positioning, 2008 (online), retrieved on Aug. 12, 2020, pp. 1-6 <https://www.pi-usa.us/fileadmin/user_upload/pi_us/files/product_datasheets/N725_Piezo_Focus_Positioner.pdf>.
Sep. 14, 2020—(CA) Examination Report—App. No. 2,850,509.
Sep. 21, 2020—(NZ) First Examination Report—App. No. 753950.
Fu et al., "Improving CRISPR-Cas nuclease specificity using truncated guide RNAs," Nature Biotechnology, vol. 32, pp. 249-284 (Jan. 26, 2014).
Lin et al., "CRISPR/Cas9 systems have off-target activity with insertions or deletions between target DNA and guide RNA sequences," Nucleic Acids Research, vol. 42, No. 11, pp. 7473-7485 (May 16, 2014).
Sep. 21, 2020—(NZ) First Examination Report—App. No. 753951.
Sep. 25, 2020—(RU) Office Action—App. No. 2019114706.
DiCarlo et al., "Genome engineering in *Saccharomyces cerevisiae* using CRISPR-Cas systems," Nucleic Acids Research, vol. 41, No. 7, pp. 4336-4343 (2013).
Gusev et al. "Rolling Circle Amplification: A New Approach to Increase Sensitivity for Immunohistochemistry and Flow Cyometry" American Journal of Pathology, vol. 159, No. 1, Jul. 2001, pp. 63-69.
Oct. 22, 2020—(KR) Second Preliminary Notice of Rejection—App. No. 10-2015-7036892.
Jan. 28, 2021—(AU) Examination Report—App. No. 753951.
Jan. 28, 2021—(AU) Examination Report—App. No. 715280.

(56) References Cited

OTHER PUBLICATIONS

Zhang et al., "The CRISPR Associated Protein Cas4 Is a 5' to 3' DNA Exonuclease with an Iron-Sulfur Cluster," PLoS ONE, 7(10), e47232 (2012).
Aug. 18, 2021—(CA) Office Action—App. No. 2,914,638.
May 25, 2021—(JP) Final Notice of Reasons for Rejection—App. No. 2019-039027.
Aug. 12, 2021—(RU) Decision to Grant—App. No. 2019114706.
Sep. 13, 2021—(MY) Substantive Examination & Search Report—App. No. PI2019003198.
Jan. 4, 2022—(JP) Notice of Reasons for Rejection—App. No. 2020-200649.
Chylinski et al., "The tracrRNA and Cas9 families of type II CRISPR-Cas immunity systems," RNA Biology, vol. 10, Iss. 5, pp. 726-737 (Apr. 5, 2013).
Deltcheva et al., "CRISPR RNA maturation by trans-encoded small RNA and host factor RNase III," Nature, vol. 471, pp. 602-607, supplementary materials (Mar. 31, 2011).
Ran et al., "Double Nicking by RNA-Guided CRISPR Cas9 for Enhanced Genome Editing Specificity," Cell, vol. 154, pp. 1380-1389 (epub Aug. 29, 2013).

\* cited by examiner

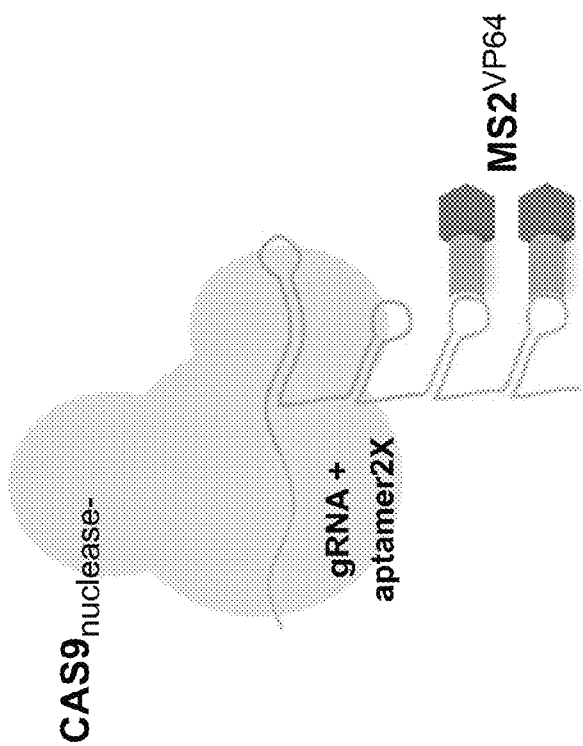
FIG. 1A
FIG. 1B
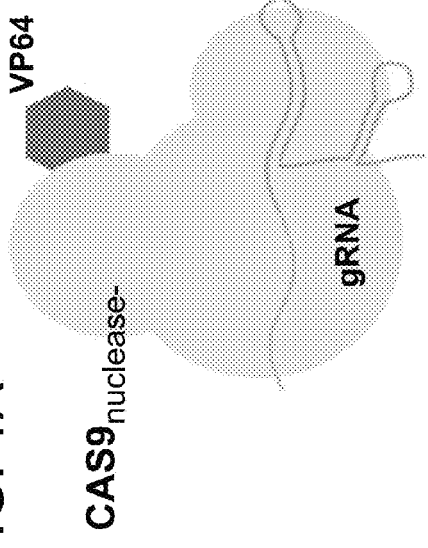
FIG. 1C

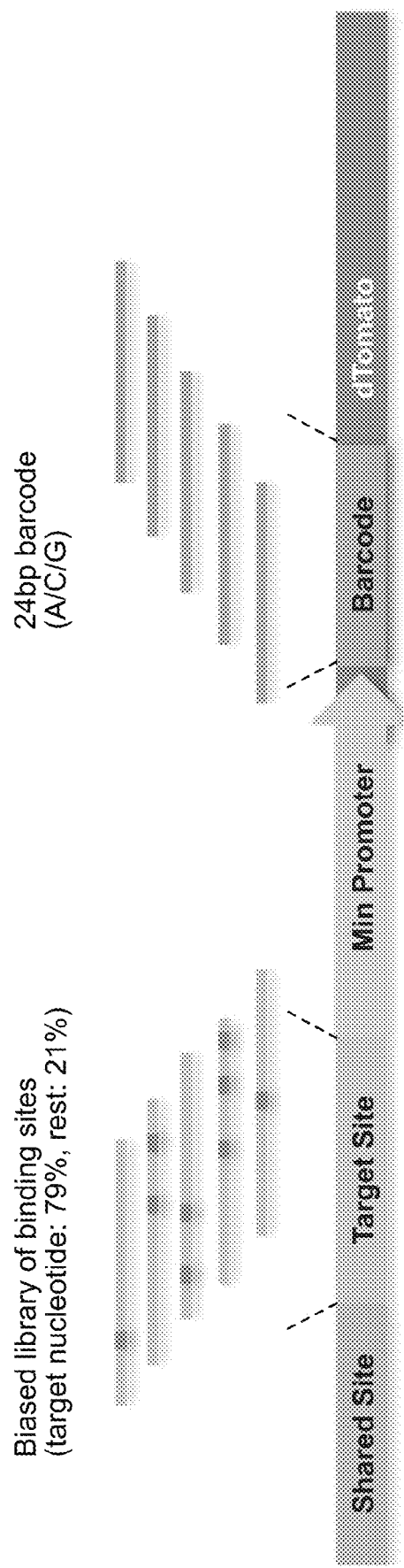

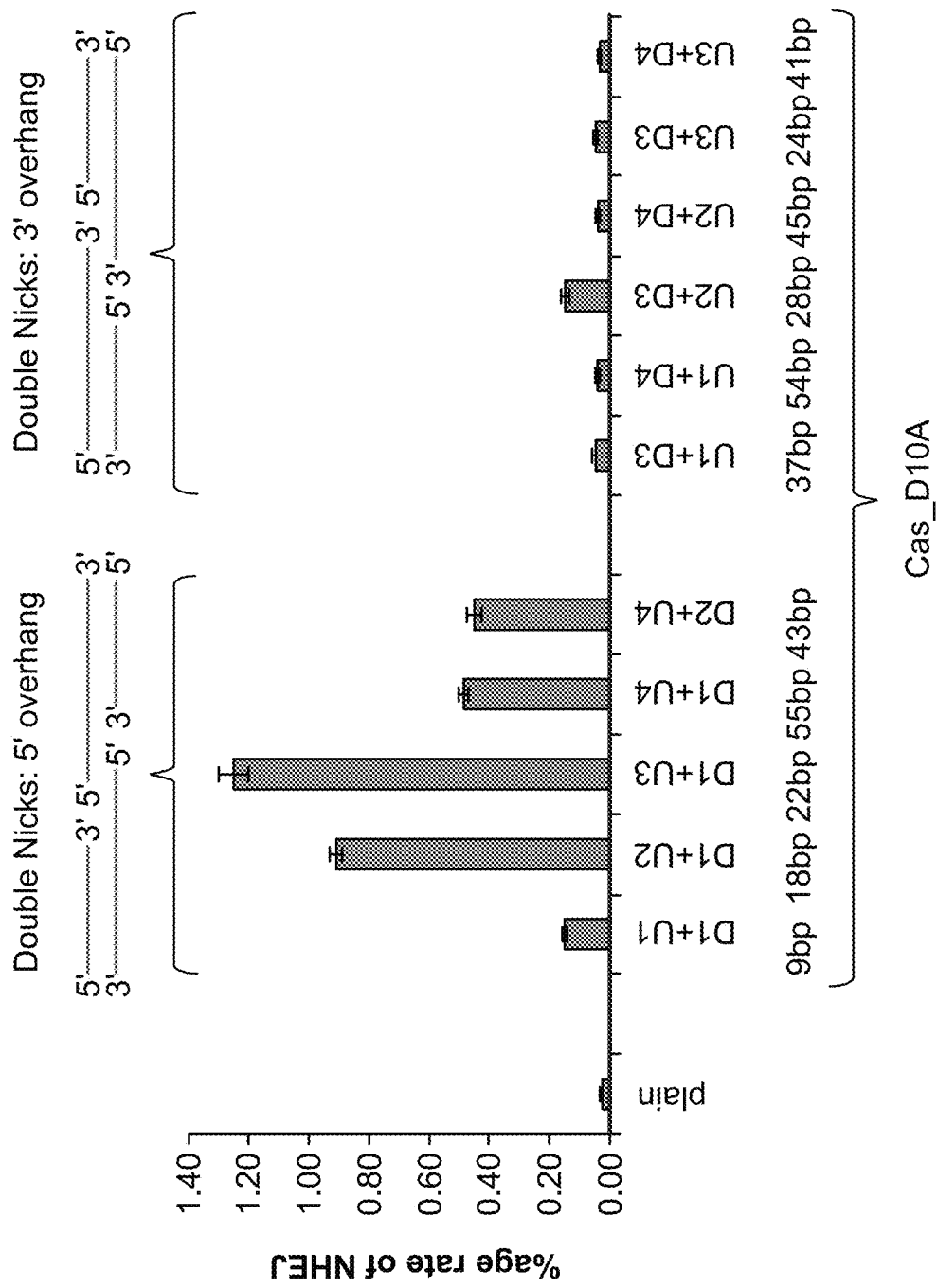

| Name | Mutations |
|---|---|
| Cas9 | wild-type |
| Cas9m1 | D10A |
| Cas9m2 | D10A+H840A |
| Cas9m3 | D10A+D839A+H840A |
| Cas9m4 | D10A+D839A+H840A+N863A |

(SEQ ID NO:64)
TAATACTTTTATCTGTCCCCTCCACCCCACAGTGGGGCCACTAGGGACAGGATTGGTGACAGAAAAGCCCC gRNA Target target locus repair donor DNA break stimulates HR

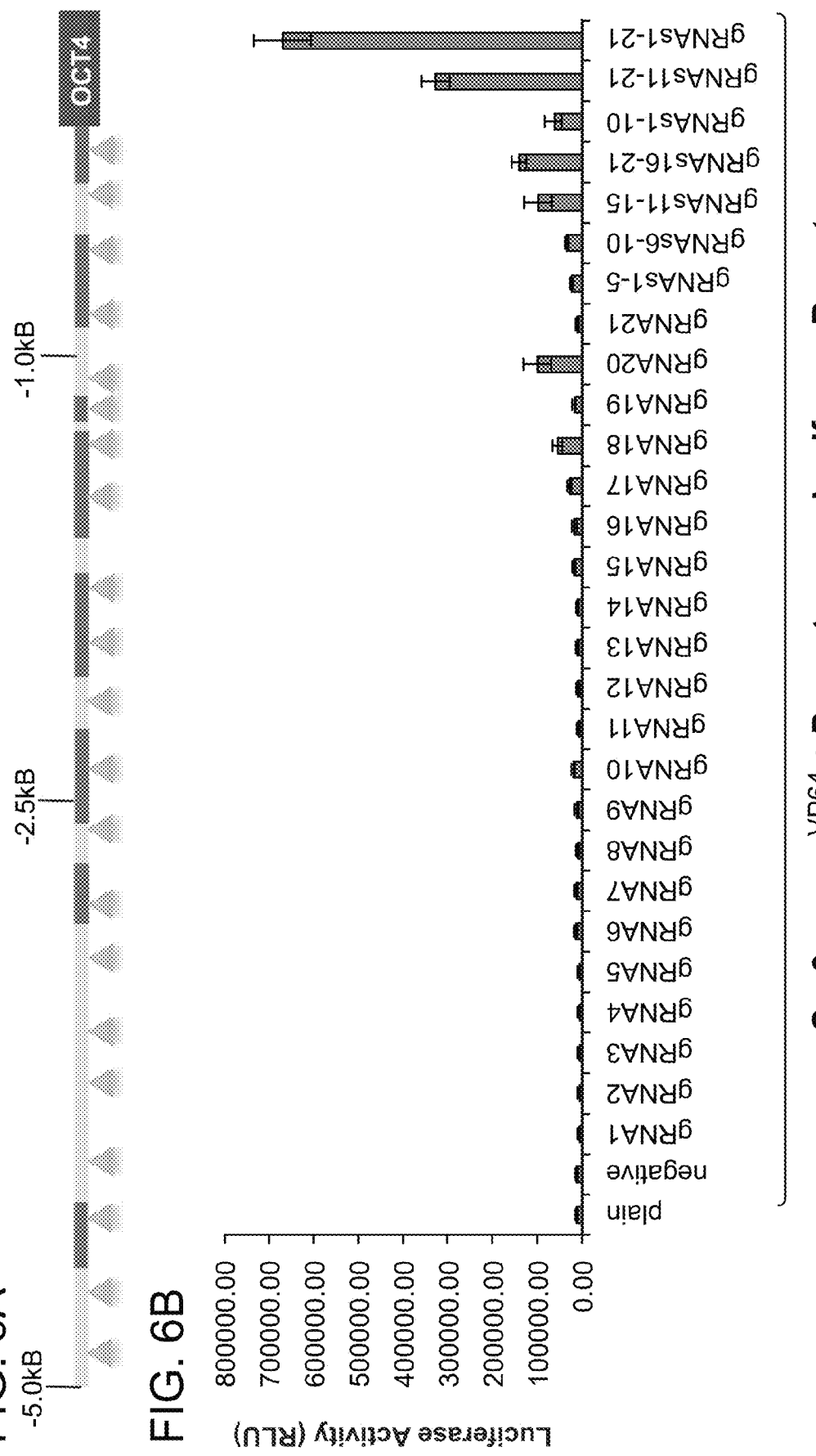

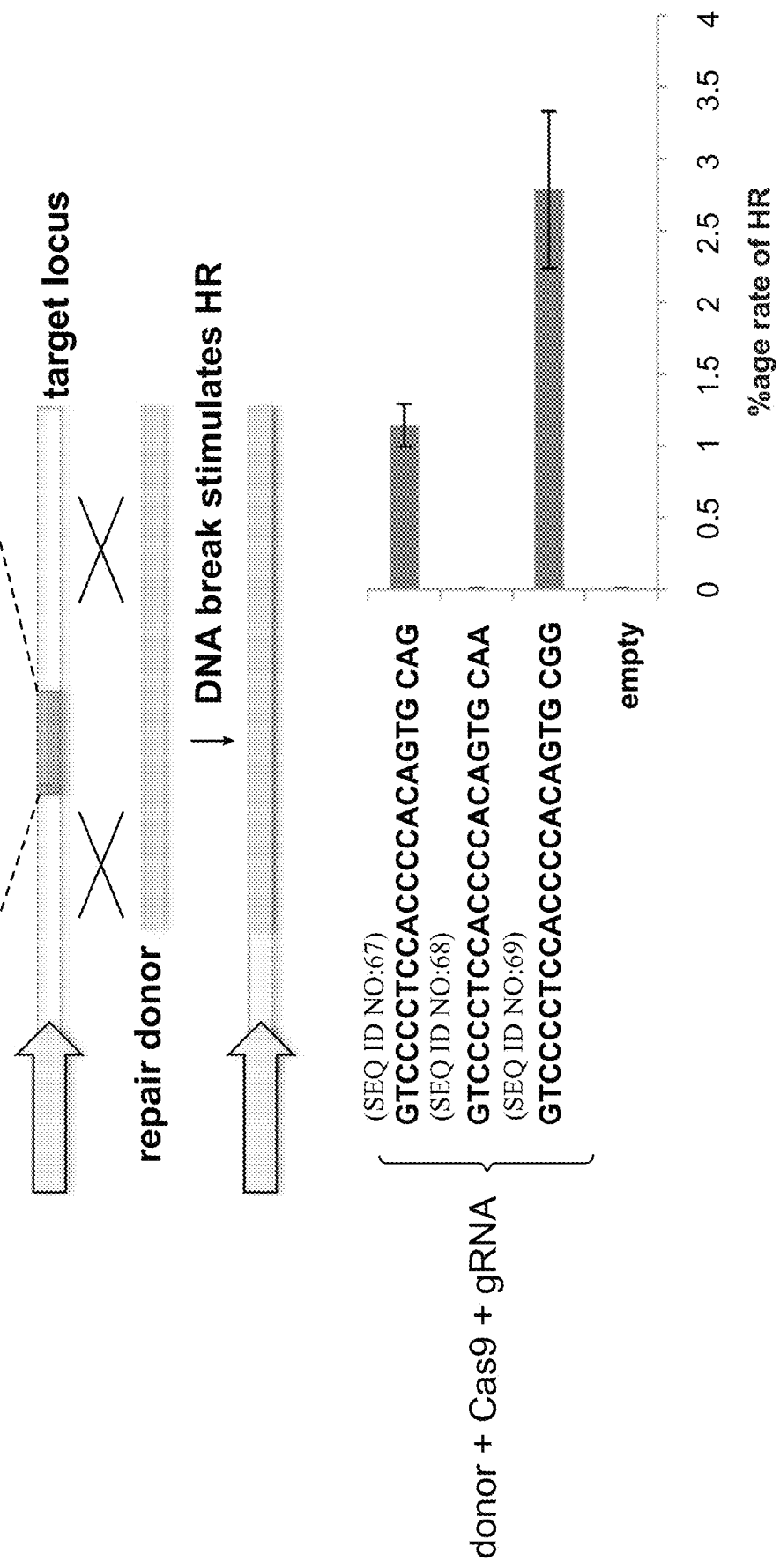

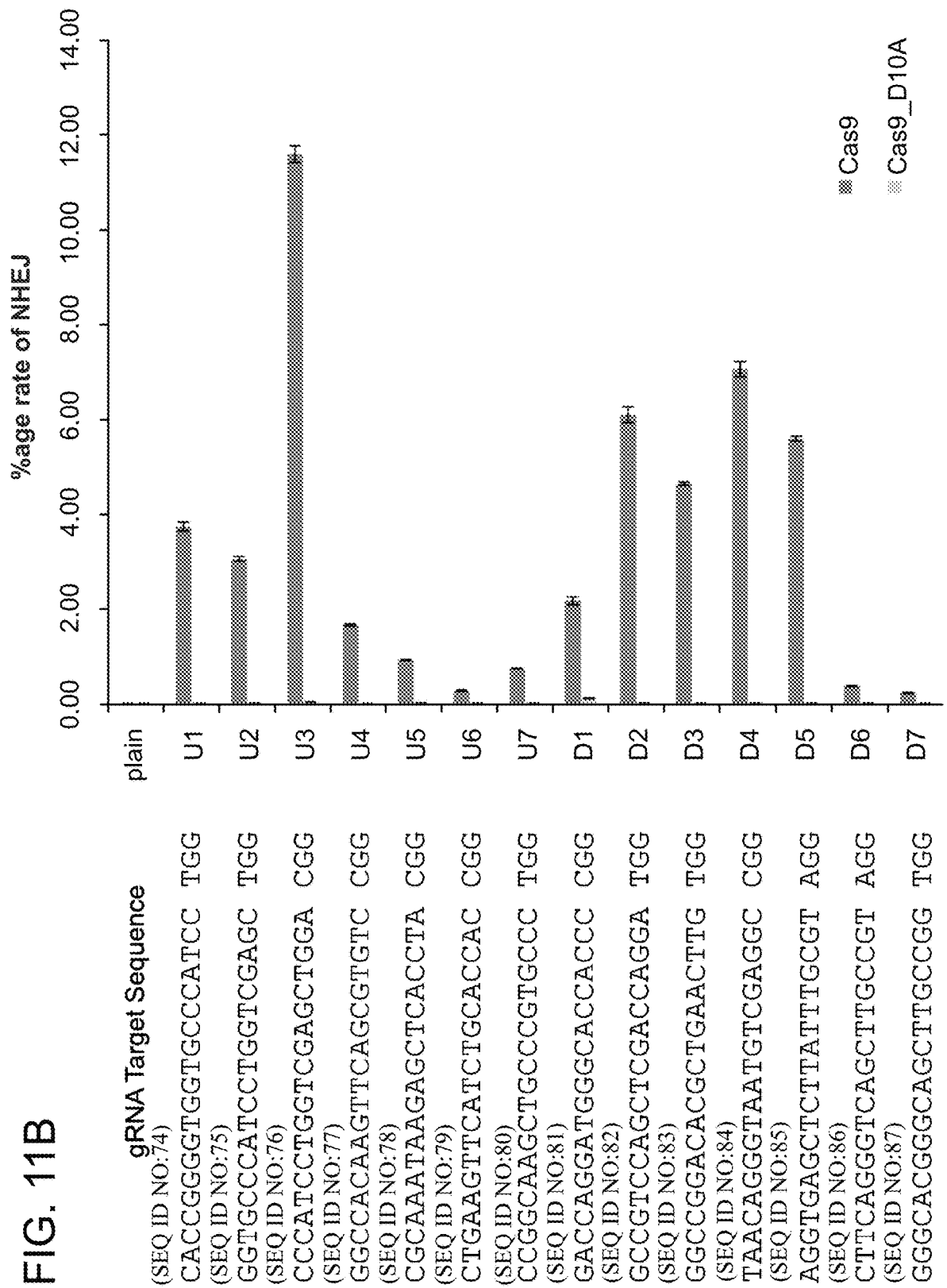

FIG. 14A
```
Target   : GAGATGATCGCCCCTTCTTC TGG  (SEQ ID NO:88)
gRNA3    : GAGATGATCGCCCCTTCTTC      (SEQ ID NO:89)
gRNA3mut : GTGATGACCGGGCCGTTCTTC     (SEQ ID NO:90)
```
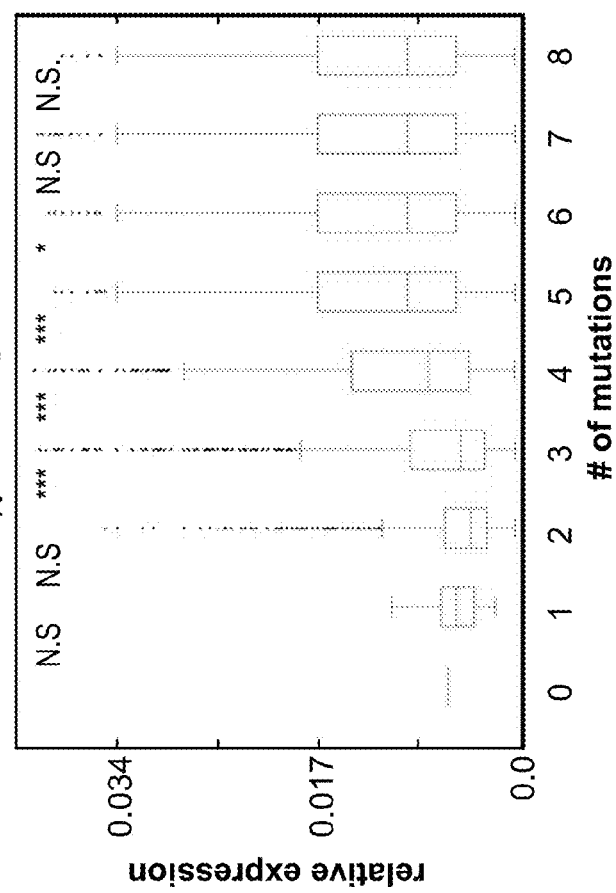
FIG. 14B
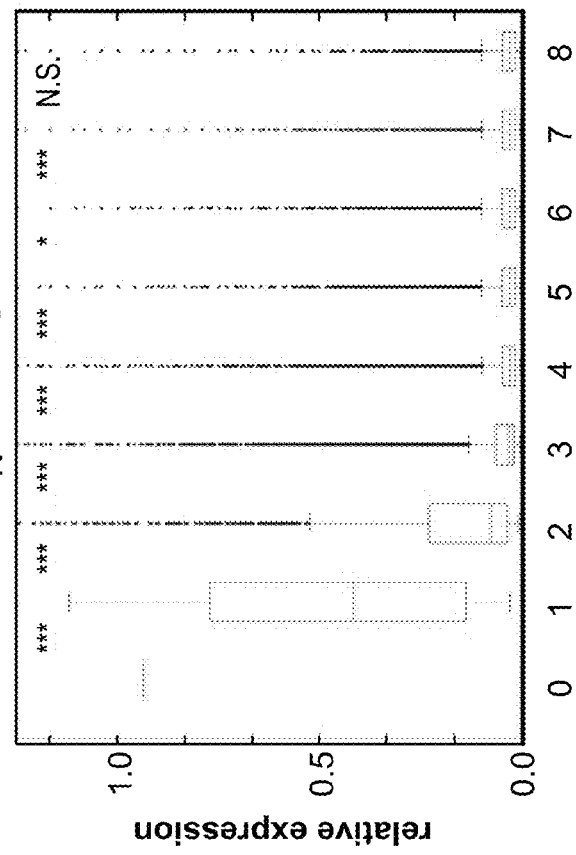
FIG. 14C

FIG. 15B-2

(SEQ ID NO:94)
GUCCCUCCACCCCACAGUC (SEQ ID NO:95)
GUCCCUCCACCCCACAGAG (SEQ ID NO:96)
GUCCCUCCACCCCACACUG (SEQ ID NO:97)
GUCCCUCCACCCCACUGUG (SEQ ID NO:98)
GUCCCUCCACCCAGAGUG (SEQ ID NO:99)
GUCCCUCCACCCCUCAGUG (SEQ ID NO:100)
GUCCCUCCACCCGACAGUG (SEQ ID NO:101)
GUCCCUCCACCGCACAGUG (SEQ ID NO:102)
GUCCCUCCACGCCACAGUG (SEQ ID NO:103)
GUCCCUCCAGCCACAGUG (SEQ ID NO:104)
GUCCCUCCUCCCCACAGUG (SEQ ID NO:105)
GUCCCUCGACCCACAGTG (SEQ ID NO:106)
GUCCCUCCACCCCACAGAC (SEQ ID NO:107)
GUCCCUCCACCCCACUCUG (SEQ ID NO:108)
GUCCCUCCACCCUGAGUG (SEQ ID NO:109)
GUCCCUCCACCGGACAGUG (SEQ ID NO:110)
GUCCCUCCAGGCCACAGUG (SEQ ID NO:111)
GUCCCUCGUCCCACAGUG

FIG. 15C
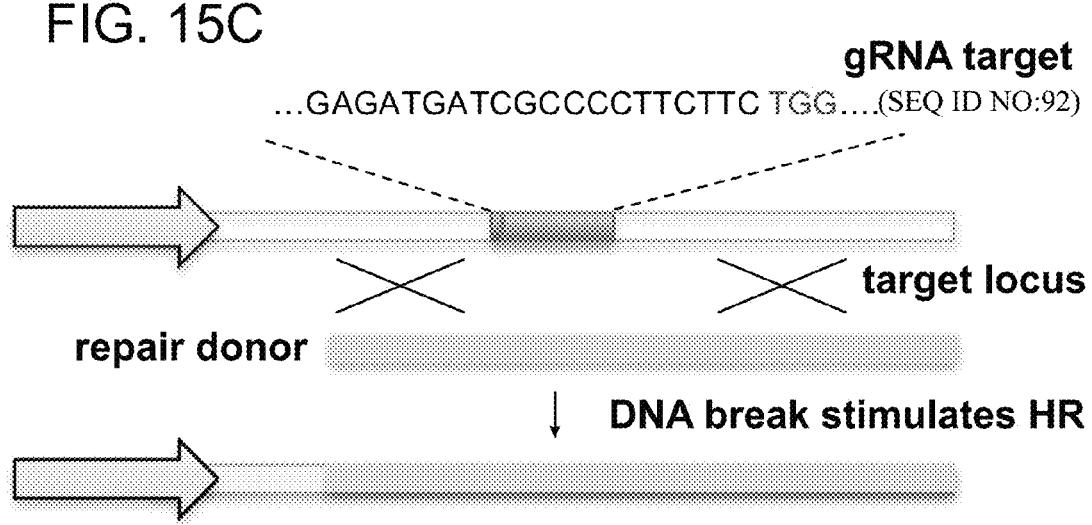
FIG. 15D-1
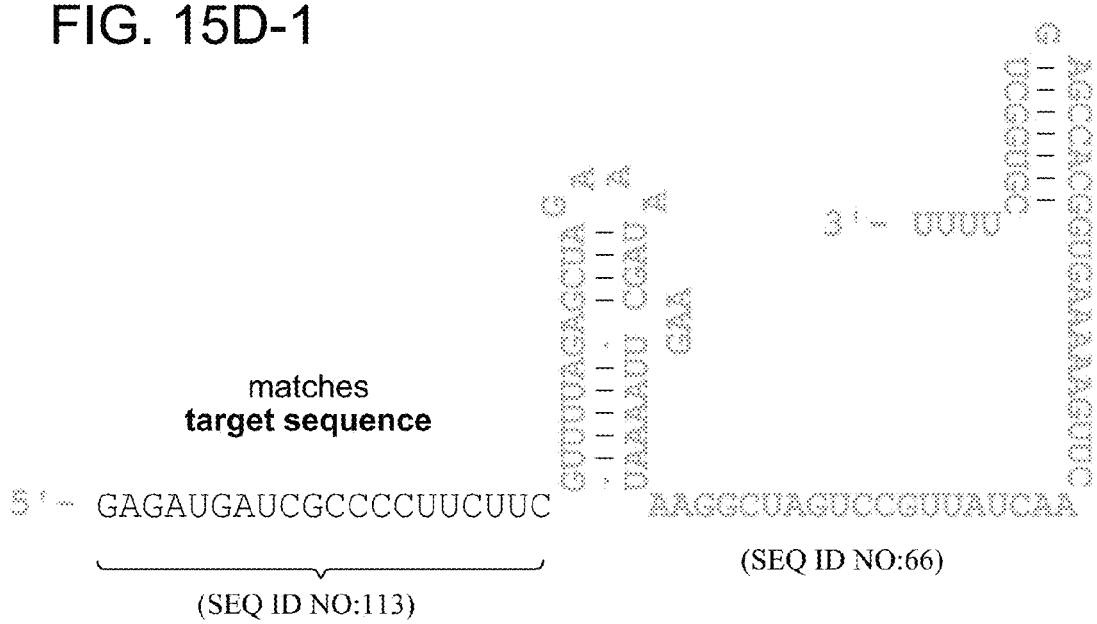
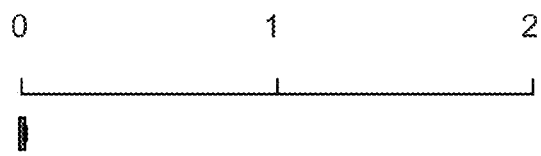

FIG. 15D-2

(SEQ ID NO:114)
GAGAUGAUCGCCCUUCUUG (SEQ ID NO:115)
GAGAUGAUCGCCCUUCUAC (SEQ ID NO:116)
GAGAUGAUCGCCCUUCAUC (SEQ ID NO:117)
GAGAUGAUCGCCCUUGUUC (SEQ ID NO:118)
GAGAUGAUCGCCCUACUUC (SEQ ID NO:119)
GAGAUGAUCGCCCAUCUUC (SEQ ID NO:120)
GAGAUGAUCGCCGUUCUUC (SEQ ID NO:121)
GAGAUGAUCGCCGCUUCUUC (SEQ ID NO:122)
GAGAUGAUCGCGCCUUCUUC (SEQ ID NO:123)
GAGAUGAUCGGCCCUUCUUC (SEQ ID NO:124)
GAGAUGAUCCCCCUUCUUC (SEQ ID NO:125)
GAGAUGAUGGCCCCUUCUUC (SEQ ID NO:126)
GAGAUGAUCGCCCUUCUAG (SEQ ID NO:127)
GAGAUGAUCGCCCUUGAUC (SEQ ID NO:128)
GAGAUGAUCGCCCAACUUC (SEQ ID NO:129)
GAGAUGAUCGCCGGUUCUUC (SEQ ID NO:130)
GAGAUGAUCGGGCCUUCUUC (SEQ ID NO:131)
GAGAUGAUGCCCCUUCUUC

FIG. 16B-1

```
        AGCCACGGUGAAAAAGUUC
       G|||||||          |
        UCGGUGC          |
              ᴬᴬᴬᴬᴬᴬ     |
         3'--            |
                         |
                         |
                    GAA  |
              A   UUAAUU CGAU
              ᴬᴬ  |||||| ||||
              ᴬ   GUUUAGCUA
                              AAGGCUAGUCCGUUAUCAA
                              (SEQ ID NO:66)

matches
                   target sequence
                 ⎧              ⎫
5'-- GGGGCCACUAGGGACAGGAU
                 ⎩              ⎭
                   (SEQ ID NO:133)
```

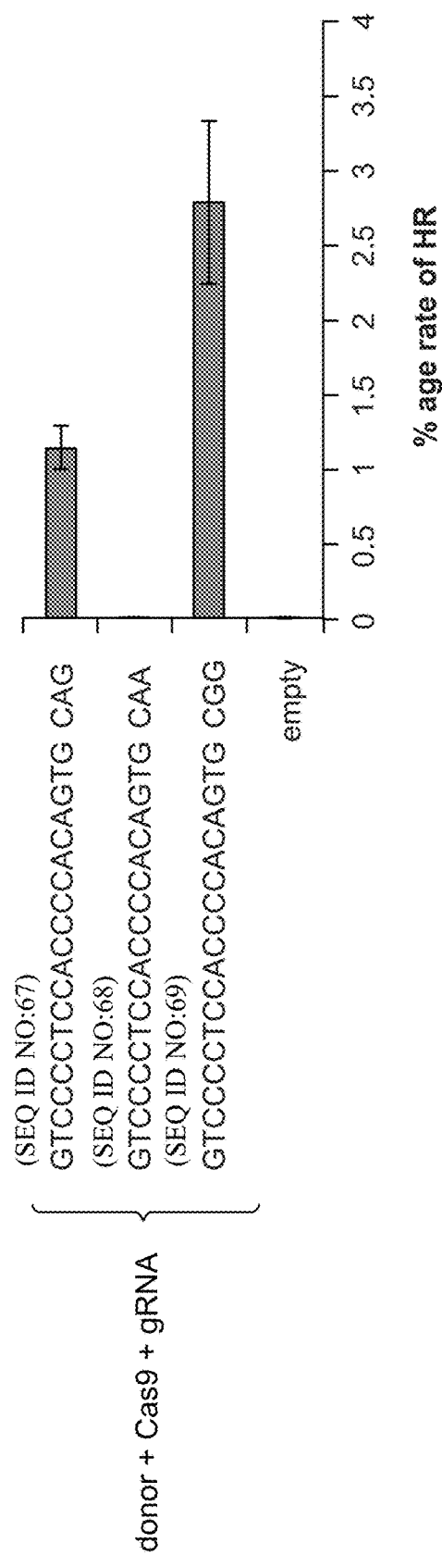

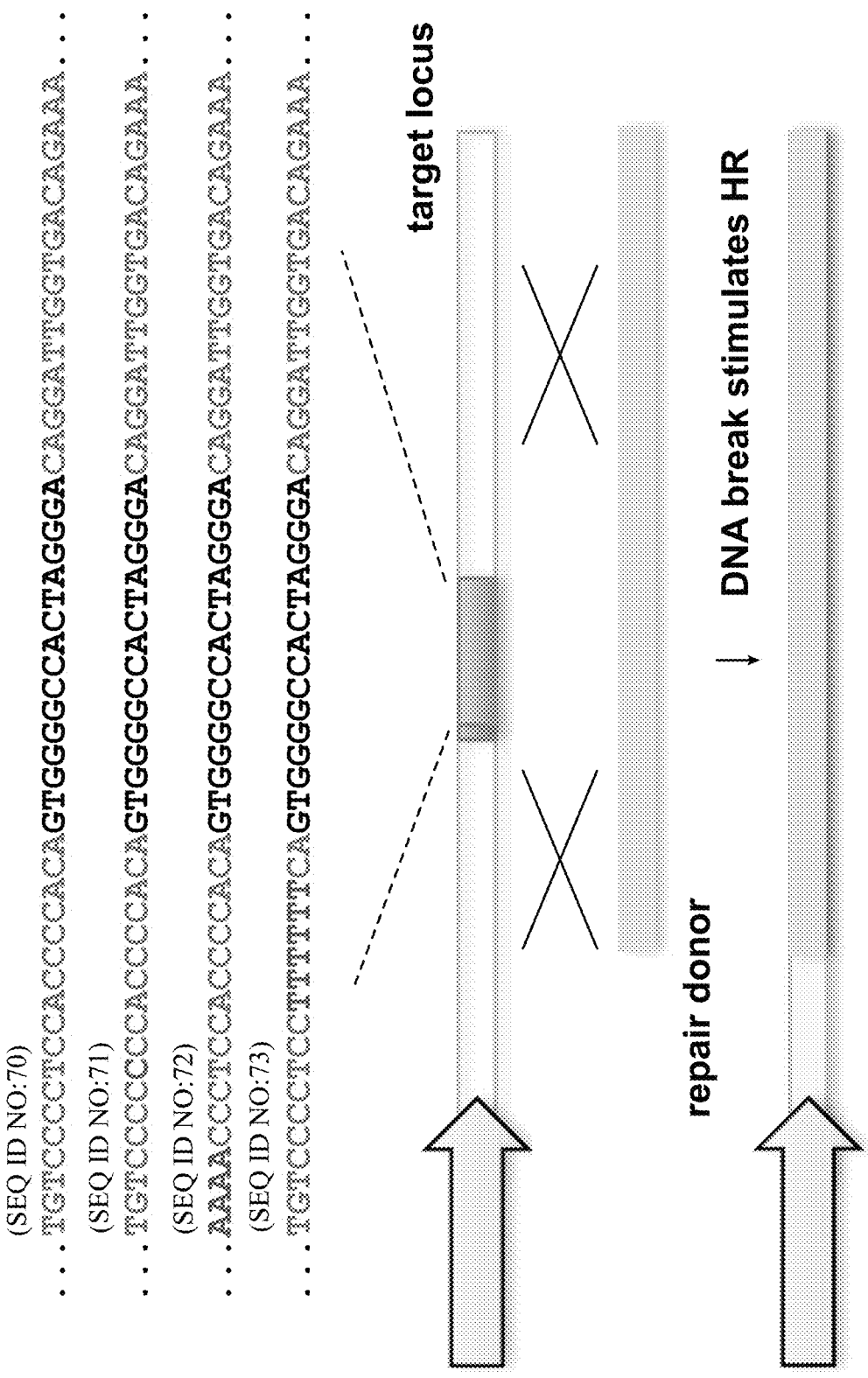

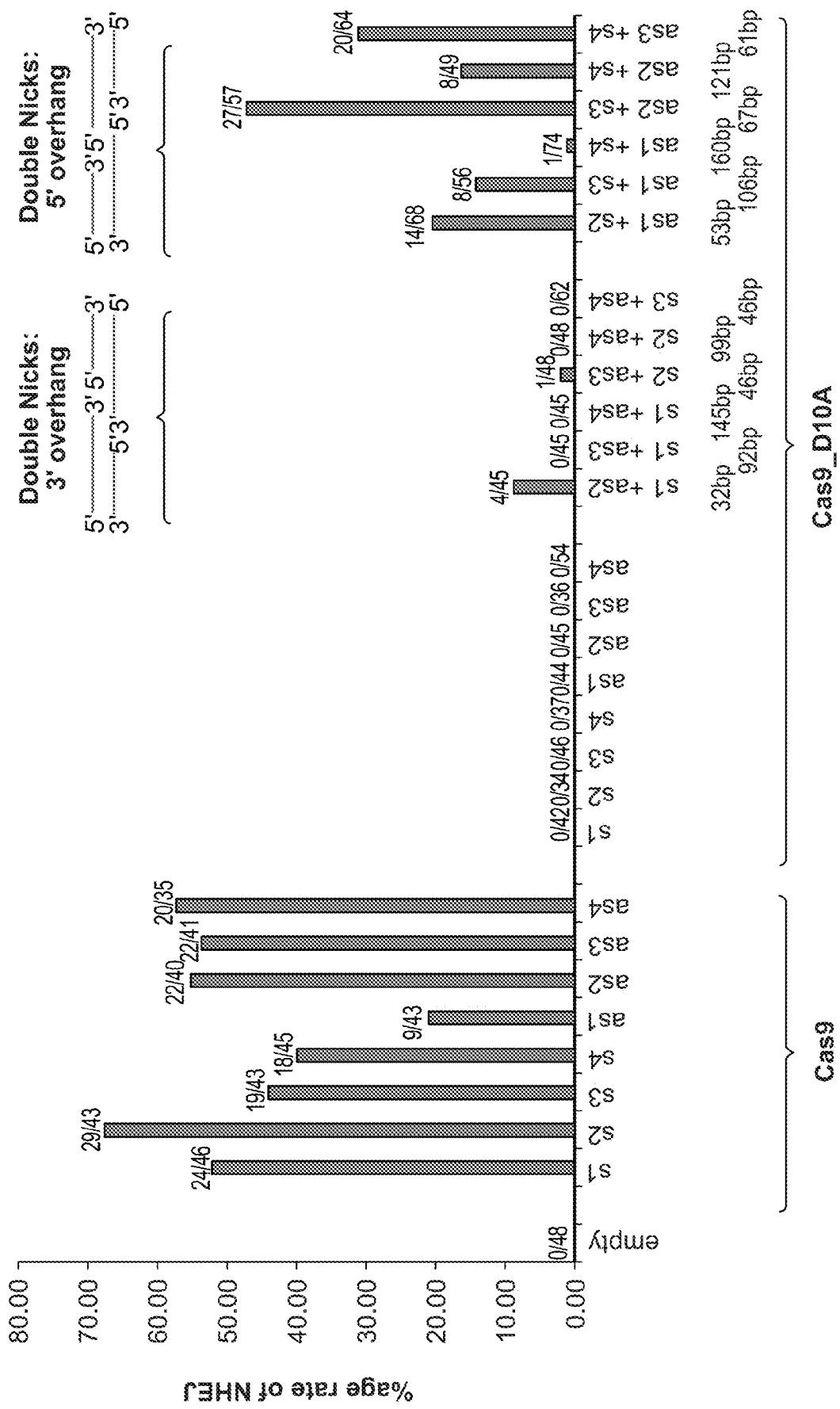

```
as2 +
AGGGCCGGTAATG----TGGCTCTGGTTCTGGGTACTTTTATCTGTCCCCTCCACCCCA------(SEQ ID NO:165)
AGGGCCGGTAATG----TGGCTCTGGTTCTGGGTACTTTTATCTGTCCCCTCCACCCCA------CAGT---GGGGCC----ACT--AGGGACAGGATTGGTGACAGAAAA (SEQ ID NO:165)
AGGGCCGGTAATG----TGGCTCTGGTTCTGGGTACTTTTATCTGTCCCCTCCACCCCA------CAGT---GGGGCC----ACT--AGGGACAGGATTGGTGACAGAAAA
AGGGCCGGTAATG----TGGCTCTGGTTCTGGGTACTTTTATCTGTCCCCTCCACCCCA------CAGT---GGGGCC----ACT--AGGGACAGGATTGGTGACAGAAAA
AGGGCCGGTAATGAATGTGGCTCTGGTTCTGGGTACTTTTATCTGTCCCCTCCACCCCA------CAGT---GGGGCC----ACT--A (SEQ ID NO:166) GACAGAAAA
AGGGCCGGTAATG----TGGCTCTGGTTCTGGGTACTTTTATCTGTCCCCTCCACCCCC------------------------------GATTGGTGACAGAAAA
AGGGCCGGTT-----------------------------------------------------(SEQ ID NO:167)
AGGGCCGGTT-------------------------------------------------------(SEQ ID NO:168)
                                                                  (SEQ ID NO:165)
AGGGCCGGTAATG----TGGCTCTGGTTCTGGGTACTTTTATCTGTCCCCTCCACCCCA------CAGT---GGGGCC----ACT--AGGGACAGGATTGGTGACAGAAAA
AGGGCCGGTAATG----TGGCTCTGGTTCTGGGTACTTTTATCTGTCCCCTCCACCCCA------CAGT---GGGGCC----ACT--AGGGACAGGATTGGTGACAGAAAA
AGGGCCGGTAATG----TGGCTCTGGTTCTGGGTACTTTTATCTGTCCCCTCCACCCCA------CAGT---GGGGCC----ACT--AGGGACAGGATTGGTGACAGAAAA
AGGGCCGGTAATG----TGGC--------------------------------------------(SEQ ID NO:169)
AGGGCCGGTAATG-----------------------------------------------------(SEQ ID NO:170)------GATTGGTGACAGAAAA
AGGGCCGGTAATG----TGGCTCTGGTTCTGGGTACTTTTATCTGTCCCCTCCACCCCA------CAGT---GGGG (SEQ ID NO:171)------GATTGGTGACAGAAAA
AGGGCCGGTAATG----TGGCTCTGGTTCTGGGTACTTTTATCTGTCCCCTCCACCCCA------CAGT---GGGG (SEQ ID NO:165) ACAGGATTGGTGACAxxAAAAA
AGGGCCGGTAATG----TGGCTCTGGTTCTGGGTACTTTTATCTGTCCCCTCCACCCCA------CAGT---GGGGCC----ACT--AGGGACAGGATTGGTGACAGAAAA
AGGGCCGGTAATG------------------------------------------------------(SEQ ID NO:172)
AGGGCCGGTAATG------------------------------------------------------(SEQ ID NO:173)------TGGTGACAGAAAA
AGGGCCGGTAATG----TGGCTCTGGTTCTGGGTACTTTTATCTGTCCCCTCCACCCCAxxCAGTxxGxCCxxCTCACxxxCAGGACAGGATTGGTGACAGAAAA
AGGGCCGGTAATG----TGGCTCTGGTTCTGGGTACTTTTATCTGTCCCCTCCACC---A (SEQ ID NO:174) CC----ACT--AGGGACAGGATTGGTGACAGAAAA
```

CCCACAGTGGGGCCACTA----------GG--GACAGGATTGTTGAC-AGAAAAGCCCCAT----------------------------------ACCCC
         (SEQ ID NO:175)
CCCACAGTGGGGCCACTA----------(SEQ ID NO:176)-----------------------------------------------------ACCCC
CCCACAGTGGGGCCACTA----------GTAGAACAGCCCCATCCTTAGGCCTTAGGCCTTAGGCCCTTAGGCCTTCCTGATATTGGGTCTAACCCC
         (SEQ ID NO:177)
CCCACAGTGGGGCCACTA----------GG--GACAGGATTGTTGAC-AGAAAAGCCCCATCCTTAGGCCTTAGGCCCTCCTAGTCTCCTGATATTGGGTCTAACCCC
         (SEQ ID NO:178)
CCCACAGTGGGGCCACTA----------GG--GACAGGATTGTTGAC-AGAAAAGCCCCATCCTTAGGCCTTAGGCCCTCCTAGTCTCCTGATATTGGGTCTAACCCC
         (SEQ ID NO:178)
CCCACAGTGGGGCCACTA----------GG--GACAGGATTGTTGAC-AGAAAAGCCCCATCCTTAGGCCTTAGGCCCTCCTAGTCTCCTGATATTGGGTCTAACCCC
         (SEQ ID NO:178)
CCCACAGTGGGGCCAC------------(SEQ ID NO:179)-----CCTTAGGCCTTAGGCCCTCCTAGTCTCCTGATATTGGGTCTAACCCC
CCCACAGTGGGGCCACTA----------GG--GACAGGATTGTTGAC-AGAAAAGCCCCATCCTTAGGCCTTAGGCCCTCCTAGTCTCCTGATATTGGGTCTAACCCC
         (SEQ ID NO:178)
CCCACAGTGGGGCCACTA----------G---(SEQ ID NO:180)------------------------------------------------
CCCACAGTGGGGCCACTA----------GG--GACAGGATTGTTGAC-AAAAAAGCCCCATCCTTACGCCTTCCTAGTCTCCTGATATTGGGCTAACCCC
         (SEQ ID NO:181)
CCCACAGTGGGGCCACTA----------GG--GAC-----------------------------TGATATTGGGTCTAACCCC
         (SEQ ID NO:182)
CCCACAGTGGGGCCACTA----------GG--GAC----------------------AGGCCTTCCTAGTCTCCTGATATTGGGTCTAACCCC
         (SEQ ID NO:183)
CCCACAGTGGGGCCACTAGGGAGGGGGG----GACAGGATTGTTGAC-AGAAAAGCCCCATCCTTAGGCCTTAGGCCCTCCTAGTCTCCTGATATTGGGTCTAACCCC
         (SEQ ID NO:178)
CCCACAGTGGGGCCACTA----------GG--GACAGGATTGTTGAC-AGAAAAGCCCCATCCTTAGGCCTTAGGCCCTCCTAGTCTCCTGATATTGGGTCTAACCCC
         (SEQ ID NO:178)
CCCACAGTGGGGCCACTA----------GG--GACAGGATTGTTGAC-AGAAAAGCCCCATCCTTAGGCCTTAGGCCCTCCTAGTCTCCTGATATTGGGTCTAACCCC
         (SEQ ID NO:178)
CCCACAGTGGGGCCACTA----------GG--ACAGGATTGTTGAC-AGAAAAGCCCCATCCTTAGGCCTTAGGCCCTCCTAGTCTCCTGATATTGGGTCTAACCCC
         (SEQ ID NO:184)
CCC-----------------------------------------------------------AGAAAAGCCCCATCCTTAGGCCTTAGGCCCTCCTAGTCTCCTGATATTGGGTCTAACCCC
CCCACAGTGGGGCCACTA----------GG--GACAGGATTGTTGAC-AGAAAAGCCCCATCCTTAGGCCTTAGGCCCTCCTAGTCTCCTGATATTGGGTCTAACCCC
         (SEQ ID NO:178)
```

RNA-GUIDED TRANSCRIPTIONAL REGULATION

RELATED APPLICATION DATA

This application is a continuation of U.S. patent application Ser. No. 16/851,360 and filed Apr. 17, 2020, which is a continuation of U.S. patent application Ser. No. 16/441,209 and filed Jun. 14, 2019, which is a continuation of U.S. patent application Ser. No. 14/319,530, filed on Jun. 30, 2014, which is a continuation of PCT application no. PCT/US2014/040868, designating the United States and filed Jun. 4, 2014; which claims the benefit U.S. Provisional Patent Application No. 61/830,787 filed on Jun. 4, 2013; each of which are hereby incorporated by reference in their entireties.

STATEMENT OF GOVERNMENT INTERESTS

This invention was made with government support under HG005550 awarded by National Institutes of Health (NIH) and under DE-FG02-02ER63445 awarded by U.S. Department of Energy (DOE). The government has certain rights in this invention.

REFERENCE TO AN ELECTRONIC SEQUENCE LISTING

The instant application contains a Sequence Listing which has been submitted electronically in XML format and is hereby incorporated by reference in its entirety. Said XML copy, created on Nov. 27, 2023, is named "Corrected Sequence_Listing_010498_01504_ST26.xml" and is 252 KB in size.

BACKGROUND

Bacterial and archaeal CRISPR-Cas systems rely on short guide RNAs in complex with Cas proteins to direct degradation of complementary sequences present within invading foreign nucleic acid. See Deltcheva, E. et al. CRISPR RNA maturation by trans-encoded small RNA and host factor RNase III. *Nature* 471, 602-607 (2011); Gasiunas, G., Barrangou, R., Horvath, P. & Siksnys, V. Cas9-crRNA ribonucleoprotein complex mediates specific DNA cleavage for adaptive immunity in bacteria. *Proceedings of the National Academy of Sciences of the United States of America* 109, E2579-2586 (2012); Jinek, M. et al. A programmable dual-RNA-guided DNA endonuclease in adaptive bacterial immunity. *Science* 337, 816-821 (2012); Sapranauskas, R. et al. The *Streptococcus thermophilus* CRISPR/Cas system provides immunity in *Escherichia coli*. *Nucleic acids research* 39, 9275-9282 (2011); and Bhaya, D., Davison, M. & Barrangou, R. CRISPR-Cas systems in bacteria and archaea: versatile small RNAs for adaptive defense and regulation. *Annual review of genetics* 45, 273-297 (2011). A recent in vitro reconstitution of the *S. pyogenes* type II CRISPR system demonstrated that crRNA ("CRISPR RNA") fused to a normally trans-encoded tracrRNA ("trans-activating CRISPR RNA") is sufficient to direct Cas9 protein to sequence-specifically cleave target DNA sequences matching the crRNA. Expressing a gRNA homologous to a target site results in Cas9 recruitment and degradation of the target DNA. See H. Deveau et al., Phage response to CRISPR-encoded resistance in *Streptococcus thermophilus*. *Journal of Bacteriology* 190, 1390 (February, 2008).

SUMMARY

Aspects of the present disclosure are directed to a complex of a guide RNA, a DNA binding protein and a double stranded DNA target sequence. According to certain aspects, DNA binding proteins within the scope of the present disclosure include a protein that forms a complex with the guide RNA and with the guide RNA guiding the complex to a double stranded DNA sequence wherein the complex binds to the DNA sequence. This aspect of the present disclosure may be referred to as co-localization of the RNA and DNA binding protein to or with the double stranded DNA. In this manner, a DNA binding protein-guide RNA complex may be used to localize a transcriptional regulator protein or domain at target DNA so as to regulate expression of target DNA.

According to certain aspects, a method of modulating expression of a target nucleic acid in a cell is provided including introducing into the cell a first foreign nucleic acid encoding one or more RNAs (ribonucleic acids) complementary to DNA (deoxyribonucleic acid), wherein the DNA includes the target nucleic acid, introducing into the cell a second foreign nucleic acid encoding an RNA guided nuclease-null DNA binding protein that binds to the DNA and is guided by the one or more RNAs, introducing into the cell a third foreign nucleic acid encoding a transcriptional regulator protein or domain, wherein the one or more RNAs, the RNA guided nuclease-null DNA binding protein, and the transcriptional regulator protein or domain are expressed, wherein the one or more RNAs, the RNA guided nuclease-null DNA binding protein and the transcriptional regulator protein or domain co-localize to the DNA and wherein the transcriptional regulator protein or domain regulates expression of the target nucleic acid.

According to one aspect, the foreign nucleic acid encoding an RNA guided nuclease-null DNA binding protein further encodes the transcriptional regulator protein or domain fused to the RNA guided nuclease-null DNA binding protein. According to one aspect, the foreign nucleic acid encoding one or more RNAs further encodes a target of an RNA-binding domain and the foreign nucleic acid encoding the transcriptional regulator protein or domain further encodes an RNA-binding domain fused to the transcriptional regulator protein or domain.

According to one aspect, the cell is a eukaryotic cell. According to one aspect, the cell is a yeast cell, a plant cell or an animal cell. According to one aspect, the cell is a mammalian cell.

According to one aspect, the RNA is between about 10 to about 500 nucleotides. According to one aspect, the RNA is between about 20 to about 100 nucleotides.

According to one aspect, the transcriptional regulator protein or domain is a transcriptional activator. According to one aspect, the transcriptional regulator protein or domain upregulates expression of the target nucleic acid. According to one aspect, the transcriptional regulator protein or domain upregulates expression of the target nucleic acid to treat a disease or detrimental condition. According to one aspect, the target nucleic acid is associated with a disease or detrimental condition.

According to one aspect, the one or more RNAs is a guide RNA. According to one aspect, the one or more RNAs is a tracrRNA-crRNA fusion. According to one aspect, the guide RNA includes a spacer sequence and a tracer mate sequence. The guide RNA may also include a tracr sequence, a portion of which hybridizes to the tracr mate sequence. The guide RNA may also include a linker nucleic acid sequence which links the tracer mate sequence and the tracr sequence to produce the tracrRNA-crRNA fusion. The spacer sequence binds to target DNA, such as by hybridization.

According to one aspect, the guide RNA includes a truncated spacer sequence. According to one aspect, the guide RNA includes a truncated spacer sequence having a 1 base truncation at the 5' end of the spacer sequence. According to one aspect, the guide RNA includes a truncated spacer sequence having a 2 base truncation at the 5' end of the spacer sequence. According to one aspect, the guide RNA includes a truncated spacer sequence having a 3 base truncation at the 5' end of the spacer sequence. According to one aspect, the guide RNA includes a truncated spacer sequence having a 4 base truncation at the 5' end of the spacer sequence. Accordingly, the spacer sequence may have a 1 to 4 base truncation at the 5' end of the spacer sequence.

According to certain embodiments, the spacer sequence may include between about 16 to about 20 nucleotides which hybridize to the target nucleic acid sequence. According to certain embodiments, the spacer sequence may include about 20 nucleotides which hybridize to the target nucleic acid sequence.

According to certain aspects, the linker nucleic acid sequence may include between about 4 and about 6 nucleic acids.

According to certain aspects, the tracr sequence may include between about 60 to about 500 nucleic acids. According to certain aspects, the tracr sequence may include between about 64 to about 500 nucleic acids. According to certain aspects, the tracr sequence may include between about 65 to about 500 nucleic acids. According to certain aspects, the tracr sequence may include between about 66 to about 500 nucleic acids. According to certain aspects, the tracr sequence may include between about 67 to about 500 nucleic acids. According to certain aspects, the tracr sequence may include between about 68 to about 500 nucleic acids. According to certain aspects, the tracr sequence may include between about 69 to about 500 nucleic acids. According to certain aspects, the tracr sequence may include between about 70 to about 500 nucleic acids. According to certain aspects, the tracr sequence may include between about 80 to about 500 nucleic acids. According to certain aspects, the tracr sequence may include between about 90 to about 500 nucleic acids. According to certain aspects, the tracr sequence may include between about 100 to about 500 nucleic acids.

According to certain aspects, the tracr sequence may include between about 60 to about 200 nucleic acids. According to certain aspects, the tracr sequence may include between about 64 to about 200 nucleic acids. According to certain aspects, the tracr sequence may include between about 65 to about 200 nucleic acids. According to certain aspects, the tracr sequence may include between about 66 to about 200 nucleic acids. According to certain aspects, the tracr sequence may include between about 67 to about 200 nucleic acids. According to certain aspects, the tracr sequence may include between about 68 to about 200 nucleic acids. According to certain aspects, the tracr sequence may include between about 69 to about 200 nucleic acids. According to certain aspects, the tracr sequence may include between about 70 to about 200 nucleic acids. According to certain aspects, the tracr sequence may include between about 80 to about 200 nucleic acids. According to certain aspects, the tracr sequence may include between about 90 to about 200 nucleic acids. According to certain aspects, the tracr sequence may include between about 100 to about 200 nucleic acids.

An exemplary guide RNA is depicted in FIG. 5B.

According to one aspect, the DNA is genomic DNA, mitochondrial DNA, viral DNA, or exogenous DNA.

According to certain aspects, a method of modulating expression of a target nucleic acid in a cell is provided including introducing into the cell a first foreign nucleic acid encoding one or more RNAs (ribonucleic acids) complementary to DNA (deoxyribonucleic acid), wherein the DNA includes the target nucleic acid, introducing into the cell a second foreign nucleic acid encoding an RNA guided nuclease-null DNA binding protein of a Type II CRISPR System that binds to the DNA and is guided by the one or more RNAs, introducing into the cell a third foreign nucleic acid encoding a transcriptional regulator protein or domain, wherein the one or more RNAs, the RNA guided nuclease-null DNA binding protein of a Type II CRISPR System, and the transcriptional regulator protein or domain are expressed, wherein the one or more RNAs, the RNA guided nuclease-null DNA binding protein of a Type II CRISPR System and the transcriptional regulator protein or domain co-localize to the DNA and wherein the transcriptional regulator protein or domain regulates expression of the target nucleic acid.

According to one aspect, the foreign nucleic acid encoding an RNA guided nuclease-null DNA binding protein of a Type II CRISPR System further encodes the transcriptional regulator protein or domain fused to the RNA guided nuclease-null DNA binding protein of a Type II CRISPR System. According to one aspect, the foreign nucleic acid encoding one or more RNAs further encodes a target of an RNA-binding domain and the foreign nucleic acid encoding the transcriptional regulator protein or domain further encodes an RNA-binding domain fused to the transcriptional regulator protein or domain.

According to one aspect, the cell is a eukaryotic cell. According to one aspect, the cell is a yeast cell, a plant cell or an animal cell. According to one aspect, the cell is a mammalian cell.

According to one aspect, the RNA is between about 10 to about 500 nucleotides. According to one aspect, the RNA is between about 20 to about 100 nucleotides.

According to one aspect, the transcriptional regulator protein or domain is a transcriptional activator. According to one aspect, the transcriptional regulator protein or domain upregulates expression of the target nucleic acid. According to one aspect, the transcriptional regulator protein or domain upregulates expression of the target nucleic acid to treat a disease or detrimental condition. According to one aspect, the target nucleic acid is associated with a disease or detrimental condition.

According to one aspect, the one or more RNAs is a guide RNA. According to one aspect, the one or more RNAs is a tracrRNA-crRNA fusion.

According to one aspect, the DNA is genomic DNA, mitochondrial DNA, viral DNA, or exogenous DNA.

According to certain aspects, a method of modulating expression of a target nucleic acid in a cell is provided including introducing into the cell a first foreign nucleic acid encoding one or more RNAs (ribonucleic acids) complementary to DNA (deoxyribonucleic acid), wherein the DNA includes the target nucleic acid, introducing into the cell a second foreign nucleic acid encoding a nuclease-null Cas9 protein that binds to the DNA and is guided by the one or more RNAs, introducing into the cell a third foreign nucleic acid encoding a transcriptional regulator protein or domain, wherein the one or more RNAs, the nuclease-null Cas9 protein, and the transcriptional regulator protein or domain are expressed, wherein the one or more RNAs, the nuclease-null Cas9 protein and the transcriptional regulator protein or domain co-localize to the DNA and wherein the transcriptional regulator protein or domain regulates expression of the target nucleic acid.

According to one aspect, the foreign nucleic acid encoding a nuclease-null Cas9 protein further encodes the transcriptional regulator protein or domain fused to the nuclease-null Cas9 protein. According to one aspect, the foreign nucleic acid encoding one or more RNAs further encodes a target of an RNA-binding domain and the foreign nucleic acid encoding the transcriptional regulator protein or domain further encodes an RNA-binding domain fused to the transcriptional regulator protein or domain.

According to one aspect, the cell is a eukaryotic cell. According to one aspect, the cell is a yeast cell, a plant cell or an animal cell. According to one aspect, the cell is a mammalian cell.

According to one aspect, the RNA is between about 10 to about 500 nucleotides. According to one aspect, the RNA is between about 20 to about 100 nucleotides.

According to one aspect, the transcriptional regulator protein or domain is a transcriptional activator. According to one aspect, the transcriptional regulator protein or domain upregulates expression of the target nucleic acid. According to one aspect, the transcriptional regulator protein or domain upregulates expression of the target nucleic acid to treat a disease or detrimental condition. According to one aspect, the target nucleic acid is associated with a disease or detrimental condition.

According to one aspect, the one or more RNAs is a guide RNA. According to one aspect, the one or more RNAs is a tracrRNA-crRNA fusion.

According to one aspect, the DNA is genomic DNA, mitochondrial DNA, viral DNA, or exogenous DNA.

According to one aspect a cell is provided that includes a first foreign nucleic acid encoding one or more RNAs complementary to DNA, wherein the DNA includes a target nucleic acid, a second foreign nucleic acid encoding an RNA guided nuclease-null DNA binding protein, and a third foreign nucleic acid encoding a transcriptional regulator protein or domain wherein the one or more RNAs, the RNA guided nuclease-null DNA binding protein and the transcriptional regulator protein or domain are members of a co-localization complex for the target nucleic acid.

According to one aspect, the foreign nucleic acid encoding an RNA guided nuclease-null DNA binding protein further encodes the transcriptional regulator protein or domain fused to an RNA guided nuclease-null DNA binding protein. According to one aspect, the foreign nucleic acid encoding one or more RNAs further encodes a target of an RNA-binding domain and the foreign nucleic acid encoding the transcriptional regulator protein or domain further encodes an RNA-binding domain fused to the transcriptional regulator protein or domain.

According to one aspect, the cell is a eukaryotic cell. According to one aspect, the cell is a yeast cell, a plant cell or an animal cell. According to one aspect, the cell is a mammalian cell.

According to one aspect, the RNA is between about 10 to about 500 nucleotides. According to one aspect, the RNA is between about 20 to about 100 nucleotides.

According to one aspect, the transcriptional regulator protein or domain is a transcriptional activator. According to one aspect, the transcriptional regulator protein or domain upregulates expression of the target nucleic acid. According to one aspect, the transcriptional regulator protein or domain upregulates expression of the target nucleic acid to treat a disease or detrimental condition. According to one aspect, the target nucleic acid is associated with a disease or detrimental condition.

According to one aspect, the one or more RNAs is a guide RNA. According to one aspect, the one or more RNAs is a tracrRNA-crRNA fusion.

According to one aspect, the DNA is genomic DNA, mitochondrial DNA, viral DNA, or exogenous DNA.

According to certain aspects, the RNA guided nuclease-null DNA binding protein is an RNA guided nuclease-null DNA binding protein of a Type II CRISPR System. According to certain aspects, the RNA guided nuclease-null DNA binding protein is a nuclease-null Cas9 protein.

According to one aspect, a method of altering a DNA target nucleic acid in a cell is provided that includes introducing into the cell a first foreign nucleic acid encoding two or more RNAs with each RNA being complementary to an adjacent site in the DNA target nucleic acid, introducing into the cell a second foreign nucleic acid encoding at least one RNA guided DNA binding protein nickase and being guided by the two or more RNAs, wherein the two or more RNAs and the at least one RNA guided DNA binding protein nickase are expressed and wherein the at least one RNA guided DNA binding protein nickase co-localizes with the two or more RNAs to the DNA target nucleic acid and nicks the DNA target nucleic acid resulting in two or more adjacent nicks.

According to one aspect, a method of altering a DNA target nucleic acid in a cell is provided that includes introducing into the cell a first foreign nucleic acid encoding two or more RNAs with each RNA being complementary to an adjacent site in the DNA target nucleic acid, introducing into the cell a second foreign nucleic acid encoding at least one RNA guided DNA binding protein nickase of a Type II CRISPR System and being guided by the two or more RNAs, wherein the two or more RNAs and the at least one RNA guided DNA binding protein nickase of a Type II CRISPR System are expressed and wherein the at least one RNA guided DNA binding protein nickase of a Type II CRISPR System co-localizes with the two or more RNAs to the DNA target nucleic acid and nicks the DNA target nucleic acid resulting in two or more adjacent nicks.

According to one aspect, a method of altering a DNA target nucleic acid in a cell is provided that includes introducing into the cell a first foreign nucleic acid encoding two or more RNAs with each RNA being complementary to an adjacent site in the DNA target nucleic acid, introducing into the cell a second foreign nucleic acid encoding at least one Cas9 protein nickase having one inactive nuclease domain and being guided by the two or more RNAs, wherein the two or more RNAs and the at least one Cas9 protein nickase are expressed and wherein the at least one Cas9 protein nickase co-localizes with the two or more RNAs to the DNA target nucleic acid and nicks the DNA target nucleic acid resulting in two or more adjacent nicks.

According to the methods of altering a DNA target nucleic acid, the two or more adjacent nicks are on the same strand of the double stranded DNA. According to one aspect, the two or more adjacent nicks are on the same strand of the double stranded DNA and result in homologous recombination. According to one aspect, the two or more adjacent nicks are on different strands of the double stranded DNA. According to one aspect, the two or more adjacent nicks are on different strands of the double stranded DNA and create double stranded breaks. According to one aspect, the two or more adjacent nicks are on different strands of the double stranded DNA and create double stranded breaks resulting in nonhomologous end joining. According to one aspect, the two or more adjacent nicks are on different strands of the double stranded DNA and are offset with respect to one another. According to one aspect, the two or more adjacent nicks are on different strands of the double stranded DNA and are offset with respect to one another and create double stranded breaks. According to one aspect, the two or more adjacent nicks are on different strands of the double stranded DNA and are offset with respect to one another and create double stranded breaks resulting in nonhomologous end joining. According to one aspect, the method further includes introducing into the cell a third foreign nucleic acid encoding a donor nucleic acid sequence wherein the two or more nicks results in homologous recombination of the target nucleic acid with the donor nucleic acid sequence.

According to one aspect, a method of altering a DNA target nucleic acid in a cell is provided including introducing into the cell a first foreign nucleic acid encoding two or more RNAs with each RNA being complementary to an adjacent site in the DNA target nucleic acid, introducing into the cell a second foreign nucleic acid encoding at least one RNA guided DNA binding protein nickase and being guided by the two or more RNAs, and wherein the two or more RNAs and the at least one RNA guided DNA binding protein nickase are expressed and wherein the at least one RNA guided DNA binding protein nickase co-localizes with the two or more RNAs to the DNA target nucleic acid and nicks the DNA target nucleic acid resulting in two or more adjacent nicks, and wherein the two or more adjacent nicks are on different strands of the double stranded DNA and create double stranded breaks resulting in fragmentation of the target nucleic acid thereby preventing expression of the target nucleic acid.

According to one aspect, a method of altering a DNA target nucleic acid in a cell is provided including introducing into the cell a first foreign nucleic acid encoding two or more RNAs with each RNA being complementary to an adjacent site in the DNA target nucleic acid, introducing into the cell a second foreign nucleic acid encoding at least one RNA guided DNA binding protein nickase of a Type II CRISPR system and being guided by the two or more RNAs, and wherein the two or more RNAs and the at least one RNA guided DNA binding protein nickase of a Type II CRISPR System are expressed and wherein the at least one RNA guided DNA binding protein nickase of a Type II CRISPR System co-localizes with the two or more RNAs to the DNA target nucleic acid and nicks the DNA target nucleic acid resulting in two or more adjacent nicks, and wherein the two or more adjacent nicks are on different strands of the double stranded DNA and create double stranded breaks resulting in fragmentation of the target nucleic acid thereby preventing expression of the target nucleic acid.

According to one aspect, a method of altering a DNA target nucleic acid in a cell is provided including introducing into the cell a first foreign nucleic acid encoding two or more RNAs with each RNA being complementary to an adjacent site in the DNA target nucleic acid, introducing into the cell a second foreign nucleic acid encoding at least one Cas9 protein nickase having one inactive nuclease domain and being guided by the two or more RNAs, and wherein the two or more RNAs and the at least one Cas9 protein nickase are expressed and wherein the at least one Cas9 protein nickase co-localizes with the two or more RNAs to the DNA target nucleic acid and nicks the DNA target nucleic acid resulting in two or more adjacent nicks, and wherein the two or more adjacent nicks are on different strands of the double stranded DNA and create double stranded breaks resulting in fragmentation of the target nucleic acid thereby preventing expression of the target nucleic acid.

According to one aspect, a cell is provided including a first foreign nucleic acid encoding two or more RNAs with each RNA being complementary to an adjacent site in a DNA target nucleic acid, and a second foreign nucleic acid encoding at least one RNA guided DNA binding protein nickase, and wherein the two or more RNAs and the at least one RNA guided DNA binding protein nickase are members of a co-localization complex for the DNA target nucleic acid.

According to one aspect, the RNA guided DNA binding protein nickase is an RNA guided DNA binding protein nickase of a Type II CRISPR System. According to one aspect, the RNA guided DNA binding protein nickase is a Cas9 protein nickase having one inactive nuclease domain.

According to one aspect, the cell is a eukaryotic cell. According to one aspect, the cell is a yeast cell, a plant cell or an animal cell. According to one aspect, the cell is a mammalian cell.

According to one aspect, the RNA includes between about 10 to about 500 nucleotides. According to one aspect, the RNA includes between about 20 to about 100 nucleotides.

According to one aspect, the target nucleic acid is associated with a disease or detrimental condition.

According to one aspect, the two or more RNAs are guide RNAs. According to one aspect, the two or more RNAs are tracrRNA-crRNA fusions.

According to one aspect, the DNA target nucleic acid is genomic DNA, mitochondrial DNA, viral DNA, or exogenous DNA.

Further features and advantages of certain embodiments of the present invention will become more fully apparent in the following description of embodiments and drawings thereof, and from the claims.

BRIEF DESCRIPTION OF THE DRAWINGS

The patent or application file contains drawings executed in color. Copies of this patent or patent application publication with the color drawings will be provided by the Office upon request and payment of the necessary fee. The foregoing and other features and advantages of the present embodiments will be more fully understood from the following detailed description of illustrative embodiments taken in conjunction with the accompanying drawings in which:

FIG. 1A and FIG. 1B are schematics of RNA-guided transcriptional activation. FIG. 1C is a design of a reporter construct. FIGS. 1E-1 and 1E-2 show assay data by FACS and IF demonstrating gRNA sequence-specific transcriptional activation from reporter constructs in the presence of Cas9N, MS2-VP64 and gRNA bearing the appropriate MS2 aptamer binding sites.

FIG. 2A depicts a methodology for evaluating the landscape of targeting by Cas9-gRNA complexes and TALEs.

FIG. 3B depicts data showing percentage rate of non-homologous end joining for off-set nicks leading to 5' overhangs and off-set nicks leading to 3' overhangs.

FIGS. 5B-1 and 5B-2 depict guide RNAs with random sequence insertions and percentage rate of homologous recombination.

FIG. 6A is a schematic of guide RNAs for the OCT4 gene. FIG. 6B depicts transcriptional activation for a promoter-luciferase reporter construct.

FIG. 9D depicts data from a nuclease mediated HR assay confirming that the predicted PAM for the S. pyogenes Cas9 is NGG and also NAG.

FIGS. 10A-1 and 10A-2 depict data from a nuclease mediated HR assay confirming that 18-mer TALEs tolerate multiple mutations in their target sequences.

FIG. 11B depicts percentage rate of non-homologous end joining for various guide RNAs.

FIG. 14A depicts the specificity profile of two gRNAs (wild-type) and mutants. Sequence differences are highlighted in red. FIGS. 14B and 14C depict that this assay was specific for the gRNA being evaluated (data re-plotted from FIG. 13D).

FIGS. 15A, 15B-1, 15B-2, 15C, 15D-1, and 15D-2 depict gRNA2 (FIGS. 15A-B) and gRNA3 (FIGS. 15C-D) bearing single or double-base mismatches (highlighted in red) in the spacer sequence versus the target.

FIGS. 16A, 16B-1, 16B-2, 16C, 16D-1, and 16D-2 depict a nuclease assay of two independent gRNA that were tested: gRNA1 (FIGS. 16A-B) and gRNA3 (FIGS. 16C-D) bearing truncations at the 5' end of their spacer.

FIGS. 17A-17B depict a nuclease mediated HR assay that shows the PAM for the S. pyogenes Cas9 is NGG and also NAG.

FIGS. 18A-18B depict a nuclease mediated HR assay that confirmed that 18-mer TALEs tolerate multiple mutations in their target sequences.

FIGS. 19A, 19B-1, 19B-2, 19C-1, and 19C-2 depict a comparison of TALE monomer specificity versus TALE protein specificity.

FIGS. 20A-20B depict data related to off-set nicking.

FIGS. 21A-21C depict off-set nicking and NHEJ profiles.

DETAILED DESCRIPTION

Figures 1, 1D:
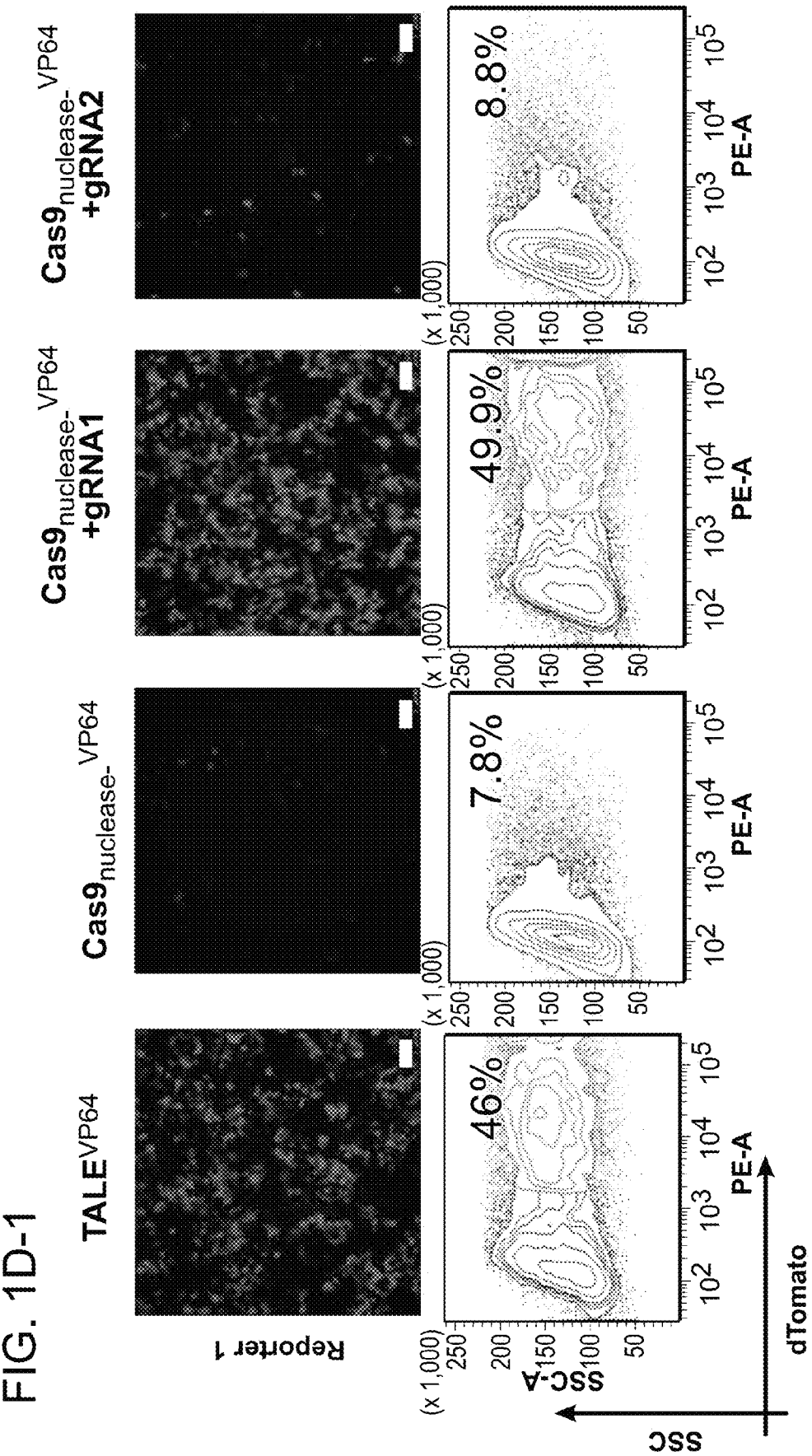
FIGS. 1D-1 and 1D-2 show data demonstrating that Cas9N-VP64 fusions display RNA-guided transcriptional activation as assayed by both fluorescence-activated cell sorting (FACS) and immunofluorescence assays (IF).

Embodiments of the present disclosure are based on the use of DNA binding proteins to co-localize transcriptional regulator proteins or domains to DNA in a manner to regulate a target nucleic acid. Such DNA binding proteins are readily known to those of skill in the art to bind to DNA for various purposes. Such DNA binding proteins may be naturally occurring. DNA binding proteins included within the scope of the present disclosure include those which may be guided by RNA, referred to herein as guide RNA. According to this aspect, the guide RNA and the RNA guided DNA binding protein form a co-localization complex at the DNA. According to certain aspects, the DNA binding protein may be a nuclease-null DNA binding protein. According to this aspect, the nuclease-null DNA binding protein may result from the alteration or modification of a DNA binding protein having nuclease activity. Such DNA binding proteins having nuclease activity are known to those of skill in the art, and include naturally occurring DNA binding proteins having nuclease activity, such as Cas9 proteins present, for example, in Type II CRISPR systems. Such Cas9 proteins and Type II CRISPR systems are well documented in the art. See Makarova et al., Nature Reviews, Microbiology, Vol. 9, June 2011, pp. 467-477 including all supplementary information hereby incorporated by reference in its entirety.

Exemplary DNA binding proteins having nuclease activity function to nick or cut double stranded DNA. Such nuclease activity may result from the DNA binding protein having one or more polypeptide sequences exhibiting nuclease activity. Such exemplary DNA binding proteins may have two separate nuclease domains with each domain responsible for cutting or nicking a particular strand of the double stranded DNA. Exemplary polypeptide sequences having nuclease activity known to those of skill in the art include the McrA-HNH nuclease related domain and the RuvC-like nuclease domain. Accordingly, exemplary DNA binding proteins are those that in nature contain one or more of the McrA-HNH nuclease related domain and the RuvC-like nuclease domain. According to certain aspects, the DNA binding protein is altered or otherwise modified to inactivate the nuclease activity. Such alteration or modification includes altering one or more amino acids to inactivate the nuclease activity or the nuclease domain. Such modification includes removing the polypeptide sequence or polypeptide sequences exhibiting nuclease activity, i.e. the nuclease domain, such that the polypeptide sequence or polypeptide sequences exhibiting nuclease activity, i.e. nuclease domain, are absent from the DNA binding protein. Other modifications to inactivate nuclease activity will be readily apparent to one of skill in the art based on the present disclosure. Accordingly, a nuclease-null DNA binding protein includes polypeptide sequences modified to inactivate nuclease activity or removal of a polypeptide sequence or sequences to inactivate nuclease activity. The nuclease-null DNA binding protein retains the ability to bind to DNA even though the nuclease activity has been inactivated. Accordingly, the DNA binding protein includes the polypeptide sequence or sequences required for DNA binding but may lack the one or more or all of the nuclease sequences exhibiting nuclease activity. Accordingly, the DNA binding protein includes the polypeptide sequence or sequences required for DNA binding but may have one or more or all of the nuclease sequences exhibiting nuclease activity inactivated.

According to one aspect, a DNA binding protein having two or more nuclease domains may be modified or altered to inactivate all but one of the nuclease domains. Such a modified or altered DNA binding protein is referred to as a DNA binding protein nickase, to the extent that the DNA binding protein cuts or nicks only one strand of double stranded DNA. When guided by RNA to DNA, the DNA binding protein nickase is referred to as an RNA guided DNA binding protein nickase.

An exemplary DNA binding protein is an RNA guided DNA binding protein of a Type II CRISPR System which lacks nuclease activity. An exemplary DNA binding protein is a nuclease-null Cas9 protein. An exemplary DNA binding protein is a Cas9 protein nickase.

In *S. pyogenes*, Cas9 generates a blunt-ended double-stranded break 3 bp upstream of the protospacer-adjacent motif (PAM) via a process mediated by two catalytic domains in the protein: an HNH domain that cleaves the complementary strand of the DNA and a RuvC-like domain that cleaves the non-complementary strand. See Jinke et al., *Science* 337, 816-821 (2012) hereby incorporated by reference in its entirety. Cas9 proteins are known to exist in many Type II CRISPR systems including the following as identified in the supplementary information to Makarova et al., *Nature Reviews, Microbiology*, Vol. 9, June 2011, pp. 467-477: Methanococcus maripaludis C7; *Corynebacterium diphtheriae*; *Corynebacterium efficiens* YS-314; *Corynebacterium glutamicum* ATCC 13032 Kitasato; *Corynebacterium glutamicum* ATCC 13032 Bielefeld; *Corynebacterium glutamicum* R; *Corynebacterium kroppenstedtii* DSM 44385; *Mycobacterium abscessus* ATCC 19977; *Nocardia farcinica* IFM10152; *Rhodococcus erythropolis* PR4; *Rhodococcus jostii* RHA1; *Rhodococcus opacus* B4 uid36573; *Acidothermus cellulolyticus* 11B; *Arthrobacter chlorophenolicus* A6; *Kribbella flavida* DSM 17836 uid43465; *Thermomonospora curvata* DSM 43183; *Bifidobacterium dentium* Bd1; *Bifidobacterium longum* DJO10A; Slackia heliotrinireducens DSM 20476; *Persephonella marina* EX H1; *Bacteroides fragilis* NCTC 9434; *Capnocytophaga ochracea* DSM 7271; *Flavobacterium psychrophilum* JIP02 86; *Akkermansia muciniphila* ATCC BAA 835; *Roseiflexus castenholzii* DSM 13941; *Roseiflexus* RS1; *Synechocystis* PCC6803; *Elusimicrobium minutum* Pei191; uncultured Termite group 1 bacterium phylotype Rs D17; *Fibrobacter succinogenes* S85; *Bacillus cereus* ATCC 10987; *Listeria innocua*; *Lactobacillus casei*; *Lactobacillus rhamnosus* GG; *Lactobacillus salivarius* UCC118; *Streptococcus agalactiae* A909; *Streptococcus agalactiae* NEM316; *Streptococcus agalactiae* 2603; *Streptococcus dysgalactiae equisimilis* GGS 124; *Streptococcus equi zooepidemicus* MGCS10565; *Streptococcus gallolyticus* UCN34 uid46061; *Streptococcus gordonii* Challis subst CH1; *Streptococcus mutans* NN2025 uid46353; *Streptococcus mutans*; *Streptococcus pyogenes* M1 GAS; *Streptococcus pyogenes* MGAS5005; *Streptococcus pyogenes* MGAS2096; *Streptococcus pyogenes* MGAS9429; *Streptococcus pyogenes* MGAS10270; *Streptococcus pyogenes* MGAS6180; *Streptococcus pyogenes* MGAS315; *Streptococcus pyogenes* SSI-1; *Streptococcus pyogenes* MGAS10750; *Streptococcus pyogenes* NZ131; *Streptococcus* thermophiles CNRZ1066; *Streptococcus* thermophiles LMD-9; *Streptococcus* thermophiles LMG 18311; *Clostridium botulinum* A3 Loch Maree; *Clostridium botulinum* B Eklund 17B; *Clostridium botulinum* Ba4 657; *Clostridium botulinum* F Langeland; *Clostridium cellulolyticum* H10; *Finegoldia magna* ATCC 29328; *Eubacterium rectale* ATCC 33656; *Mycoplasma gallisepticum*; *Mycoplasma* mobile 163K; *Mycoplasma penetrans*; *Mycoplasma synoviae* 53; *Streptobacillus moniliformis* DSM 12112; *Bradyrhizobium* BTAi1; *Nitrobacter hamburgensis* X14; *Rhodopseudomonas palustris* BisB18; *Rhodopseudomonas palustris* BisB5; *Parvibaculum lavamentivorans* DS-1; *Dinoroseobacter shibae* DFL 12; *Gluconacetobacter diazotrophicus* Pal 5 FAPERJ; *Gluconacetobacter diazotrophicus* Pal 5 JGI; *Azospirillum* B510 uid46085; *Rhodospirillum rubrum* ATCC 11170; Diaphorobacter TPSY uid29975; *Verminephrobacter eiseniae* EF01-2; *Neisseria meningitidis* 053442; *Neisseria meningitides* alpha14; *Neisseria meningitides* Z2491; *Desulfovibrio salexigens* DSM 2638; *Campylobacter jejuni* doylei 269 97; *Campylobacter jejuni* 81116; *Campylobacter jejuni*; *Campylobacter lari* RM2100; *Helicobacter hepaticus*; *Wolinella succinogenes*; *Tolumonas auensis* DSM 9187; *Pseudoalteromonas atlantica* T6c; *Shewanella pealeana* ATCC 700345; *Legionella pneumophila* Paris; *Actinobacillus succinogenes* 130Z; *Pasteurella multocida*; *Francisella tularensis novicida* U112; *Francisella tularensis* holarctica; *Francisella tularensis* FSC 198; *Francisella tularensis tularensis*; *Francisella tularensis* WY96-3418; and *Treponema denticola* ATCC 35405. Accordingly, aspects of the present disclosure are directed to a Cas9 protein present in a Type II CRISPR system, which has been rendered nuclease null or which has been rendered a nickase as described herein.

The Cas9 protein may be referred by one of skill in the art in the literature as Csn1. The *S. pyogenes* Cas9 protein sequence that is the subject of experiments described herein is shown below. See Deltcheva et al., *Nature* 471, 602-607 (2011) hereby incorporated by reference in its entirety.

(SEQ ID NO: 1)
MDKKYSIGLDIGTNSVGWAVITDEYKVPSKKFKVLGNTDRHSIKKNLIGA

LLFDSGETAEATRLKRTARRRYTRRKNRICYLQEIFSNEMAKVDDSFFHR

LEESFLVEEDKKHERHPIFGNIVDEVAYHEKYPTIYHLRKKLVDSTDKAD

LRLIYLALAHMIKFRGHFLIEGDLNPDNSDVDKLFIQLVQTYNQLFEENP

INASGVDAKAILSARLSKSRRLENLIAQLPGEKKNGLFGNLIALSLGLTP

NFKSNFDLAEDAKLQLSKDTYDDDLDNLLAQIGDQYADLFLAAKNLSDAI

LLSDILRVNTEITKAPLSASMIKRYDEHHQDLTLLKALVRQQLPEKYKEI

FFDQSKNGYAGYIDGGASQEEFYKFIKPILEKMDGTEELLVKLNREDLLR

KQRTFDNGSIPHQIHLGELHAILRRQEDFYPFLKDNREKIEKILTFRIPY

YVGPLARGNSRFAWMTRKSEETITPWNFEEVVDKGASAQSFIERMTNFDK

NLPNEKVLPKHSLLYEYFTVYNELTKVKYVTEGMRKPAFLSGEQKKAIVD

LLFKTNRKVTVKQLKEDYFKKIECFDSVEISGVEDRFNASLGTYHDLLKI

IKDKDFLDNEENEDILEDIVLTLTLFEDREMIEERLKTYAHLFDDKVMKQ

LKRRRYTGWGRLSRKLINGIRDKQSGKTILDFLKSDGFANRNFMQLIHDD

SLTFKEDIQKAQVSGQGDSLHEHIANLAGSPAIKKGILQTVKVVDELVKV

MGRHKPENIVIEMARENQTTQKGQKNSRERMKRIEEGIKELGSQILKEHP

VENTQLQNEKLYLYYLQNGRDMYVDQELDINRLSDYDVDHIVPQSFLKDD

SIDNKVLTRSDKNRGKSDNVPSEEVVKKMKNYWRQLLNAKLITQRKFDNL

TKAERGGLSELDKAGFIKRQLVETRQITKHVAQILDSRMNTKYDENDKLI

REVKVITLKSKLVSDFRKDFQFYKVREINNYHHAHDAYLNAVVGTALIKK

YPKLESEFVYGDYKVYDVRKMIAKSEQEIGKATAKYFFYSNIMNFFKTEI

TLANGEIRKRPLIETNGETGEIVWDKGRDFATVRKVLSMPQVNIVKKTEV

QTGGFSKESILPKRNSDKLIARKKDWDPKKYGGFDSPTVAYSVLVVAKVE

KGKSKKLKSVKELLGITIMERSSFEKNPIDFLEAKGYKEVKKDLIIKLPK

YSLFELENGRKRMLASAGELQKGNELALPSKYVNFLYLASHYEKLKGSPE

DNEQKQLFVEQHKHYLDEIIEQISEFSKRVILADANLDKVLSAYNKHRDK

PIREQAENIIHLFTLTNLGAPAAFKYFDTTIDRKRYTSTKEVLDATLIHQ

SITGLYETRIDLSQLGGD-

According to certain aspects of methods of RNA-guided genome regulation described herein, Cas9 is altered to reduce, substantially reduce or eliminate nuclease activity. According to one aspect, Cas9 nuclease activity is reduced, substantially reduced or eliminated by altering the RuvC nuclease domain or the HNH nuclease domain. According to one aspect, the RuvC nuclease domain is inactivated. According to one aspect, the HNH nuclease domain is inactivated. According to one aspect, the RuvC nuclease domain and the HNH nuclease domain are inactivated. According to an additional aspect, Cas9 proteins are provided where the RuvC nuclease domain and the HNH nuclease domain are inactivated. According to an additional aspect, nuclease-null Cas9 proteins are provided insofar as the RuvC nuclease domain and the HNH nuclease domain are inactivated. According to an additional aspect, a Cas9 nickase is provided where either the RuvC nuclease domain or the HNH nuclease domain is inactivated, thereby leaving the remaining nuclease domain active for nuclease activity. In this manner, only one strand of the double stranded DNA is cut or nicked.

According to an additional aspect, nuclease-null Cas9 proteins are provided where one or more amino acids in Cas9 are altered or otherwise removed to provide nuclease-null Cas9 proteins. According to one aspect, the amino acids include D10 and H840. See Jinke et al., *Science* 337, 816-821 (2012). According to an additional aspect, the amino acids include D839 and N863. According to one aspect, one or more or all of D10, H840, D839 and H863 are substituted with an amino acid which reduces, substantially eliminates or eliminates nuclease activity. According to one aspect, one or more or all of D10, H840, D839 and H863 are substituted with alanine. According to one aspect, a Cas9 protein having one or more or all of D10, H840, D839 and H863 substituted with an amino acid which reduces, substantially eliminates or eliminates nuclease activity, such as alanine, is referred to as a nuclease-null Cas9 or Cas9N and exhibits reduced or eliminated nuclease activity, or nuclease activity is absent or substantially absent within levels of detection. According to this aspect, nuclease activity for a Cas9N may be undetectable using known assays, i.e. below the level of detection of known assays.

According to one aspect, the nuclease null Cas9 protein includes homologs and orthologs thereof which retain the ability of the protein to bind to the DNA and be guided by the RNA. According to one aspect, the nuclease null Cas9 protein includes the sequence as set forth for naturally occurring Cas9 from *S. pyogenes* and having one or more or all of D10, H840, D839 and H863 substituted with alanine and protein sequences having at least 30%, 40%, 50%, 60%, 70%, 80%, 90%, 95%, 98% or 99% homology thereto and being a DNA binding protein, such as an RNA guided DNA binding protein.

According to one aspect, the nuclease null Cas9 protein includes the sequence as set forth for naturally occurring Cas9 from *S. pyogenes* excepting the protein sequence of the RuvC nuclease domain and the HNH nuclease domain and also protein sequences having at least 30%, 40%, 50%, 60%, 70%, 80%, 90%, 95%, 98% or 99% homology thereto and being a DNA binding protein, such as an RNA guided DNA binding protein. In this manner, aspects of the present disclosure include the protein sequence responsible for DNA binding, for example, for co-localizing with guide RNA and binding to DNA and protein sequences homologous thereto, and need not include the protein sequences for the RuvC nuclease domain and the HNH nuclease domain (to the extent not needed for DNA binding), as these domains may be either inactivated or removed from the protein sequence of the naturally occurring Cas9 protein to produce a nuclease null Cas9 protein.

Figure 4A:
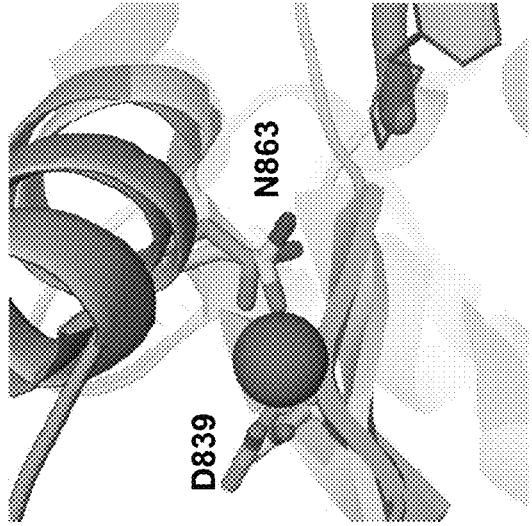
FIG. 4A is a schematic of a metal coordinating residue in RuvC PDB ID: 4EP4 (blue) position D7 (left), a schematic of HNH endonuclease domains from PDB IDs: 3M7K (orange) and 4H9D (cyan) including a coordinated Mg-ion (gray sphere) and DNA from 3M7K (purple) (middle) and a list of mutants analyzed (right).
Figure 4A:
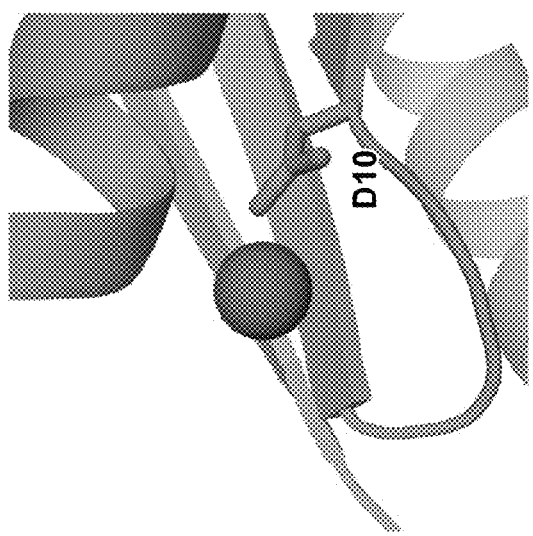

For purposes of the present disclosure, FIG. 4A depicts metal coordinating residues in known protein structures with homology to Cas9. Residues are labeled based on position in Cas9 sequence. Left: RuvC structure, PDB ID: 4EP4 (blue) position D7, which corresponds to D10 in the Cas9 sequence, is highlighted in a Mg-ion coordinating position. Middle: Structures of HNH endonuclease domains from PDB IDs: 3M7K (orange) and 4H9D (cyan) including a coordinated Mg-ion (gray sphere) and DNA from 3M7K (purple). Residues D92 and N113 in 3M7K and 4H9D positions D53 and N77, which have sequence homology to Cas9 amino acids D839 and N863, are shown as sticks. Right: List of mutants made and analyzed for nuclease activity: Cas9 wildtype; $Cas9_{m1}$ which substitutes alanine for D10; $Cas9_{m2}$ which substitutes alanine for D10 and alanine for H840; $Cas9_{m3}$ which substitutes alanine for D10, alanine for H840, and alanine for D839; and Cas9$_{m4}$ which substitutes alanine for D10, alanine for H840, alanine for D839, and alanine for N863.

Figure 4B:
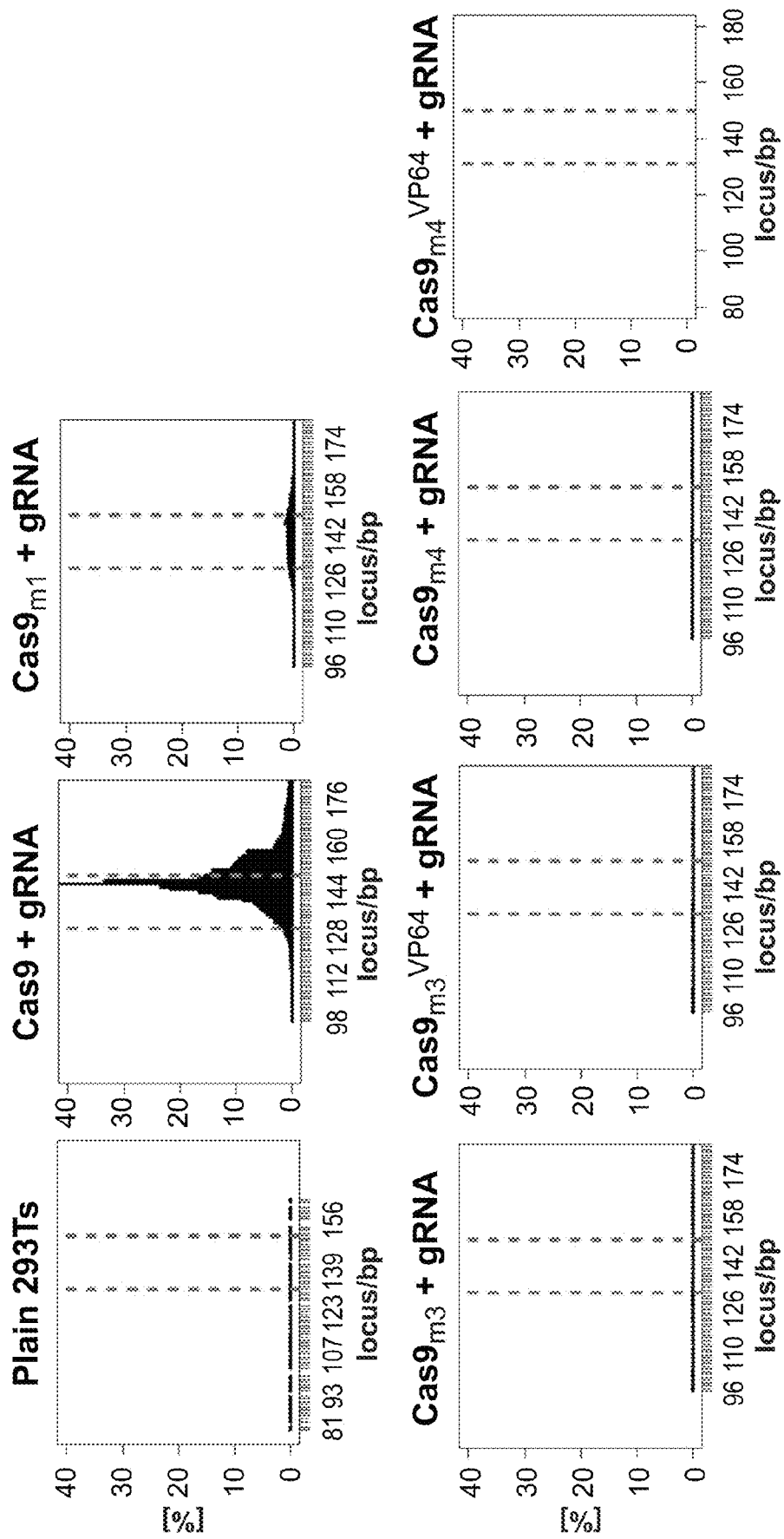
FIG. 4B depicts data showing undetectable nuclease activity for Cas9 mutants m3 and m4, and also their respective fusions with VP64.
Figure 4C:
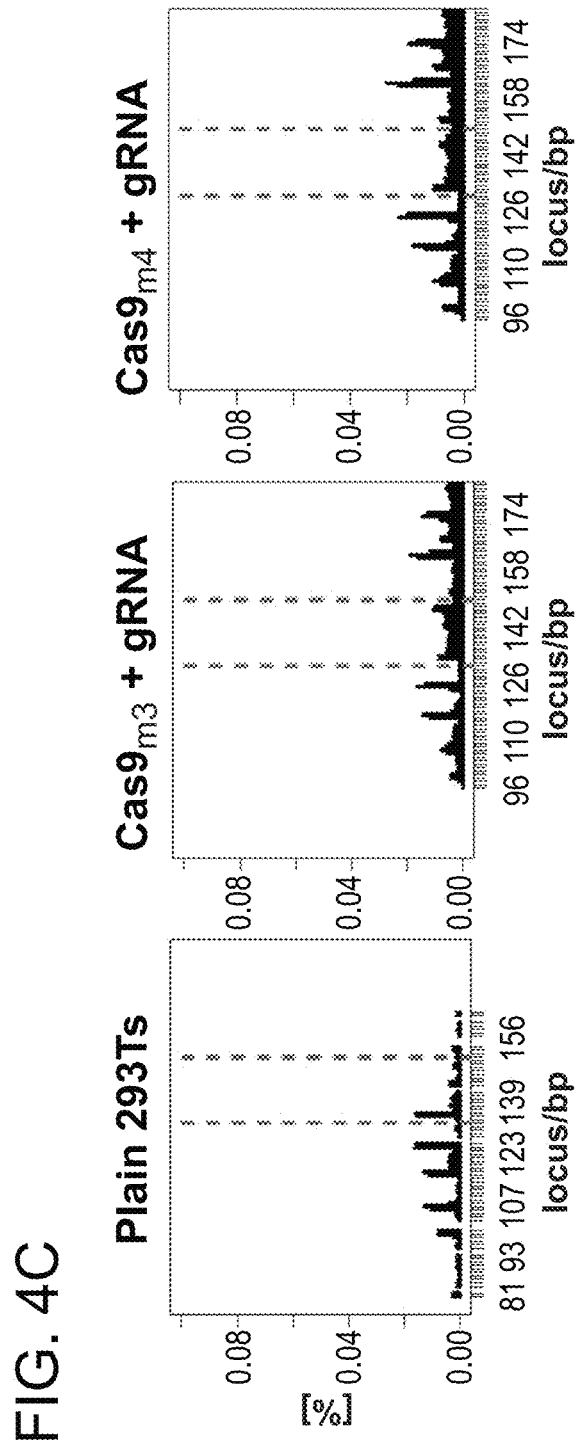
FIG. 4C is a higher-resolution examination of the data in FIG. 4B.

As shown in FIG. 4B, the Cas9 mutants: m3 and m4, and also their respective fusions with VP64 showed undetectable nuclease activity upon deep sequencing at targeted loci. The plots show the mutation frequency versus genomic position, with the red lines demarcating the gRNA target. FIG. 4C is a higher-resolution examination of the data in FIG. 4B and confirms that the mutation landscape shows comparable profile as unmodified loci.

According to one aspect, an engineered Cas9-gRNA system is provided which enables RNA-guided genome regulation in human cells by tethering transcriptional activation domains to either a nuclease-null Cas9 or to guide RNAs. According to one aspect of the present disclosure, one or more transcriptional regulatory proteins or domains (such terms are used interchangeably) are joined or otherwise connected to a nuclease-deficient Cas9 or one or more guide RNA (gRNA). The transcriptional regulatory domains correspond to targeted loci. Accordingly, aspects of the present disclosure include methods and materials for localizing transcriptional regulatory domains to targeted loci by fusing, connecting or joining such domains to either Cas9N or to the gRNA.

According to one aspect, a Cas9N-fusion protein capable of transcriptional activation is provided. According to one aspect, a VP64 activation domain (see Zhang et al., *Nature Biotechnology* 29, 149-153 (2011) hereby incorporated by reference in its entirety) is joined, fused, connected or otherwise tethered to the C terminus of Cas9N. According to one method, the transcriptional regulatory domain is provided to the site of target genomic DNA by the Cas9N protein. According to one method, a Cas9N fused to a transcriptional regulatory domain is provided within a cell along with one or more guide RNAs. The Cas9N with the transcriptional regulatory domain fused thereto bind at or near target genomic DNA. The one or more guide RNAs bind at or near target genomic DNA. The transcriptional regulatory domain regulates expression of the target gene. According to a specific aspect, a Cas9N-VP64 fusion activated transcription of reporter constructs when combined with gRNAs targeting sequences near the promoter, thereby displaying RNA-guided transcriptional activation.

According to one aspect, a gRNA-fusion protein capable of transcriptional activation is provided. According to one aspect, a VP64 activation domain is joined, fused, connected or otherwise tethered to the gRNA. According to one method, the transcriptional regulatory domain is provided to the site of target genomic DNA by the gRNA. According to one method, a gRNA fused to a transcriptional regulatory domain is provided within a cell along with a Cas9N protein. The Cas9N binds at or near target genomic DNA. The one or more guide RNAs with the transcriptional regulatory protein or domain fused thereto bind at or near target genomic DNA. The transcriptional regulatory domain regulates expression of the target gene. According to a specific aspect, a Cas9N protein and a gRNA fused with a transcriptional regulatory domain activated transcription of reporter constructs, thereby displaying RNA-guided transcriptional activation.

Figures 1, 1D, 2:
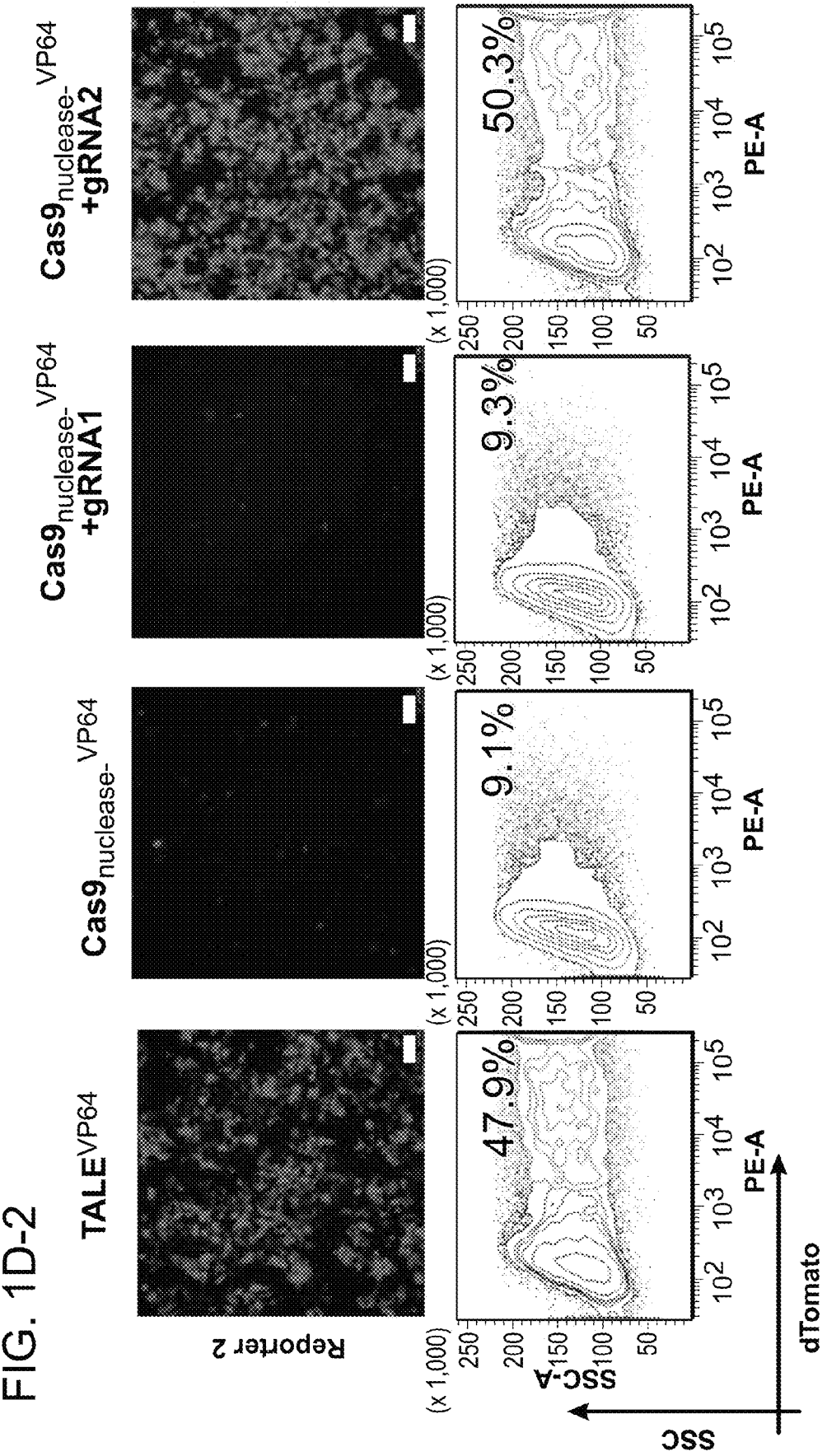
Figure 5A:
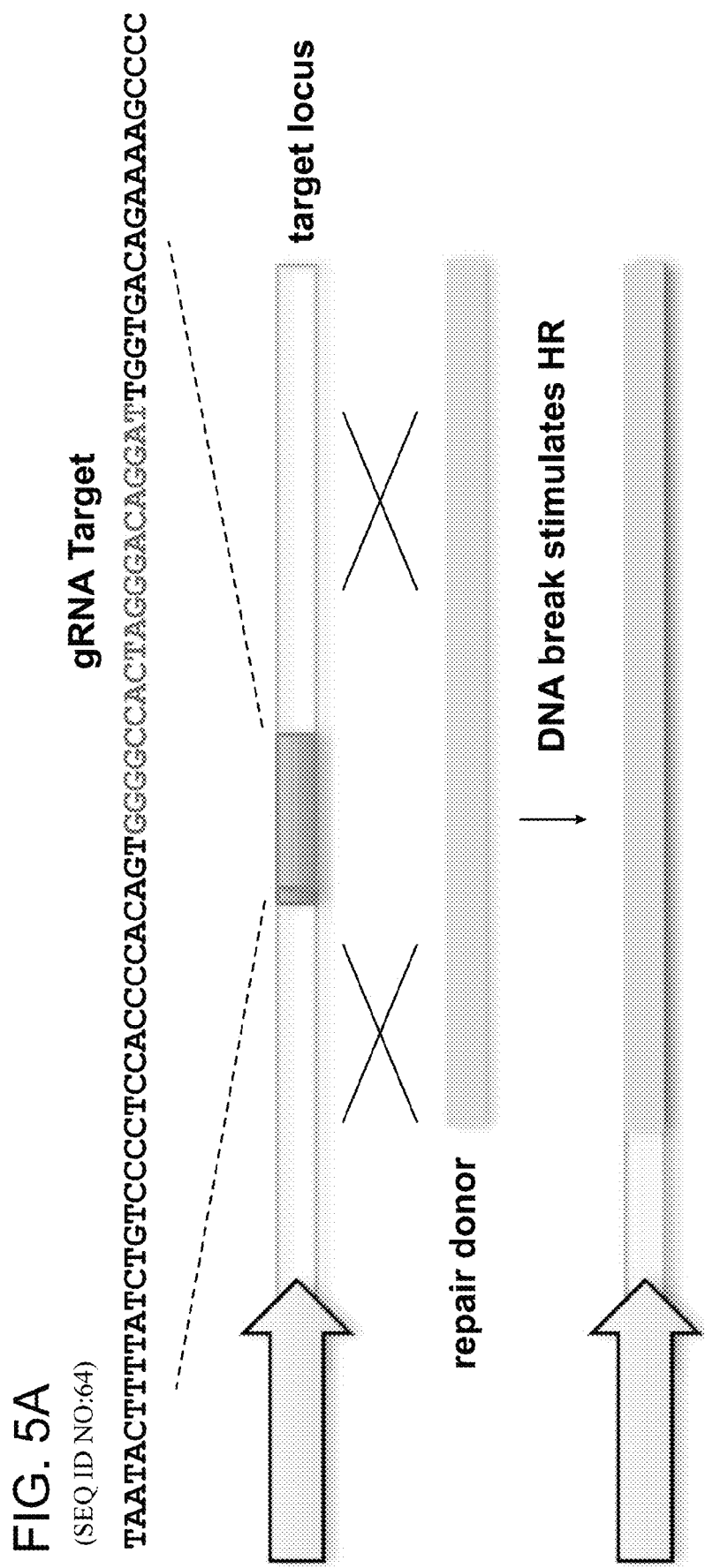
FIG. 5A is a schematic of a homologous recombination assay to determine Cas9-gRNA activity.
Figures 1, 5B:
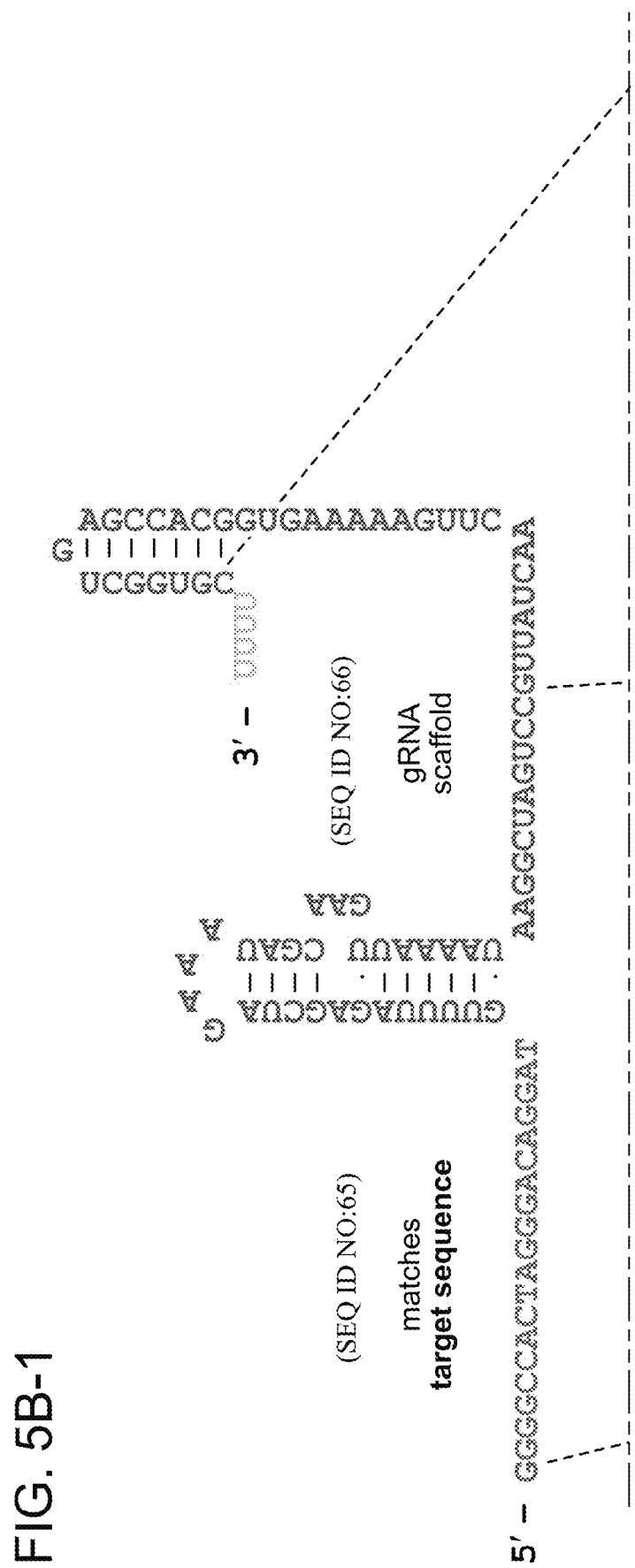
Figures 2, 5B:
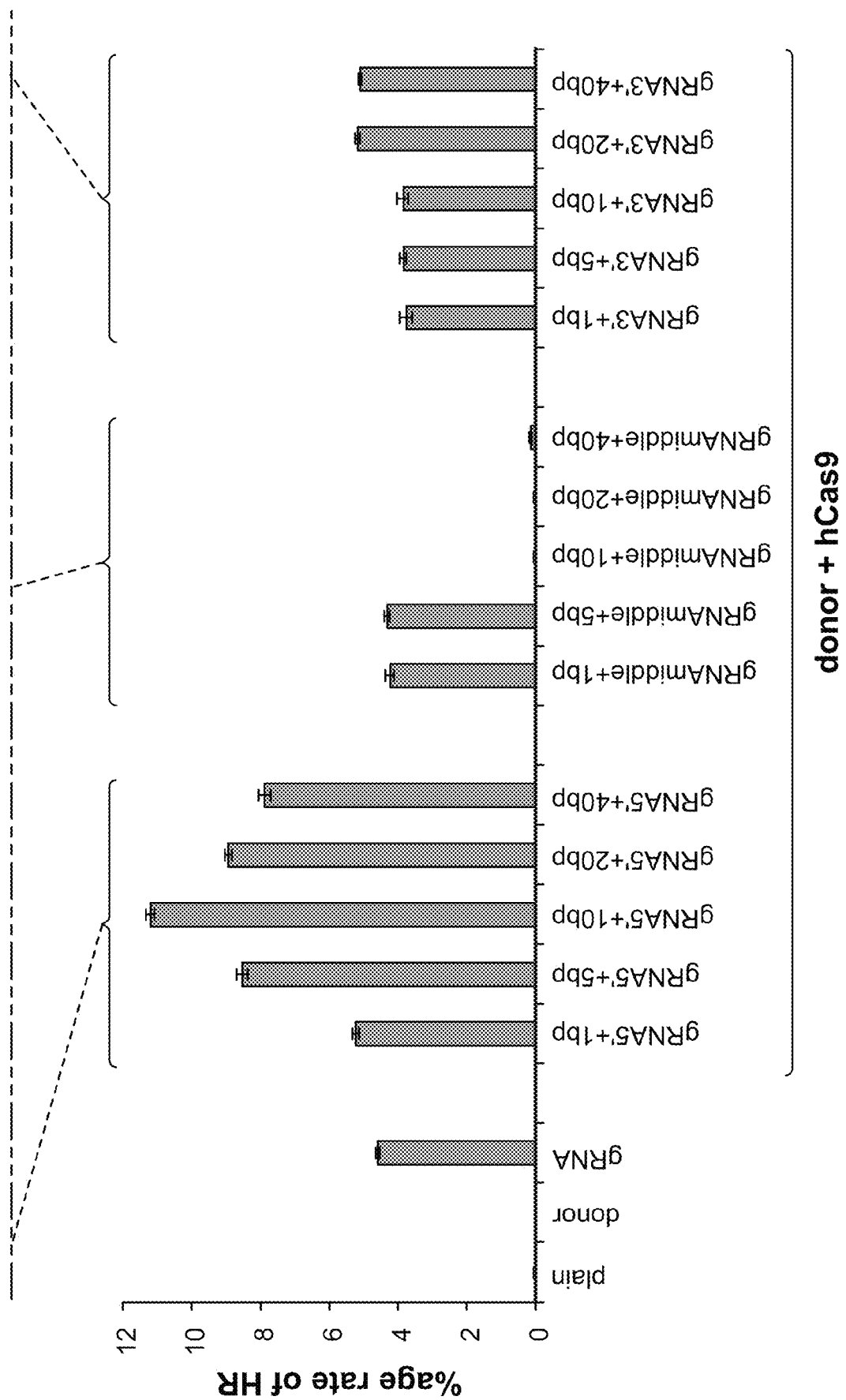

The gRNA tethers capable of transcriptional regulation were constructed by identifying which regions of the gRNA will tolerate modifications by inserting random sequences into the gRNA and assaying for Cas9 function. gRNAs bearing random sequence insertions at either the 5' end of the crRNA portion or the 3' end of the tracrRNA portion of a chimeric gRNA retain functionality, while insertions into the tracrRNA scaffold portion of the chimeric gRNA result in loss of function. See FIG. 5A-B summarizing gRNA flexibility to random base insertions. FIG. 5A is a schematic of a homologous recombination (HR) assay to determine Cas9-gRNA activity. As shown in FIGS. 5B-1 and 5B-2, gRNAs bearing random sequence insertions at either the 5' end of the crRNA portion or the 3' end of the tracrRNA portion of a chimeric gRNA retain functionality, while insertions into the tracrRNA scaffold portion of the chimeric gRNA result in loss of function. The points of insertion in the gRNA sequence are indicated by red nucleotides. Without wishing to be bound by scientific theory, the increased activity upon random base insertions at the 5' end may be due to increased half-life of the longer gRNA.

To attach VP64 to the gRNA, two copies of the MS2 bacteriophage coat-protein binding RNA stem-loop were appended to the 3' end of the gRNA. See Fusco et al., *Current Biology*: CB13, 161-167 (2003) hereby incorporated by reference in its entirety. These chimeric gRNAs were expressed together with Cas9N and MS2-VP64 fusion protein. Sequence-specific transcriptional activation from reporter constructs was observed in the presence of all 3 components.

Figures 1, 1E:
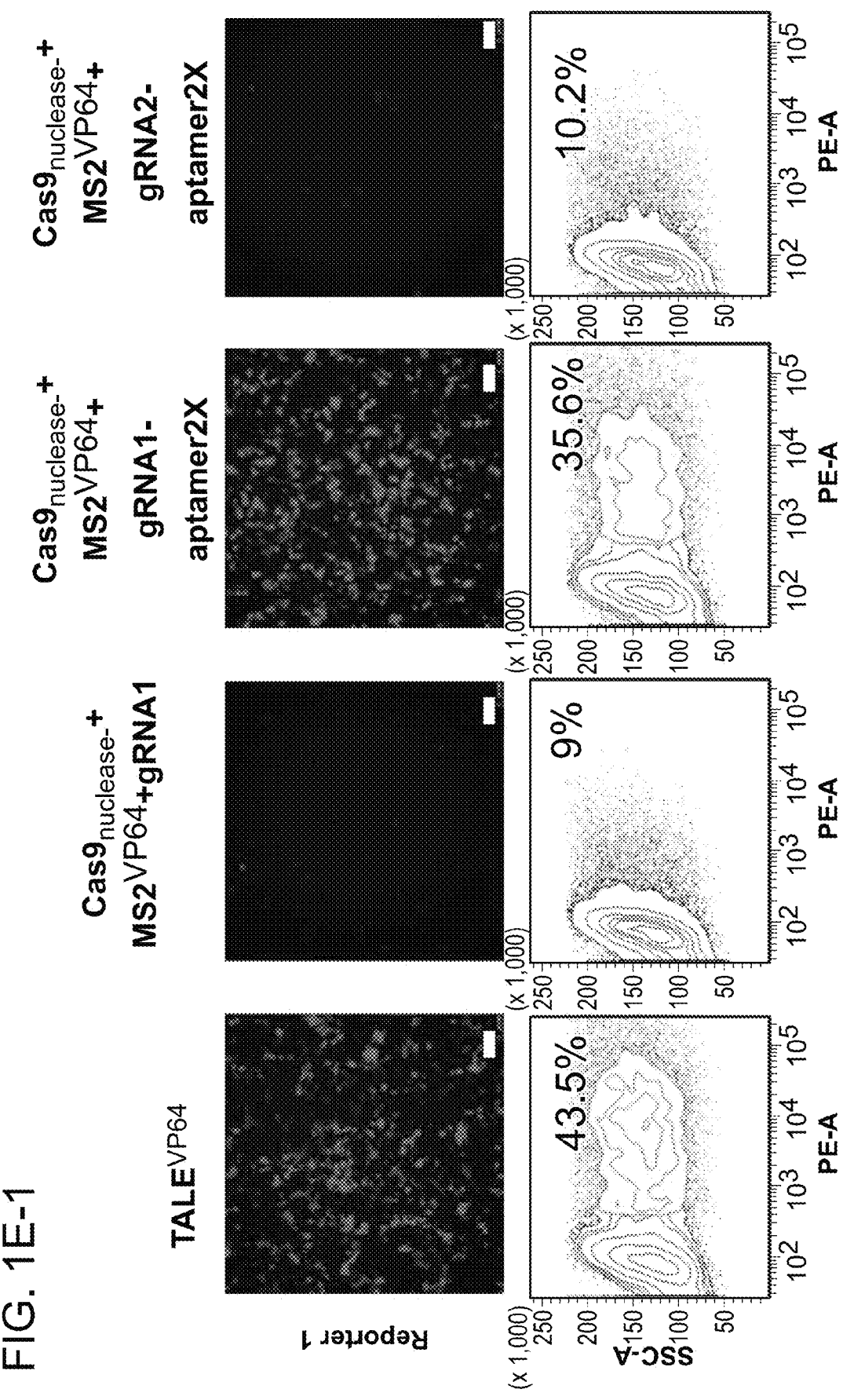
Figures 1, 1E, 2:
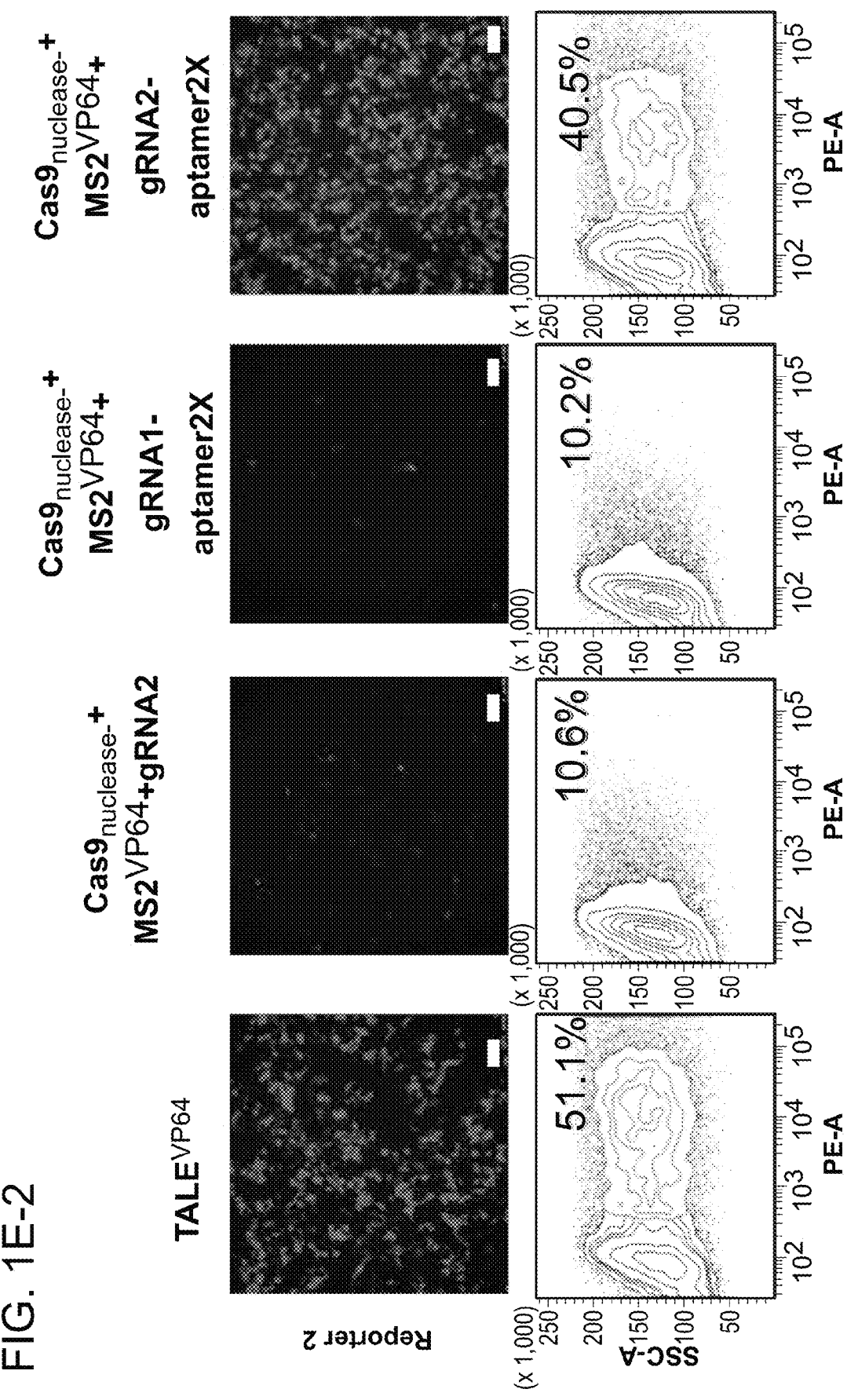

FIG. 1A is a schematic of RNA-guided transcriptional activation. As shown in FIG. 1A, to generate a Cas9N-fusion protein capable of transcriptional activation, the VP64 activation domain was directly tethered to the C terminus of Cas9N. As shown in FIG. 1B, to generate gRNA tethers capable of transcriptional activation, two copies of the MS2 bacteriophage coat-protein binding RNA stem-loop were appended to the 3' end of the gRNA. These chimeric gRNAs were expressed together with Cas9N and MS2-VP64 fusion protein. FIG. 1C shows design of reporter constructs used to assay transcriptional activation. The two reporters bear distinct gRNA target sites, and share a control TALE-TF target site. As shown in FIGS. 1D-1 and 1D-2, Cas9N-VP64 fusions display RNA-guided transcriptional activation as assayed by both fluorescence-activated cell sorting (FACS) and immunofluorescence assays (IF). Specifically, while the control TALE-TF activated both reporters, the Cas9N-VP64 fusion activates reporters in a gRNA sequence specific manner. As shown in FIGS. 1E-1 and 1E-2, gRNA sequence-specific transcriptional activation from reporter constructs only in the presence of all 3 components: Cas9N, MS2-VP64 and gRNA bearing the appropriate MS2 aptamer binding sites was observed by both FACS and IF.

Figure 1F:
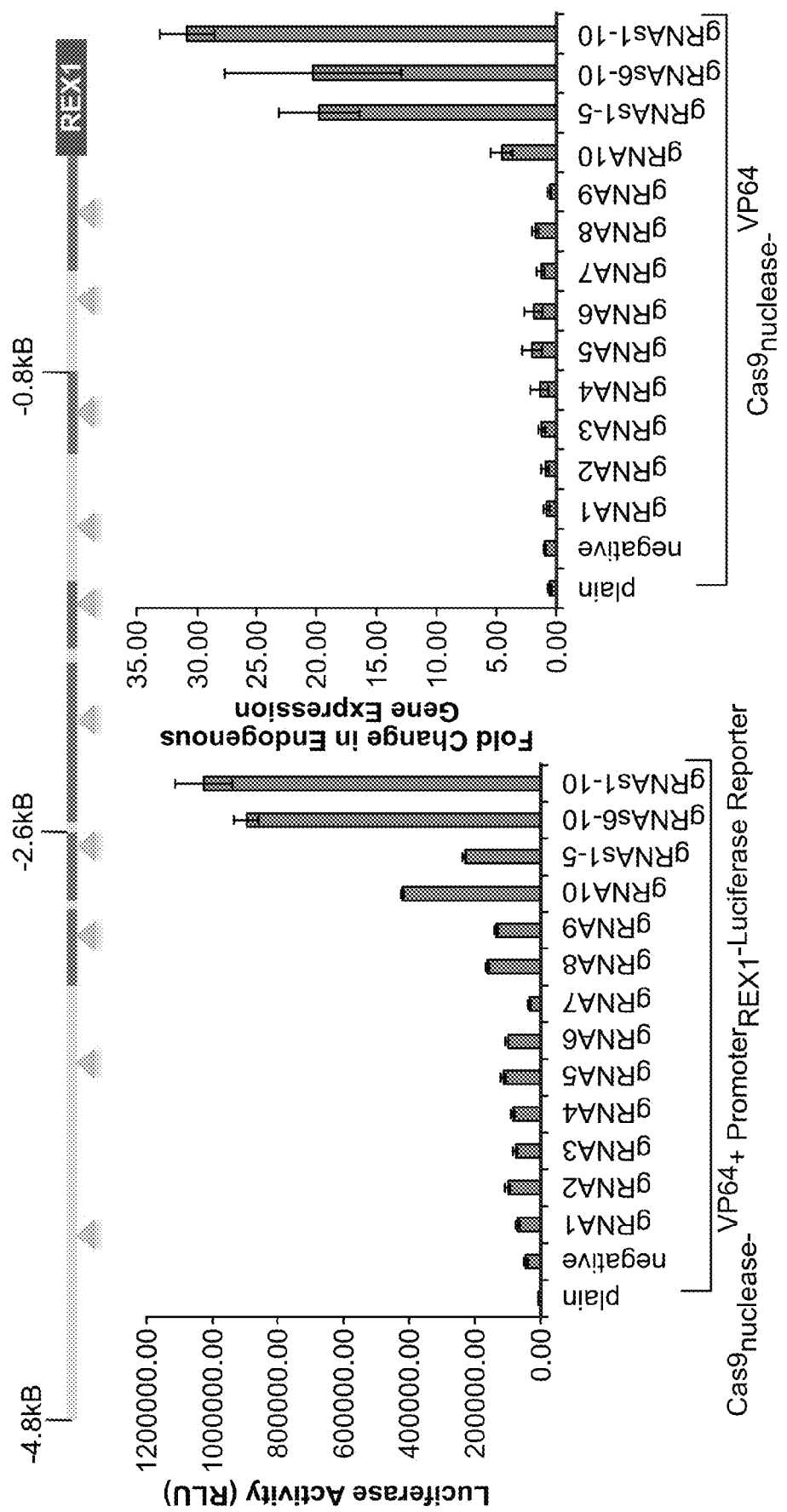
FIG. 1F depicts data demonstrating transcriptional induction by individual gRNAs and multiple gRNAs.

According to certain aspects, methods are provided for regulating endogenous genes using Cas9N, one or more gRNAs and a transcriptional regulatory protein or domain. According to one aspect, an endogenous gene can be any desired gene, referred to herein as a target gene. According to one exemplary aspect, genes target for regulation included ZFP42 (REX1) and POU5F1 (OCT4), which are both tightly regulated genes involved in maintenance of pluripotency. As shown in FIG. 1F, 10 gRNAs targeting a ~5 kb stretch of DNA upstream of the transcription start site (DNase hypersensitive sites are highlighted in green) were designed for the REX1 gene. Transcriptional activation was assayed using either a promoter-luciferase reporter construct (see Takahashi et al., Cell 131 861-872 (2007) hereby incorporated by reference in its entirety) or directly via qPCR of the endogenous genes.

Figure 6C:
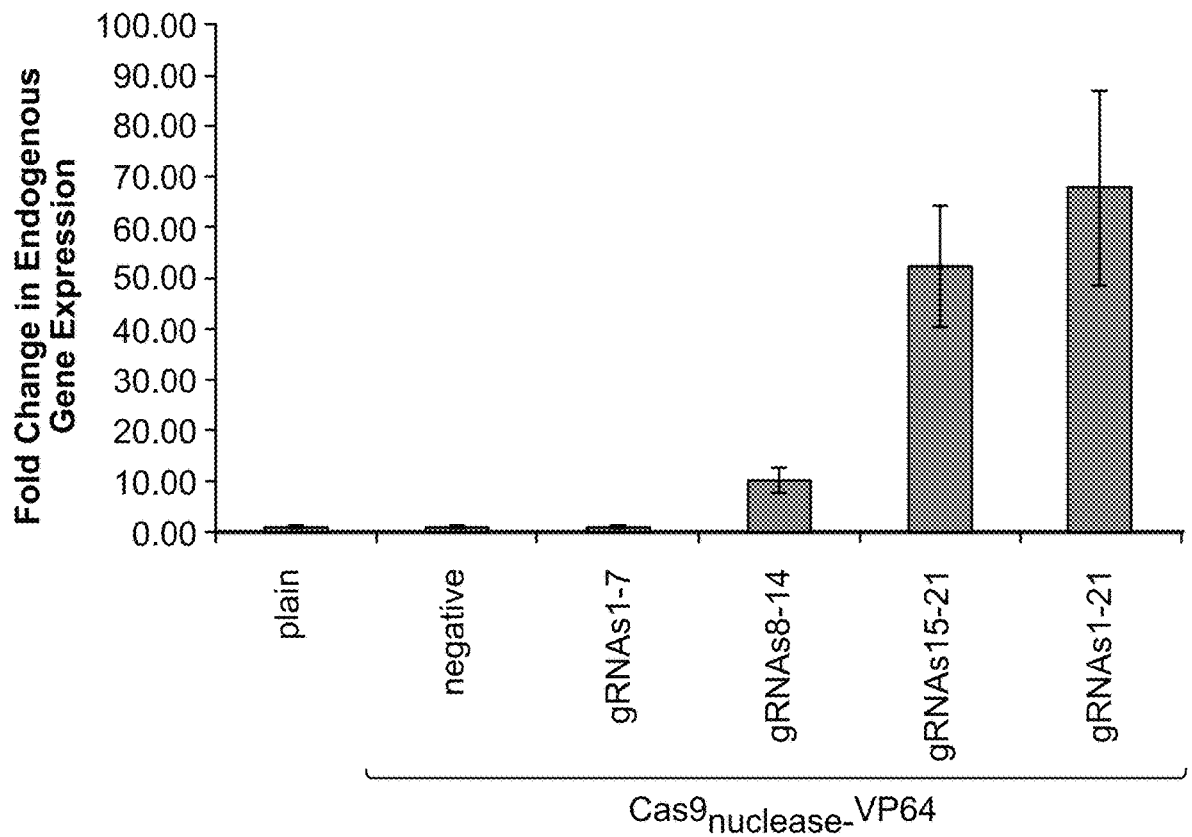
FIG. 6C depicts transcriptional activation via qPCR of endogenous genes.

FIG. 6A-C is directed to RNA-guided OCT4 regulation using Cas9N-VP64. As shown in FIG. 6A, 21 gRNAs targeting a ~5 kb stretch of DNA upstream of the transcription start site were designed for the OCT4 gene. The DNase hypersensitive sites are highlighted in green. FIG. 6B shows transcriptional activation using a promoter-luciferase reporter construct. FIG. 6C shows transcriptional activation directly via qPCR of the endogenous genes. While introduction of individual gRNAs modestly stimulated transcription, multiple gRNAs acted synergistically to stimulate robust multi-fold transcriptional activation.

Figure 7A:
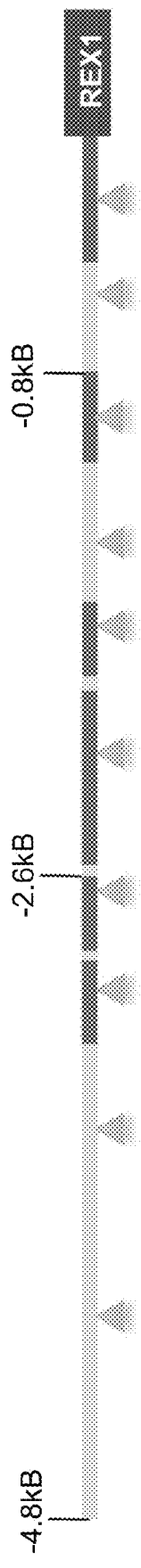
FIG. 7A is a schematic of guide RNAs for the REX1 gene.
Figure 7B:
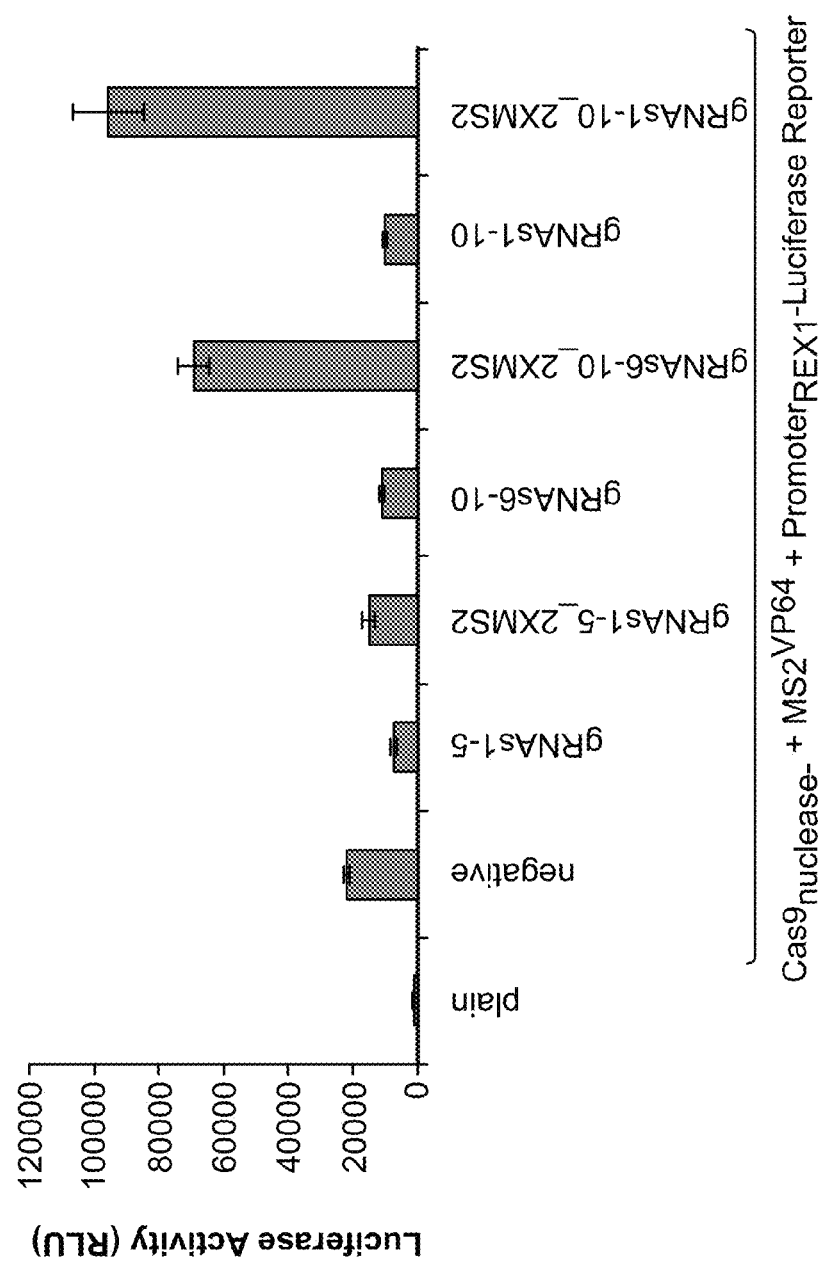
FIG. 7B depicts transcriptional activation for a promoter-luciferase reporter construct.
Figure 7C:
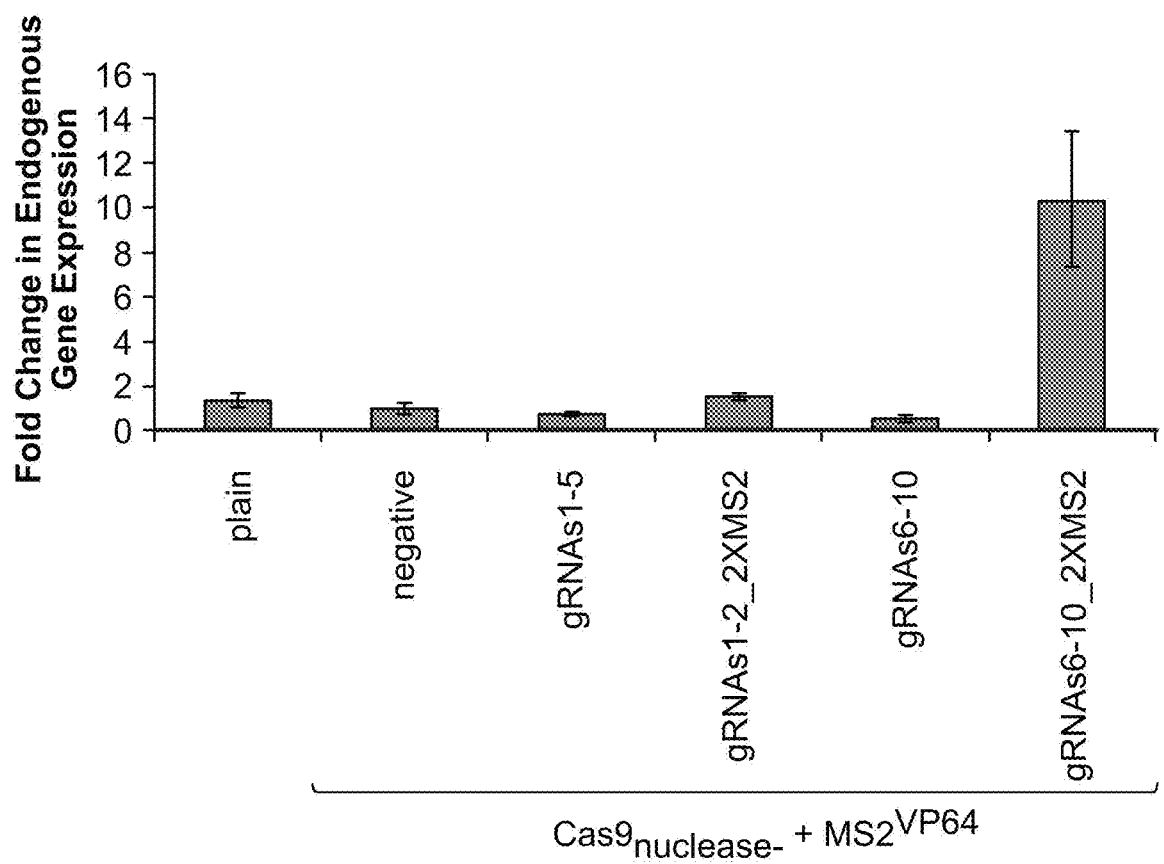
FIG. 7C depicts transcriptional activation via qPCR of endogenous genes.

FIG. 7A-C is directed to RNA-guided REX1 regulation using Cas9N, MS2-VP64 and gRNA+2X-MS2 aptamers. As shown in FIG. 7A, 10 gRNAs targeting a ~5 kb stretch of DNA upstream of the transcription start site were designed for the REX1 gene. The DNase hypersensitive sites are highlighted in green. FIG. 7B shows transcriptional activation using a promoter-luciferase reporter construct. FIG. 7C shows transcriptional activation directly via qPCR of the endogenous genes. While introduction of individual gRNAs modestly stimulated transcription, multiple gRNAs acted synergistically to stimulate robust multi-fold transcriptional activation. In one aspect, the absence of the 2X-MS2 aptamers on the gRNA does not result in transcriptional activation. See Maeder et al., *Nature Methods* 10, 243-245 (2013) and Perez-Pinera et al., *Nature Methods* 10, 239-242 (2013) each of which are hereby incorporated by reference in its entirety.

Accordingly, methods are directed to the use of multiple guide RNAs with a Cas9N protein and a transcriptional regulatory protein or domain to regulate expression of a target gene.

Both the Cas9 and gRNA tethering approaches were effective, with the former displaying ~1.5-2 fold higher potency. This difference is likely due to the requirement for 2-component as opposed to 3-component complex assembly. However, the gRNA tethering approach in principle enables different effector domains to be recruited by distinct gRNAs so long as each gRNA uses a different RNA-protein interaction pair. See Karyer-Bibens et al., *Biology of the Cell/Under the Auspices of the European Cell Biology Organization* 100, 125-138 (2008) hereby incorporated by reference in its entirety. According to one aspect of the present disclosure, different target genes may be regulated using specific guide RNA and a generic Cas9N protein, i.e. the same or a similar Cas9N protein for different target genes. According to one aspect, methods of multiplex gene regulation are provided using the same or similar Cas9N.

Methods of the present disclosure are also directed to editing target genes using the Cas9N proteins and guide RNAs described herein to provide multiplex genetic and epigenetic engineering of human cells. With Cas9-gRNA targeting being an issue (see Jiang et al., *Nature Biotechnology* 31, 233-239 (2013) hereby incorporated by reference in its entirety), methods are provided for in-depth interrogation of Cas9 affinity for a very large space of target sequence variations. Accordingly, aspects of the present disclosure provide direct high-throughput readout of Cas9 targeting in human cells, while avoiding complications introduced by dsDNA cut toxicity and mutagenic repair incurred by specificity testing with native nuclease-active Cas9.

Further aspects of the present disclosure are directed to the use of DNA binding proteins or systems in general for the transcriptional regulation of a target gene. One of skill in the art will readily identify exemplary DNA binding systems based on the present disclosure. Such DNA binding systems need not have any nuclease activity, as with the naturally occurring Cas9 protein. Accordingly, such DNA binding systems need not have nuclease activity inactivated. One exemplary DNA binding system is TALE. As a genome editing tool, usually TALE-FokI dimers are used, and for genome regulation TALE-VP64 fusions have been shown to be highly effective. According to one aspect, TALE specificity was evaluated using the methodology shown in FIG. 2A. A construct library in which each element of the library comprises a minimal promoter driving a dTomato fluorescent protein is designed. Downstream of the transcription start site m, a 24 bp (A/C/G) random transcript tag is inserted, while two TF binding sites are placed upstream of the promoter: one is a constant DNA sequence shared by all library elements, and the second is a variable feature that bears a 'biased' library of binding sites which are engineered to span a large collection of sequences that present many combinations of mutations away from the target sequence the programmable DNA targeting complex was designed to bind. This is achieved using degenerate oligonucleotides engineered to bear nucleotide frequencies at each position such that the target sequence nucleotide appears at a 79% frequency and each other nucleotide occurs at 7% frequency. See Patwardhan et al., *Nature Biotechnology* 30, 265-270 (2012) hereby incorporated by reference in its entirety. The reporter library is then sequenced to reveal the associations between the 24 bp dTomato transcript tags and their corresponding 'biased' target site in the library element. The large diversity of the transcript tags assures that sharing of tags between different targets will be extremely rare, while the biased construction of the target sequences means that sites with few mutations will be associated with more tags than sites with more mutations. Next, transcription of the dTomato reporter genes is stimulated with either a control-TF engineered to bind the shared DNA site, or the target-TF that was engineered to bind the target site. The abundance of each expressed transcript tag is measured in each sample by conducting RNAseq on the stimulated cells, which is then mapped back to their corresponding binding sites using the association table established earlier. The control-TF is expected to excite all library members equally since its binding site is shared across all library elements, while the target-TF is expected to skew the distribution of the expressed members to those that are preferentially targeted by it. This assumption is used in step 5 to compute a normalized expression level for each binding site by dividing the tag counts obtained for the target-TF by those obtained for the control-TF.

Figure 2B:
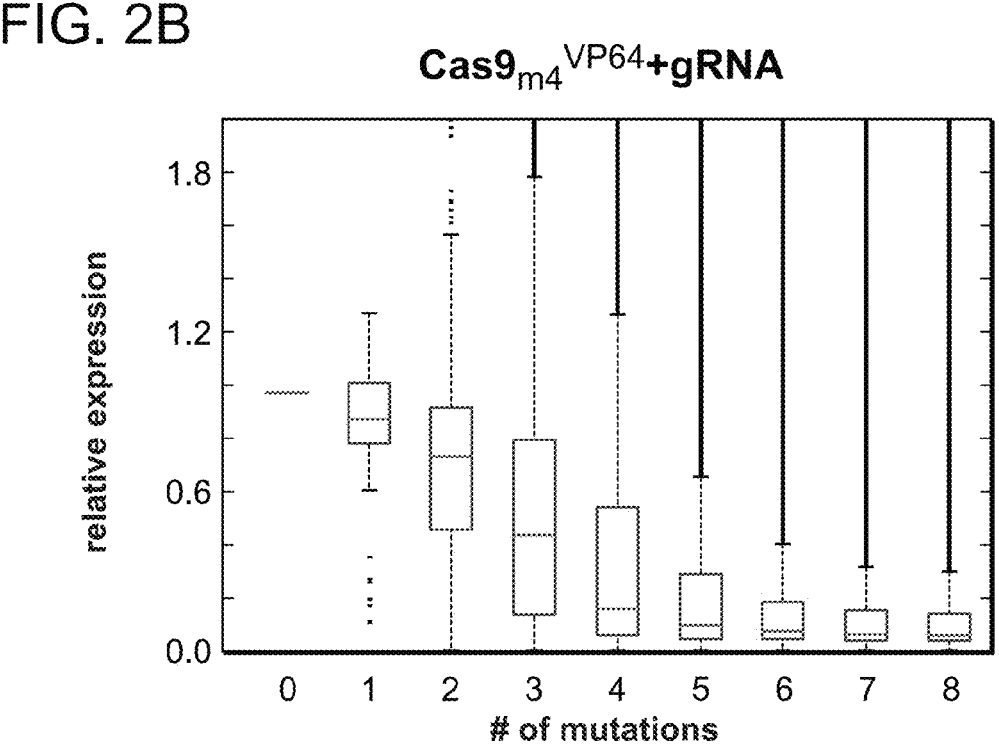
FIG. 2B depicts data demonstrating that a Cas9-gRNA complex is on average tolerant to 1-3 mutations in its target sequences.
Figure 2C:
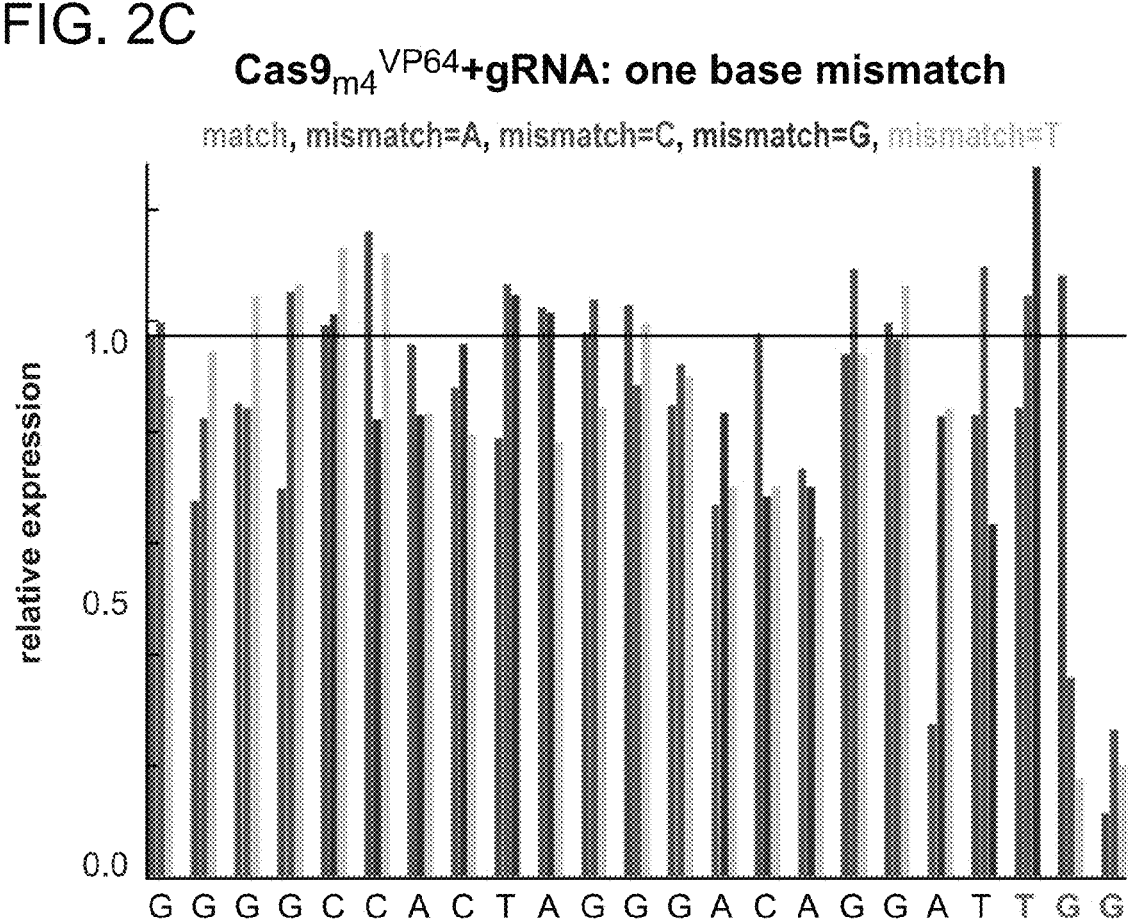
FIG. 2C depicts data demonstrating that the Cas9-gRNA complex is largely insensitive to point mutations, except those localized to the PAM sequence.
Figure 2D:
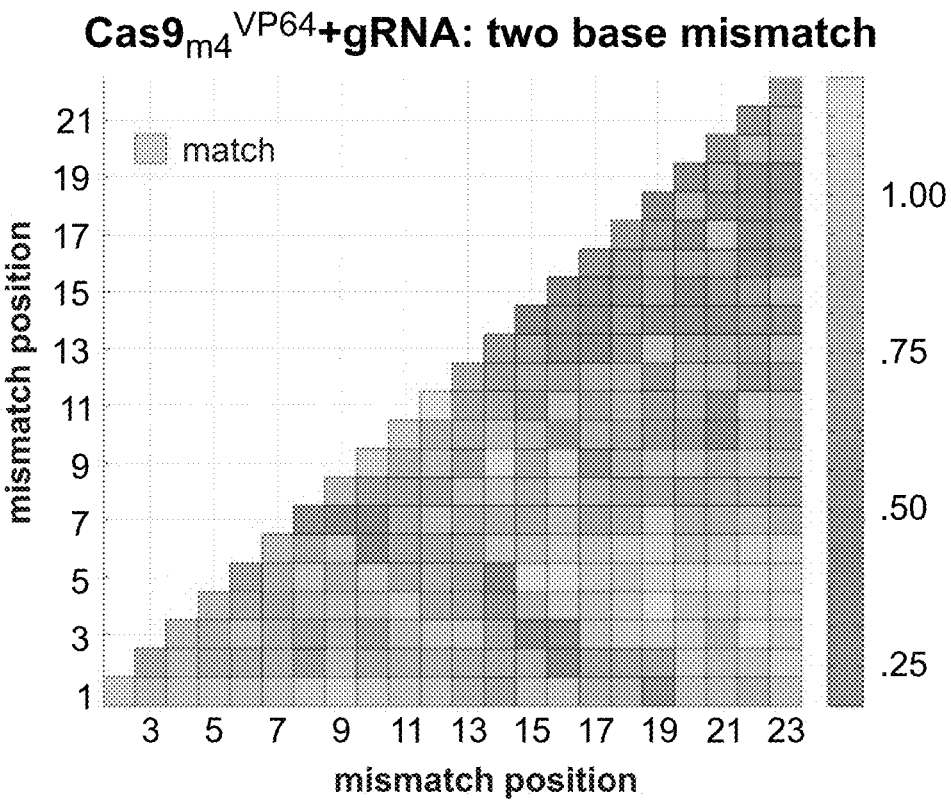
FIG. 2D depicts heat plot data demonstrating that introduction of 2 base mismatches significantly impairs the Cas9-gRNA complex activity.

As shown in FIG. 2B, the targeting landscape of a Cas9-gRNA complex reveals that it is on average tolerant to 1-3 mutations in its target sequences. As shown in FIG. 2C, the Cas9-gRNA complex is also largely insensitive to point mutations, except those localized to the PAM sequence. Notably this data reveals that the predicted PAM for the *S. pyogenes* Cas9 is not just NGG but also NAG. As shown in FIG. 2D, introduction of 2 base mismatches significantly impairs the Cas9-gRNA complex activity, however only when these are localized to the 8-10 bases nearer the 3' end of the gRNA target sequence (in the heat plot the target sequence positions are labeled from 1-23 starting from the 5' end).

Figure 2E:
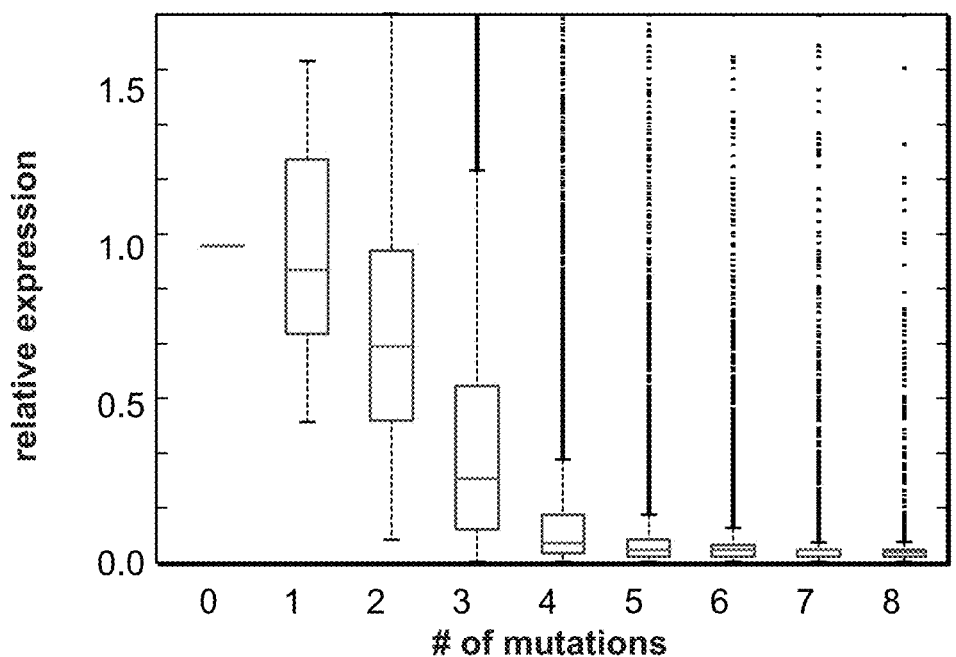
FIG. 2E depicts data demonstrating that an 18-mer TALE reveals is on average tolerant to 1-2 mutations in its target sequence.
Figure 2F:
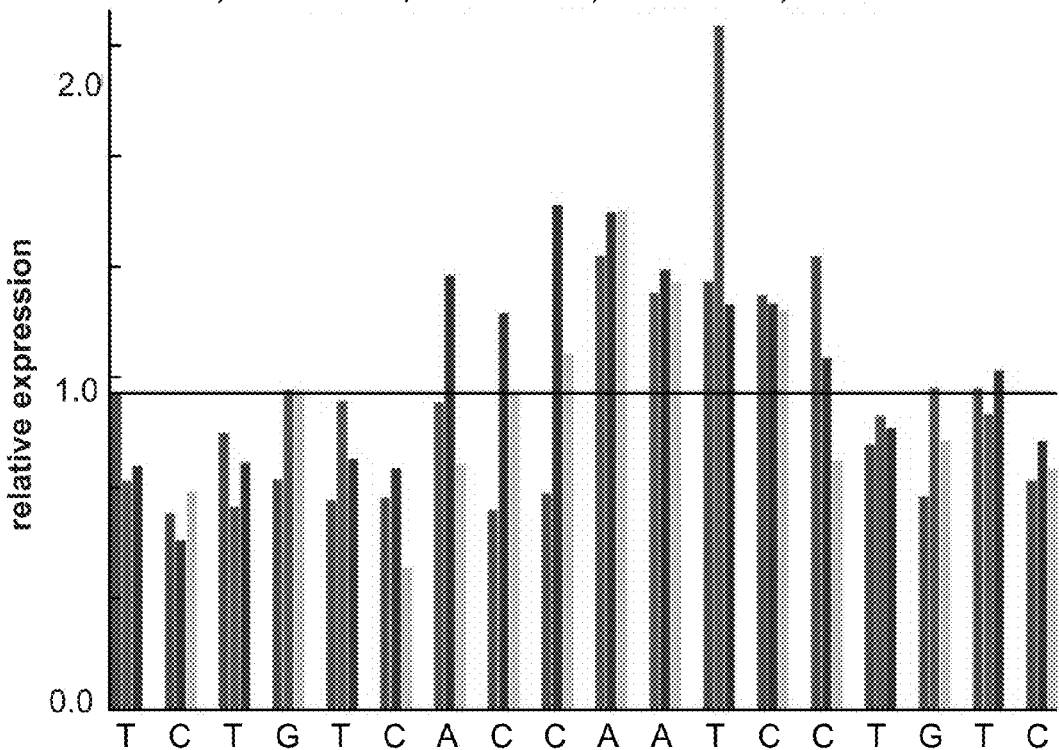
FIG. 2F depicts data demonstrating the 18-mer TALE is, similar to the Cas9-gRNA complexes, largely insensitive to single base mismatched in its target.
Figure 2G:
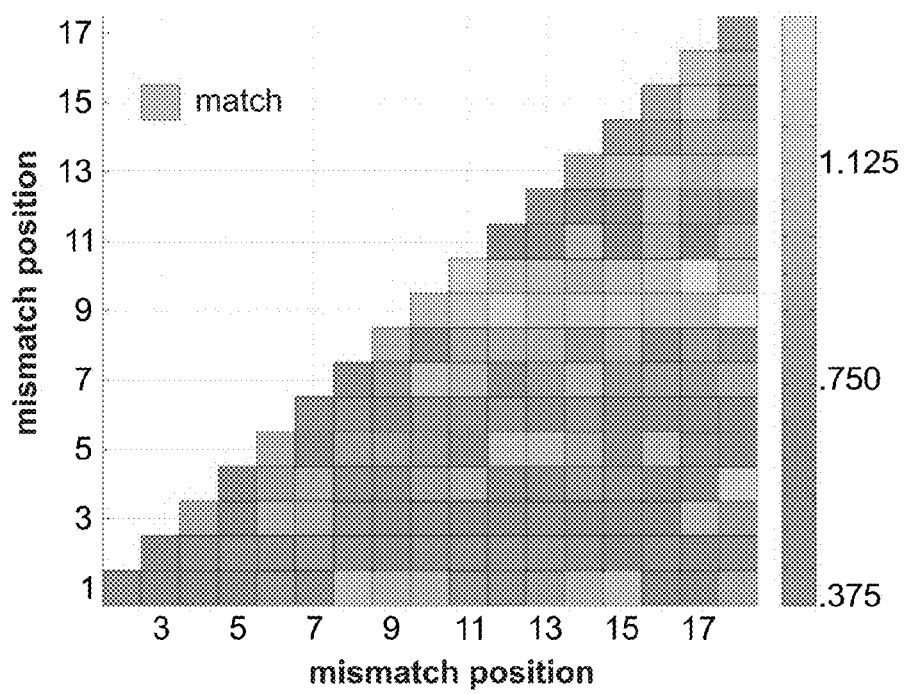
FIG. 2G depicts heat plot data demonstrating that introduction of 2 base mismatches significantly impairs the 18-mer TALE activity.

The mutational tolerance of another widely used genome editing tool, TALE domains, was determined using the transcriptional specificity assay described herein. As shown in FIG. 2E, the TALE off-targeting data for an 18-mer TALE reveals that it can tolerate on average 1-2 mutations in its target sequence, and fails to activate a large majority of 3 base mismatch variants in its targets. As shown in FIG. 2F, the 18-mer TALE is, similar to the Cas9-gRNA complexes, largely insensitive to single base mismatched in its target. As shown in FIG. 2G, introduction of 2 base mismatches significantly impairs the 18-mer TALE activity. TALE activity is more sensitive to mismatches nearer the 5' end of its target sequence (in the heat plot the target sequence positions are labeled from 1-18 starting from the 5' end).

Figures 1, 10A:
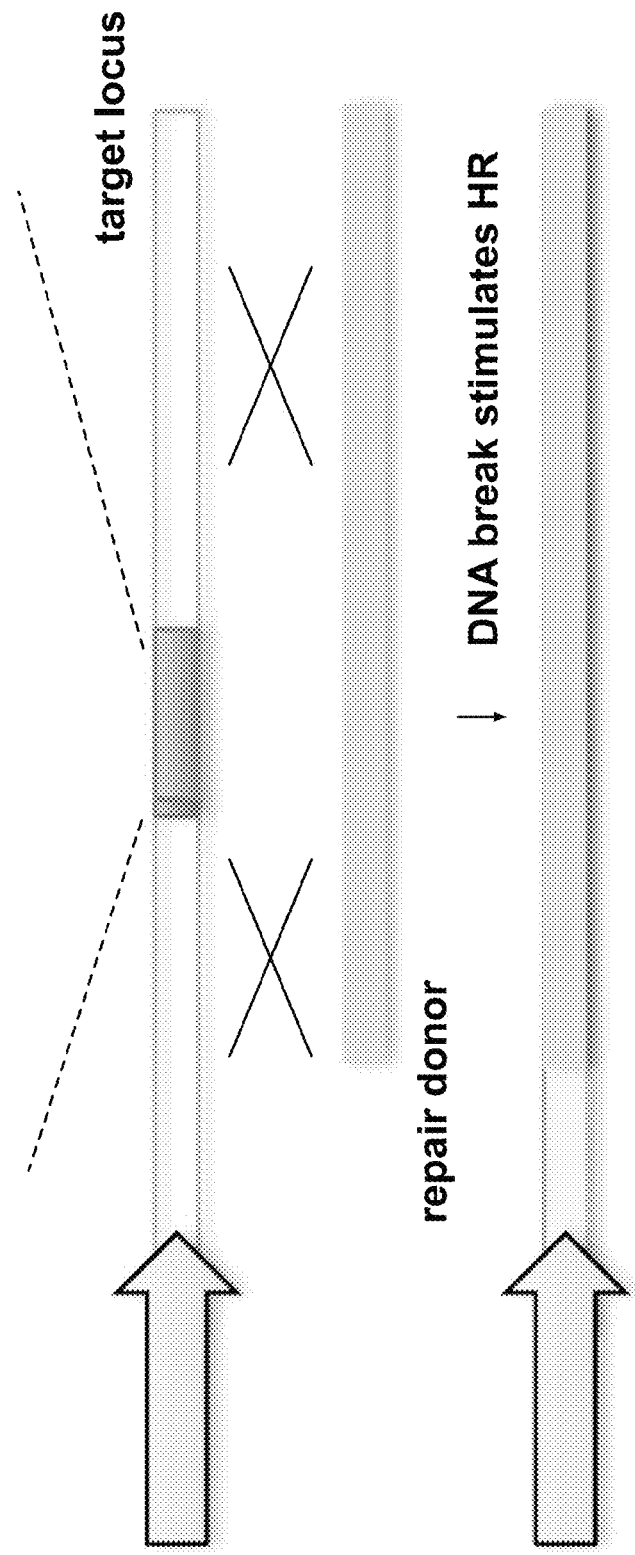
Figures 2, 10A:
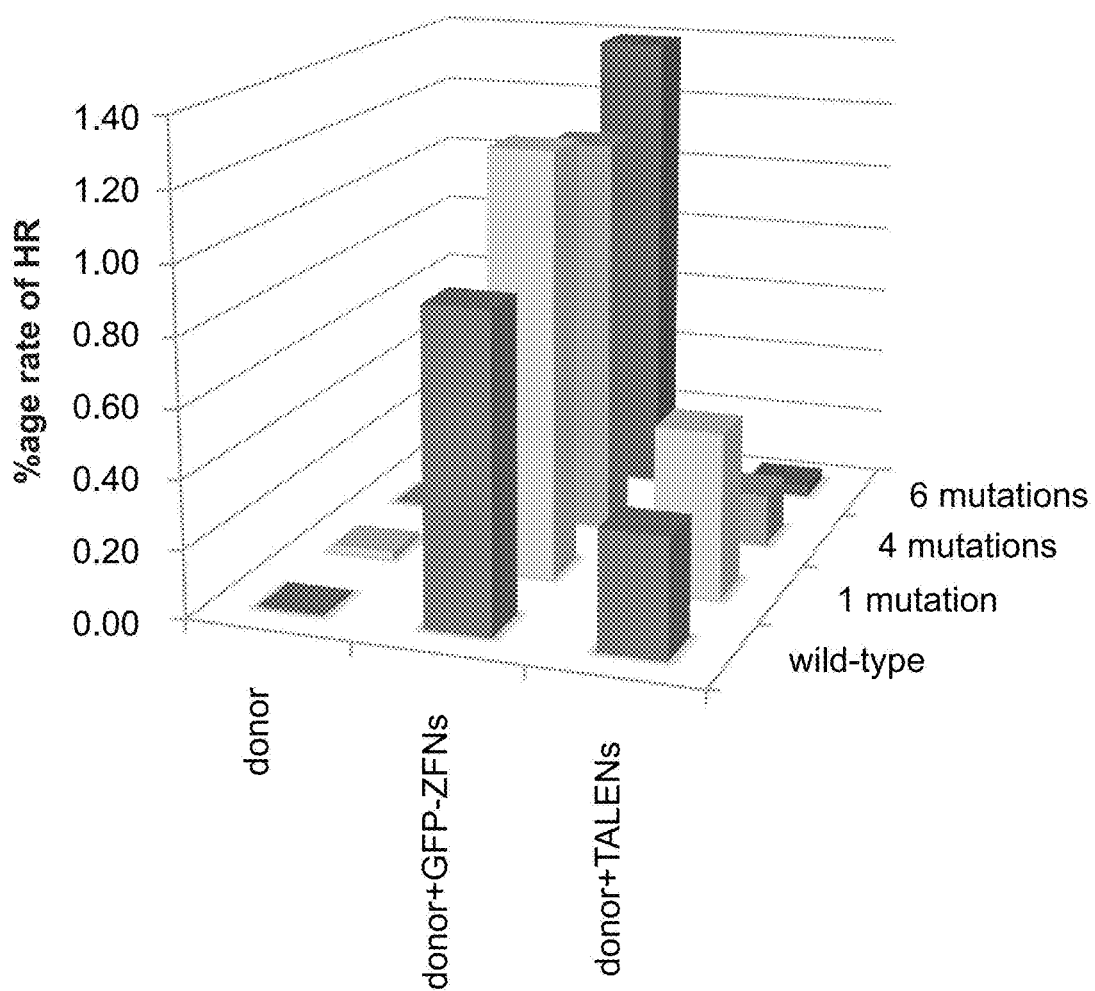
Figure 10B:
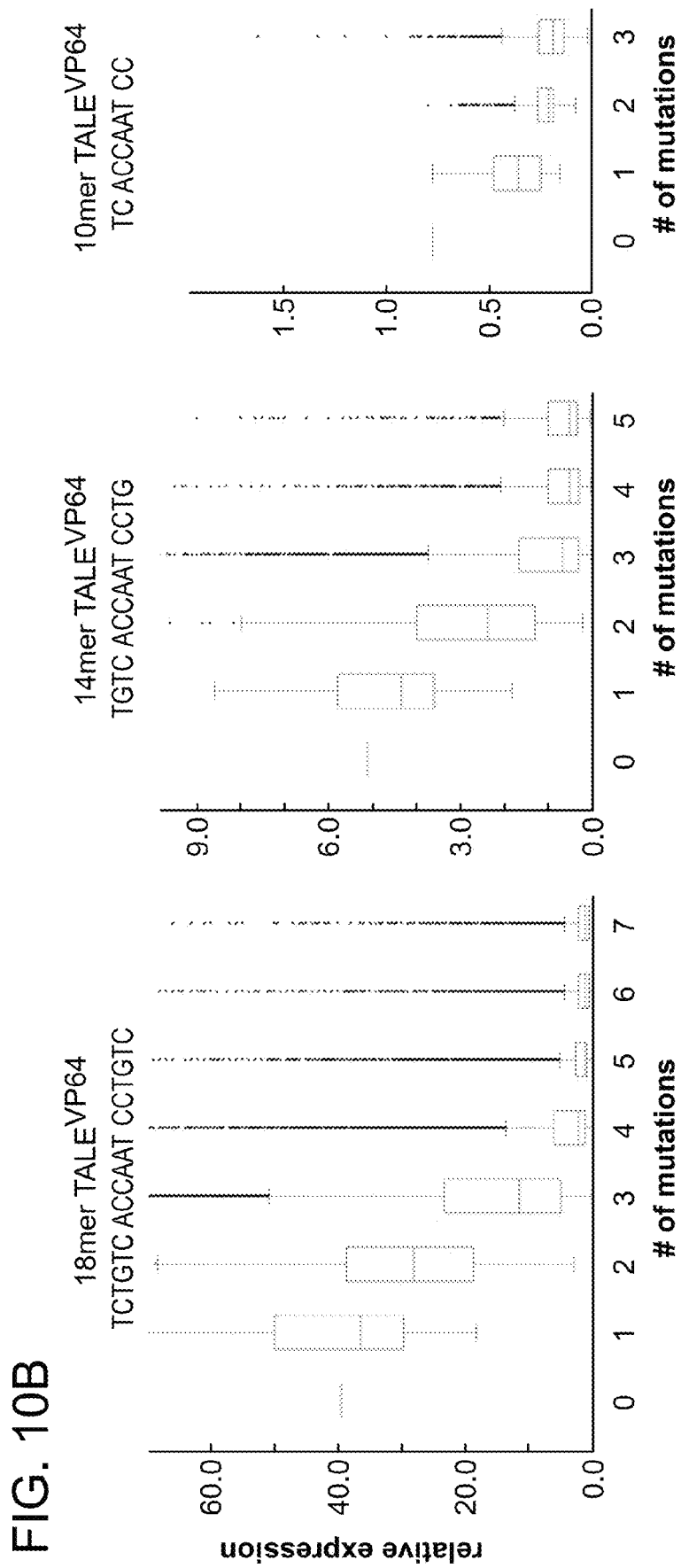
FIG. 10B depicts data from analysis of the targeting landscape of TALEs of 3 different sizes (18-mer, 14-mer and 10-mer).
Figure 10C:
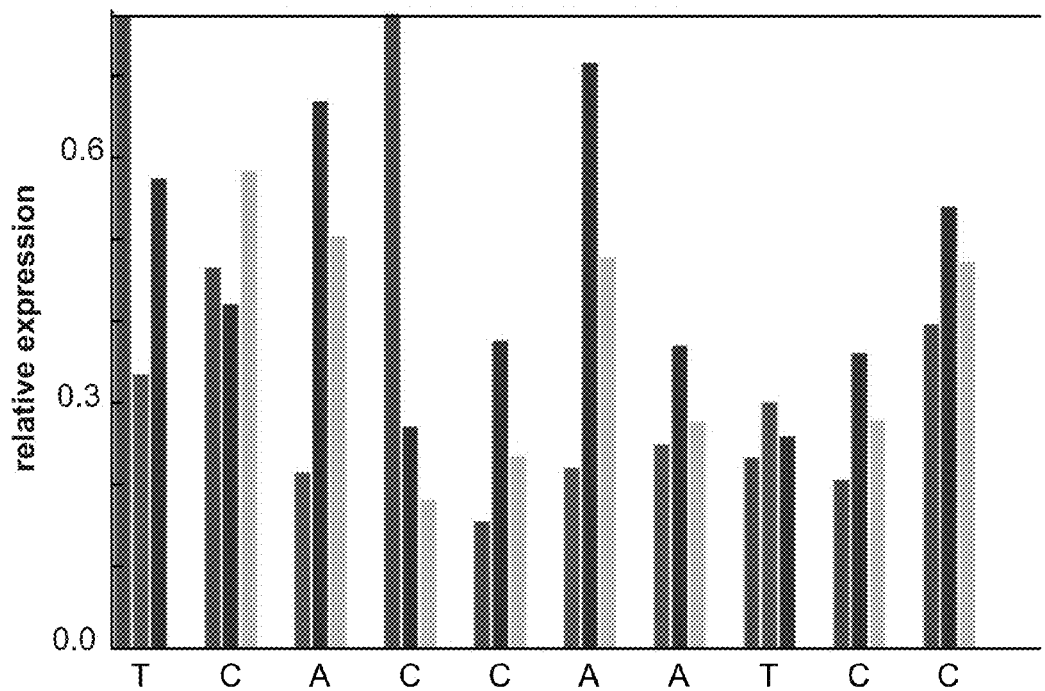
FIG. 10C depicts data for 10-mer TALEs show near single-base mismatch resolution.
Figure 10D:
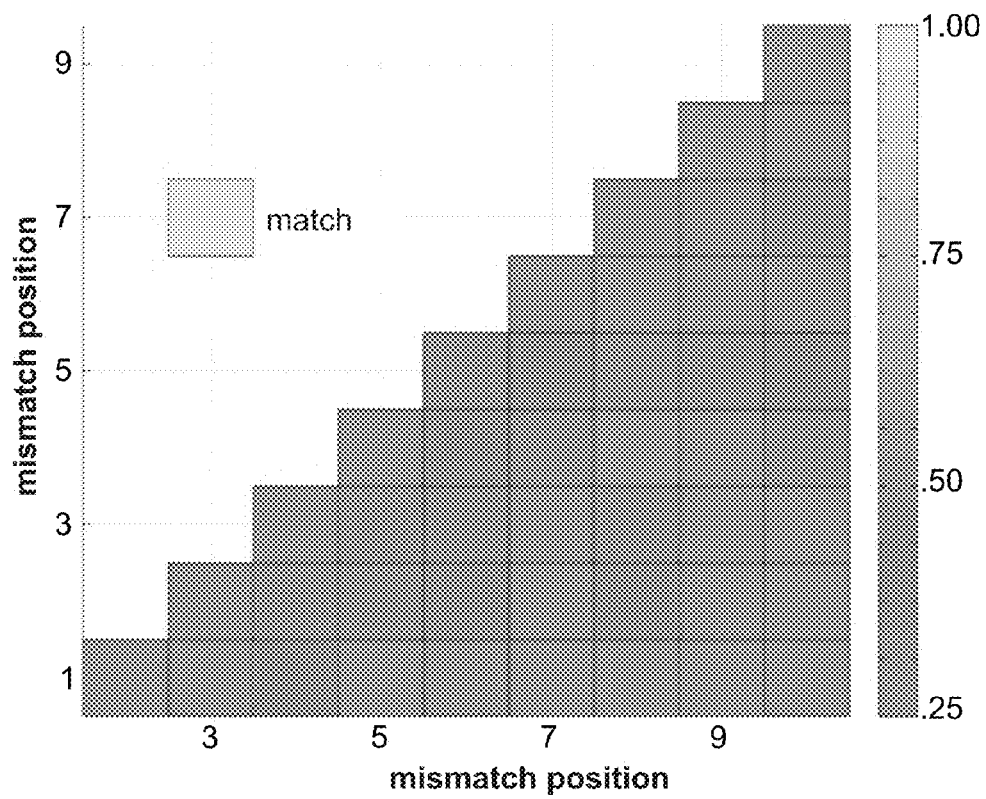
FIG. 10D depicts heat plot data for 10-mer TALEs show near single-base mismatch resolution.

Results were confirmed using targeted experiments in a nuclease assay which is the subject of FIGS. 10A-C directed to evaluating the landscape of targeting by TALEs of different sizes. As shown in FIGS. 10A-1 and 10A-2, using a nuclease mediated HR assay, it was confirmed that 18-mer TALEs tolerate multiple mutations in their target sequences. As shown in FIG. 10B, using the approach described in FIG. 2, the targeting landscape of TALEs of 3 different sizes (18-mer, 14-mer and 10-mer) was analyzed. Shorter TALEs (14-mer and 10-mer) are progressively more specific in their targeting but also reduced in activity by nearly an order of magnitude. As shown in FIGS. 10C and 10D, 10-mer TALEs show near single-base mismatch resolution, losing almost all activity against targets bearing 2 mismatches (in the heat plot the target sequence positions are labeled from 1-10 starting from the 5' end). Taken together, these data imply that engineering shorter TALEs can yield higher specificity in genome engineering applications, while the requirement for FokI dimerization in TALE nuclease applications is essential to avoid off-target effect. See Kim et al., *Proceedings of the National Academy of Sciences of the United States of America* 93, 1156-1160 (1996) and Pattanayak et al., *Nature Methods* 8, 765-770 (2011) each of which are hereby incorporated by reference in its entirety.

Figure 8A:
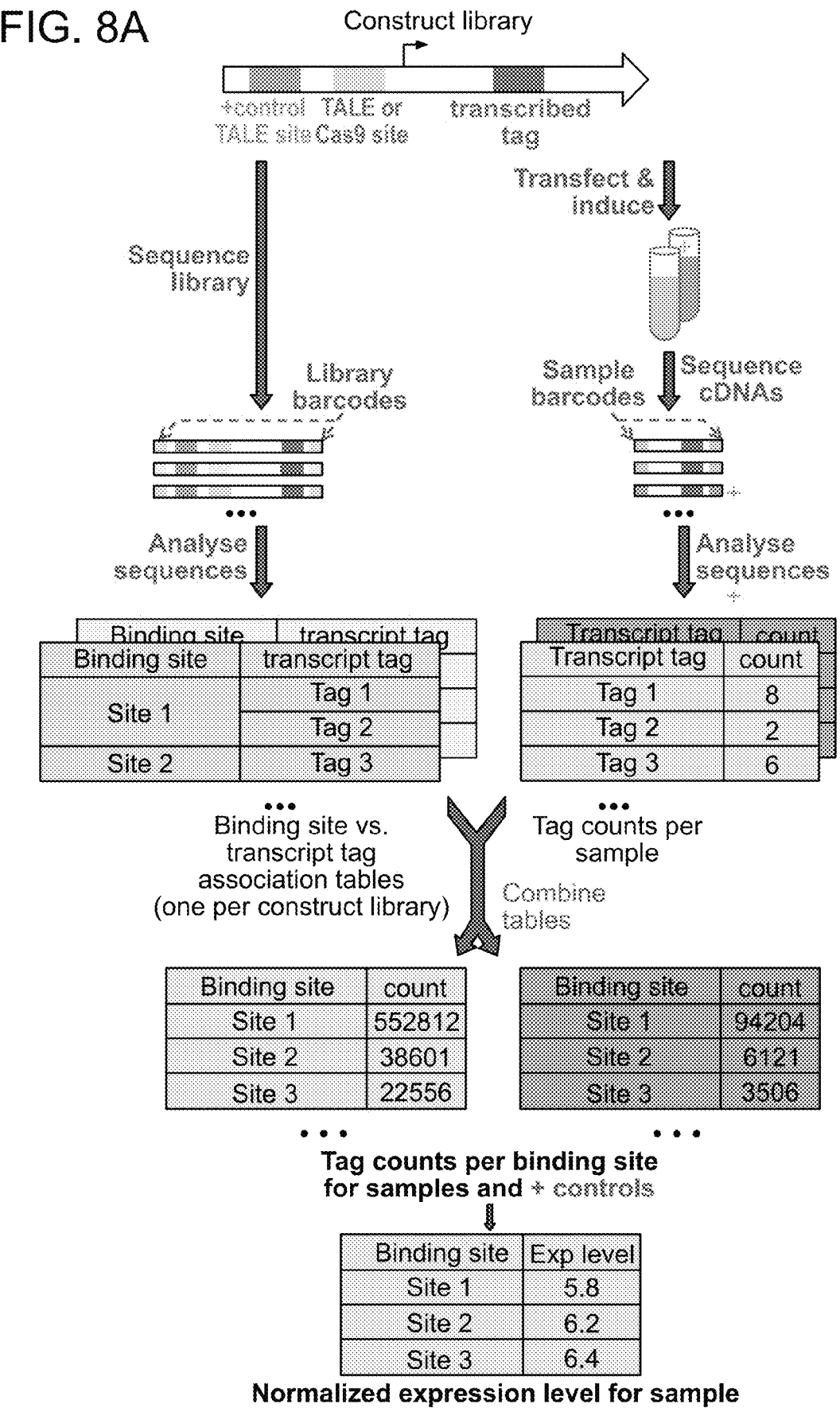
FIG. 8A depicts in schematic a high level specificity analysis processing flow for calculation of normalized expression levels.
Figure 8B:
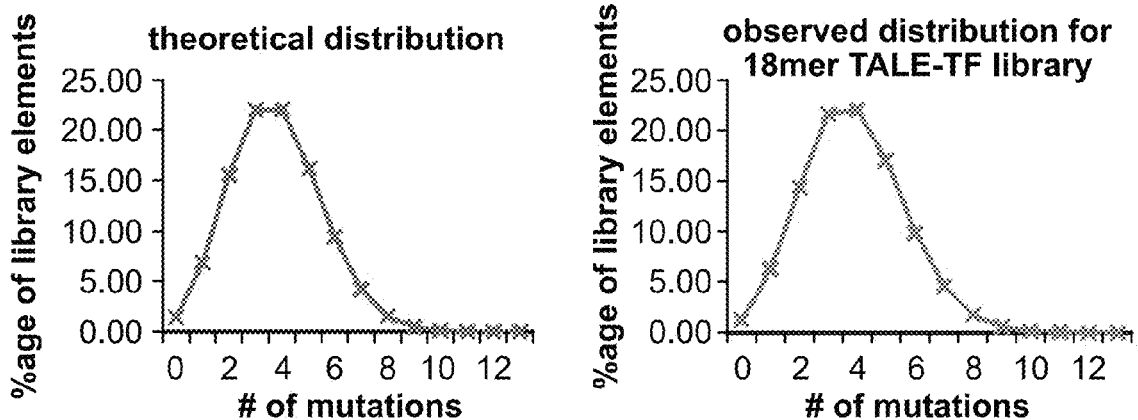
FIG. 8B depicts data of distributions of percentages of binding sites by numbers of mismatches generated within a biased construct library. Left: Theoretical distribution. Right: Distribution observed from an actual TALE construct library.
Figure 8C:
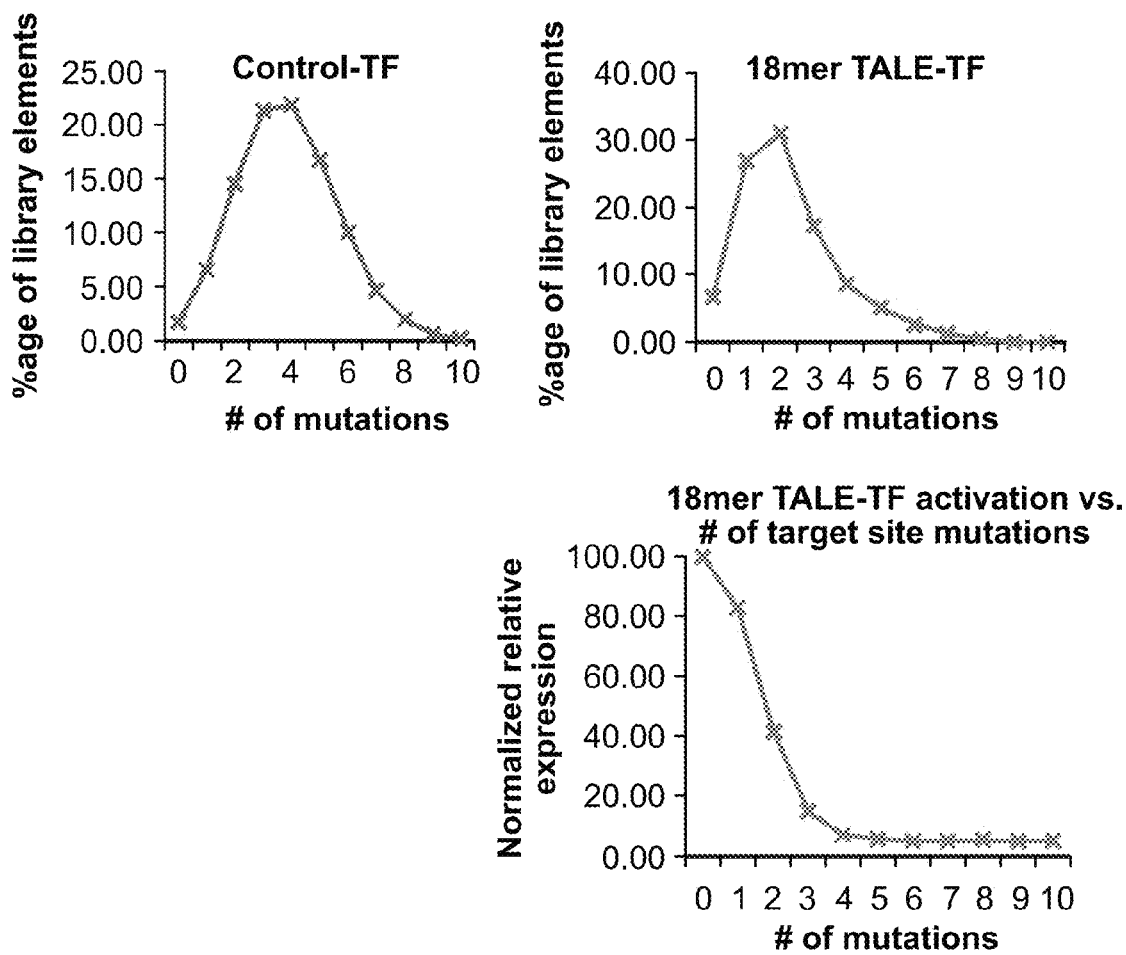
FIG. 8C depicts data of distributions of percentages of tag counts aggregated to binding sites by numbers of mismatches. Left: Distribution observed from the positive control sample. Right: Distribution observed from a sample in which a non-control TALE was induced.

FIG. 8A-C is directed to high level specificity analysis processing flow for calculation of normalized expression levels illustrated with examples from experimental data. As shown in FIG. 8A, construct libraries are generated with a biased distribution of binding site sequences and random sequence 24 bp tags that will be incorporated into reporter gene transcripts (top). The transcribed tags are highly degenerate so that they should map many-to-one to Cas9 or TALE binding sequences. The construct libraries are sequenced ($3^{rd}$ level, left) to establish which tags co-occur with binding sites, resulting in an association table of binding sites vs. transcribed tags ($4^{th}$ level, left). Multiple construct libraries built for different binding sites may be sequenced at once using library barcodes (indicated here by the light blue and light yellow colors; levels 1-4, left). A construct library is then transfected into a cell population and a set of different Cas9/gRNA or TALE transcription factors are induced in samples of the populations (2n d level, right). One sample is always induced with a fixed TALE activator targeted to a fixed binding site sequence within the construct (top level, green box); this sample serves as a positive control (green sample, also indicated by a + sign). cDNAs generated from the reporter mRNA molecules in the induced samples are then sequenced and analyzed to obtain tag counts for each tag in a sample ($3^{rd}$ and $4^{th}$ level, right). As with the construct library sequencing, multiple samples, including the positive control, are sequenced and analyzed together by appending sample barcodes. Here the light red color indicates one non-control sample that has been sequenced and analyzed with the positive control (green). Because only the transcribed tags and not the construct binding sites appear in each read, the binding site vs. tag association table obtained from construct library sequencing is then used to tally up total counts of tags expressed from each binding site in each sample ($5^{th}$ level). The tallies for each non-positive control sample are then converted to normalized expression levels for each binding site by dividing them by the tallies obtained in the positive control sample. Examples of plots of normalized expression levels by numbers of mismatches are provided in FIGS. 2B and 2E, and in FIG. 9A and FIG. 10B.

Not covered in this overall process flow are several levels of filtering for erroneous tags, for tags not associable with a construct library, and for tags apparently shared with multiple binding sites. FIG. 8B depicts example distributions of percentages of binding sites by numbers of mismatches generated within a biased construct library. Left: Theoretical distribution. Right: Distribution observed from an actual TALE construct library. FIG. 8C depicts example distributions of percentages of tag counts aggregated to binding sites by numbers of mismatches. Left: Distribution observed from the positive control sample. Right: Distribution observed from a sample in which a non-control TALE was induced. As the positive control TALE binds to a fixed site in the construct, the distribution of aggregated tag counts closely reflects the distribution of binding sites in FIG. 8B, while the distribution is skewed to the left for the non-control TALE sample because sites with fewer mismatches induce higher expression levels. Below: Computing the relative enrichment between these by dividing the tag counts obtained for the target-TF by those obtained for the control-TF reveals the average expression level versus the number of mutations in the target site.

Figure 9A:
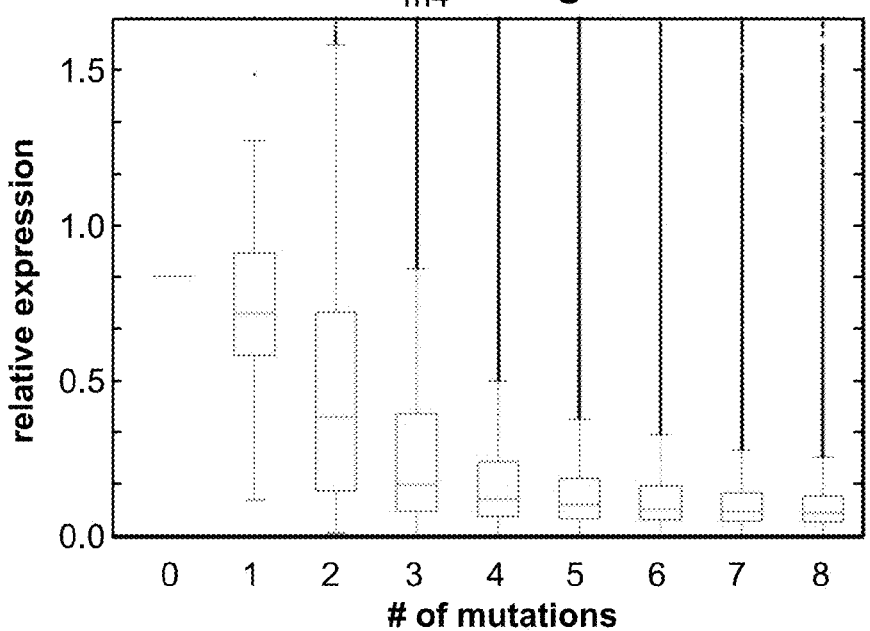
FIG. 9A depicts data for analysis of the targeting landscape of a Cas9-gRNA complex showing tolerance to 1-3 mutations in its target sequence.
Figure 9B:
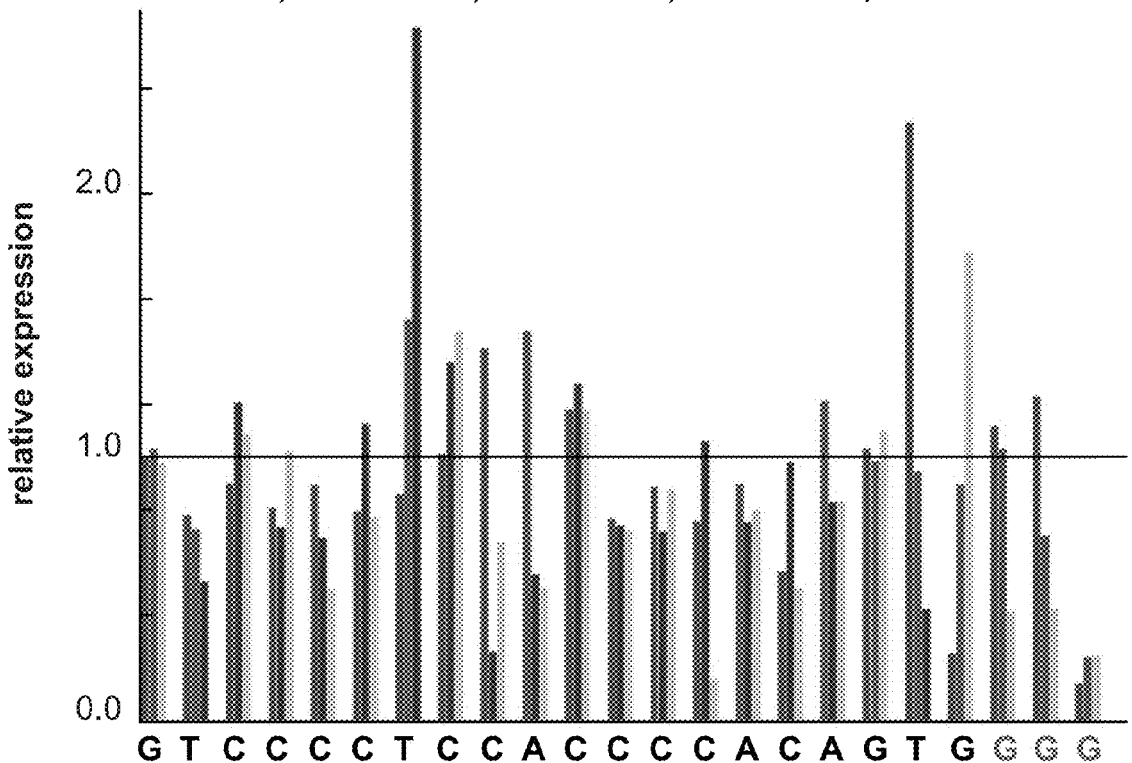
FIG. 9B depicts data for analysis of the targeting landscape of a Cas9-gRNA complex showing insensitivity to point mutations, except those localized to the PAM sequence.
Figure 9C:
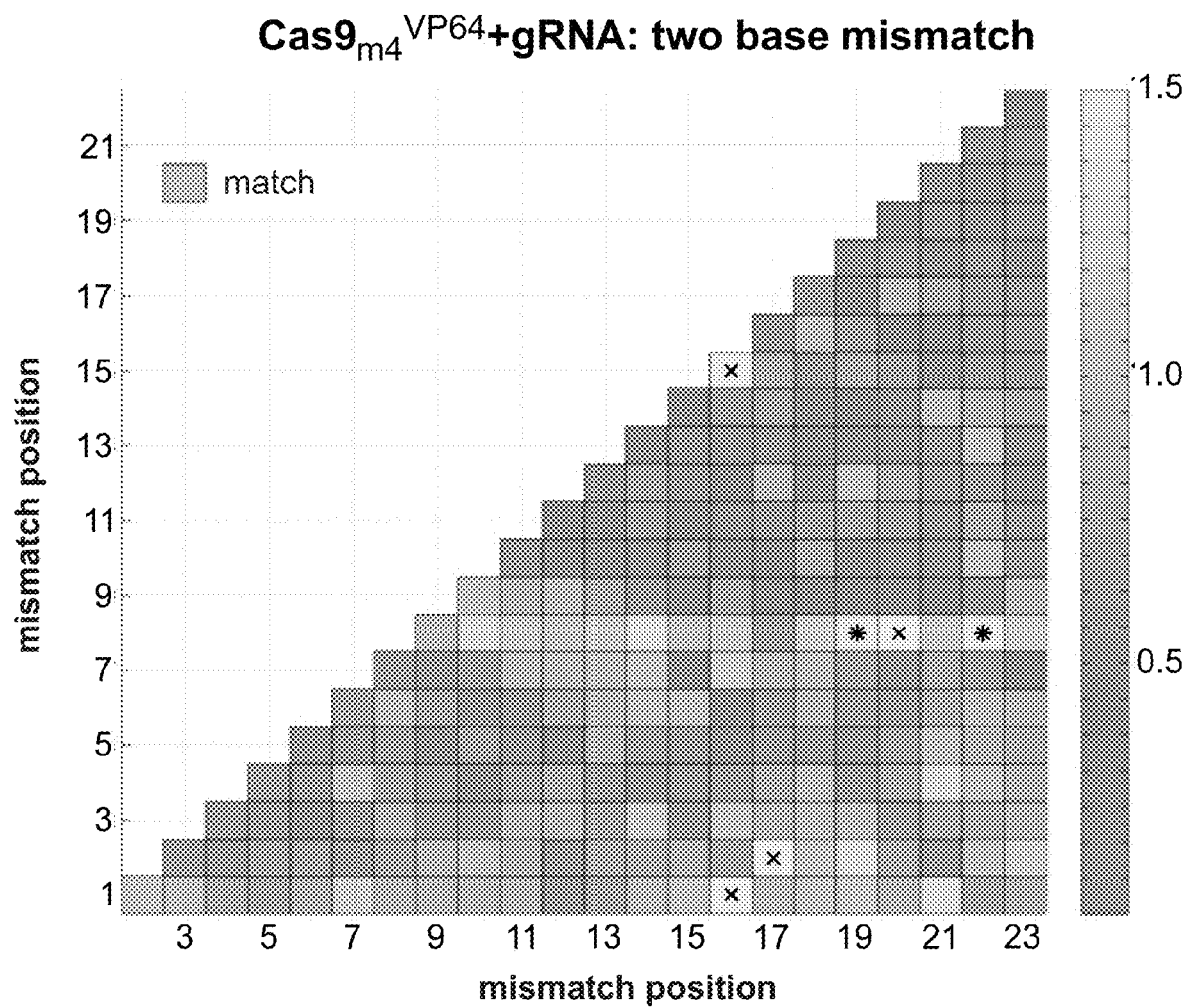
FIG. 9C depicts heat plot data for analysis of the targeting landscape of a Cas9-gRNA complex showing that introduction of 2 base mismatches significantly impairs activity.

These results are further reaffirmed by specificity data generated using a different Cas9-gRNA complex. As shown in FIG. 9A, a different Cas9-gRNA complex is tolerant to 1-3 mutations in its target sequence. As shown in FIG. 9B, the Cas9-gRNA complex is also largely insensitive to point mutations, except those localized to the PAM sequence. As shown in FIG. 9C, introduction of 2 base mismatches however significantly impairs activity (in the heat plot the target sequence positions are labeled from 1-23 starting from the 5' end). As shown in FIG. 9D, it was confirmed using a nuclease mediated HR assay that the predicted PAM for the *S. pyogenes* Cas9 is NGG and also NAG.

According to certain aspects, binding specificity is increased according to methods described herein. Because synergy between multiple complexes is a factor in target gene activation by Cas9N-VP64, transcriptional regulation applications of Cas9N is naturally quite specific as individual off-target binding events should have minimal effect. According to one aspect, off-set nicks are used in methods of genome-editing. A large majority of nicks seldom result in NHEJ events, (see Certo et al., *Nature Methods* 8, 671-676 (2011) hereby incorporated by reference in its entirety) thus minimizing the effects of off-target nicking. In contrast, inducing off-set nicks to generate double stranded breaks (DSBs) is highly effective at inducing gene disruption. According to certain aspects, 5' overhangs generate more significant NHEJ events as opposed to 3' overhangs. Similarly, 3' overhangs favor HR over NHEJ events, although the total number of HR events is significantly lower than when a 5' overhang is generated. Accordingly, methods are provided for using nicks for homologous recombination and off-set nicks for generating double stranded breaks to minimize the effects of off-target Cas9-gRNA activity.

Figure 3A:
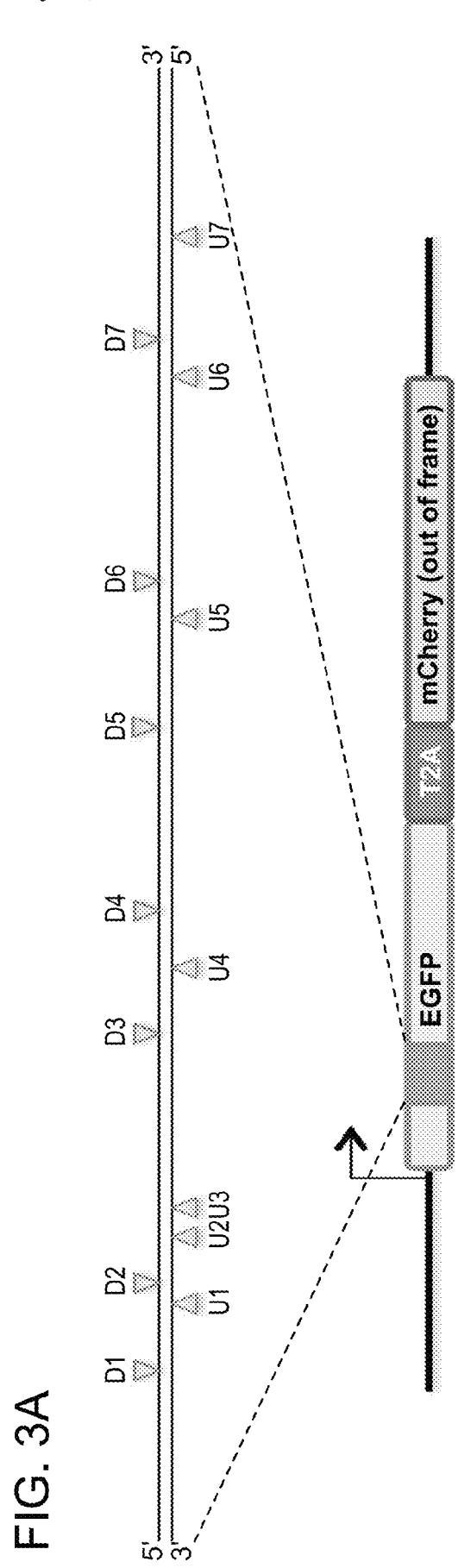
FIG. 3A depicts a schematic of a guide RNA design.
Figure 3C:
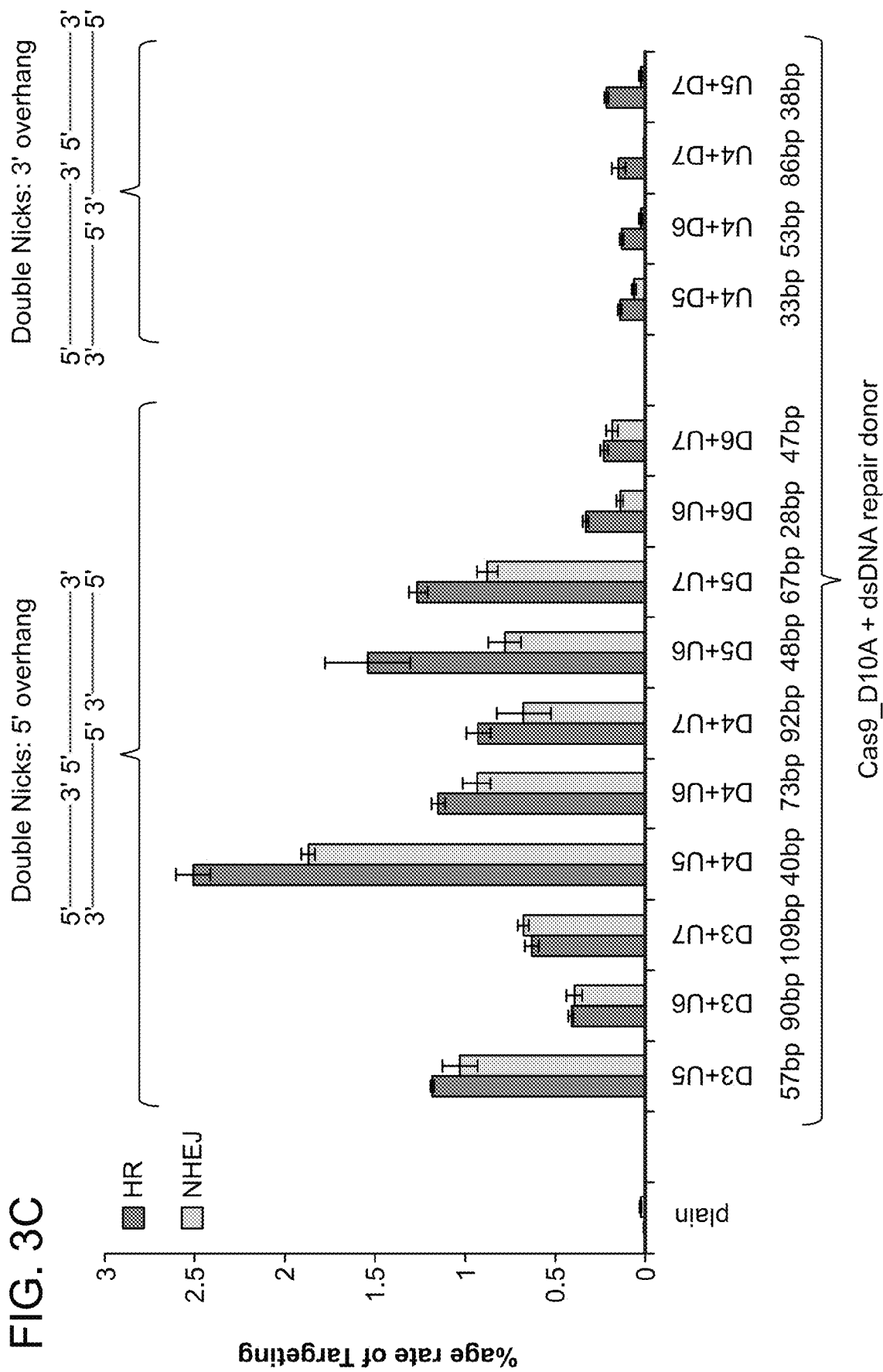
FIG. 3C depicts data showing percentage rate of targeting for off-set nicks leading to 5' overhangs and off-set nicks leading to 3' overhangs.

FIG. 3A-C is directed to multiplex off-set nicking and methods for reducing the off-target binding with the guide RNAs. As shown in FIG. 3A, the traffic light reporter was used to simultaneously assay for HR and NHEJ events upon introduction of targeted nicks or breaks. DNA cleavage events resolved through the HDR pathway restore the GFP sequence, whereas mutagenic NHEJ causes frameshifts rendering the GFP out of frame and the downstream mCherry sequence in frame. For the assay, 14 gRNAs covering a 200 bp stretch of DNA: 7 targeting the sense strand (U1-7) and 7 the antisense strand (D1-7) were designed. Using the Cas9D10A mutant, which nicks the complementary strand, different two-way combinations of the gRNAs were used to induce a range of programmed 5' or 3' overhangs (the nicking sites for the 14 gRNAs are indicated). As shown in FIG. 3B, inducing off-set nicks to generate double stranded breaks (DSBs) is highly effective at inducing gene disruption. Notably off-set nicks leading to 5' overhangs result in more NHEJ events as opposed to 3' overhangs. As shown in FIG. 3C, generating 3' overhangs also favors the ratio of HR over NHEJ events, but the total number of HR events is significantly lower than when a 5' overhang is generated.

Figure 11A:
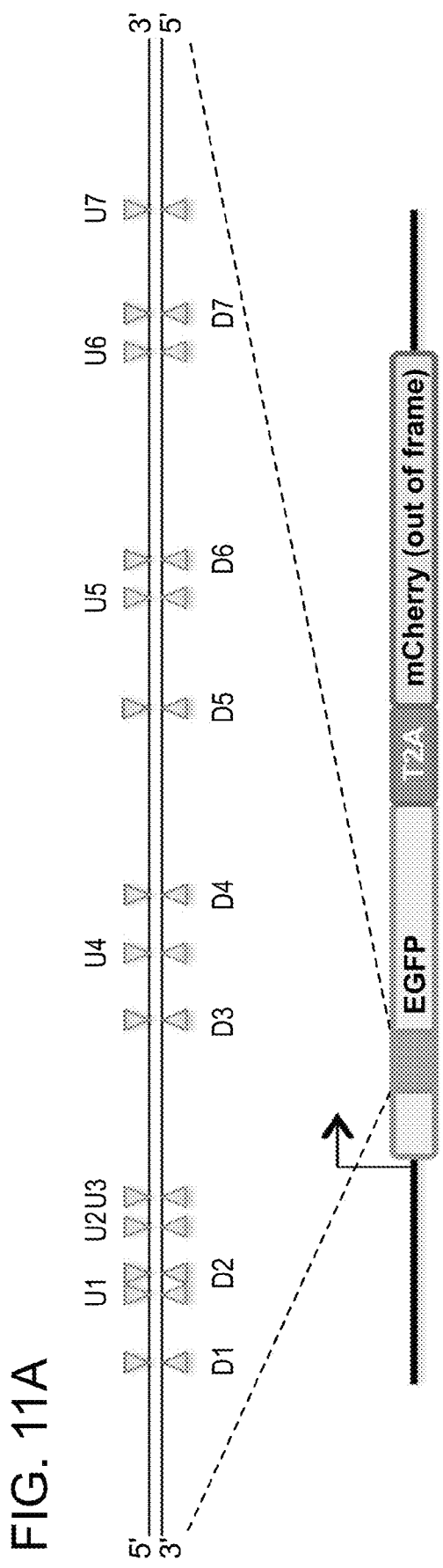
FIG. 11A depicts designed guide RNAs.

FIG. 11A-B is directed to Cas9D10A nickase mediated NHEJ. As shown in FIG. 11A, the traffic light reporter was used to assay NHEJ events upon introduction of targeted nicks or double-stranded breaks. Briefly, upon introduction of DNA cleavage events, if the break goes through mutagenic NHEJ, the GFP is translated out of frame and the downstream mCherry sequences are rendered in frame resulting in red fluorescence. 14 gRNAs covering a 200 bp stretch of DNA: 7 targeting the sense strand (U1-7) and 7 the antisense strand (D1-7) were designed. As shown in FIG. 11B, it was observed that unlike the wild-type Cas9 which results in DSBs and robust NHEJ across all targets, most nicks (using the Cas9D10A mutant) seldom result in NHEJ events. All 14 sites are located within a contiguous 200 bp stretch of DNA and over 10-fold differences in targeting efficiencies were observed.

According to certain aspects, methods are described herein of modulating expression of a target nucleic acid in a cell that include introducing one or more, two or more or a plurality of foreign nucleic acids into the cell. The foreign nucleic acids introduced into the cell encode for a guide RNA or guide RNAs, a nuclease-null Cas9 protein or proteins and a transcriptional regulator protein or domain. Together, a guide RNA, a nuclease-null Cas9 protein and a transcriptional regulator protein or domain are referred to as a co-localization complex as that term is understood by one of skill in the art to the extent that the guide RNA, the nuclease-null Cas9 protein and the transcriptional regulator protein or domain bind to DNA and regulate expression of a target nucleic acid. According to certain additional aspects, the foreign nucleic acids introduced into the cell encode for a guide RNA or guide RNAs and a Cas9 protein nickase. Together, a guide RNA and a Cas9 protein nickase are referred to as a co-localization complex as that term is understood by one of skill in the art to the extent that the guide RNA and the Cas9 protein nickase bind to DNA and nick a target nucleic acid.

Cells according to the present disclosure include any cell into which foreign nucleic acids can be introduced and expressed as described herein. It is to be understood that the basic concepts of the present disclosure described herein are not limited by cell type. Cells according to the present disclosure include eukaryotic cells, prokaryotic cells, animal cells, plant cells, fungal cells, archael cells, eubacterial cells and the like. Cells include eukaryotic cells such as yeast cells, plant cells, and animal cells. Particular cells include mammalian cells. Further, cells include any in which it would be beneficial or desirable to regulate a target nucleic acid. Such cells may include those which are deficient in expression of a particular protein leading to a disease or detrimental condition. Such diseases or detrimental conditions are readily known to those of skill in the art. According to the present disclosure, the nucleic acid responsible for expressing the particular protein may be targeted by the methods described herein and a transcriptional activator resulting in upregulation of the target nucleic acid and corresponding expression of the particular protein. In this manner, the methods described herein provide therapeutic treatment.

Target nucleic acids include any nucleic acid sequence to which a co-localization complex as described herein can be useful to either regulate or nick. Target nucleic acids include genes. For purposes of the present disclosure, DNA, such as double stranded DNA, can include the target nucleic acid and a co-localization complex can bind to or otherwise co-localize with the DNA at or adjacent or near the target nucleic acid and in a manner in which the co-localization complex may have a desired effect on the target nucleic acid. Such target nucleic acids can include endogenous (or naturally occurring) nucleic acids and exogenous (or foreign) nucleic acids. One of skill based on the present disclosure will readily be able to identify or design guide RNAs and Cas9 proteins which co-localize to a DNA including a target nucleic acid. One of skill will further be able to identify transcriptional regulator proteins or domains which likewise co-localize to a DNA including a target nucleic acid. DNA includes genomic DNA, mitochondrial DNA, viral DNA or exogenous DNA.

Foreign nucleic acids (i.e. those which are not part of a cell's natural nucleic acid composition) may be introduced into a cell using any method known to those skilled in the art for such introduction. Such methods include transfection, transduction, viral transduction, microinjection, lipofection, nucleofection, nanoparticle bombardment, transformation, conjugation and the like. One of skill in the art will readily understand and adapt such methods using readily identifiable literature sources.

Transcriptional regulator proteins or domains which are transcriptional activators include VP16 and VP64 and others readily identifiable by those skilled in the art based on the present disclosure.

Diseases and detrimental conditions are those characterized by abnormal loss of expression of a particular protein. Such diseases or detrimental conditions can be treated by upregulation of the particular protein. Accordingly, methods of treating a disease or detrimental condition are provided where the co-localization complex as described herein associates or otherwise binds to DNA including a target nucleic acid, and the transcriptional activator of the co-localization complex upregulates expression of the target nucleic acid. For example upregulating PRDM16 and other genes promoting brown fat differentiation and increased metabolic uptake can be used to treat metabolic syndrome or obesity. Activating anti-inflammatory genes are useful in autoimmunity and cardiovascular disease. Activating tumor suppressor genes is useful in treating cancer. One of skill in the art will readily identify such diseases and detrimental conditions based on the present disclosure.

The following examples are set forth as being representative of the present disclosure. These examples are not to be construed as limiting the scope of the present disclosure as these and other equivalent embodiments will be apparent in view of the present disclosure, figures and accompanying claims.

Example I

Cas9 Mutants

Sequences homologous to Cas9 with known structure were searched to identify candidate mutations in Cas9 that could ablate the natural activity of its RuvC and HNH domains. Using HHpred (world wide website toolkit.tuebingen.mpg.de/hhpred), the full sequence of Cas9 was queried against the full Protein Data Bank (January 2013). This search returned two different HNH endonucleases that had significant sequence homology to the HNH domain of Cas9; PacI and a putative endonuclease (PDB IDs: 3M7K and 4H9D respectively). These proteins were examined to find residues involved in magnesium ion coordination. The corresponding residues were then identified in the sequence alignment to Cas9. Two Mg-coordinating side-chains in each structure were identified that aligned to the same amino acid type in Cas9. They are 3M7K D92 and N113, and 4H9D D53 and N77. These residues corresponded to Cas9 D839 and N863. It was also reported that mutations of Pad residues D92 and N113 to alanine rendered the nuclease catalytically deficient. The Cas9 mutations D839A and N863A were made based on this analysis. Additionally, HHpred also predicts homology between Cas9 and the N-terminus of a *Thermus thermophilus* RuvC (PDB ID: 4EP4). This sequence alignment covers the previously reported mutation D1 OA which eliminates function of the RuvC domain in Cas9. To confirm this as an appropriate mutation, the metal binding residues were determined as before. In 4EP4, D7 helps to coordinate a magnesium ion. This position has sequence homology corresponding to Cas9 D10, confirming that this mutation helps remove metal binding, and thus catalytic activity from the Cas9 RuvC domain.

Example II

Plasmid Construction

The Cas9 mutants were generated using the Quickchange kit (Agilent technologies). The target gRNA expression constructs were either (1) directly ordered as individual gBlocks from IDT and cloned into the pCR-BluntII-TOPO vector (Invitrogen); or (2) custom synthesized by Genewiz; or (3) assembled using Gibson assembly of oligonucleotides into the gRNA cloning vector (plasmid #41824). The vectors for the HR reporter assay involving a broken GFP were constructed by fusion PCR assembly of the GFP sequence bearing the stop codon and appropriate fragment assembled into the EGIP lentivector from Addgene (plasmid #26777). These lentivectors were then used to establish the GFP reporter stable lines. TALENs used in this study were constructed using standard protocols. See Sanjana et al., Nature Protocols 7, 171-192 (2012) hereby incorporated by reference in its entirety. Cas9N and MS2 VP64 fusions were performed using standard PCR fusion protocol procedures. The promoter luciferase constructs for OCT4 and REX1 were obtained from Addgene (plasmid #17221 and plasmid #17222).

Example III

Cell Culture and Transfections

HEK 293T cells were cultured in Dulbecco's modified Eagle's medium (DMEM, Invitrogen) high glucose supplemented with 10% fetal bovine serum (FBS, Invitrogen), penicillin/streptomycin (pen/strep, Invitrogen), and non-essential amino acids (NEAA, Invitrogen). Cells were maintained at 37° C. and 5% $CO_2$ in a humidified incubator.

Transfections involving nuclease assays were as follows: $0.4 \times 10^6$ cells were transfected with 2 µg Cas9 plasmid, 2 µg gRNA and/or 2 µg DNA donor plasmid using Lipofectamine 2000 as per the manufacturer's protocols. Cells were harvested 3 days after transfection and either analyzed by FACS, or for direct assay of genomic cuts the genomic DNA of ~$1 \times 10^6$ cells was extracted using DNAeasy kit (Qiagen). For these PCR was conducted to amplify the targeting region with genomic DNA derived from the cells and amplicons were deep sequenced by MiSeq Personal Sequencer (Illumina) with coverage>200,000 reads. The sequencing data was analyzed to estimate NHEJ efficiencies.

For transfections involving transcriptional activation assays: $0.4 \times 10^6$ cells were transfected with (1) 2 µg Cas9N-VP64 plasmid, 2 µg gRNA and/or 0.25 µg of reporter construct; or (2) 2 µg Cas9N plasmid, 2 µg MS2-VP64, 2 µg gRNA-2XMS2aptamer and/or 0.25 µg of reporter construct. Cells were harvested 24-48 hrs post transfection and assayed using FACS or immunofluorescence methods, or their total RNA was extracted and these were subsequently analyzed by RT-PCR. Here standard taqman probes from Invitrogen for OCT4 and REX1 were used, with normalization for each sample performed against GAPDH.

For transfections involving transcriptional activation assays for specificity profile of Cas9-gRNA complexes and TALEs: $0.4 \times 10^6$ cells were transfected with (1) 2 µg Cas9N-VP64 plasmid, 2 µg gRNA and 0.25 µg of reporter library; or (2) 2 µg TALE-TF plasmid and 0.25 µg of reporter library; or (3) 2 µg control-TF plasmid and 0.25 µg of reporter library. Cells were harvested 24 hrs post transfection (to avoid the stimulation of reporters being in saturation mode). Total RNA extraction was performed using RNAeasy-plus kit (Qiagen), and standard RT-per performed using Superscript-III (Invitrogen). Libraries for next-generation sequencing were generated by targeted per amplification of the transcript-tags.

Example IV

Computational and Sequence Analysis for Calculation of Cas9-TF and TALE-TF Reporter Expression Levels The high-level logic flow for this process is depicted in FIG. 8A, and additional details are given here. For details on construct library composition, see FIGS. 8A (level 1) and 8B.

Sequencing: For Cas9 experiments, construct library (FIG. 8A, level 3, left) and reporter gene cDNA sequences (FIG. 8A, level 3, right) were obtained as 150 bp overlapping paired end reads on an Illumina MiSeq, while for TALE experiments, corresponding sequences were obtained as 51 bp non-overlapping paired end reads on an Illumina HiSeq.

Construct library sequence processing: Alignment: For Cas9 experiments, novoalign V2.07.17 (world wide website novocraft.com/main/index/php) was used to align paired reads to a set of 250 bp reference sequences that corresponded to 234 bp of the constructs flanked by the pairs of 8 bp library barcodes (see FIG. 8A, $3^{rd}$ level, left). In the reference sequences supplied to novoalign, the 23 bp degenerate Cas9 binding site regions and the 24 bp degenerate transcript tag regions (see FIG. 8A, first level) were specified as Ns, while the construct library barcodes were explicitly provided. For TALE experiments, the same procedures were used except that the reference sequences were 203 bp in length and the degenerate binding site regions were 18 bp vs. 23 bp in length. Validity checking: Novoalign output for comprised files in which left and right reads for each read pair were individually aligned to the reference sequences. Only read pairs that were both uniquely aligned to the reference sequence were subjected to additional validity conditions, and only read pairs that passed all of these conditions were retained. The validity conditions included: (i) Each of the two construct library barcodes must align in at least 4 positions to a reference sequence barcode, and the two barcodes must to the barcode pair for the same construct library. (ii) All bases aligning to the N regions of the reference sequence must be called by novoalign as As, Cs, Gs or Ts. Note that for neither Cas9 nor TALE experiments did left and right reads overlap in a reference N region, so that the possibility of ambiguous novoalign calls of these N bases did not arise. (iii) Likewise, no novoalign-called inserts or deletions must appear in these regions. (iv) No Ts must appear in the transcript tag region (as these random sequences were generated from As, Cs, and Gs only). Read pairs for which any one of these conditions were violated were collected in a rejected read pair file. These validity checks were implemented using custom perl scripts.

Induced sample reporter gene cDNA sequence processing: Alignment: SeqPrep (downloaded from world wide website github.com/jstjohn/SeqPrep) was first used to merge the overlapping read pairs to the 79 bp common segment, after which novoalign (version above) was used to align these 79 bp common segments as unpaired single reads to a set of reference sequences (see FIG. 8A, $3^{rd}$ level, right) in which (as for the construct library sequencing) the 24 bp degenerate transcript tag was specified as Ns while the sample barcodes were explicitly provided. Both TALE and Cas9 cDNA sequence regions corresponded to the same 63 bp regions of cDNA flanked by pairs of 8 bp sample barcode sequences. Validity checking: The same conditions were applied as for construct library sequencing (see above) except that: (a) Here, due prior SeqPrep merging of read pairs, validity processing did not have to filter for unique alignments of both reads in a read pair but only for unique alignments of the merged reads. (b) Only transcript tags appeared in the cDNA sequence reads, so that validity processing only applied these tag regions of the reference sequences and not also to a separate binding site region.

Assembly of table of binding sites vs. transcript tag associations: Custom perl was used to generate these tables from the validated construct library sequences (FIG. 8A, $4^{th}$ level, left). Although the 24 bp tag sequences composed of A, C, and G bases should be essentially unique across a construct library (probability of sharing=~2.8e-11), early analysis of binding site vs. tag associations revealed that a non-negligible fraction of tag sequences were in fact shared by multiple binding sequences, likely mainly caused by a combination of sequence errors in the binding sequences, or oligo synthesis errors in the oligos used to generate the construct libraries. In addition to tag sharing, tags found associated with binding sites in validated read pairs might also be found in the construct library read pair reject file if it was not clear, due to barcode mismatches, which construct library they might be from. Finally, the tag sequences themselves might contain sequence errors. To deal with these sources of error, tags were categorized with three attributes: (i) safe vs. unsafe, where unsafe meant the tag could be found in the construct library rejected read pair file; shared vs. nonshared, where shared meant the tag was found associated with multiple binding site sequences, and 2+vs. 1-only, where 2+ meant that the tag appeared at least twice among the validated construct library sequences and so presumed to be less likely to contain sequence errors. Combining these three criteria yielded 8 classes of tags associated with each binding site, the most secure (but least abundant) class comprising only safe, nonshared, 2+ tags; and the least secure (but most abundant) class comprising all tags regardless of safety, sharing, or number of occurrences.

Computation of normalized expression levels: Custom perl code was used to implement the steps indicated in FIG. 8A, levels 5-6. First, tag counts obtained for each induced sample were aggregated for each binding site, using the binding site vs. transcript tag table previously computed for the construct library (see FIG. 8C). For each sample, the aggregated tag counts for each binding site were then divided by the aggregated tag counts for the positive control sample to generate normalized expression levels. Additional considerations relevant to these calculations included:

1. For each sample, a subset of "novel" tags were found among the validity-checked cDNA gene sequences that could not be found in the binding site vs. transcript tag association table. These tags were ignored in the subsequent calculations.
2. The aggregations of tag counts described above were performed for each of the eight classes of tags described above in binding site vs. transcript tag association table. Because the binding sites in the construct libraries were biased to generate sequences similar to a central sequence frequently, but sequences with increasing numbers of mismatches increasingly rarely, binding sites with few mismatches generally aggregated to large numbers of tags, while binding sites with more mismatches aggregated to smaller numbers. Thus, although use of the most secure tag class was generally desirable, evaluation of binding sites with two or more mismatches might be based on small numbers of tags per binding site, making the secure counts and ratios less statistically reliable even if the tags themselves were more reliable. In such cases, all tags were used. Some compensation for this consideration obtains from the fact that the number of separate aggregated tag counts for n mismatching positions grew with the number of combinations of mismatching positions (equal to $$\binom{L}{n}3^n$$

and so dramatically increases with n; thus the averages of aggregated tag counts for different numbers n of mismatches (shown in FIGS. 2b, 2e, and in FIGS. 9A and 10B) are based on a statistically very large set of aggregated tag counts for $n \geq 2$.

3. Finally, the binding site built into the TALE construct libraries was 18 bp and tag associations were assigned based on these 18 bp sequences, but some experiments were conducted with TALEs programmed to bind central 14 bp or 10 bp regions within the 18 bp construct binding site regions. In computing expression levels for these TALEs, tags were aggregated to binding sites based on the corresponding regions of the 18 bp binding sites in the association table, so that binding site mismatches outside of this region were ignored.

Example V

RNA-Guided SOX2 and NANOG Regulation Using Cas9$_N$.VP64

Figure 12A:
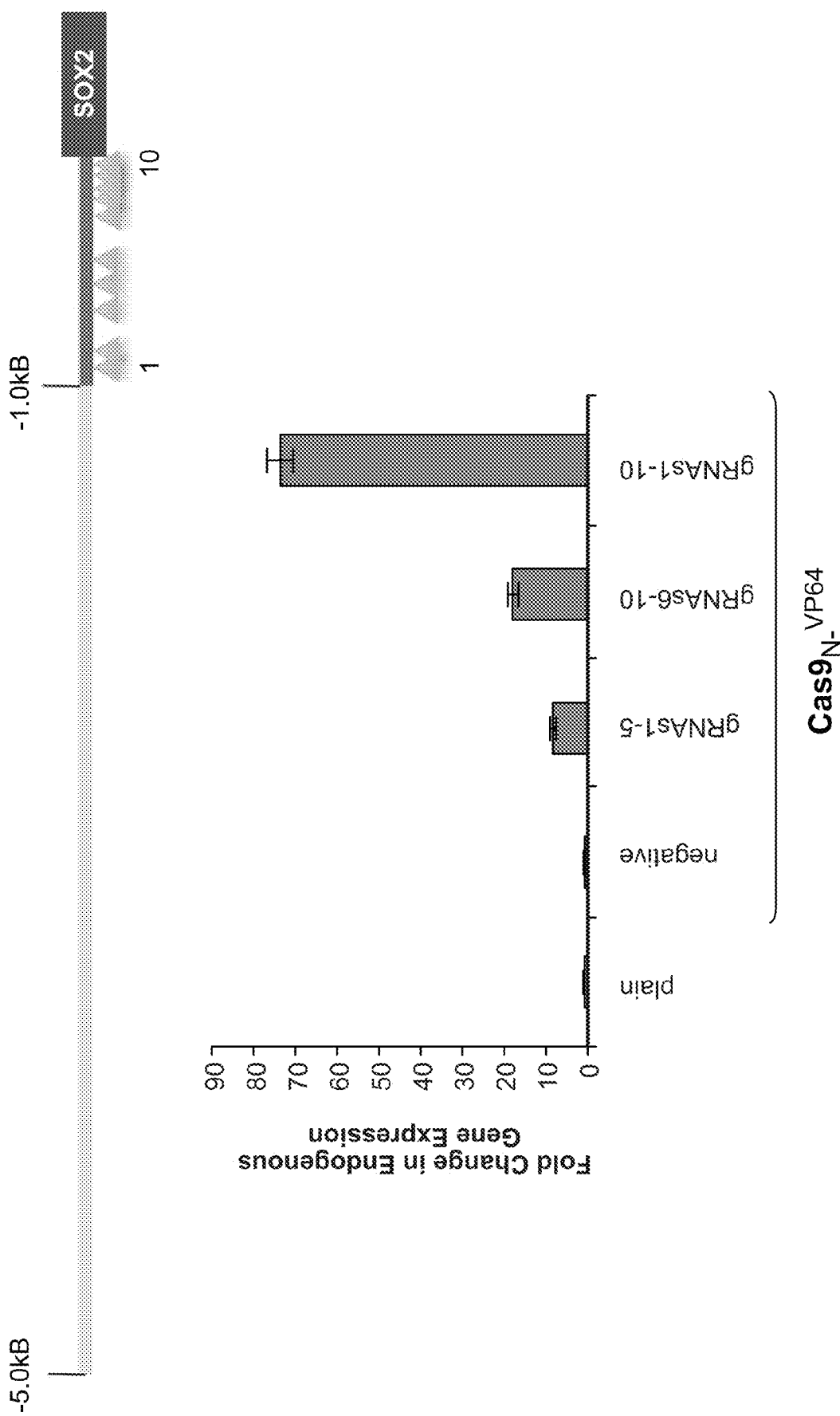
FIG. 12A depicts the Sox2 gene.
Figure 12B:
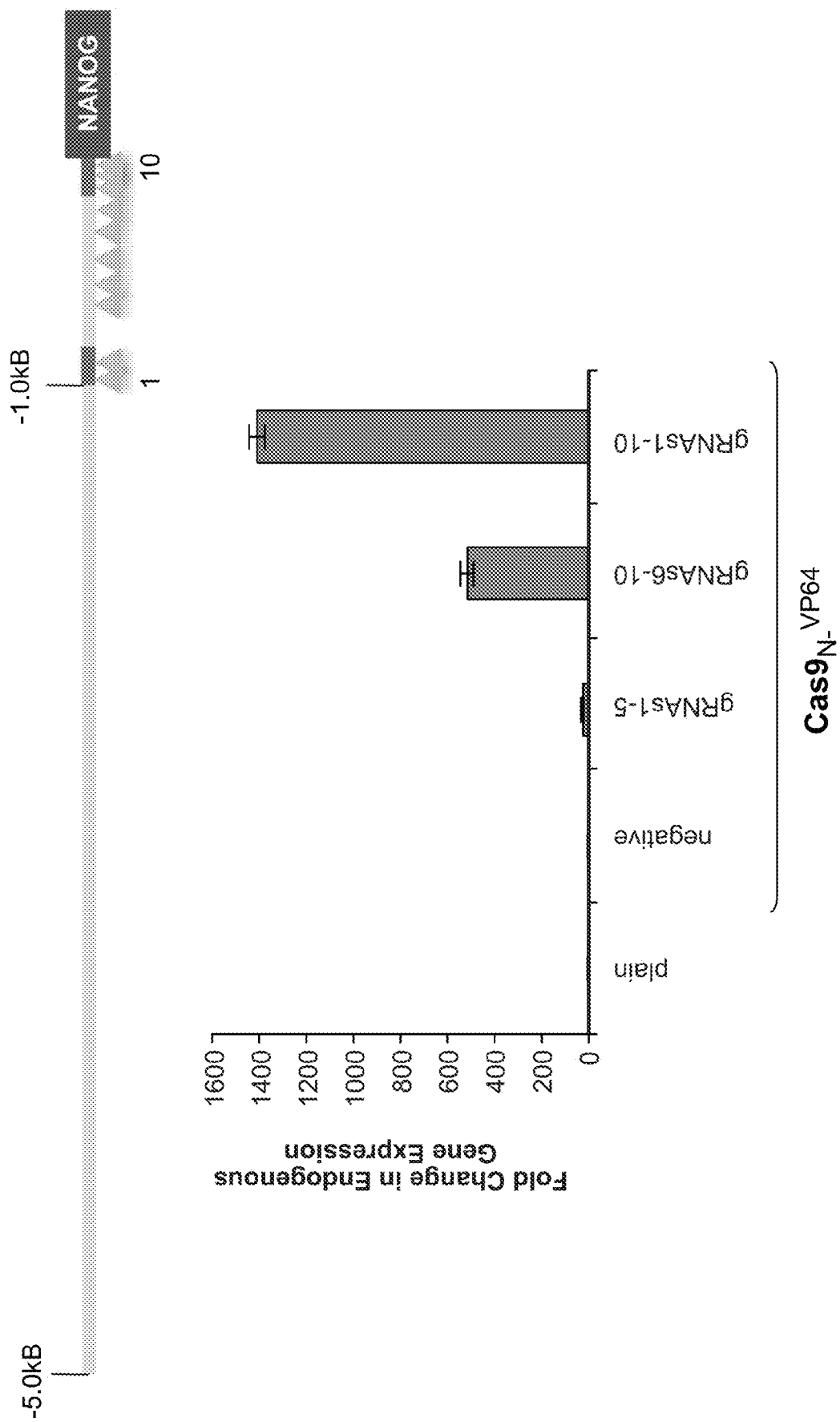
FIG. 12B depicts the Nanog gene.

The sgRNA (aptamer-modified single guide RNA) tethering approach described herein allows different effector domains to be recruited by distinct sgRNAs so long as each sgRNA uses a different RNA-protein interaction pair, enabling multiplex gene regulation using the same Cas9N-protein. For the FIG. 12A SOX2 and FIG. 12B NANOG genes, 10 gRNAs were designed targeting a ~1 kb stretch of DNA upstream of the transcription start site. The DNase hypersensitive sites are highlighted in green. Transcriptional activation via qPCR of the endogenous genes was assayed. In both instances, while introduction of individual gRNAs modestly stimulated transcription, multiple gRNAs acted synergistically to stimulate robust multi-fold transcriptional activation. Data are means+/−SEM (N=3). As shown in FIG. 12A-B, two additional genes, SOX2 and NANOG, were regulated via sgRNAs targeting within an upstream ~1 kb stretch of promoter DNA. The sgRNAs proximal to the transcriptional start site resulted in robust gene activation.

Example VI

Evaluating the Landscape of Targeting by Cas9-gRNA Complexes

Figure 13A:
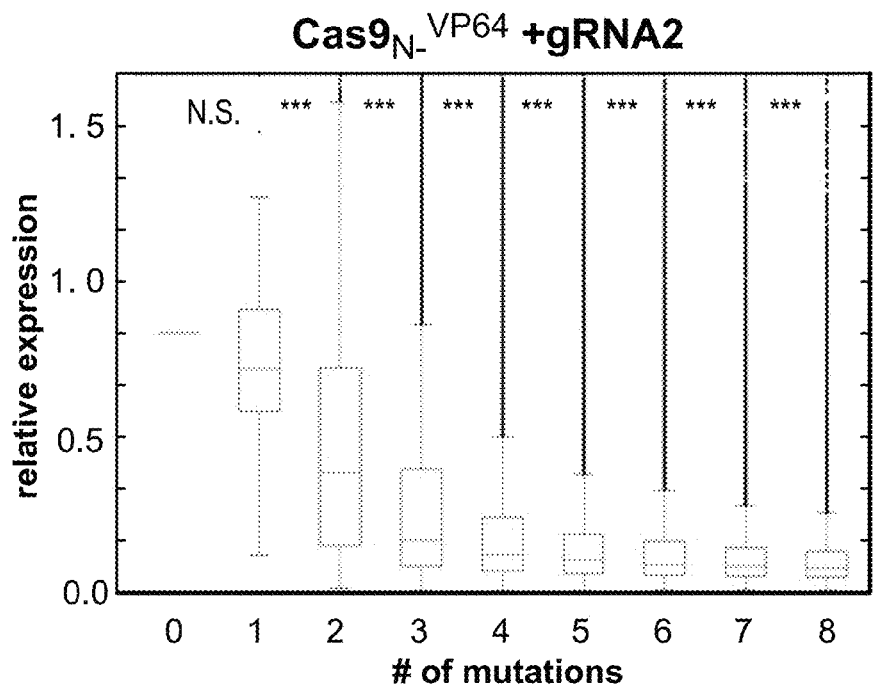
FIGS. 13A-13F depict the targeting landscape of two additional Cas9-gRNA complexes.
Figure 13B:
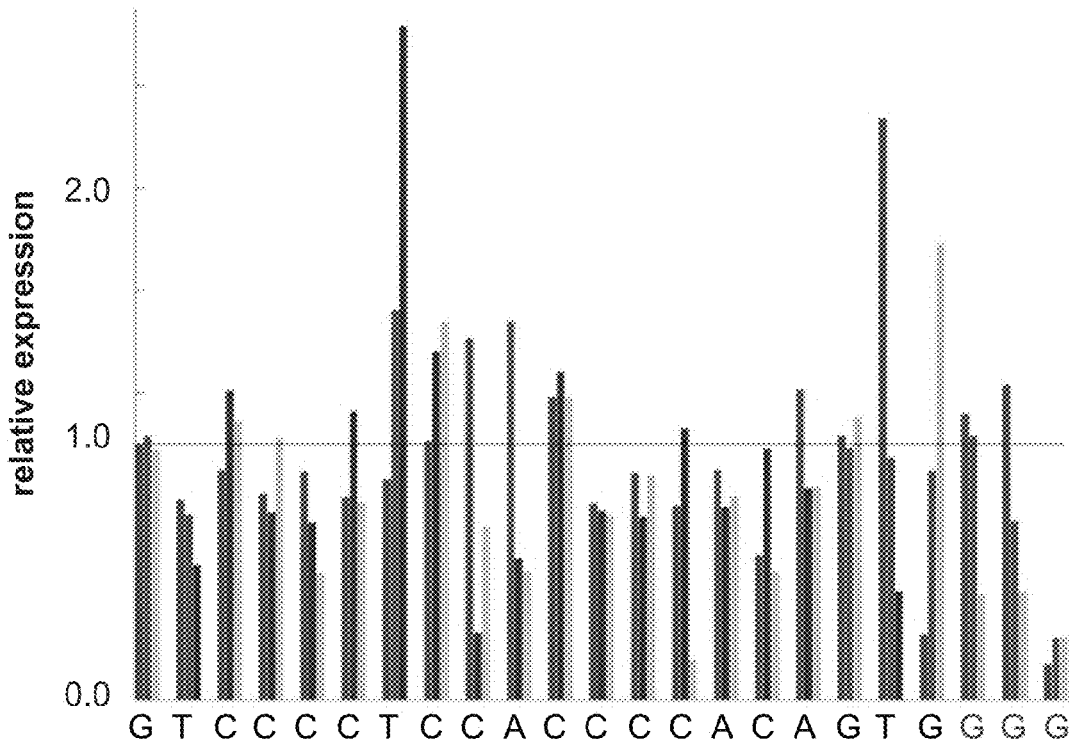
Figure 13C:
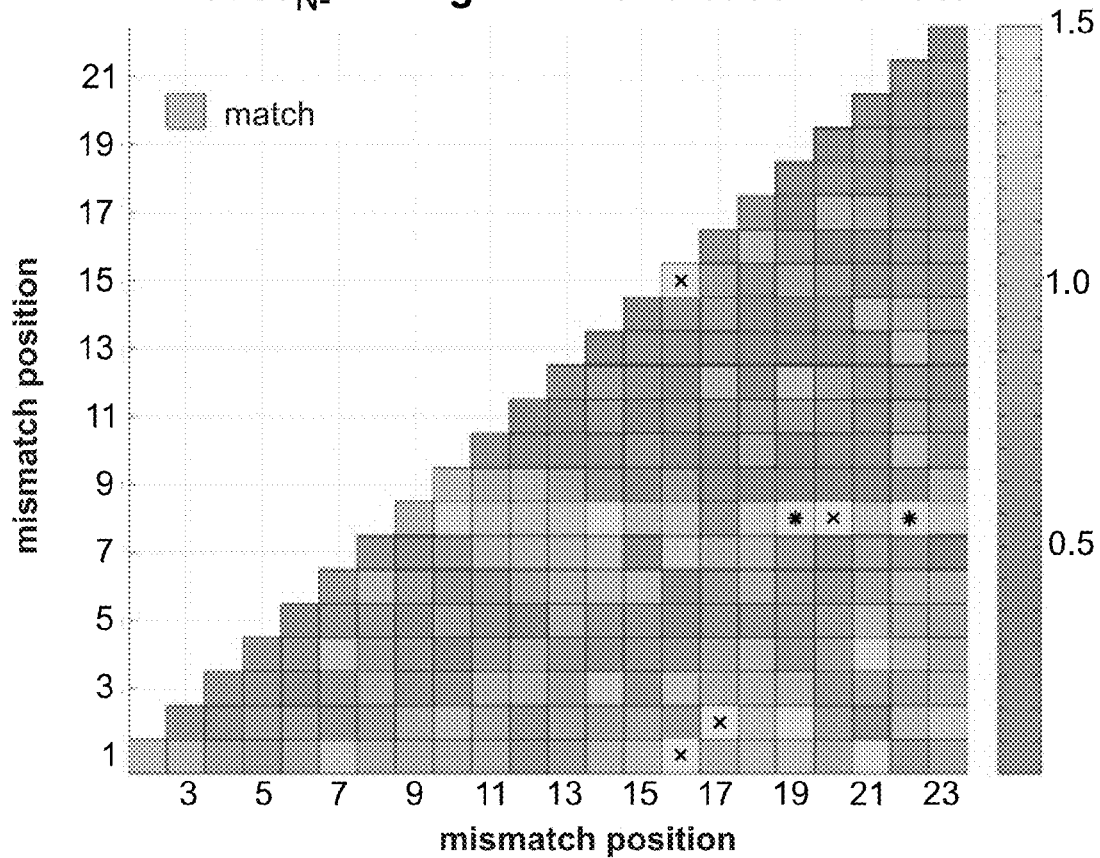
Figure 13D:
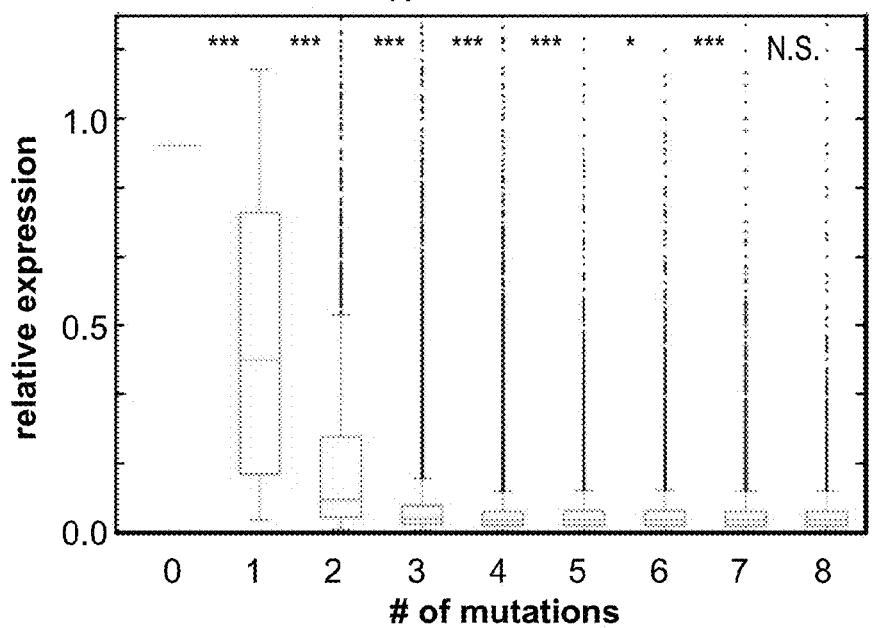
Figure 13E:
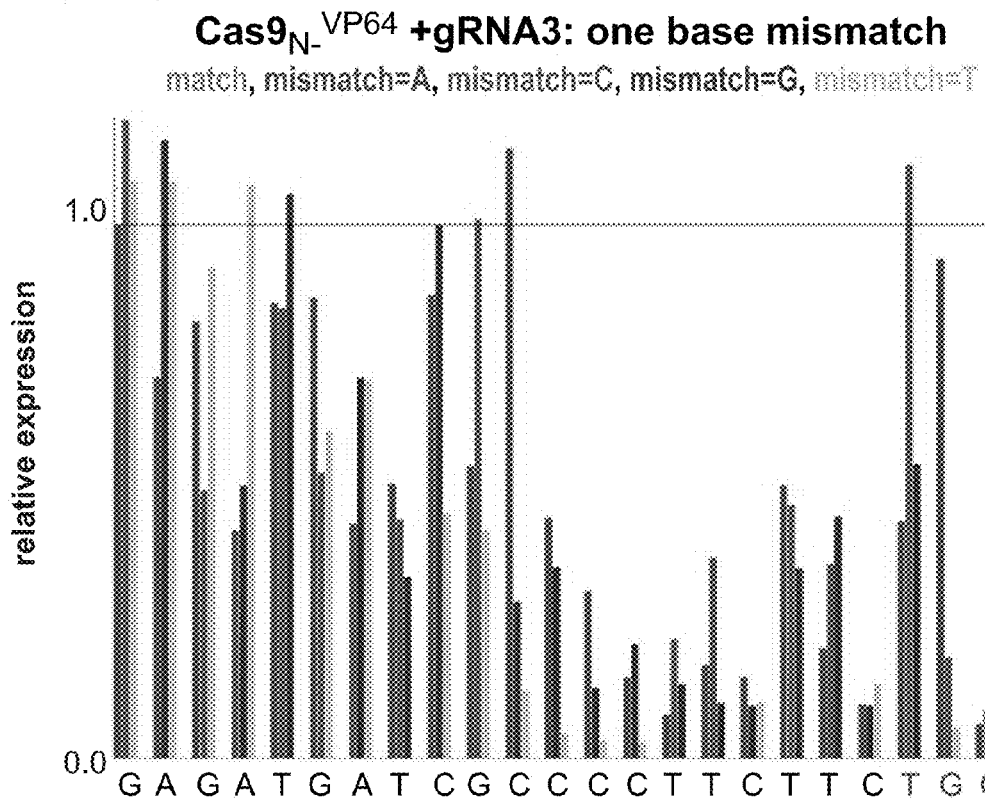
Figure 13F:
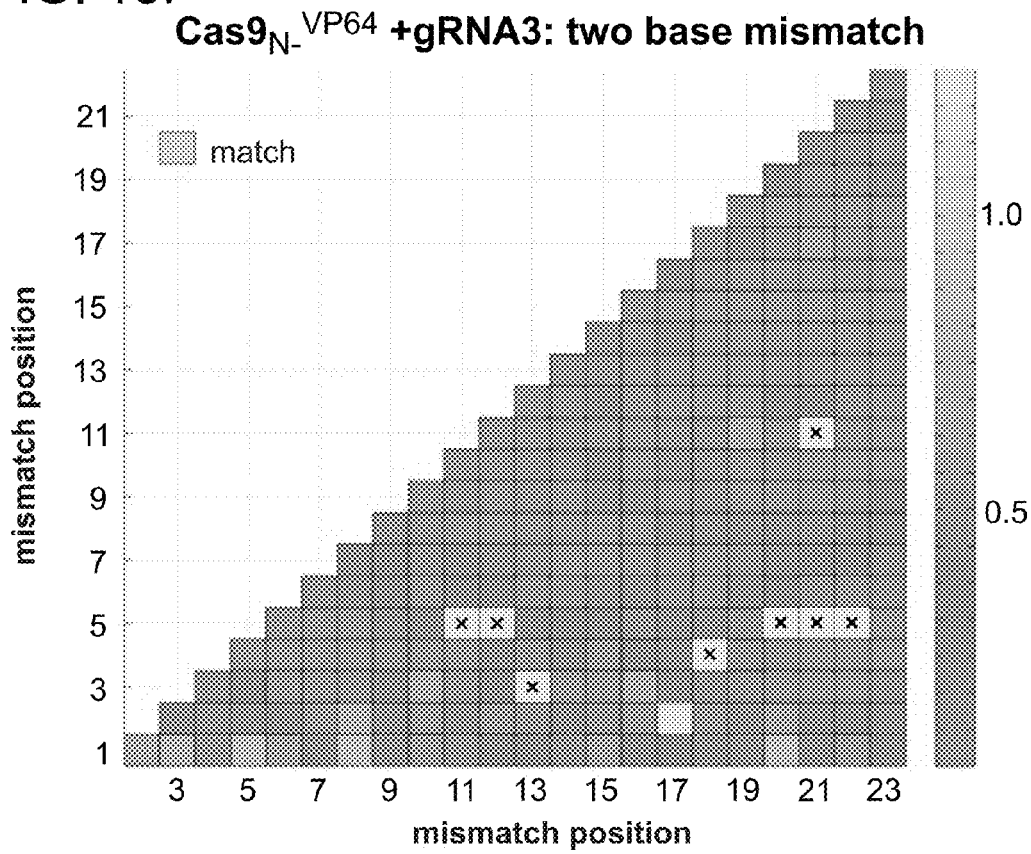
Figure 15A:
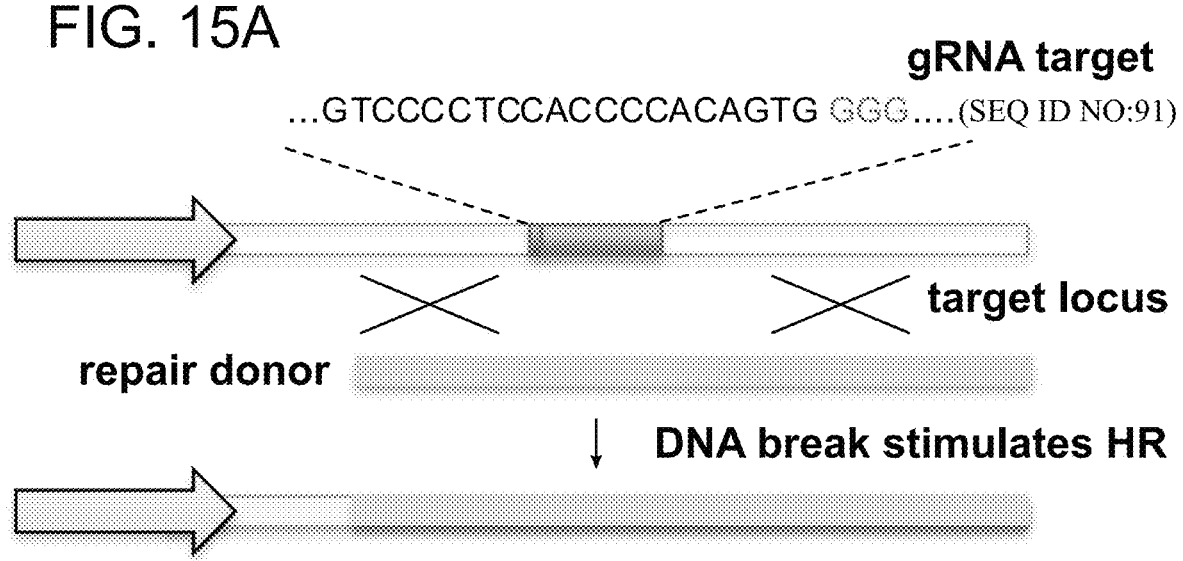
Figures 1, 15B:
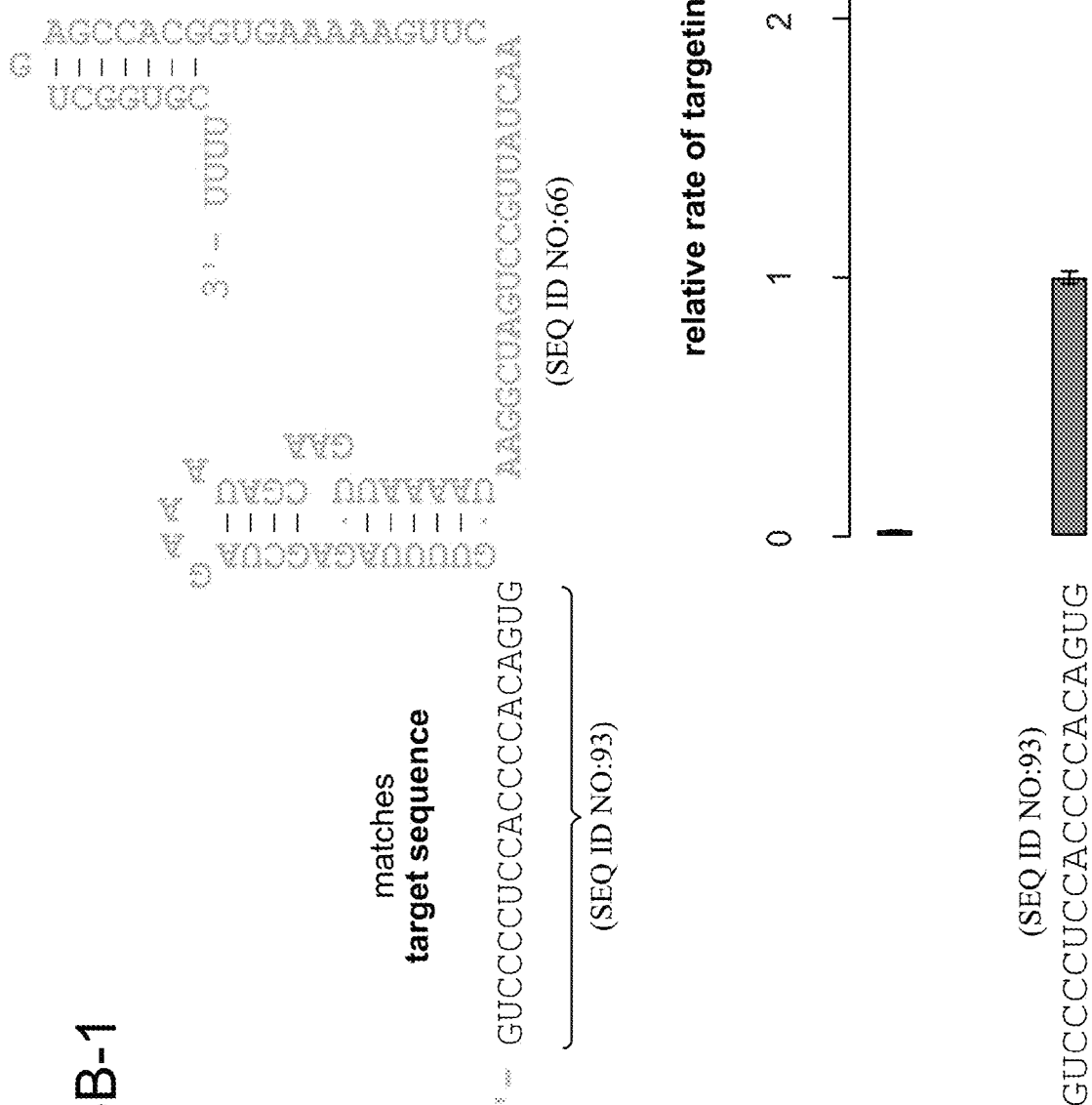
Figure 16A:
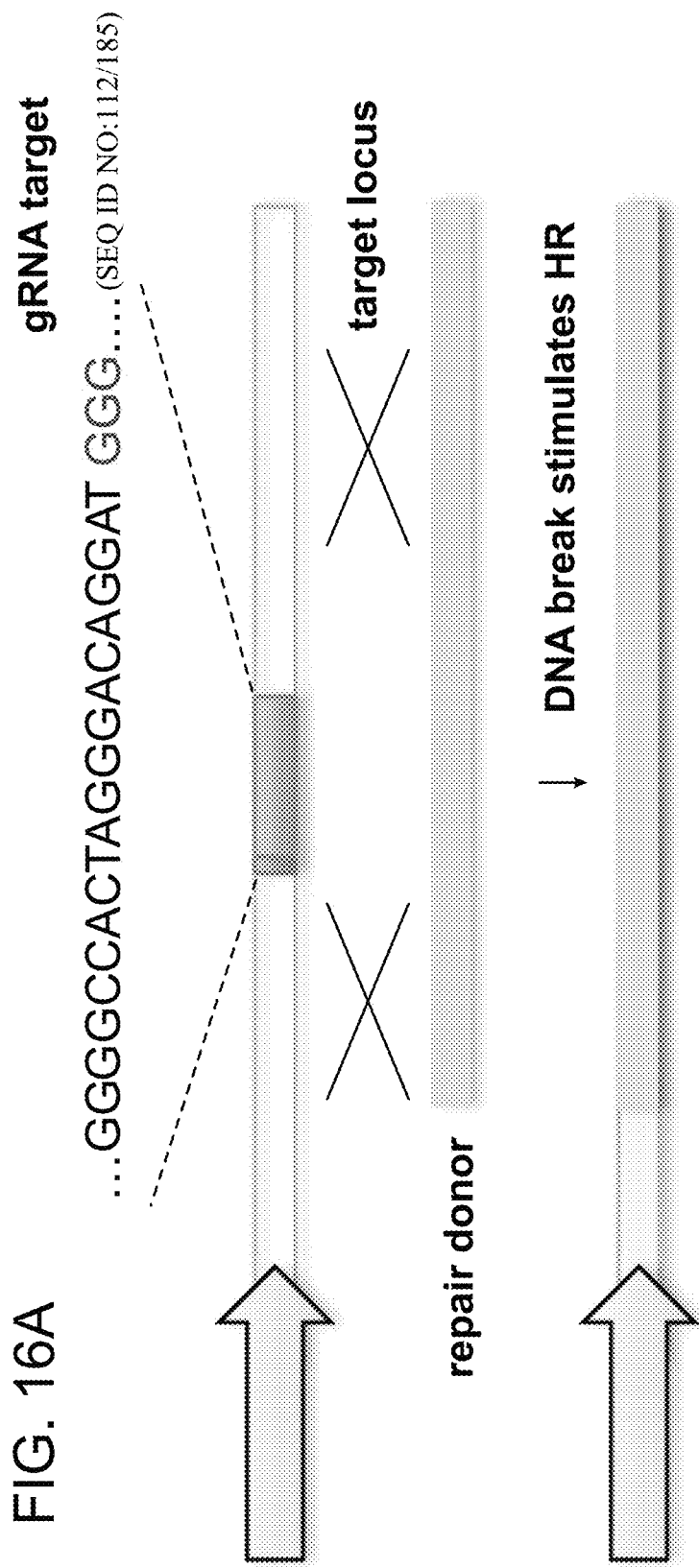
Figures 2, 16B:
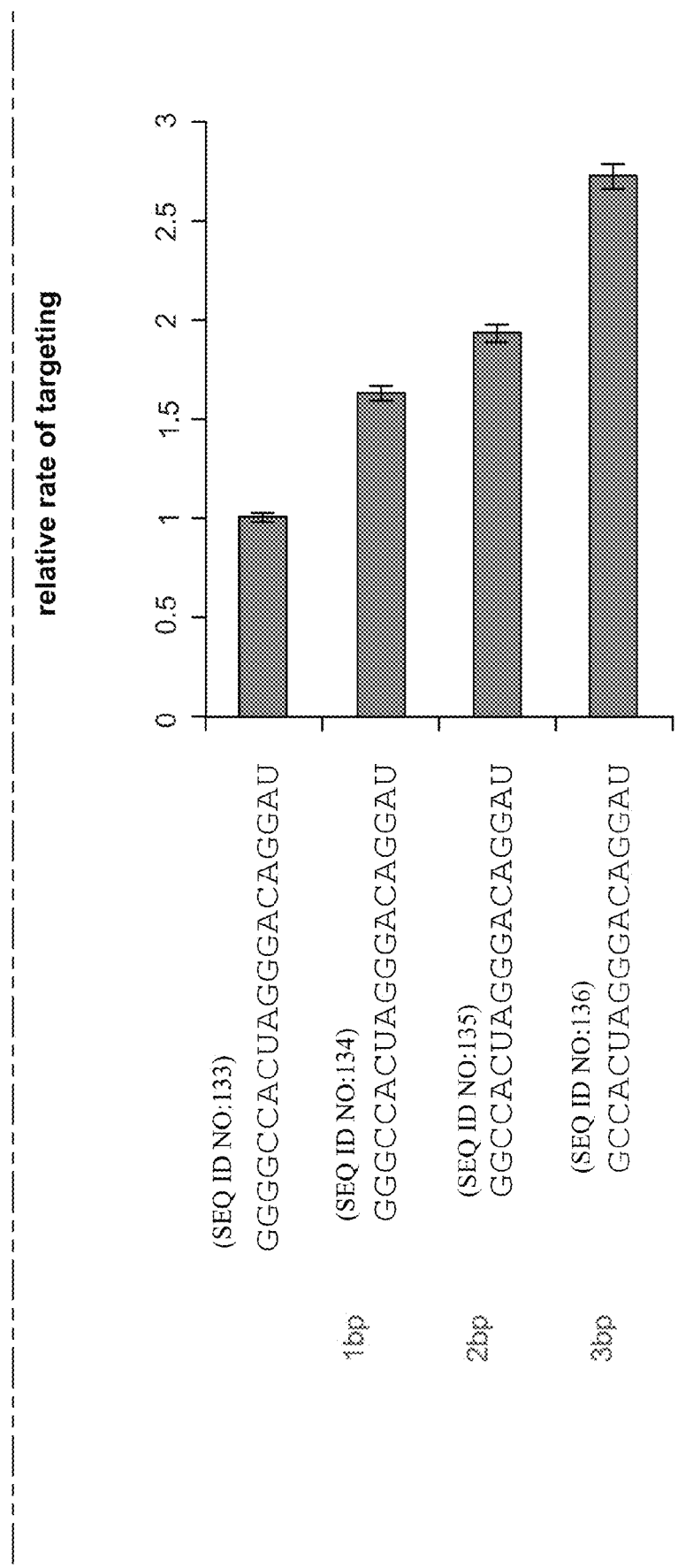
Figure 16C:
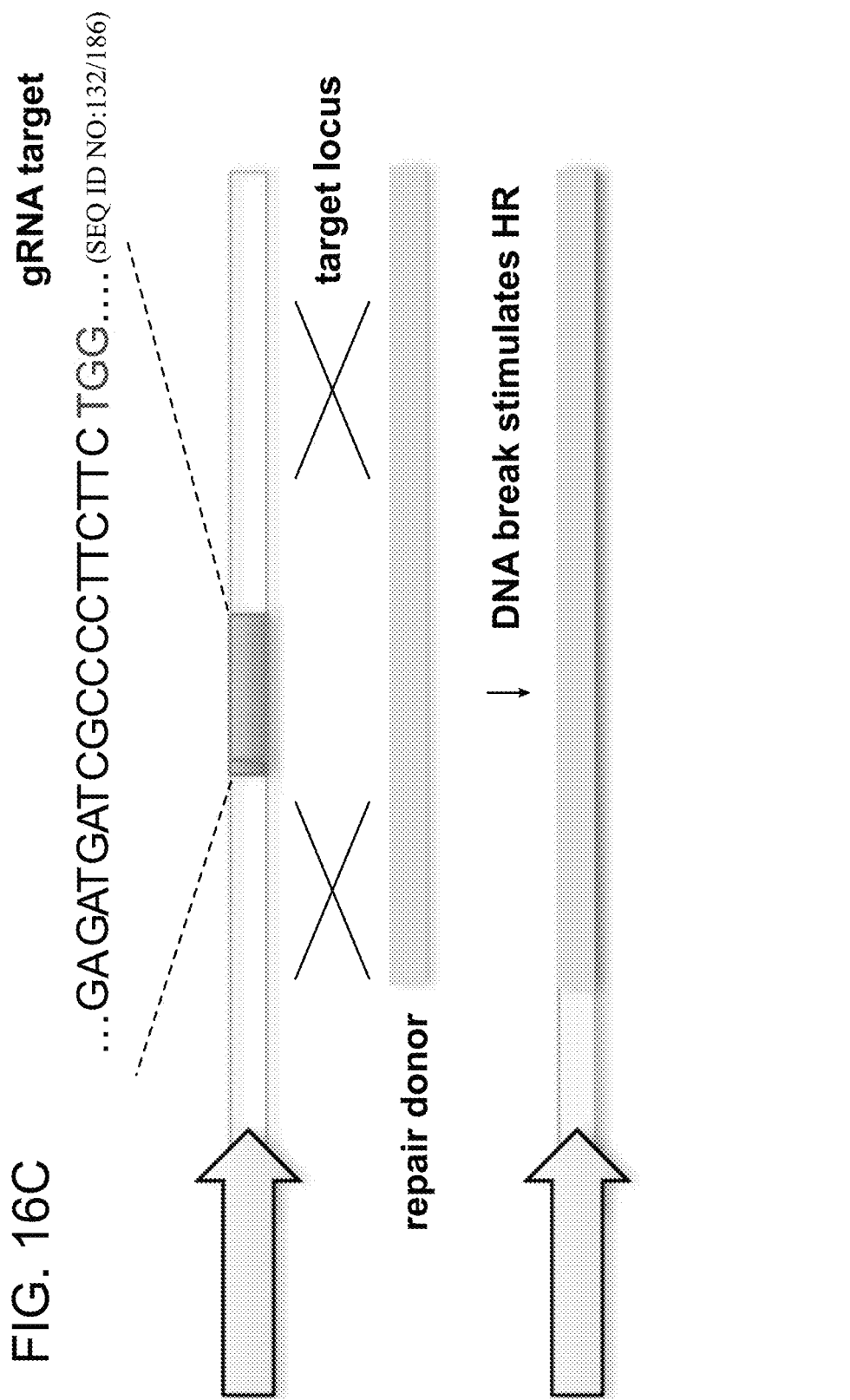
Figures 1, 16D:
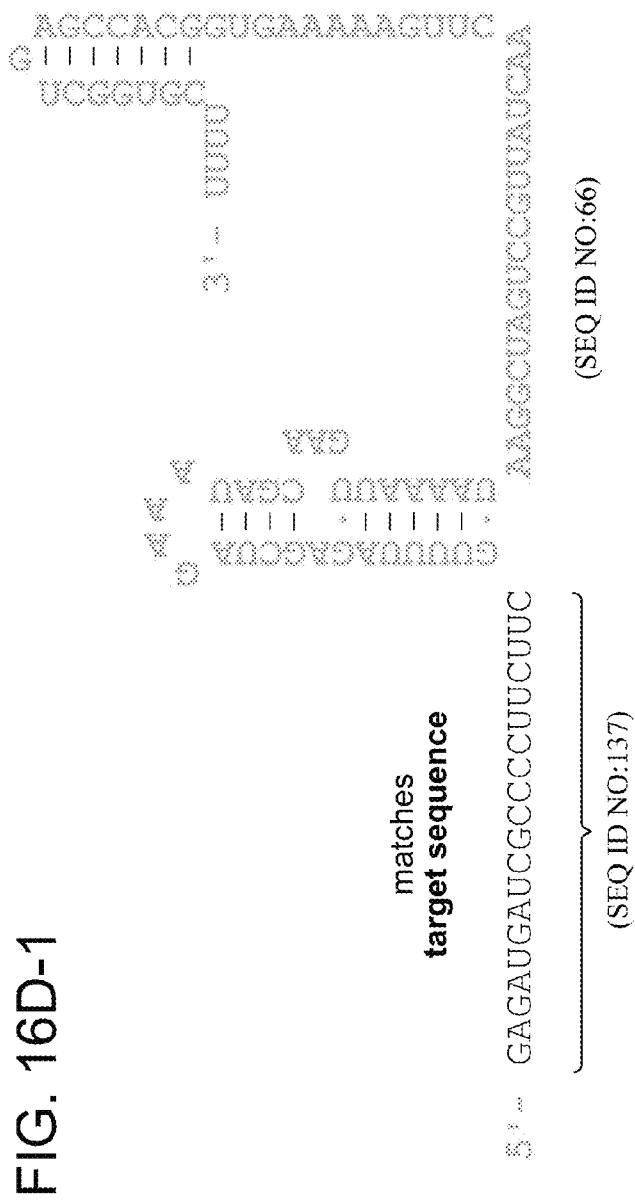
Figures 2, 16D:
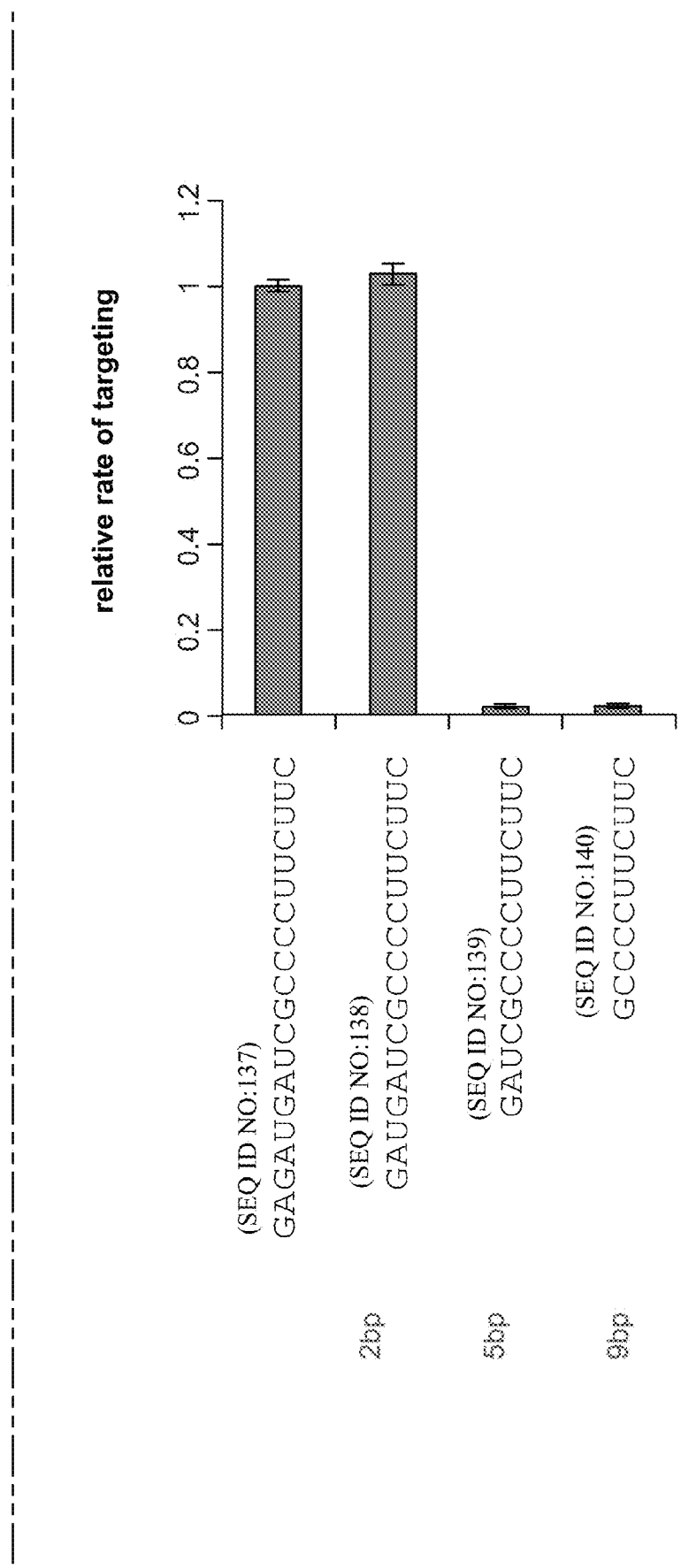

Using the approach described in FIG. 2, the targeting landscape of two additional Cas9-gRNA complexes (FIG. 13A-C) and (FIG. 13D-F) was analyzed. The two gRNAs have vastly different specificity profiles with gRNA2 tolerating up to 2-3 mismatches and gRNA3 only up to 1. These aspects are reflected in both the one base mismatch (FIG. 13B, 13E) and two base mismatch plots (FIG. 13C, 13F). In FIGS. 13C and 13F, base mismatch pairs for which insufficient data were available to calculate a normalized expression level are indicated as gray boxes containing an 'x', while, to improve data display, mismatch pairs whose normalized expression levels are outliers that exceed the top of the color scale are indicated as yellow boxes containing an asterisk '*'. Statistical significance symbols are: * for P<0.0005/n,  for P<0.005/n, * for P<0.05/n, and N.S. (Non-Significant) for P>=0.05/n, where n is the number of comparisons (refer Table 2).

Example VII

Validations, Specificity of Reporter Assay

As shown in FIG. 14A-C, specificity data was generated using two different sgRNA:Cas9 complexes. It was confirmed that the assay was specific for the sgRNA being evaluated, as a corresponding mutant sgRNA was unable to stimulate the reporter library. FIG. 14A: The specificity profile of two gRNAs (wild-type and mutant; sequence differences are highlighted in red) were evaluated using a reporter library designed against the wild-type gRNA target sequence. FIG. 14B: It was confirmed that this assay was specific for the gRNA being evaluated (data re-plotted from FIG. 13D), as the corresponding mutant gRNA is unable to stimulate the reporter library. Statistical significance symbols are: * for P<0.0005/n,  for P<0.005/n, * for P<0.05/n, and N.S. (Non-Significant) for P>=0.05/n, where n is the number of comparisons (refer Table 2). Different sgRNAs can have different specificity profiles (FIGS. 13A, 13D), specifically, sgRNA2 tolerates up to 3 mismatches and sgRNA3 only up to 1. The greatest sensitivity to mismatches was localized to the 3' end of the spacer, albeit mismatches at other positions were also observed to affect activity.

Example VIII

Validations, Single and Double-Base gRNA Mismatches

As shown in FIGS. 15A, 15B-1, 15B-2, 15C, 15D-1, and 15D-2, it was confirmed by targeted experiments that single-base mismatches within 12 bp of the 3' end of the spacer in the assayed sgRNAs resulted in detectable targeting. However, 2 bp mismatches in this region resulted in significant loss of activity. Using a nuclease assay, 2 independent gRNAs were tested: gRNA2 (FIGS. 15A-15B-2) and gRNA3 (FIGS. 15C-15D-2) bearing single or double-base mismatches (highlighted in red) in the spacer sequence versus the target. It was confirmed that single-base mismatches within 12 bp of the 3' end of the spacer in the assayed gRNAs result in detectable targeting, however 2 bp mismatches in this region result in rapid loss of activity. These results further highlight the differences in specificity profiles between different gRNAs consistent with the results in FIG. 13. Data are means+/− SEM (N=3).

Example IX

Validations, 5' gRNA Truncations

As shown in FIGS. 16A, 16B-1, 16B-2, 16C, 16D-1, and 16D-2, truncations in the 5' portion of the spacer resulted in retention of sgRNA activity. Using a nuclease assay, 2 independent gRNA were tested: gRNA I (FIGS. 16A-16B-2) and gRNA3 (FIGS. 16C-16D-2) bearing truncations at the 5' end of their spacer. It was observed that 1-3 bp 5' truncations are well tolerated, but larger deletions lead to loss of activity. Data are means+/— SEM (N=3).

Example X

Validations, S. pyogenes PAM

Figure 17A:
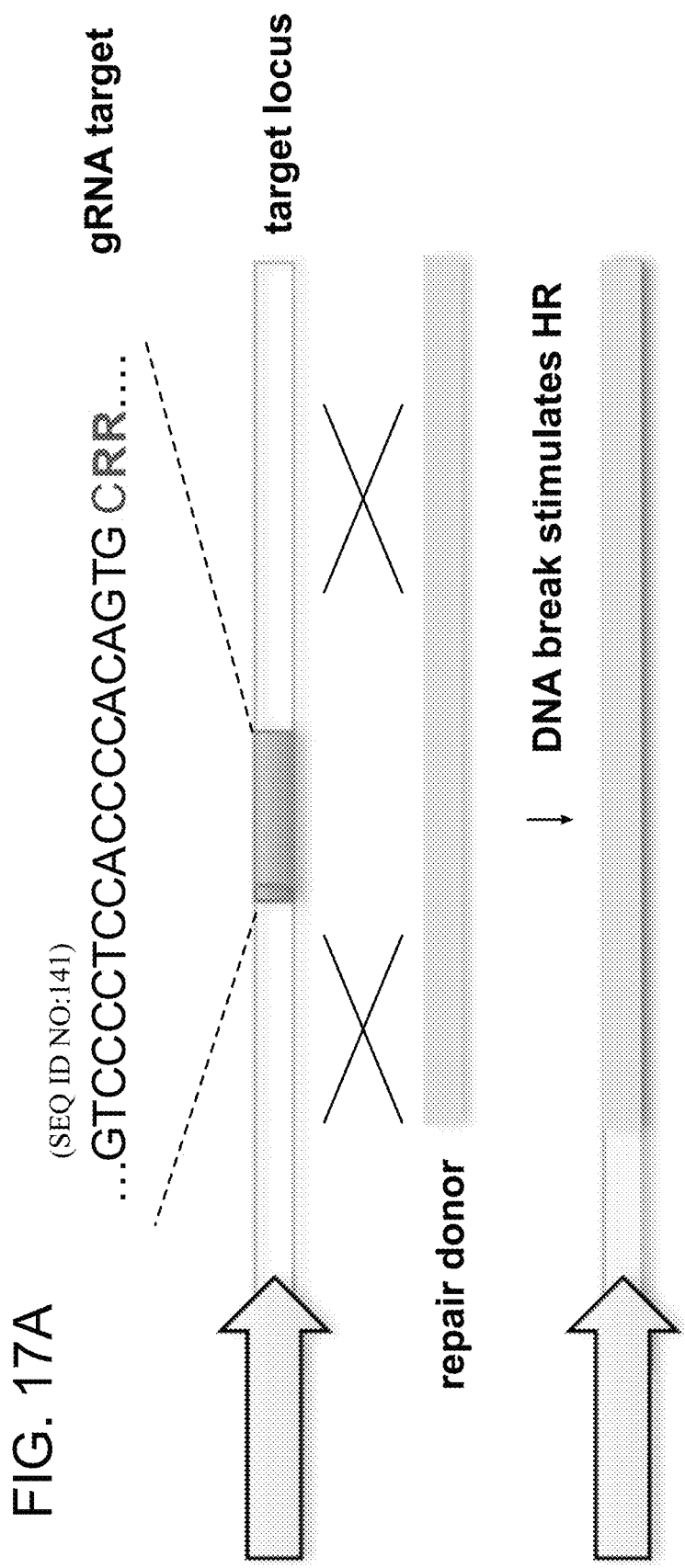

As shown in FIGS. 17A-B, it was confirmed using a nuclease mediated HR assay that the PAM for the S. pyogenes Cas9 is NGG and also NAG. Data are means+/− SEM (N=3). According to an additional investigation, a generated set of about 190K Cas9 targets in human exons that had no alternate NGG targets sharing the last 13 nt of the targeting sequence was scanned for the presence of alternate NAG sites or for NGG sites with a mismatch in the prior 13 nt. Only 0.4% were found to have no such alternate targets.

Example XI

Validations, TALE Mutations

Figure 18B:
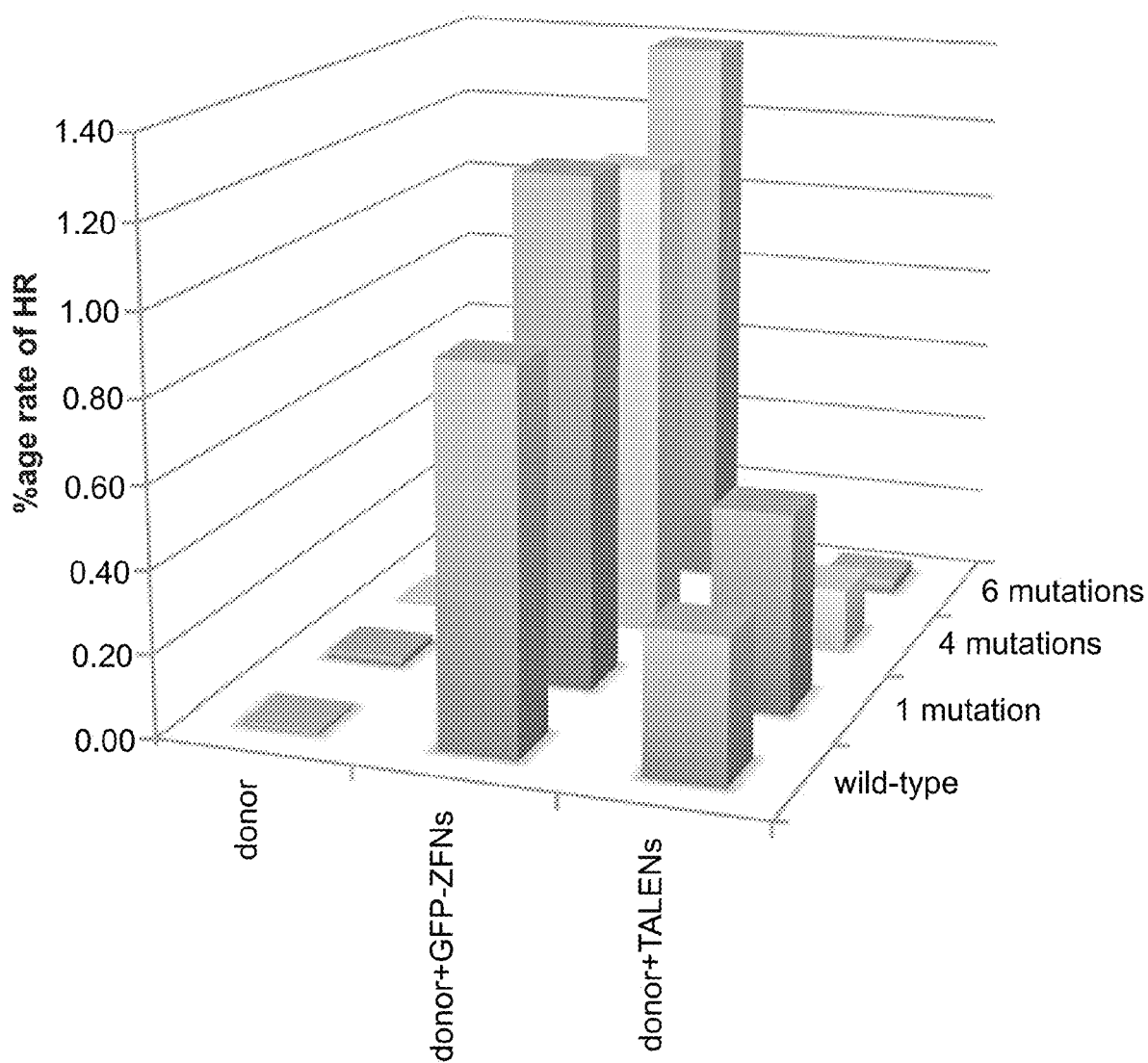

Using a nuclease mediated HR assay (FIG. 18A-B) it was confirmed that 18-mer TALEs tolerate multiple mutations in their target sequences. As shown in FIG. 18A-B certain mutations in the middle of the target lead to higher TALE activity, as determined via targeted experiments in a nuclease assay.

Example XII

TALE Monomer Specificity Versus TALE Protein Specificity

Figure 19A:
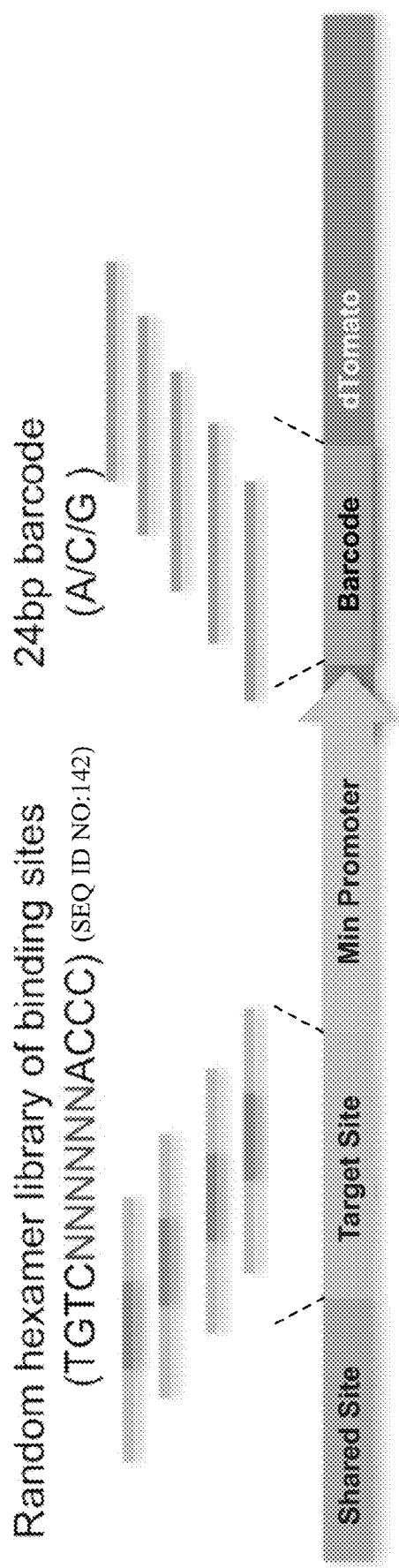
Figures 1, 19B:
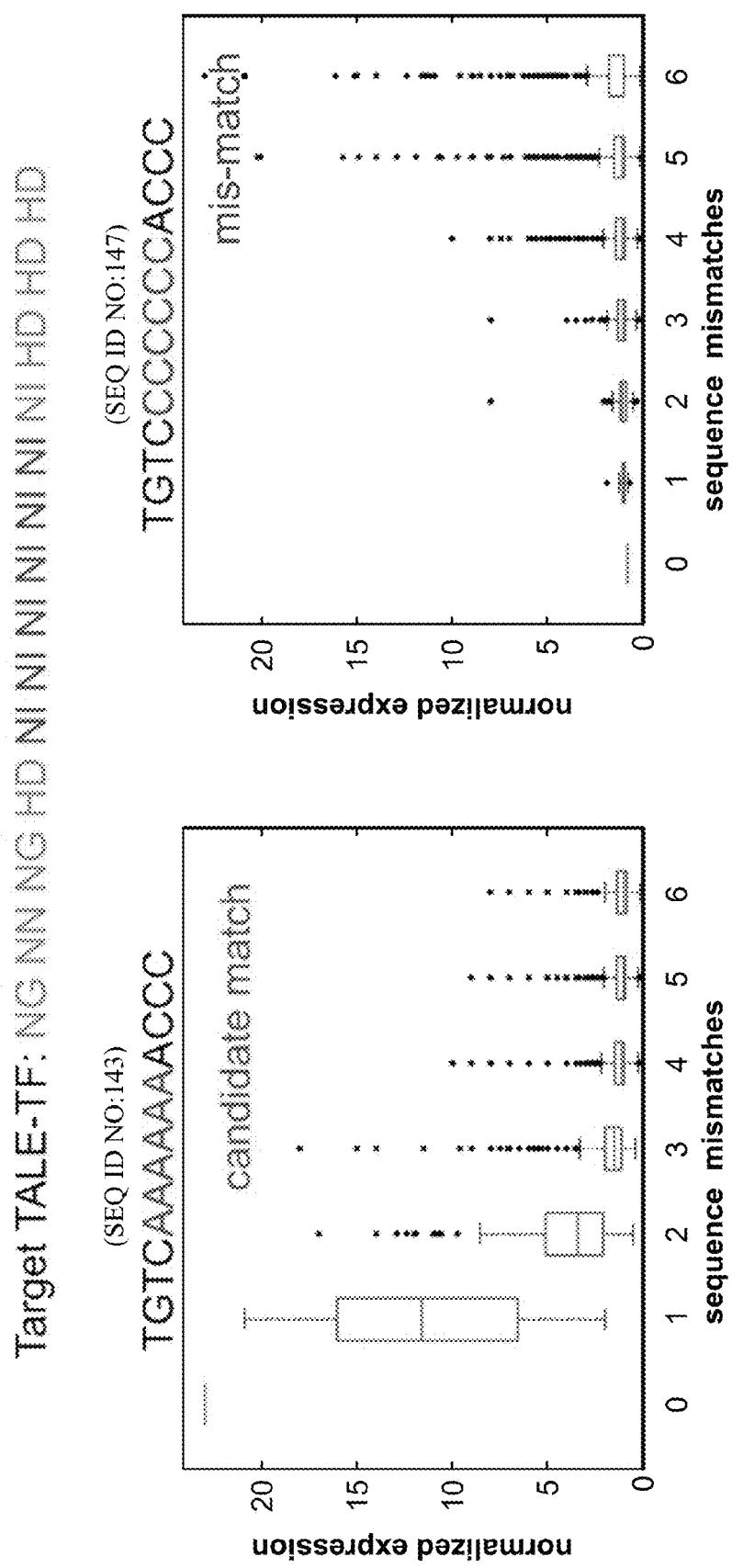
Figures 2, 19B:
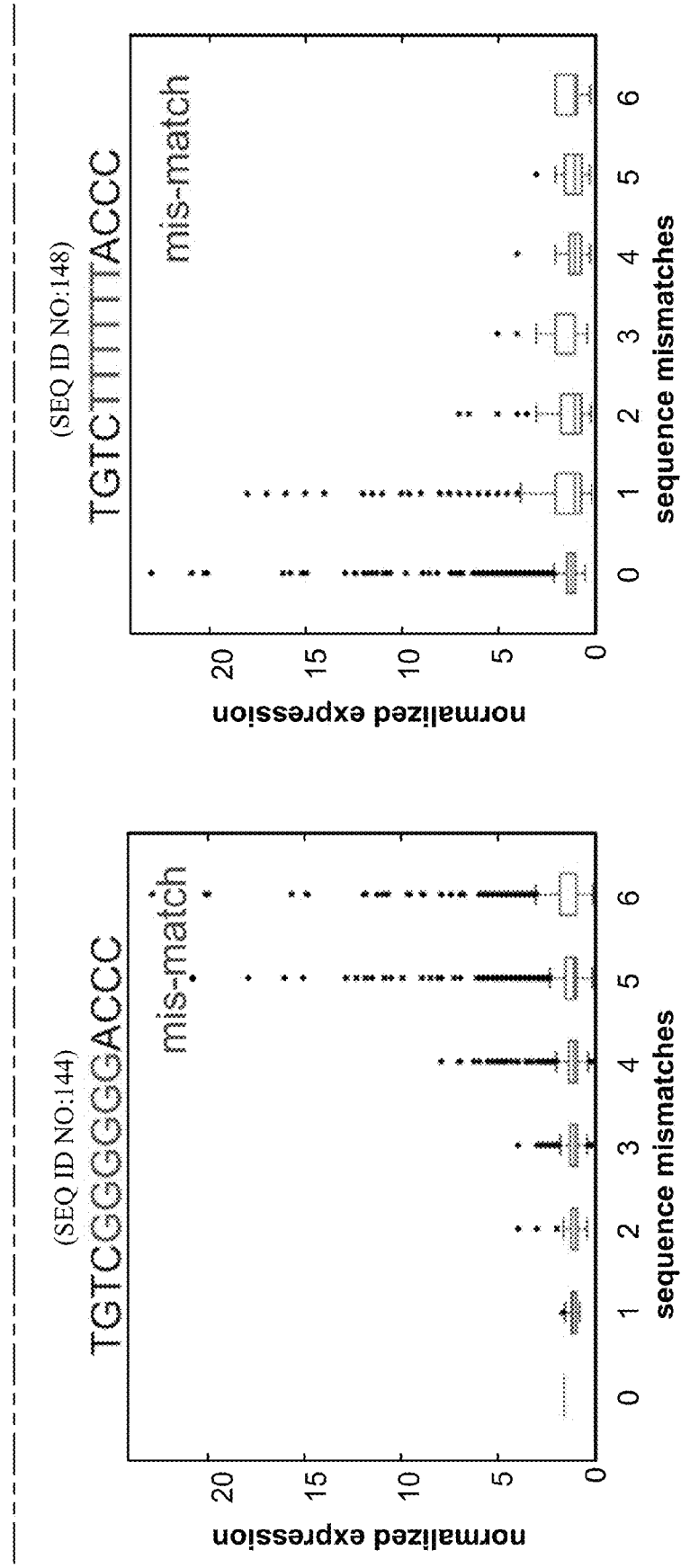
Figures 1, 19C:
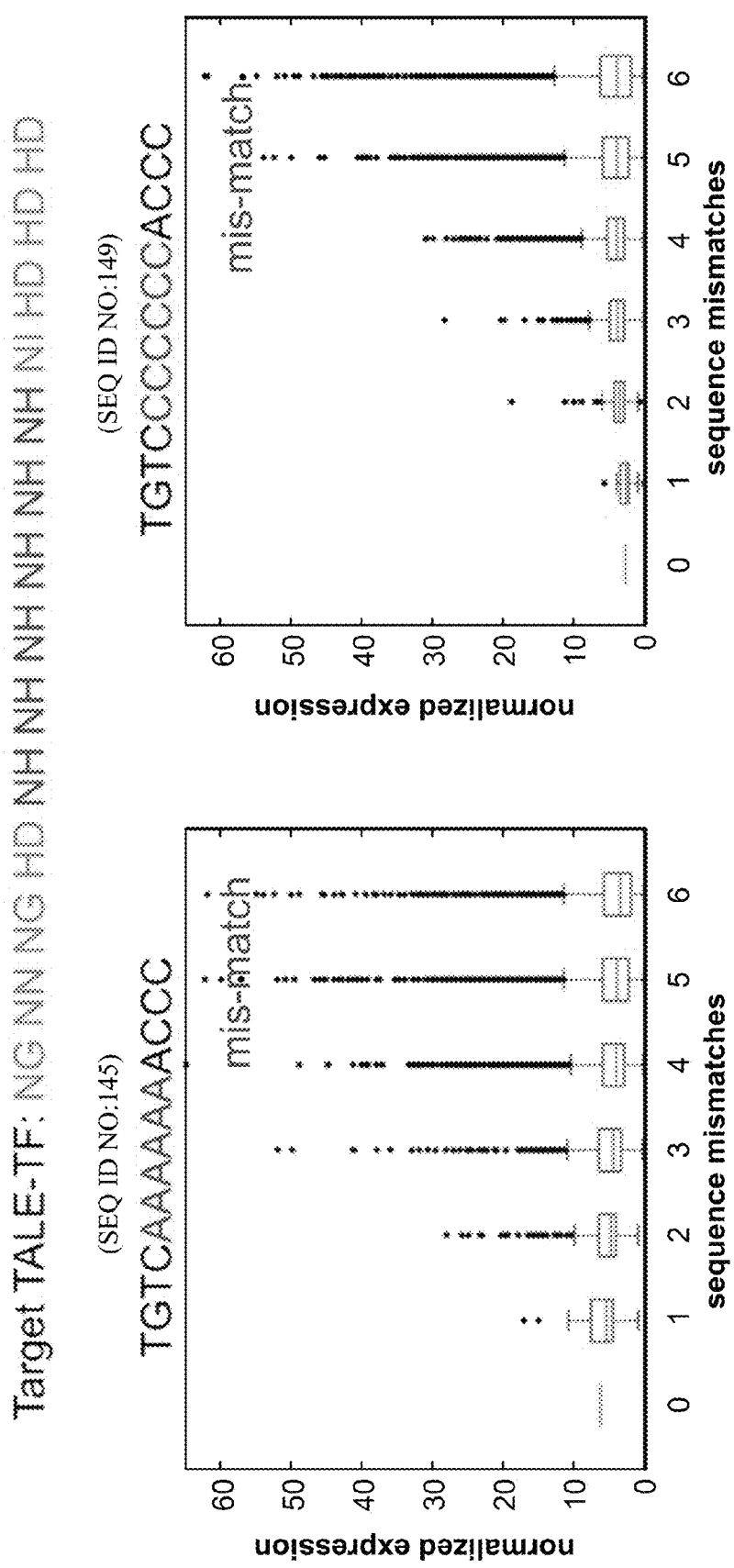
Figures 2, 19C:
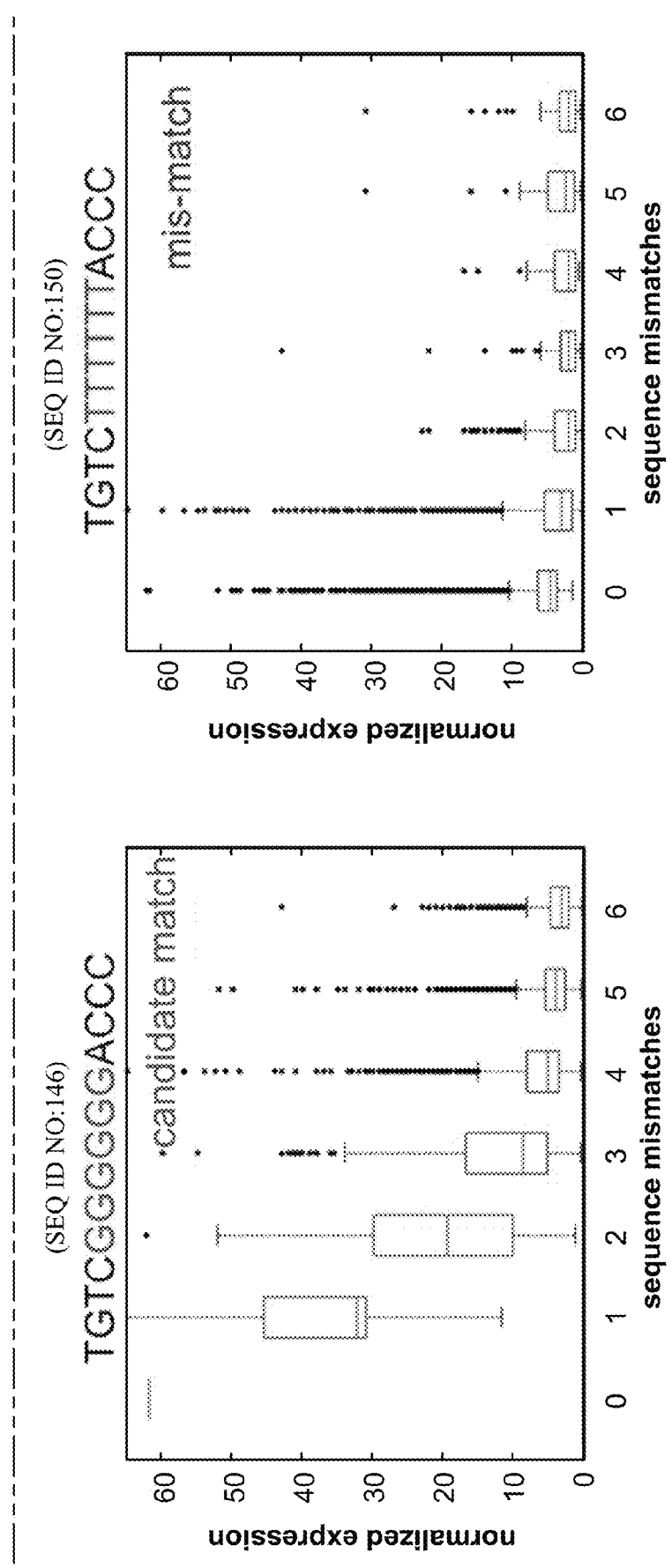

To decouple the role of individual repeat-variable diresidues (RVDs), it was confirmed that choice of RVDs did contribute to base specificity but TALE specificity is also a function of the binding energy of the protein as a whole. FIGS. 19A-19C-2 show a comparison of TALE monomer specificity versus TALE protein specificity. FIG. 19A: Using a modification of approach described in FIG. 2, the targeting landscape of 2 14-mer TALE-TFs bearing a contiguous set of 6 NI or 6 NH repeats was analyzed. In this approach, a reduced library of reporters bearing a degenerate 6-mer sequence in the middle was created and used to assay the TALE-TF specificity. FIGS. 19B-1-19C-2: In both instances, it was noted that the expected target sequence is enriched (i.e. one bearing 6 As for NI repeats, and 6 Gs for NH repeats). Each of these TALEs still tolerate 1-2 mismatches in the central 6-mer target sequence. While choice of monomers does contribute to base specificity, TALE specificity is also a function of the binding energy of the protein as a whole. According to one aspect, shorter engineered TALEs or TALEs bearing a composition of high and low affinity monomers result in higher specificity in genome engineering applications and FokI dimerization in nuclease applications allows for further reduction in off-target effects when using shorter TALEs.

Example XIII

Off-Set Nicking, Native Locus

Figure 20A:
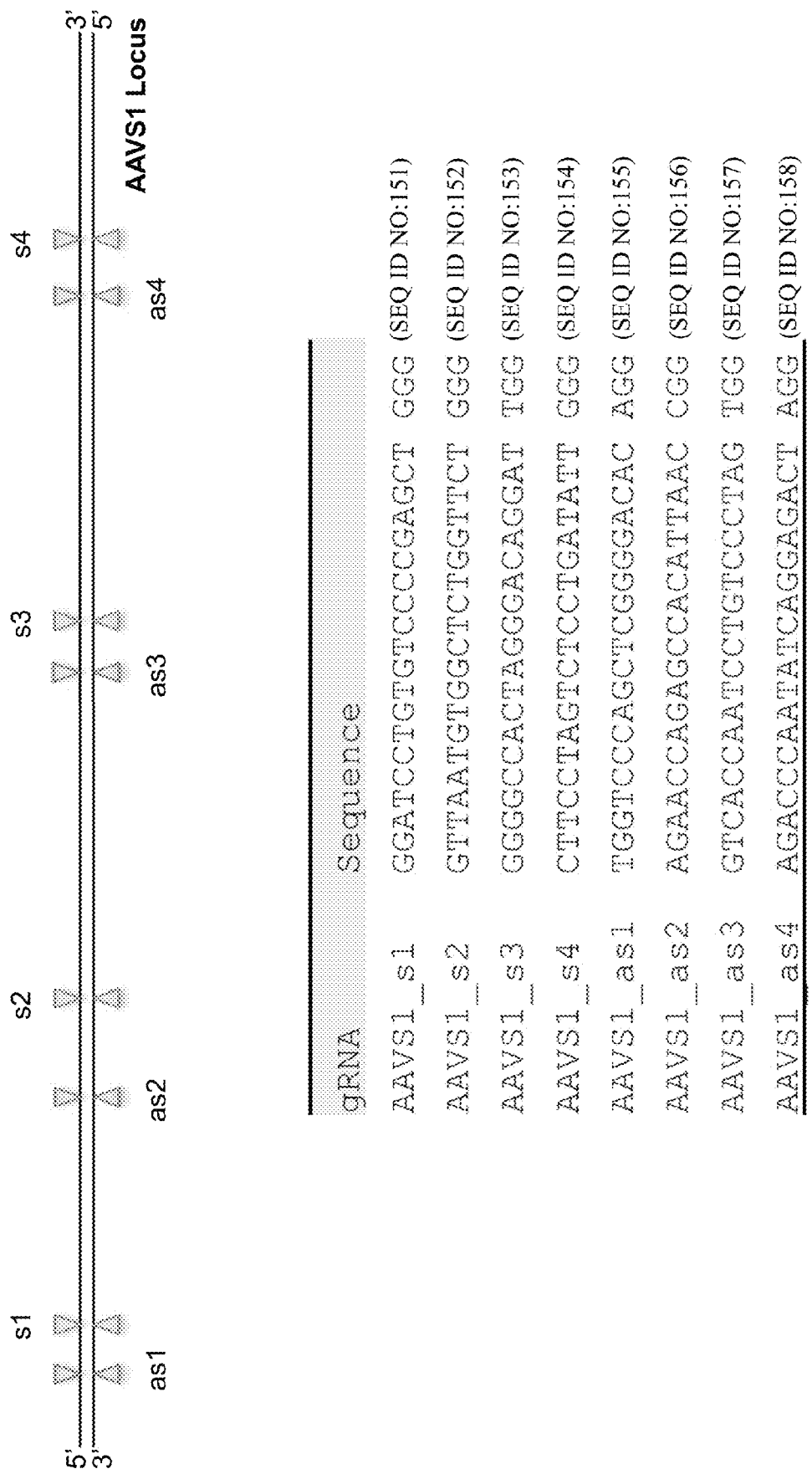

FIG. 20A-B shows data related to off-set nicking. In the context of genome-editing, off-set nicks were created to generate DSBs. A large majority of nicks do not result in non-homologous end joining (NHEJ) mediated indels and thus when inducing off-set nicks, off-target single nick events will likely result in very low indel rates. Inducing off-set nicks to generate DSBs is effective at inducing gene disruption at both integrated reporter loci and at the native AAVS1 genomic locus.

FIG. 20A: The native AAVS1 locus with 8 gRNAs covering a 200 bp stretch of DNA was targeted: 4 targeting the sense strand (s1-4) and 4 the antisense strand (as1-4). Using the Cas9D10A mutant, which nicks the complementary strand, different two-way combinations of the gRNAs was used to induce a range of programmed 5' or 3' overhangs. FIG. 20B: Using a Sanger sequencing based assay, it was observed that while single gRNAs did not induce detectable NHEJ events, inducing off-set nicks to generate DSBs is highly effective at inducing gene disruption. Notably off-set nicks leading to 5' overhangs result in more NHEJ events as opposed to 3' overhangs. The number of Sanger sequencing clones is highlighted above the bars, and the predicted overhang lengths are indicated below the corresponding x-axis legends.

Example XIV

Off-Set Nicking, NHEJ Profiles

FIG. 21A-C is directed to off-set nicking and NHEJ profiles. Representative Sanger sequencing results of three different off-set nicking combinations is shown with positions of the targeting gRNAs highlighted by boxes. Furthermore, consistent with the standard model for homologous recombination (HR) mediated repair, engineering of 5' overhangs via off-set nicks generated more robust NHEJ events than 3' overhangs (FIG. 3B). In addition to a stimulation of NHEJ, robust induction of HR was observed when the 5' overhangs were created. Generation of 3' overhangs did not result in improvement of HR rates (FIG. 3C).

Example XV

Table 1 gRNA Targets for Endogenous Gene Regulation

Targets in the REX1, OCT4, SOX2 and NANOG promoters used in Cas9-gRNA mediated activation experiments are listed and set forth as SEQ ID NOs:11-61.

gRNA Name gRNA Target

TABLE 1 gRNA Targets for Endogenous Gene Regulation Targets in the REX1, OCT4, SOX2 and NANOG promoters used in Cas9-gRNA mediated activation experiments are listed (SEQ ID NOs: 11-61).

| gRNA | gRNA Target |
|---|---|
| REX1 1 | ctggcggatcactcgcggtt agg |
| REX1 2 | cctcggcctccaaaagtgct agg |
| REX1 3 | acgctgattcctgcagatca ggg |
| REX1 4 | ccaggaatacgtatccacca ggg |
| REX1 5 | gccacacccaagcgatcaaa tgg |
| REX1 6 | aaataatacattctaaggta agg |
| REX1 7 | gctactggggaggctgaggc agg |
| REX1 8 | tagcaatacagtcacattaa tgg |
| REX1 9 | ctcatgtgatcccccgtct cgg |
| REX1 10 | ccgggcagagagtgaacgcg cgg |
| OCT4 1 | ttccttccctctcccgtgct tgg |
| OCT4 2 | tctctgcaaagccctggag agg |
| OCT4 3 | aatgcagttgccgagtgcag tgg |
| OCT4 4 | cctcagcctcctaaagtgct ggg |
| OCT4 5 | gagtccaaatcctctttact agg |
| OCT4 6 | gagtgtctggatttgggata agg |
| OCT4 7 | cagcacctcatctcccagtg agg |
| OCT4 8 | tctaaaacccagggaatcat ggg |
| OCT4 9 | cacaaggcagccagggatcc agg |
| OCT4 10 | gatggcaagctgagaaacac tgg |
| OCT4 11 | tgaaatgcacgcatacaatt agg |
| OCT4 12 | ccagtccagacctggccttc tgg |
| OCT4 13 | cccagaaaaacagaccctga agg |
| OCT4 14 | aagggttgagcacttgttta ggg |
| OCT4 15 | atgtctgagttttggttgag agg |

TABLE 1-continued gRNA Targets for Endogenous Gene Regulation
Targets in the REX1, OCT4, SOX2 and NANOG
promoters used in Cas9-gRNA mediated activation
experiments are listed (SEQ ID NOs: 11-61).

| gRNA | gRNA Target |
|---|---|
| OCT4 16 | ggtcccttgaaggggaagta ggg |
| OCT4 17 | tggcagtctactcttgaaga tgg |
| OCT4 18 | ggcacagtgccagaggtctg tgg |
| OCT4 19 | taaaaataaaaaaactaaca ggg |
| OCT4 20 | tctgtggggacctgcactg agg |
| OCT4 21 | ggccagaggtcaaggctagt ggg |
| SOX2 1 | cacgaccgaaacccttctta cgg |
| SOX2 2 | gttgaatgaagacagtctag tgg |
| SOX2 3 | taagaacagagcaagttacg tgg |
| SOX2 4 | tgtaaggtaagagaggagag cgg |
| SOX2 5 | tgacacaccaactcctgcac tgg |
| SOX2 6 | tttacccacttccttcgaaa agg |
| SOX2 7 | gtggctggcaggctggctct ggg |
| SOX2 8 | ctcccccggcctcccccgcg cgg |
| SOX2 9 | caaaacccggcagcgaggct ggg |
| SOX2 10 | aggagccgccgcgcgctgat tgg |
| NANOG 1 | cacacacacccacacgagat ggg |
| NANOG 2 | gaagaagctaaagagccaga ggg |
| NANOG 3 | atgagaatttcaataacctc agg |
| NANOG 4 | tcccgctctgttgcccaggc tgg |
| NANOG 5 | cagacacccaccaccatgct tgg |
| NANOG 6 | tcccaatttactgggattac agg |
| NANOG 7 | tgatttaaaagttggaaacg tgg |
| NANOG 8 | tctagttccccacctagtct ggg |
| NANOG 9 | gattaactgagaattcacaa ggg |
| NANOG 10 | cgccaggaggggtgggtcta agg |

Example XVI

Table 2

Summary of Statistical Analysis of Cas9-gRNA and TALE Specificity Data

Table 2(a) P-values for comparisons of normalized expression levels of TALE or Cas9-VP64 activators binding to target sequences with particular numbers of target site mutations. Normalized expression levels have been indicated by boxplots in the figures indicated in the Figure column, where the boxes represent the distributions of these levels by numbers of mismatches from the target site. P-values were computed using t-tests for each consecutive pair of numbers of mismatches in each boxplot, where the t-tests were either one sample or two sample t-tests (see Methods). Statistical significance was assessed using Bonferroni-corrected P-value thresholds, where the correction was based on the number of comparisons within each boxplot. Statistical significance symbols are: * for P<0.0005/n,  for P<0.005/n, * for P<0.05/n, and N.S. (Non-Significant) for P>=0.05/n, where n is the number of comparisons. Table 2(b) Statistical characterization of seed region in FIG. 2D: log 10 (P-values) indicating the degree of separation between expression values for Cas9N VP64+ gRNA binding to target sequences with two mutations for those position pairs mutated within candidate seed regions at the 3' end of the 20 bp target site vs. all other position pairs. The greatest separation, indicated by the largest −log 10 (P-values) (highlighted above), is found in the last 8-9 bp of the target site. These positions may be interpreted as indicating the start of the "seed" region of this target site. See the section "Statistical characterization of seed region" in Methods for information on how the P-values were computed.

a

| Figure | Expression level comparison: mutations vs mutations | | t-test | P-value | Symbol |
|---|---|---|---|---|---|
| 2b | 0 | 1 | 1-samp | 7.8E−05 | ** |
|  | 1 | 2 | 2-samp | 1.4E−06 | *** |
|  | 2 | 3 | 2-samp | 4.0E−61 | *** |
|  | 3 | 4 | 2-samp | 0 | *** |
|  | 4 | 5 | 2-samp | 0 | *** |
|  | 5 | 6 | 2-samp | 1.0E−217 | *** |
|  | 6 | 7 | 2-samp | 1.7E−43 | *** |
|  | 7 | 8 | 2-samp | 3.76E−02 | N.S. |
| 2e | 0 | 1 | 1-samp | 8.9E−01 | N.S. |
|  | 1 | 2 | 2-samp | 1.9E−06 | *** |
|  | 2 | 3 | 2-samp | 5.0E−147 | *** |
|  | 3 | 4 | 2-samp | 0 | *** |
|  | 4 | 5 | 2-samp | 0 | *** |
|  | 5 | 6 | 2-samp | 4.2E−62 | *** |
|  | 6 | 7 | 2-samp | 1.6E−03 | * |
|  | 7 | 8 | 2-samp | 4.7E−01 | N.S. |
| S7a | 0 | 1 | 1-samp | 5.2E−02 | N.S. |
|  | 1 | 2 | 2-samp | 2.8E−05 | *** |
|  | 2 | 3 | 2-samp | 3.5E−21 | *** |
|  | 3 | 4 | 2-samp | 1.4E−58 | *** |
|  | 4 | 5 | 2-samp | 8.3E−101 | *** |
|  | 5 | 6 | 2-samp | 6.8E−94 | *** |
|  | 6 | 7 | 2-samp | 1.8E−61 | *** |
|  | 7 | 8 | 2-samp | 8.1E−24 | *** |
| S7d and S8d | 0 | 1 | 1-samp | 2.3E−18 | *** |
|  | 1 | 2 | 2-samp | 2.4E−08 | *** |
|  | 2 | 3 | 2-samp | 6.2E−54 | *** |
|  | 3 | 4 | 2-samp | 4.0E−141 | *** |
|  | 4 | 5 | 2-samp | 1.9E−20 | *** |
|  | 5 | 6 | 2-samp | 1.2E−03 | * |
|  | 6 | 7 | 2-samp | 3.8E−05 | *** |
|  | 7 | 8 | 2-samp | 9.4E−01 | N.S. |
| S8c | 0 | 1 | 1-samp | 7.2E−03 | N.S. |
|  | 1 | 2 | 2-samp | 5.0E−01 | N.S. |
|  | 2 | 3 | 2-samp | 3.9E−84 | *** |
|  | 3 | 4 | 2-samp | 8.5E−153 | *** |
|  | 4 | 5 | 2-samp | 8.6E−76 | *** |
|  | 5 | 6 | 2-samp | 1.6E−03 | * |
|  | 6 | 7 | 2-samp | 7.1E−01 | N.S. |
|  | 7 | 8 | 2-samp | 7.8E−02 | N.S. |
| S13a (left) | 0 | 1 | 1-samp | 7.3E−01 | N.S. |
|  | 1 | 2 | 2-samp | 2.4E−06 | *** |
|  | 2 | 3 | 2-samp | 7.2E−140 | *** |
|  | 3 | 4 | 2-samp | 0 | *** |
|  | 4 | 5 | 2-samp | 0 | *** |
|  | 5 | 6 | 2-samp | 1.0E−72 | *** |
|  | 6 | 7 | 2-samp | 4.0E−03 | * |
| S13a (middle) | 0 | 1 | 1-samp | 9.4E−02 | N.S. |
|  | 1 | 2 | 2-samp | 5.2E−09 | *** | a

| Figure | Expression level comparison: mutations vs mutations | | t-test | P-value | Symbol |
|---|---|---|---|---|---|
| S13a (right) | 2 | 3 | 2-samp | 7.9E−86 | *** |
| | 3 | 4 | 2-samp | 2.9E−53 | *** |
| | 4 | 5 | 2-samp | 3.5E−10 | *** |
| | 0 | 1 | 1-samp | 1.3E−13 | *** |
| | 1 | 2 | 2-samp | 1.1E−04 | *** |
| | 2 | 3 | 2-samp | 3.7E−08 | *** | b

| seed start position | Number position pairs | | log10 |
|---|---|---|---|
| | both in | not both | P-value |
| 2 | 171 | 19 | 3.11 |
| 3 | 153 | 37 | 1.46 |
| 4 | 136 | 54 | 2.01 |
| 5 | 120 | 70 | 3.34 |
| 6 | 105 | 85 | 5.65 |
| 7 | 91 | 99 | 7.34 |
| 8 | 78 | 112 | 6.61 |
| 9 | 66 | 124 | 7.1 |
| 10 | 55 | 135 | 9.72 |
| 11 | 45 | 145 | 9.83 |
| 12 | 36 | 154 | 10.44 |
| 13 | 28 | 162 | 10.72 |
| 14 | 21 | 169 | 8.97 |
| 15 | 15 | 175 | 5.61 |
| 16 | 10 | 180 | 3.34 |
| 17 | 6 | 184 | 2.26 |
| 18 | 3 | 187 | 1.16 |

Example XVII

Sequences of Proteins and RNAs in the Examples

A. Sequences of the $Cas9_N$-VP64 activator constructs based on the m4 mutant are displayed below. Three versions were constructed with the $Cas9_{m4}^{VP64}$ and $Cas9_{m4}^{VP64}N$ fusion protein formats showing highest activity. Corresponding vectors for the m3 and m2 mutants (FIG. 4A) were also constructed (NLS and VP64 domains are highlighted).
>$Cas9_{m4}^{VP64}$ (SEQ ID NO: 2)
gccaccATGGACAAGAAGTACTCCATTGGGCTCGCTATCGGCACAAACAG
CGTCGGCTGGGCCGTCATTACGGACGAGTACAAGGTGCCGAGCAAAAAT
TCAAAGTTCTGGGCAATACCGATCGCCACAGCATAAAGAAGAACCTCATT
GGCGCCCTCCTGTTCGACTCCGGGGAGACGGCCGAAGCCACGCGGCTCAA
AAGAACAGCACGGCGCAGATATACCCGCAGAAAGAATCGGATCTGCTACC
TGCAGGAGATCTTTAGTAATGAGATGGCTAAGGTGGATGACTCTTTCTTC
CATAGGCTGGAGGAGTCCTTTTTGGTGGAGGAGGATAAAAAGCACGAGCG
CCACCCAATCTTTGGCAATATCGTGGACGAGGTGGCGTACCATGAAAGT
ACCCAACCATATATCATCTGAGGAAGAAGCTTGTAGACAGTACTGATAAG
GCTGACTTGCGGTTGATCTATCTCGCGCTGGCGCATATGATCAAATTTCG
GGGACACTTCCTCATCGAGGGGGACCTGAACCCAGACAACAGCGATGTCG
ACAAACTCTTTATCCAACTGGTTCAGACTTACAATCAGCTTTTCGAAGAG
AACCCGATCAACGCATCCGGAGTTGACGCCAAAGCAATCCTGAGCGCTAG
GCTGTCCAAATCCCGGCGGCTCGAAAACCTCATCGCACAGCTCCCTGGGG
AGAAGAAGAACGGCCTGTTTGGTAATCTTATCGCCCTGTCACTCGGGCTG
ACCCCCAACTTTAAATCTAACTTCGACCTGGCCGAAGATGCCAAGCTTCA
ACTGAGCAAAGACACCTACGATGATGATCTCGACAATCTGCTGGCCCAGA
TCGGCGACCAGTACGCAGACCTTTTTTTGGCGGCAAAGAACCTGTCAGAC
GCCATTCTGCTGAGTGATATTCTGCGAGTGAACACGGAGATCACCAAAGC
TCCGCTGAGCGCTAGTATGATCAAGCGCTATGATGAGCACCACCAAGACT
TGACTTTGCTGAAGGCCCTTGTCAGACAGCAACTGCCTGAGAAGTACAAG
GAAATTTTCTTCGATCAGTCTAAAAATGGCTACGCCGGATACATTGACGG
CGGAGCAAGCCAGGAGGAATTTTACAAATTTATTAAGCCCATCTTGGAAA
AAATGGACGGCACCGAGGAGCTGCTGGTAAAGCTTAACAGAGAAGATCTG
TTGCGCAAACAGCGCACTTTCGACAATGGAAGCATCCCCCACCAGATTCA
CCTGGGCGAACTGCACGCTATCCTCAGGCGGCAAGAGGATTTCTACCCCT
TTTTGAAAGATAACAGGGAAAAGATTGAGAAAATCCTCACATTTCGGATA
CCCTACTATGTAGGCCCCCTCGCCCGGGGAAATTCCAGATTCGCGTGGAT
GACTCGCAAATCAGAAGAGACCATCACTCCCTGGAACTTCGAGGAAGTCG
TGGATAAGGGGGCCTCTGCCCAGTCCTTCATCGAAAGGATGACTAACTTT
GATAAAAATCTGCCTAACGAAAAGGTGCTTCCTAAACACTCTCTGCTGTA
CGAGTACTTCACAGTTTATAACGAGCTCACCAAGGTCAAATACGTCACAG
AAGGGATGAGAAAGCCAGCATTCCTGTCTGGAGAGCAGAAGAAAGCTATC
GTGGACCTCCTCTTCAAGACGAACCGGAAAGTTACCGTGAAACAGCTCAA
AGAAGACTATTTCAAAAAGATTGAATGTTTCGACTCTGTTGAAATCAGCG
GAGTGGAGGATCGCTTCAACGCATCCCTGGGAACGTATCACGATCTCCTG
AAAATCATTAAAGACAAGGACTTCCTGGACAATGAGGAGAACGAGGACAT
TCTTGAGGACATTGTCCTCACCCTTACGTTGTTTGAAGATAGGGAGATGA
TTGAAGAACGCTTGAAAACTTACGCTCATCTCTTCGACGACAAAGTCATG
AAACAGCTCAAGAGGCGCCGATATACAGGATGGGGCGGCTGTCAAGAAA
ACTGATCAATGGGATCCGAGACAAGCAGAGTGGAAAGACAATCCTGGATT
TTCTTAAGTCCGATGGATTTGCCAACCGGAACTTCATGCAGTTGATCCAT
GATGACTCTCTCACCTTTAAGGAGGACATCCAGAAAGCACAAGTTTCTGG
CCAGGGGACAGTCTTCACGAGCACATCGCTAATCTTGCAGGTAGCCCAG
CTATCAAAAGGGAATACTGCAGACCGTTAAGGTCGTGGATGAACTCGTC
AAAGTAATGGGAAGGCATAAGCCCGAGAATATCGTTATCGAGATGGCCCG
AGAGAACCAAACTACCCAGAAGGGACAGAAGAACAGTAGGGAAAGGATGA
AGAGGATTGAAGAGGGTATAAAAGAACTGGGGTCCCAAATCCTTAAGGAA
CACCCAGTTGAAAACACCCAGCTTCAGAATGAGAAGCTCTACCTGTACTA
CCTGCAGAACGGCAGGGACATGTACGTGGATCAGGAACTGGACATCAATC -continued GGCTCTCCGACTACGACGTGGCTGCTATCGTGCCCCAGTCTTTTCTCAAA
GATGATTCTATTGATAATAAAGTGTTGACAAGATCCGATAAAgcTAGAGG
GAAGAGTGATAACGTCCCCTCAGAAGAAGTTGTCAAGAAAATGAAAAATT
ATTGGCGGCAGCTGCTGAACGCCAAACTGATCACACAACGGAAGTTCGAT
AATCTGACTAAGGCTGAACGAGGTGGCCTGTCTGAGTTGGATAAAGCCGG
CTTCATCAAAAGGCAGCTTGTTGAGACACGCCAGATCACCAAGCACGTGG
CCCAAATTCTCGATTCACGCATGAACACCAAGTACGATGAAAATGACAAA
CTGATTCGAGAGGTGAAAGTTATTACTCTGAAGTCTAAGCTGGTCTCAGA
TTTCAGAAAGGACTTTCAGTTTTATAAGGTGAGAGAGATCAACAATTACC
ACCATGCGCATGATGCCTACCTGAATGCAGTGGTAGGCACTGCACTTATC
AAAAAATATCCCAAGCTTGAATCTGAATTTGTTTACGGAGACTATAAAGT
GTACGATGTTAGGAAAATGATCGCAAAGTCTGAGCAGGAAATAGGCAAGG
CCACCGCTAAGTACTTCTTTTACAGCAATATTATGAATTTTTTCAAGACC
GAGATTACACTGGCCAATGGAGAGATTCGGAAGCGACCACTTATCGAAAC
AAACGGAGAAACAGGAGAAATCGTGTGGGACAAGGGTAGGGATTTCGCGA
CAGTCCGGAAGGTCCTGTCCATGCCGCAGGTGAACATCGTTAAAAAGACC
GAAGTACAGACCGGAGGCTTCTCCAAGGAAAGTATCCTCCCGAAAAGGAA
CAGCGACAAGCTGATCGCACGCAAAAAAGATTGGGACCCCAAGAAATACG
GCGGATTCGATTCTCCTACAGTCGCTTACAGTGTACTGGTTGTGGCCAAA
GTGGAGAAAGGGAAGTCTAAAAAACTCAAAAGCGTCAAGGAACTGCTGGG
CATCACAATCATGGAGCGATCAAGCTTCGAAAAAAACCCCATCGACTTTC
TCGAGGCGAAAGGATATAAAGAGGTCAAAAAAGACCTCATCATTAAGCTT
CCCAAGTACTCTCTCTTTGAGCTTGAAAACGGCCGGAAACGAATGCTCGC
TAGTGCGGGCGAGCTGCAGAAAGGTAACGAGCTGGCACTGCCCTCTAAAT
ACGTTAATTTCTTGTATCTGGCCAGCCACTATGAAAAGCTCAAAGGGTCT
CCCGAAGATAATGAGCAGAAGCAGCTGTTCGTGGAACAACACAAACACTA
CCTTGATGAGATCATCGAGCAAATAAGCGAATTCTCCAAAAGAGTGATCC
TCGCCGACGCTAACCTCGATAAGGTGCTTTCTGCTTACAATAAGCACAGG
GATAAGCCCATCAGGGAGCAGGCAGAAAACATTATCCACTTGTTTACTCT
GACCAACTTGGGCGCGCCTGCAGCCTTCAAGTACTTCGACACCACCATAG
ACAGAAAGCGGTACACCTCTACAAAGGAGGTCCTGGACGCCACACTGATT
CATCAGTCAATTACGGGGCTCTATGAAACAAGAATCGACCTCTCTCAGCT
CGGTGGAGACAGCAGGGCTGACCCCAAGAAGAAGAGGAAGGTGGAGGCCA
GCGGTTCCGGACGGGCTGACGCATTGGACGATTTTGATCTGGATATGCTG
GGAAGTGACGCCCTCGATGATTTTGACCTTGACATGCTTGGTTCGGATGC
CCTTGATGACTTTGACCTCGACATGCTCGGCAGTGACGCCCTTGATGATT
CGACCTGGACATGCTGATTAACTCTAGATGA >Cas9$_{m4}^{VP64}$N Sequences (SEQ ID NO: 3)
gccaccATGCCCAAGAAGAAGAGGAAGGTGGGAAGGGGGATGGACAAGAA
GTACTCCATTGGGCTCGCTATCGGCACAAACAGCGTCGGCTGGGCCGTCA TTACGGACGAGTACAAGGTGCCGAGCAAAAAATTCAAAGTTCTGGGCAAT
ACCGATCGCCACAGCATAAAGAAGAACCTCATTGGCGCCCTCCTGTTCGA
CTCCGGGGAGACGGCCGAAGCCACGCGGCTCAAAAGAACAGCACGGCGCA
GATATACCCGCAGAAAGAATCGGATCTGCTACCTGCAGGAGATCTTTAGT
AATGAGATGGCTAAGGTGGATGACTCTTTCTTCCATAGGCTGGAGGAGTC
CTTTTTTGGTGGAGGAGGATAAAAAGCACGAGCGCCACCCAATCTTTGGCA
ATATCGTGGACGAGGTGGCGTACCATGAAAAGTACCCAACCATATATCAT
CTGAGGAAGAAGCTTGTAGACAGTACTGATAAGGCTGACTTGCCGGTTGAT
CTATCTCGCGCTGGCGCATATGATCAAATTTCGGGGACACTTCCTCATCG
AGGGGGACCTGAACCCAGACAACAGCGATGTCGACAAACTCTTTATCCAA
CTGGTTCAGACTTACAATCAGCTTTTCGAAGAGAACCCGATCAACGCATC
CGGAGTTGACGCCAAAGCAATCCTGAGCGCTAGGCTGTCCAAATCCCGGC
GGCTCGAAAACCTCATCGCACAGCTCCCTGGGGAGAAGAAGAACGGCCTG
TTTGGTAATCTTATCGCCCTGTCACTCGGGCTGACCCCCAACTTTAAATC
TAACTTCGACCTGGCCGAAGATGCCAAGCTTCAACTGAGCAAAGACACCT
ACGATGATGATCTCGACAATCTGCTGGCCCAGATCGGCGACCAGTACGCA
GACCTTTTTTTGGCGGCAAAGAACCTGTCAGACGCCATTCTGCTGAGTGA
TATTCTGCGAGTGAACACGGAGATCACCAAAGCTCCGCTGAGCGCTAGTA
TGATCAAGCGCTATGATGAGCACCACCAAGACTTGACTTTGCTGAAGGCC
CTTGTCAGACAGCAACTGCCTGAGAAGTACAAGGAAATTTTCTTCGATCA
GTCTAAAAATGGCTACGCCGGATACATTGACGGCGGAGCAAGCCAGGAGG
AATTTTACAAATTTATTAAGCCCATCTTGGAAAAAATGGACGGCACCGAG
GAGCTGCTGGTAAAGCTTAACAGAGAAGATCTGTTGCGCAAACAGCGCAC
TTTCGACAATGGAAGCATCCCCCACCAGATTCACCTGGGCGAACTGCACG
CTATCCTCAGGCGGCAAGAGGATTTCTACCCCTTTTTGAAAGATAACAGG
GAAAAGATTGAGAAAATCCTCACATTTCGGATACCCTACTATGTAGGCCC
CCTCGCCCGGGGAAATTCCAGATTCGCGTGGATGACTCGCAAATCAGAAG
AGACCATCACTCCCTGGAACTTCGAGGAAGTCGTGGATAAGGGGGCCTCT
GCCCAGTCCTTCATCGAAAGGATGACTAACTTTGATAAAAATCTGCCTAA
CGAAAAGGTGCTTCCTAAACACTCTCTGCTGTACGAGTACTTCACAGTTT
ATAACGAGCTCACCAAGGTCAAATACGTCACAGAAGGGATGAGAAAGCCA
GCATTCCTGTCTGGAGAGCAGAAGAAAGCTATCGTGGACCTCCTCTTCAA
GACGAACCGGAAAGTTACCGTGAAACAGCTCAAAGAAGACTATTTCAAAA
AGATTGAATGTTTCGACTCTGTTGAAATCAGCGGAGTGGAGGATCGCTTC
AACGCATCCCTGGGAACGTATCACGATCTCCTGAAAATCATTAAAGACAA
GGACTTCCTGGACAATGAGGAGAACGAGGACATTCTTGAGGACATTGTCC
TCACCCTTACGTTGTTTGAAGATAGGGAGATGATTGAAGAACGCTTGAAA
ACTTACGCTCATCTCTTCGACGACAAAGTCATGAAACAGCTCAAGAGGCG
CCGATATACAGGATGGGGCGGCTGTCAAGAAAACTGATCAATGGGATCC
GAGACAAGCAGAGTGGAAAGACAATCCTGGATTTTCTTAAGTCCGATGGA

```
TTTGCCAACCGGAACTTCATGCAGTTGATCCATGATGACTCTCTCACCTT

TAAGGAGGACATCCAGAAAGCACAAGTTTCTGGCCAGGGGGACAGTCTTC

ACGAGCACATCGCTAATCTTGCAGGTAGCCCAGCTATCAAAAAGGGAATA

CTGCAGACCGTTAAGGTCGTGGATGAACTCGTCAAAGTAATGGGAAGGCA

TAAGCCCGAGAATATCGTTATCGAGATGGCCCGAGAGAACCAAACTACCC

AGAAGGGACAGAAGAACAGTAGGGAAAGGATGAAGAGGATTGAAGAGGGT

ATAAAAGAACTGGGGTCCCAAATCCTTAAGGAACACCCAGTTGAAAACAC

CCAGCTTCAGAATGAGAAGCTCTACCTGTACTACCTGCAGAACGGCAGGG

ACATGTACGTGGATCAGGAACTGGACATCAATCGGCTCTCCGACTACGAC

GTGGCTGCTATCGTGCCCCAGTCTTTTCTCAAAGATGATTCTATTGATAA

TAAAGTGTTGACAAGATCCGATAAAgcTAGAGGGAAGAGTGATAACGTCC

CCTCAGAAGAAGTTGTCAAGAAAATGAAAAATTATTGGCGGCAGCTGCTG

AACGCCAAACTGATCACACAACGGAAGTTCGATAATCTGACTAAGGCTGA

ACGAGGTGGCCTGTCTGAGTTGGATAAAGCCGGCTTCATCAAAAGGCAGC

TTGTTGAGACACGCCAGATCACCAAGCACGTGGCCCAAATTCTCGATTCA

CGCATGAACACCAAGTACGATGAAAATGACAAACTGATTCGAGAGGTGAA

AGTTATTACTCTGAAGTCTAAGCTGGTCTCAGATTTCAGAAAGGACTTTC

AGTTTTATAAGGTGAGAGAGATCAACAATTACCACCATGCGCATGATGCC

TACCTGAATGCAGTGGTAGGCACTGCACTTATCAAAAAATATCCCAAGCT

TGAATCTGAATTTGTTTACGGAGACTATAAAGTGTACGATGTTAGGAAAA

TGATCGCAAAGTCTGAGCAGGAAATAGGCAAGGCCACCGCTAAGTACTTC

TTTTACAGCAATATTATGAATTTTTTCAAGACCGAGATTACACTGGCCAA

TGGAGAGATTCGGAAGCGACCACTTATCGAAACAAACGGAGAAACAGGAG

AAATCGTGTGGGACAAGGGTAGGGATTTCGCGACAGTCCGGAAGGTCCTG

TCCATGCCGCAGGTGAACATCGTTAAAAAGACCGAAGTACAGACCGGAGG

CTTCTCAAGGAAAGTATCCTCCCGAAAAGGAACAGCGACAAGCTGATCG

CACGCAAAAAAGATTGGGACCCCAAGAAATACGGCGGATTCGATTCTCCT

ACAGTCGCTTACAGTGTACTGGTTGTGGCCAAAGTGGAGAAAGGGAAGTC

TAAAAAACTCAAAAGCGTCAAGGAACTGCTGGGCATCACAATCATGGAGC

GATCAAGCTTCGAAAAAAACCCCATCGACTTTCTCGAGGCGAAAGGATAT

AAAGAGGTCAAAAAAGACCTCATCATTAAGCTTCCCAAGTACTCTCTCTT

TGAGCTTGAAAACGGCCGGAAACGAATGCTCGCTAGTGCGGGCGAGCTGC

AGAAAGGTAACGAGCTGGCACTGCCCTCTAAATACGTTAATTTCTTGTAT

CTGGCCAGCCACTATGAAAAGCTCAAAGGGTCTCCCGAAGATAATGAGCA

GAAGCAGCTGTTCGTGGAACAACACAAACACTACCTTGATGAGATCATCG

AGCAAATAAGCGAATTCTCCAAAAGAGTGATCCTCGCCGACGCTAACCTC

GATAAGGTGCTTTCTGCTTACAATAAGCACAGGGATAAGCCCATCAGGGA

GCAGGCAGAAAACATTATCCACTTGTTTACTCTGACCAACTTGGGCGCGC

CTGCAGCCTTCAAGTACTTCGACACCACCATAGACAGAAAGCGGTACACC

TCTACAAAGGAGGTCCTGGACGCCACACTGATTCATCAGTCAATTACGGG

GCTCTATGAAACAAGAATCGACCTCTCTCAGCTCGGTGGAGACAGCAGGG

CTGACCCCAAGAAGAAGAGGAAGGTGGAGGCCAGCGGTTCCGGACGGGCT

GACGCATTGGACGATTTTGATCTGGATATGCTGGGAAGTGACGCCCTCGA

TGATTTTGACCTTGACATGCTTGGTTCGGATGCCCTTGATGACTTTCAGG

TCGACATGCTCGGCAGTGACGCCCTTGATCATTTCGACCTGGACATGCTG

ATTAACTCTAGATGA

>Cas9$_{m4}$$^{VP64}$C (SEQ ID NO: 4)
gccaccATGGACAAGAAGTACTCCATTGGGCTCGCTATCGGCACAAACAG

CGTCGGCTGGGCCGTCATTACGGACGAGTACAAGGTGCCGAGCAAAAAT

TCAAAGTTCTGGGCAATACCGATCGCCACAGCATAAAGAAGAACCTCATT

GGCGCCCTCCTGTTCGACTCCGGGGAGACGGCCGAAGCCACGCGGCTCAA

AAGAACAGCACGGCGCAGATATACCCGCAGAAAGAATCGGATCTGCTACC

TGCAGGAGATCTTTAGTAATGAGATGGCTAAGGTGGATGACTCTTTCTTC

CATAGGCTGGAGGAGTCCTTTTTGGTGGAGGAGGATAAAAAGCACGAGCG

CCACCCAATCTTTGGCAATATCGTGGACGAGGTGGCGTACCATGAAAAGT

ACCCAACCATATATCATCTGAGGAAGAAGCTTGTAGACAGTACTGATAAG

GCTGACTTGCGGTTGATCTATCTCGCGCTGGCGCATATGATCAAATTTCG

GGGACACTTCCTCATCGAGGGGGACCTGAACCCAGACAACAGCGATGTCG

ACAAACTCTTTATCCAACTGGTTCAGACTTACAATCAGCTTTTCGAAGAG

AACCCGATCAACGCATCCGGAGTTGACGCCAAAGCAATCCTGAGCGCTAG

GCTGTCCAAATCCCGGCGGCTCGAAAACCTCATCGCACAGCTCCCTGGGG

AGAAGAAGAACGGCCTGTTTGGTAATCTTATCGCCCTGTCACTCGGGCTG

ACCCCCAACTTTAAATCTAACTTCGACCTGGCCGAAGATGCCAAGCTTCA

ACTGAGCAAAGACACCTACGATGATGATCTCGACAATCTGCTGGCCCAGA

TCGGCGACCAGTACGCAGACCTTTTTTTGGCGGCAAAGAACCTGTCAGAC

GCCATTCTGCTGAGTGATATTCTGCGAGTGAACACGGAGATCACCAAAGC

TCCGCTGAGCGCTAGTATGATCAAGCGCTATGATGAGCACCACCAAGACT

TGACTTTGCTGAAGGCCCTTGTCAGACAGCAACTGCCTGAGAAGTACAAG

GAAATTTTCTTCGATCAGTCTAAAAATGGCTACGCCGGATACATTGACGG

CGGAGCAAGCCAGGAGGAATTTTACAAATTTATTAAGCCCATCTTGGAAA

AAATGGACGGCACCGAGGAGCTGCTGGTAAAGCTTAACAGAGAAGATCTG

TTGCGCAAACAGCGCACTTTCGACAATGGAAGCATCCCCCACCAGATTCA

CCTGGGCGAACTGCACGCTATCCTCAGGCGGCAAGAGGATTTCTACCCCT

TTTTGAAAGATAACAGGGAAAAGATTGAGAAAATCCTCACATTTCGGATA

CCCTACTATGTAGGCCCCCTCGCCCGGGGAAATTCCAGATTCGCGTGGAT

GACTCGCAAATCAGAAGAGACCATCACTCCCTGGAACTTCGAGGAAGTCG

TGGATAAGGGGGCCTCTGCCCAGTCCTTCATCGAAAGGATGACTAACTTT

GATAAAAATCTGCCTAACGAAAAGGTGCTTCCTAAACACTCTCTGCTGTA

CGAGTACTTCACAGTTTATAACGAGCTCACCAAGGTCAAATACGTCACAG
```

-continued

AAGGGATGAGAAAGCCAGCATTCCTGTCTGGAGAGCAGAAGAAAGCTATC

GTGGACCTCCTCTTCAAGACGAACCGGAAAGTTACCGTGAAACAGCTCAA

AGAAGACTATTTCAAAAAGATTGAATGTTTCGACTCTGTTGAAATCAGCG

GAGTGGAGGATCGCTTCAACGCATCCCTGGGAACGTATCACGATCTCCTG

AAAATCATTAAAGACAAGGACTTCCTGGACAATGAGGAGAACGAGGACAT

TCTTGAGGACATTGTCCTCACCCTTACGTTGTTTGAAGATAGGGAGATGA

TTGAAGAACGCTTGAAAACTTACGCTCATCTCTTCGACGACAAAGTCATG

AAACAGCTCAAGAGGCGCCGATATACAGGATGGGGGCGGCTGTCAAGAAA

ACTGATCAATGGGATCCGAGACAAGCAGAGTGGAAAGACAATCCTGGATT

TTCTTAAGTCCGATGGATTTGCCAACCGGAACTTCATGCAGTTGATCCAT

GATGACTCTCTCACCTTTAAGGAGGACATCCAGAAAGCACAAGTTTCTGG

CCAGGGGGACAGTCTTCACGAGCACATCGCTAATCTTGCAGGTAGCCCAG

CTATCAAAAAGGGAATACTGCAGACCGTTAAGGTCGTGGATGAACTCGTC

AAAGTAATGGGAAGGCATAAGCCCGAGAATATCGTTATCGAGATGGCCCG

AGAGAACCAAACTACCCAGAAGGGACAGAAGAACAGTAGGGAAAGGATGA

AGAGGATTGAAGAGGGTATAAAAGAACTGGGGTCCCAAATCCTTAAGGAA

CACCCAGTTGAAAACACCCAGCTTCAGAATGAGAAGCTCTACCTGTACTA

CCTGCAGAACGGCAGGGACATGTACGTGGATCAGGAACTGGACATCAATC

GGCTCTCCGACTACGACGTGGCTGCTATCGTGCCCCAGTCTTTTCTCAAA

GATGATTCTATTGATAATAAAGTGTTGACAAGATCCGATAAAgcTAGAGG

GAAGAGTGATAACGTCCCCTCAGAAGAAGTTGTCAAGAAAATGAAAAATT

ATTGGCGGCAGCTGCTGAACGCCAAACTGATCACACAACGGAAGTTCGAT

AATCTGACTAAGGCTGAACGAGGTGGCCTGTCTGAGTTGGATAAAGCCGG

CTTCATCAAAAGGCAGCTTGTTGAGACACGCCAGATCACCAAGCACGTGG

CCCAAATTCTCGATTCACGCATGAACACCAAGTACGATGAAAATGACAAA

CTGATTCGAGAGGTGAAAGTTATTACTCTGAAGTCTAAGCTGGTCTCAGA

TTTCAGAAAGGACTTTCAGTTTTATAAGGTGAGAGAGATCAACAATTACC

ACCATGCGCATGATGCCTACCTGAATGCAGTGGTAGGCACTGCACTTATC

AAAAAATATCCCAAGCTTGAATCTGAATTTGTTTACGGAGACTATAAAGT

GTACGATGTTAGGAAAATGATCGCAAAGTCTGAGCAGGAAATAGGCAAGG

CCACCGCTAAGTACTTCTTTTACAGCAATATTATGAATTTTTTCAAGACC

GAGATTACACTGGCCAATGGAGAGATTCGGAAGCGACCACTTATCGAAAC

AAACGGAGAAACAGGAGAAATCGTGTGGGACAAGGGTAGGGATTTCGCGA

CAGTCCGGAAGGTCCTGTCCATGCCGCAGGTGAACATCGTTAAAAAGACC

GAAGTACAGACCGGAGGCTTCTCCAAGGAAAGTATCCTCCCGAAAAGGAA

CAGCGACAAGCTGATCGCACGCAAAAAAGATTGGGACCCCAAGAAATACG

GCGGATTCGATTCTCCTACAGTCGCTTACAGTGTACTGGTTGTGGCCAAA

GTGGAGAAAGGGAAGTCTAAAAAACTCAAAAGCGTCAAGGAACTGCTGGG

CATCACAATCATGGAGCGATCAAGCTTCGAAAAAAACCCCATCGACTTTC

TCGAGGCGAAAGGATATAAAGAGGTCAAAAAAGACCTCATCATTAAGCTT

CCCAAGTACTCTCTCTTTGAGCTTGAAAACGGCCGGAAACGAATGCTCGC

-continued

TAGTGCGGGCGAGCTGCAGAAAGGTAACGAGCTGGCACTGCCCTCTAAAT

ACGTTAATTTCTTGTATCTGGCCAGCCACTATGAAAAGCTCAAAGGGTCT

CCCGAAGATAATGAGCAGAAGCAGCTGTTCGTGGAACAACACAAACACTA

CCTTGATGAGATCATCGAGCAAATAAGCGAATTCTCCAAAAGAGTGATCC

TCGCCGACGCTAACCTCGATAAGGTGCTTTCTGCTTACAATAAGCACAGG

GATAAGCCCATCAGGGAGCAGGCAGAAAACATTATCCACTTGTTTACTCT

GACCAACTTGGGCGCGCCTGCAGCCTTCAAGTACTTCGACACCACCATAG

ACAGAAAGCGGTACACCTCTACAAAGGAGGTCCTGGACGCCACACTGATT

CATCAGTCAATTACGGGGCTCTATGAAACAAGAATCGACCTCTCTCAGCT

CGGTGGAGACAGCAGGGCTGACCCCAAGAAGAAGAGGAAGGTGGAGGCA

GCGGTTCCGGACGGGCTGACGCATTGGACGATTTTGATCTGGATATGCTG

GGAAGTGACGCCCTCGATGATTTTGACCTTGACATGCTTGGTCTGGACAT

GCTGATTAACTCTAGAGCGGCCGCAGATCCAAAAAAGAAGAGAAAGGTAG

ATCCAAAAAAGAAGAGAAAGGTAGATCCAAAAAAGAAGAGAAAGGTAGAT

ACGGCCGCATAG

B. Sequences of the MS2-activator constructs and corresponding gRNA backbone vector with 2X MS2 aptamer domains is provided below (NLS, VP64, gRNA spacer, and MS2-binding RNA stem loop domains are highlighted). Two versions of the former were constructed with the MS2$^{VP64}$N fusion protein format showing highest activity.

>MS2$_{VP64}$N (SEQ ID NO: 5)
gccaccATGGGACCTAAGAAAAAGAGGAAGGTGGCGGCCGCTTCTAGAAT

GGCTTCTAACTTTACTCAGTTCGTTCTCGTCGACAATGGCGGAACTGGCG

ACGTGACTGTCGCCCCAAGCAACTTCGCTAACGGGATCGCTGAATGGATC

AGCTCTAACTCGCGTTCACAGGCTTACAAAGTAACCTGTAGCGTTCGTCA

GAGCTCTGCGCAGAATCGCAAATACACCATCAAAGTCGAGGTGCCTAAAG

GCGCCTGGCGTTCGTACTTAAATATGGAACTAACCATTCCAATTTTCGCC

ACGAATTCCGACTGCGAGCTTATTGTTAAGGCAATGCAAGGTCTCCTAAA

AGATGGAAACCCGATTCCCTCAGCAATCGCAGCAAACTCCGGCATCTACG

AGGCCAGC*GGTTCCGGACGGGCTGACGCATTGGACGATTTTGATCTGGAT*

*ATGCTGGGAAGTGACGCCCTCGATGATTTTGACCTTGACATGCTTGGTCG*

*GATGCCCTTGATGACTTTGACCTCGACATGCTCGGCAGTGACGCCCTTGA*

*TCATTTCGACCTGGACATGCTGATTAACTCTAGATGA*

>MS2$_{VP64}$C (SEQ ID NO: 6)
gccaccATGGGACCTAAGAAAAAGAGGAAGGTGGCGGCCGCTTCTAGAAT

GGCTTCTAACTTTACTCAGTTCGTTCTCGTCGACAATGGCGGAACTGGCG

ACGTGACTGTCGCCCCAAGCAACTTCGCTAACGGGATCGCTGAATGGATC

AGCTCTAACTCGCGTTCACAGGCTTACAAAGTAACCTGTAGCGTTCGTCA

GAGCTCTGCGCAGAATCGCAAATACACCATCAAAGTCGAGGTGCCTAAAG

```
GCGCCTGGCGTTCGTACTTAAATATGGAACTAACCATTCCAATTTTCGCC

ACGAATTCCGACTGCGAGCTTATTGTTAAGGCAATGCAAGGTCTCCTAAA

AGATGGAAACCCGATTCCCTCAGCAATCGCAGCAAACTCCGGCATCTACG

AGGCCAGCGGTTCCGGACGGGCTGACGCATTGGACGATTTTGATCTGGAT

ATGCTGGGAAGTGACGCCCTCGATCATTTTGACCTTGACATGCTTGGTTC

GGATGCCCTTGATGACTTGACCTCGACATGCTCGGCAGTGACGCCCTTGA

TGATTTCGACCTGGACATGCTGATTAACTCTAGAGCGGCCGCAGATCCAA

AAAAGAAGAGAAAGGTAGATCCAAAAAAGAAGAGAAAGGTAGATCCAAAA

AAGAAGAGAAAGGTAGATACGGCCGCATAG
```

>gRNA<sub>2XMS2</sub>

```
                                     (SEQ ID NO: 7)
TGTACAAAAAAGCAGGCTTTAAAGGAACCAATTCAGTCGACTGGATCCGG

TACCAAGGTCGGGCAGGAAGAGGGCCTATTTCCCATGATTCCTTCATATT

TGCATATACGATACAAGGCTGTTAGAGAGATAATTAGAATTAATTTGACT

GTAAACACAAAGATATTAGTACAAAATACGTGACGTAGAAAGTAATAATT

TCTTGGGTAGTTTGCAGTTTTAAAATTATGTTTTAAAATGGACTATCATA

TGCTTACCGTAACTTGAAAGTATTTCGATTTCTTGGCTTTATATATCTTG

TGGAAAGGACGAAACACCGNNNNNNNNNNNNNNNNNNNNGTTTTAGAGCT

AGAAATAGCAAGTTAAAATAAGGCTAGTCCGTTATCAACTTGAAAAAGTG

GCACCGAGTCGGTGCTCTGCAGGTCGACTCTAGAAAACATGAGGATCACC

CATGTCTGCAGTATTCCCGGGTTCATTAGATCCTAAGGTACCTAATTGCC

TAGAAAACATGAGGATCACCCATGTCTGCAGGTCGACTCTAGAAATTTTT

TCTAGAC
```

C. dTomato fluorescence based transcriptional activation reporter sequences are listed below (ISceI control-TF target, gRNA targets, minCMV promoter and FLAG tag+dTomato sequences are highlighted).

>TF Reporter 1

```
                                      (SEQ ID NO: 8)
TAGGGATAACAGGGTAATAGTGTCCCCTCCACCCCACAGTGGGGCGAGGTA

GGCGTGTACGGTGGGAGGCCTATATAAGCAGAGCTCGTTTAGTGAACCGT

CAGATCGCCTGGAGAATTCgccaccatgGACTACAAGGATGACGACGATA

AAACTTCCGGTGGCGGACTGGGTTCCACCGTGAGCAAGGGCGAGGAGGTC

ATCAAAGAGTTCATGCGCTTCAAGGTGCGCATGGAGGGCTCCATGAACGG

CCACGAGTTCGAGATCGAGGGCGAGGGCGAGGGCCGCCCCTACGAGGGCACCCAGA

CCGCCAAGCTGAAGGTGACCAAGGGCGGCCCCCTGCCCTTCGCCTGGGAC

ATCCTGTCCCCCAGTTCATGTACGGCTCCAAGGCGTACGTGAAGCACCC

CGCCGACATCCCCGATTACAAGAAGCTGTCCTTCCCCGAGGGCTTCAAGT

GGGAGCGCGTGATGAACTTCGAGGACGGCGGTCTGGTGACCGTGACCCAG

GACTCCTCCCTGCAGGACGGCACGCTGATCTACAAGGTGAAGATGCGCGG

CACCAACTTCCCCCCGACGGCCCCGTAATGCAGAAGAAGACCAGGGCTGG

GAGGCCTCCACCGAGCGCCTGTACCCCGCGCGGCGTGCTGAAGGGCGAG

ATCCACCAGGCCCTGAAGCTGAAGGACGGCGGCCACTACCTGGTGGAGTT

CAAGACCATCTACATGGCCAAGAAGCCCGTGCAACTGCCCGGCTACTACT

ACGTGGACACCAAGCTGGACATCACCTCCCACAACGAGGACTACACCATC

GTGGAACAGTACGAGCGCTCCGAGGGCCGCCACCACCTGTTCCTGTACGG

CATGGACGAGCTGTACAAGTAA
```

>TF Reporter 2

```
(SEQ ID NO: 9)
TAGGGATAACAGGGTAATAGTGGGGCCACTAGGGACAGGATTGGCGAGGT

AGGCGTGTACGGTGGGAGGCCTATATAAGCAGAGCTCGTTTAGTGAACCG

TCAGATCGCCTGGAGAATTCgccaccatgGACTACAAGGATGACGACGAT

AAAACTTCCGGTGGCGGACTGGGTTCCACCGTGAGCAAGGGCGAGGAGGT

CATCAAAGAGTTCATGCGCTTCAAGGTGCGCATGGAGGGCTCCATGAACG

GCCACGAGTTCGAGATCGAGGGCGAGGGCGAGGGCCGCCCCTACGAGGGC

ACCCAGACCGCCAAGCTGAAGGTGACCAAGGGCGGCCCCCTGCCCTTCGC

CTGGGACATCCTGTCCCCCCAGTTCATGTACGGCTCCAAGGCGTACGTGA

AGCACCCCGCCGACATCCCCGATTACAAGAAGCTGTCCTTCCCCGAGGGC

TTCAAGTGGGAGCGCGTGATGAACTTCGAGGACGGCGGTCTGGTGACCGT

GACCCAGGACTCCTCCCTGCAGGACGGCACGCTGATCTACAAGGTGAAGA

TGCGCGGCACCAACTTCCCCCCCGACGGCCCCGTAATGCAGAAGAAGACCA

TGGGCTGGGAGGCCTCCACCGAGCGCCTGTACCCCGCGACGGCGTGCTG

AAGGGCGAGATCCACCAGGCCCTGAAGCGAAGGACGGCGGCCACTACCTG

GTGGAGTTCAAGACCATCTACATGGCCAAGAAGCCCGTGCAACGCCCGGC

TACTACTACGTGGACACCAAGCTGGACATCACCTCCCACAACGAGGACTA

CACCATCGTGGAACAGTACGAGCGCTCCGAGGGCCGCCACCACCTGTTCC

TGTACGGCATGGACGAGCTGTACAAGTAA
```

D. General format of the reporter libraries used for TALE and Cas9-gRNA specificity assays is provided below (ISceI control-TF target, gRNA/TALE target site (23 bp for gRNAs and 18 bp for TALEs), minCMV promoter, RNA barcode, and dTomato sequences are highlighted).

>Specificity Reporter Libraries

```
(SEQ ID NO: 10)
TAGGGATAACAGGGTAATAGTNNNNNNNNNNNNNNNNNNNNNNNGCAGGT

AGGCGTGTACGGTGGGAGGCCTATATAAGCAGAGCTCGTTTAGTGAACCG

TCAGATCGCCTGGAGAATTCgccaccatgGACTACAAGGATGACGACGAT

AAANNNNNNNNNNNNNNNNNNNNNNNNNACTTCCGGTGGCGGACTGGGTTC

CACCGTGAGCAAGGGCGAGGAGGTCATCAAAGAGTTCATGCGCTTCAAGG

TGCGCATGGAGGGCTCCATGAACGGCCACGAGTTCGAGATCGAGGGCGAG

GGCGAGGGCCGCCCCTACGAGGGCACCCAGACCGCCAAGCTGAAGGTGAC

CAAGGGCGGCCCCCTGCCCTTCGCCTGGGACATCCTGTCCCCCAGTTCA

TGTACGGCTCCAAGGCGTACGTGAAGCACCCCGCCGACATCCCCGATACA

AGAAGCTGTCCTTCCCCGAGGGCTTCAAGTGGGAGCGCGTGATGAACTTCG
```

-continued

AGGACGGCGGTCTGGTGACCGTGACCCAGGACTCCTCCCTGCAGGACGGC

ACGCTGATCTACAAGGTGAAGATGCGCGGCACCAACTTCCCCCCCGACGG

CCCCGTAATGCAGAAGAAGACCATGGGCTGGGAGGCCTCCACCGAGCGCC

TGTACCCCGCGACGGCGTGCTGAAGGGCGAGATCCACCAGGCCCTGAAG

-continued

CTGAAGGACGGCGCCACTACCTGGTGGAGTTCAAGACCATCTACATGGC

CAAGAAGCCCGTGCAACTGCCCGGCTACTACTACGTGGACACCAAGCTGG

ACATCACCTCCCACAACGAGGACTACACCATCGTGGAACAGTACGAGCGC

TCCGAGGGCCGCCACCACCTGTTCCTGTACGGCATGGACGAGCTGTACAA

GTAAGAATTC

---

SEQUENCE LISTING

```
Sequence total quantity: 187
SEQ ID NO: 1           moltype = AA  length = 1368
FEATURE                Location/Qualifiers
source                 1..1368
                       mol_type = protein
                       organism = Streptococcus pyogenes
SEQUENCE: 1
MDKKYSIGLD IGTNSVGWAV ITDEYKVPSK KFKVLGNTDR HSIKKNLIGA LLFDSGETAE   60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDH  840
IVPQSFLKDD SIDNKVLTRS DKNRGKSDNV PSEEVVKKMK NYWRQLLNAK LITQRKFDNL  900
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGTALIKK YPKLESEFVY GDYKVYDVRK 1020
MIAKSEQEIG KATAKYFFYS NIMNFFKTEI TLANGEIRKR PLIETNGETG EIVWDKGRDF 1080
ATVRKVLSMP QVNIVKKTEV QTGGFSKESI LPKRNSDKLI ARKKDWDPKK YGGFDSPTVA 1140
YSVLVVAKVE KGKSKKLKSV KELLGITIME RSSFEKNPID FLEAKGYKEV KKDLIIKLPK 1200
YSLFELENGR KRMLASAGEL QKGNELALPS KYVNFLYLAS HYEKLKGSPE DNEQKQLFVE 1260
QHKHYLDEII EQISEFSKRV ILADANLDKV LSAYNKHRDK PIREQAENII HLFTLTNLGA 1320
PAAFKYFDTT IDRKRYTSTK EVLDATLIHQ SITGLYETRI DLSQLGGD              1368

SEQ ID NO: 2           moltype = DNA  length = 4332
FEATURE                Location/Qualifiers
misc_feature           1..4332
                       note = VP64-activator construct
source                 1..4332
                       mol_type = other DNA
                       organism = synthetic construct
SEQUENCE: 2
gccaccatgg acaagaagta ctccattggg ctcgctatcg gcacaaacag cgtcggctgg   60
gccgtcatta cggacgagta caaggtgccg agcaaaaaat tcaaagttct gggcaatacc  120
gatcgccaca gcataaagaa gaacctcatt ggcgccctcc tgttcgactc cggggagacg  180
gccgaagcca cgcggctcaa aagaacagca cggcgcagat atacccgcag aaagaatcgg  240
atctgctacc tgcaggagat ctttagtaat gagatggcta aggtggatga ctctttcttc  300
cataggctgg aggagtcctt tttggtggag gaggataaaa agcacgagcg ccacccaatc  360
tttggcaata tcgtggacga ggtggcgtac catgaaaagt acccaaccat atatcatctg  420
aggaagaagc ttgtagacag tactgataag gctgacttgc ggttgatcta tctcgcgctg  480
gcgcatatga tcaaatttcg gggacacttc ctcatcgagg gggacctgaa cccagacaac  540
agcgatgtcg acaaactctt tatccaactg gttcagactt acaatcagct tttcgaagag  600
aacccgatca acgcatccgg agttgacgcc aaagcaatcc tgagcgctag gctgtccaaa  660
tccggcggc tcgaaaacct catcgcacag ctccctgggg agaagaagaa cggcctgttt  720
ggtaatctta tcgccctgtc actcgggctg accccccaact ttaaatctaa cttcgacctg  780
gccgaagatg ccaagcttca actgagcaaa gacacctacg atgatgatct cgacaatctg  840
ctggcccaga tcggcgacca gtacgcagac ttttttttgg cggcaaagaa cctgtcagac  900
gccattctgc tgagtgatat tctgcgagtg aacacggaga tcaccaaagc tccgctgagc  960
gctagtatga tcaagcgcta tgatgagcac caccaagact gactttgct gaaggccctt 1020
gtcagacagc aactgcctga agtacaag gaaattttct cgatcagtc taaaaatggc 1080
tacgccggat acattgacgg cggagcaagc caggaggaat tttacaaatt tattaagccc 1140
atcttggaaa aaatggacgg caccgaggag ctgctggtaa agcttaacag agaagatctg 1200
ttgcgcaaac agcgcacttt cgacaatgga agcatccgca accagatttca ccatctggaa 1260
ctgcacgcta tcctcaggcg gcaagaggat ttctaccct ttttgaaaga taacagggaa 1320
aagattgaga aaatcctcac atttcggata ccctactatg taggccccct cgccggggga 1380
aattccagat tcgcgtggat gactcgcaaa tcagaagaga ccatcactcc ctggaacttc 1440
gaggaagtcg tggataaggg ggcctctgcc cagtccttca tcgaaaggat gactaacttt 1500
gataaaaatc tgcctaacga aaaggtgctt cctaaacact ctctgctgta cgagtacttc 1560
```

-continued

```
acagtttata acgagctcac caaggtcaaa tacgtcacag aagggatgag aaagccagca 1620
ttcctgtctg gagagcagaa gaaagctatc gtggacctcc tcttcaagac gaaccggaaa 1680
gttaccgtga aacagctcaa agaagactat ttcaaaaaga ttgaatgttt cgactctgtt 1740
gaaatcagcg gagtggagga tcgcttcaac gcatccctgg gaacgtatca cgatctcctg 1800
aaaatcatta aagacaagga cttcctggac aatgaggaga acgaggacat tcttgaggac 1860
attgtcctca cccttacgtt gtttgaagat agggagatga ttgaagaacg cttgaaaact 1920
tacgctcatc tcttcgacga caaagtcatg aaacagctca agaggcgcc atatacagga 1980
tgggggcggc tgtcaagaaa actgatcaat gggatccgag acaagcagag tggaaagaca 2040
atcctggatt ttcttaagtc cgatggattt gccaaccgga acttcatgca gttgatccat 2100
gatgactctc tcacctttaa ggaggacatc cagaaagcac aagtttctgg ccaggggac 2160
agtcttcacg agcacatcgc taatcttgca ggtagcccag ctatcaaaaa gggaatactg 2220
cagaccgtta aggtcgtgga tgaactcgtc aaagtaatgg gaaggcataa gcccgagaat 2280
atcgttatcg agatggcccg agagaaccaa actacccaga agggacagaa gaacagtagg 2340
gaaaggatga agaggattga agagggtata aaagaactgg ggtcccaaat ccttaaggaa 2400
cacccagttg aaaacaccca gcttcagaat gagaagctct acctgtacta cctgcagaac 2460
ggcagggaca tgtacgtgga tcaggaactg gacatcaatc ggctctccga ctacgacgtg 2520
gctgctatcg tgccccagtc ttttctcaaa gatgattcta ttgataataa agtgttgaca 2580
agatccgata aagctagagg gaagagtgat aacgtcccct cagaagaagt tgtcaagaaa 2640
atgaaaaatt attggcggca gctgctgaac gccaaactga tcacacaacg gaagttcgat 2700
aatctgacta aggctgaacg aggtggcctg tctgagttgg ataaagccgg cttcatcaaa 2760
aggcagcttg ttgagacacg ccagatcacc aagcacgtgg cccaaattct cgattcacgc 2820
atgaacacca agtacgatga aaatgacaaa ctgattcgaa aggtgaaagt tattactctg 2880
aagtctaagc tggtctcaga tttcagaaag gactttcagt tttataaggt gagagagatc 2940
aacaattacc accatgcgca tgatgcctac ctgaatgcag tggtaggcac tgcacttatc 3000
aaaaaatatc caagcttgaa atctgaattt gtttacggag actataaagt gtacgatgtt 3060
aggaaaatga tcgcaaagtc tgagcaggaa ataggcaagg ccaccgctaa gtacttcttt 3120
tacagcaata ttatgaattt ttcaagacc gagattacac tggccaatgg agagattcgg 3180
aagcgaccac ttatcgaaac aaacggagaa acaggagaaa tcgtgtggga caagggtagg 3240
gatttcgcga cagtccggaa ggtcctgtcc atgccgcagg tgaacatcgt taaaaagacc 3300
gaagtcacga ccggaggctt ctccaaggaa agtatcctcc cgaaaaggaa cagcgacaag 3360
ctgatcgcac gcaaaaaaga ttgggacccc aagaaatacg gcggattcga ttctcctaca 3420
gtcgcttaca gtgtactggt tgtggccaaa gtggagaaag gaagtctaa aaaactcaaa 3480
agcgtcaagg aactgctggg catcacaatc atggagcgat caagcttcga aaaaaacccc 3540
atcgactttc tcgaggcgaa aggatataaa gaggtcaaga aagacctcat cattaagctt 3600
cccaagtact ctctctttga gcttgaaaac ggccggaaac gaatgctcgc tagtcgggc 3660
gagctgcaga aggtaacga gctggcactg ccctctaaat acgttaattt cttgtatctg 3720
gccagccact atgaaaagct caaagggtct cccgaagata tgagcagaa gcagctgttc 3780
gtggaacaac acaaacacta ccttgatgag atcatcgagc aaataagcga attctccaaa 3840
agagtgatcc tcgccgacgc taacctcgat aaggtgcttt ctgcttacaa taagcacagg 3900
gataagccca tcagggagca ggcagaaaac attatccact tgtttactct gaccaacttg 3960
ggcgcgcctg cagccttcaa gtacttcgac accaccatag acagaaagcg gtacacctct 4020
acaaaggagg tcctggacgc cacactgatt catcagtcaa ttacgggct ctatgaaaca 4080
agaatcgacc tctctcagct cggtgagac agcagggctg accccaagaa gaagaggaag 4140
gtggaggcca gcggttccgg acgggctgac gcattggacg attttgatct ggatatgctg 4200
ggaagtgacg ccctcgatga ttttgacctt gacatgcttg gttcggatgc ccttgatgac 4260
tttgacctcg acatgctcgg cagtgacgcc cttgatgatt cgacctgga catgctgatt 4320
aactctagat ga                                                   4332
```

SEQ ID NO: 3         moltype = DNA   length = 4365
FEATURE              Location/Qualifiers
misc_feature        1..4365
                    note = VP64-activator construct
source              1..4365
                    mol_type = other DNA
                    organism = synthetic construct
SEQUENCE: 3

```
gccaccatgc ccaagaagaa gaggaaggtg gaaggggga tggacaagaa gtactccatt 60
gggctcgcta tcggcacaaa cagcgtcggc tgggccgtca ttacggacga gtacaaggtg 120
ccgagcaaaa aattcaaagt tctgggcaat accgatcgcc acagcataaa gaagaacctc 180
attggcgccc tcctgttcga ctccggggag acggccgaag ccacgcggct caaaagaaca 240
gcacggcgca gatatacccg cagaaagaat cggatctgct acctgcagga gatctttagt 300
aatgagatgg ctaaggtgga tgactctttc ttccataggc tggaggagtc cttttttggtg 360
gaggaggata aaaagcacga gcgccaccca atctttgcca atatcgtgga cgaggtggcg 420
taccatgaaa agtacccaac catatatcat ctgaggaaga agcttgtaga cagtactgat 480
aaggctgact tgcggttgat ctatctcgcg ctggcgcata tgatcaaatt tcggggacac 540
ttcctcatcg aggggaccct gaacccagac aacagcgatg tcgacaaact ctttatccaa 600
ctggttcaga cttacaatca gctttttgaa gagaacccga tcaacgcatc ggagttgac 660
gccaaagcaa tcctgagcgc taggctgtcc aaatcccggc ggctcgaaaa cctcatcgca 720
cagctccctg gggagaagaa gaacggcctg tttggtaatc ttatcgccct gtcactcgga 780
ctgaccccca actttaaatc taacttcgac ctggccgaag atgccaagct tcaactgagc 840
aaagacacct acgatgatga tctcgacaat ctgctggccc agatcggcga ccagtacgca 900
gaccttttt tggcggcaaa gaacctgtca gacgccattc tgctgagtga tattctgcga 960
gtgaacacgg agatcaccaa agctccgctg agcgctagta tgatcaagcg ctatgatgag 1020
caccaccaag acttgacttt gctgaaggcc cttgtcagac agcaactgcc tgaaagtac 1080
aaggaaattt tcttcgatca gtctaaaaat ggctacgccg gatacattga cggcggagca 1140
agccaggagg aattttacaa atttattaag cccatcttgg aaaaaatgga cggcaccgag 1200
gagctgctgt aaagcttaa cagagaagat ctgttgcgca acagcgcac tttcgacaat 1260
gaagcatcc cccaccagat tcacctgggc gaactgcacg ctatcctcag gcggcaagag 1320
gatttctacc ccttttttgaa agataacagg gaaaagattg agaaaatcct cacatttcgg 1380
```

```
atacccctact atgtaggccc cctcgcccgg ggaaattcca gattcgcgtg gatgactcgc  1440
aaatcagaag agaccatcac tccctggaac ttcgaggaag tcgtggataa ggggggcctct  1500
gcccagtcct tcatcgaaag gatgactaac tttgataaaa atctgcctaa cgaaaaggtg  1560
cttcctaaac actctctgct gtacgagtac ttcacagttt ataacgagct caccaaggtc  1620
aaatacgtca cagaagggat gagaaagcca gcattcctgt ctggagagca gaagaaagct  1680
atcgtggacc tcctcttcaa gacgaaccgg aaagttaccg tgaaacagct caaagaagac  1740
tatttcaaaa agattgaatg tttcgactct gttgaaatca gcggagtgga ggatcgcttc  1800
aacgcatccc tggaacgtac tcacgatctc ctgaaaatca ttaaagacaa ggacttcctg  1860
gacaatgagg agaacgagga cattcttgag gacattgtcc tcaccctttac gttgtttgaa  1920
gatagggaga tgattgaaga acgcttgaaa acttacgctc atctcttcga cgacaaagtc  1980
atgaaacagc tcaagaggcg ccgatataca ggatgggggc ggctgtcaag aaaactgatc  2040
aatgggatcc gagacaagca gagtggaaag acaatcctgg attttcttaa gtccgatgga  2100
tttgccaacc ggaacttcat gcagttgatc catgatgact ctctcaccct taaggaggac  2160
atccagaaag cacaagtttc tggccagggg gacagtcttc acgagcacat cgctaatctt  2220
gcaggtagcc cagctatcaa aaagggaata ctgcagaccg ttaaggtcgt ggatgaactc  2280
gtcaaagtaa tgggaaggca taagcccgag aatatcgtta tcgagatggc ccgagagaac  2340
caaactaccc agaagggaca aagaacagt agggaaagga tgaagaggat tgaagagggt  2400
ataaaagaac tggggtccca aatccttaag gaacacccag ttgaaaacac ccagcttcag  2460
aatgagaagc tctacctgta ctacctgcag aacggcaggg acatgtacgt ggatcaggaa  2520
ctggacatca atcggctctc cgactacgac gtggctgcta tcgtgcccca gtcttttctc  2580
aaagatgatt ctattgataa taagtgttg acaagatccg ataaagctag agggaagagt  2640
gataacgtcc cctcagaaga agtttgtcaag aaaatgaaaa attattggcg gcagctgctg  2700
aacgccaaac tgatcacaca acggaagttc gataatctga ctaaggctga acgaggtggc  2760
ctgtctgagt tggataaagc cggcttcatc aaaaggcagc ttgttgagac acgccagatc  2820
accaagcacg tggcccaaat tctcgattca cgcatgaaca ccaagtacga tgaaaatgac  2880
aaactgattc gagaggtgaa gtattact ctgaagtcta agctggtctc agatttcaga  2940
aaggactttc agttttataa ggtgagagag atcaacaatt accaccatgc gcatgatgcc  3000
tacctgaatg cagtggtagg cactgcactt atcaaaaaat atcccaagct gaatctgaa  3060
tttgtttacg gagactataa agtgtacgat gttaggaaaa tgatcgcaaa gtctgagcag  3120
gaaataggca aggccaccgc taagtacttc ttttacagca atattatgaa tttttttcag  3180
accgagatta cactggccaa tggagagatt cggaagcgac cacttatcga acaaacgga  3240
gaaacaggag aaatcgtgtg ggacaagggt agggatttcg cgacagtccg gaaggtcctg  3300
tccatgccgc aggtgaacat cgttaaaaag accgaagtac agaccggagg cttctccaag  3360
gaaagtatcc tcccgaaaag gaacagcgac aagctgatcg cacgcaaaaa agattgggac  3420
cccaagaaat acggcggatt cgattctcct acagtgtact ggttgtggcc  3480
aaagtggaga agggaagtc taaaaaactc aaaagcgtca aggaactgct gggcatcaca  3540
atcatgagc gatcaagctt cgaaaaaac cccatcgact ttctcgaggc gaaaggatat  3600
aaagaggtca aaaagacct catcattaag cttcccaagt actctctctt tgagcttgaa  3660
aacggccgga aacgaatgct cgctagtgcg ggcgagctgc agaaaggtaa cgagctggca  3720
ctgccctcta aatacgttaa ttttcttgtat ctggccagcc actatgaaaa gctcaaaggg  3780
tctcccgaag ataatgagca gaagcagctg ttcgtggaac aacacaaaca ctaccttgat  3840
gagatcatcg agcaaataag cgaattctcc aaaagagtga tcctcgccga cgctaacctc  3900
gataaggtgc tttctgctta caataagcac agggataagc ccatcaggga gcaggcagaa  3960
aacattatcc acttgtttac tctgaccaac ttgggcgcgc ctgcagcctt caagtacttc  4020
gacaccacca tagacagaaa gcggtacacc tctacaaagg aggtcctgga cgccacactg  4080
attcatcagt caattacggg gctctatgaa acaagaatcg acctctctca gctcggtgga  4140
gacagcaggg ctgaccccaa gaagaagagg aaggtggagg ccagcggttc cggacgggct  4200
gacgcattgg acgattttga tctggatatg ctgggaagtg acgccctcga tgattttgac  4260
cttgacatgc ttggttcgga tgccttgat gactttgacc tcgacatgct cggcagtgac  4320
gcccttgatg atttcgacct ggacatgctg attaactcta gatga           4365
```

```
SEQ ID NO: 4              moltype = DNA   length = 4425
FEATURE                   Location/Qualifiers
misc_feature              1..4425
                          note = VP64-activator construct
source                    1..4425
                          mol_type = other DNA
                          organism = synthetic construct
SEQUENCE: 4
gccaccatgg acaagaagta ctccattggg ctcgctatcg gcacaaacag cgtcggctgg  60
gccgtcatta cggacgagta caaggtgccg agcaaaaaat tcaaagttct gggcaatacc  120
gatcgccaca gcataaagaa gaacctcatt ggcgccctcc tgttcgactc ggggagacg  180
gccgaagcca cgcggctcaa aagaacagca cggcgcagat atacccgcag aaagaatcgg  240
atctgctacc tgcaggagat ctttagtaat gagatggctc aggtggatga ctctttcttc  300
cataggctgg aggagtcctt tttggtggag gaggataaaa agcacgagcg ccacccaatc  360
tttgcaata tcgtggacga ggtggcgtac catgaaaagt acccaaccat atatcatctg  420
aggaagaagc ttgtagacag tactgataag gctgacttgc ggttgatcta tctcgcgctg  480
gcgcatatga tcaaatttcg gggacacttc ctcatcgagg gggacctgaa cccagacaac  540
agcgatgtcg acaaactctt tatccaactg gttcagactc acaatcagct tttcgaagag  600
aacccgatca acgcatccgg agttgacgcc aaagcaatcc tgagcgctag gctgtccaaa  660
tcccggcggc tcgaaaacct catcgcacag ctccctgggg agaagaagaa cggcctgttt  720
ggtaatctta tcgccctgtc actcgggctg accccaact ttaaatctaa cttcgacctg  780
gccgaagatg ccaagcttca actgagcaaa gacacctacg atgatgatct cgacaatctg  840
ctggcccaga tcggcgacca gtacgcagac cttttttggg caaagaa cctgtcagac  900
gccattctgc tgagtgatat tctgcgagtc aacacggaga tcaccaaagc tccgctgagc  960
gctagtatga tcaagcgcta tgatgagcac caccaagact tgactttgct gaaggccctt  1020
gtcagacagc aactgcctga aagtacaag gaaattttct tcgatcagtc taaaaatggc  1080
tacgccggat acattgacgg cggagcaagc caggaggaat tttacaaatt tattaagccc  1140
atcttggaaa aaatggacgg caccgaggag ctgctggtaa agcttaacag agaagatctg  1200
```

-continued

```
ttgcgcaaac agcgcacttt cgacaatgga agcatccccc accagattca cctgggcgaa   1260
ctgcacgcta tcctcaggcg gcaagaggat ttctacccct ttttgaaaga taacagggaa   1320
aagattgaga aaatcctcac atttcggata ccctactatg taggcccct cgcccgggga   1380
aattccagat tcgcgtggat gactcgcaaa tcagaagaga ccatcactcc ctggaacttc   1440
gaggaagtcg tggataaggg ggcctctgcc cagtccttca tcgaaaggat gactaacttt   1500
gataaaaatc tgcctaacga aaaggtgctt cctaaacact ctctgctgta cgagtacttc   1560
acagtttata acgagctcac caaggtcaaa tacgtcacag aagggatgag aaagccagca   1620
ttcctgtctg gagagcagaa gaaagctatc gtggacctcc tcttcaagac gaaccggaaa   1680
gttaccgtga aacagctcaa agaagactat ttcaaaaaga ttgaatgttt cgactctgtt   1740
gaaatcagcg gagtggagga tcgcttcaac gcatccctgg gaacgtatca cgatctcctg   1800
aaaatcatta aagacaagga cttcctggac aatgaggaga acgaggacat tcttgaggac   1860
attgtcctca cccttacgtt gtttgaagat agggagatga ttgaagaacg cttgaaaact   1920
tacgctcatc tcttcgacga caaagtcatg aaacagctca agaggcgccg atatacagga   1980
tggggcggc tgtcaagaaa actgatcaat gggatccgag acaagcagag tggaaagaca   2040
atcctggatt ttcttaagtc cgatggattt gccaaccgga acttcatgca gttgatccat   2100
gatgactctc tcacctttaa ggaggacatc cagaaagcac aagtttctgg ccaggggac   2160
agtcttcacg agcacatcgc taatcttgca ggtagcccag ctatcaaaaa gggaatactg   2220
cagaccgtta aggtcgtgga tgaactcgtc aaagtaatgg gaaggcataa gcccgagaat   2280
atcgttatcg agatggcccg agagaaccaa actacccaga agggacagaa gaacagtagg   2340
gaaaggatga gaggattga gagggtata aagaactggg gtcccaaat ccttaaggaa   2400
cacccagttg aaaacaccca gcttcagaat gagaagctct acctgtacta cctgcagaac   2460
ggcagggaca tgtacgtgga tcaggaactg gacatcaatc ggctctccga ctacgacgtg   2520
gctgctatcg tgccccagtc ttttctcaaa gatgattcta ttgataataa agtgttgaca   2580
agatccgata aagctagagg gaagagtgat aacgtcccct cagaagaagt tgtcaagaaa   2640
atgaaaaatt attggcggca gctgctgaac gccaaactga tcacacaacg gaagttcgat   2700
aatctgacta aggctgaacg aggtgggctg tctgagttgg ataaagccgg cttcatcaaa   2760
aggcagcttg ttgagacacg ccagatcacc aagcacgtgg cccaaattct cgattcacgc   2820
atgaacacca agtacgatga aaatgacaaa ctgattcgag aggtgaaagt tattactctg   2880
aagtctaagc tggtctcaga tttcagaaag gactttcagt tttataaggt gagagagatc   2940
aacaattacc accatgcgca tgatgcctac ctgaatgcaa tggtaggcac tgcacttatt   3000
aaaaaatatc ccaagcttga atctgaattt gtttacggag actataaagt gtacgatgtt   3060
aggaaaatga tcgcaaagtc tgagcaggaa ataggcaagg ccaccgctaa gtacttcttt   3120
tacagcaata ttatgaattt tttcaagacc gagattacac tggccaatgg agagattcgg   3180
aagcgaccac ttatcgaaac aaacggagaa acaggagaaa tcgtctgtgga caagggtagg   3240
gatttcgcga cagtccggaa ggtcctgtcc atgccgcagg tgaacatcgt taaaaagacc   3300
gaagtacaga ccggaggctt ctccaaggaa agtatcctcc cgaaaaggaa cagcgacaag   3360
ctgatcgcac gcaaaaaaga ttgggacccc aagaaatacg gcggattcga ttctcctaca   3420
gtcgcttaca gtgtactggt tgtggccaaa gtggagaaag ggaagtctaa aaaactcaaa   3480
agcgtcaagg aactgctggg catcacaatc atggagcgat caagcttcga aaaaaacccc   3540
atcgactttc tcgaggcgaa aggatataaa gaggtcaaaa aagacctcat cattaagctt   3600
cccaagtact ctctctttga gcttgaaaac ggccggaaac gaatgctcgc tagtgcgggc   3660
gagctgcaga aaggtaacga gctggcactg ccctctaaat acgttaattt cttgtatctg   3720
gccagccact atgaaaagct caaaggtgtc cccgaagata atgagcagaa gcagctgttc   3780
gtggaacaac acaaacacta ccttgatgag atcatcgagc aaataagcga attctccaaa   3840
agagtgatcc tcgccgacgc taacctcgat aaggtgcttt ctgcttacaa taagcacagg   3900
gataagccca tcagggagca ggcagaaaac attatccact tgtttactct gaccaacttg   3960
ggcgcgcctg cagccttcaa gtacttcgac accaccatag acagaaagcg gtacacctct   4020
acaaaggagg tcctgacgc cacactgatt catcagtcaa ttacggggct ctatgaaaca   4080
agaatcgacc tctctcagct cggtggagac agcagggctg accccaagaa gaagaggaag   4140
gtggaggcca gcggttccgg acgggctgac gcattggacg attttgatct ggatatgctg   4200
ggaagtgcag ccctcgatga tttttgacctt gacatgcttg gttcggatgc ccttgatgac   4260
tttgacctcg acatgctcgg cagtgacgcc cttgatgatt tcgacctgga catgctgatt   4320
aactctagag cggccgcaga tccaaaaaag aagagaaagg tagatccaaa aagaagagaaa   4380
aaggtagatc caaaaagaaa gagaaaggta gatacggccg catag              4425
```

```
SEQ ID NO: 5           moltype = DNA   length = 587
FEATURE                Location/Qualifiers
misc_feature           1..587
                       note = MS2-activator construct
source                 1..587
                       mol_type = other DNA
                       organism = synthetic construct
SEQUENCE: 5
ccaccatggg acctaagaaa aagaggaagg tggcggccgc ttctagaatg gcttctaact   60
ttactcagtt cgttctcgtc gacaatggcg gaactggcga cgtgactgtc gccccaagca   120
acttcgctaa cgggatcgct gaatggatca gctctaactc gcgttcacag gcttacaaag   180
taacctgtag cgttcgtcag agctctgcgc agaatcgcaa ataccaccatc aaagtcgagg   240
tgcctaaagg cgcctggcgt tcgtacttaa atatgaact aaccattcca attttcgcca   300
cgaattccga ctgcgagctt attgttaagg caatgcaagg tctcctaaaa gatggaaacc   360
cgattccctc agcaatcgca gcaaactccg gcatctacga ggccagcggt tccgacgggg   420
ctgacgcatt ggacgatttt gatctggata tgctgggaag tgacgccctc gatgattttg   480
accttgacat gcttggttcg gatgcccttg atgactttga cctcgacatg ctcggcagtg   540
acgcccttga tgatttcgac ctggacatgc tgattaactc tagatga              587
```

```
SEQ ID NO: 6           moltype = DNA   length = 681
FEATURE                Location/Qualifiers
misc_feature           1..681
                       note = MS2-activator construct
source                 1..681
```

```
                        mol_type = other DNA
                        organism = synthetic construct
SEQUENCE: 6
gccaccatgg gacctaagaa aaagaggaag gtggcggccg cttctagaat ggcttctaac    60
tttactcagt tcgttctcgt cgacaatggc ggaactggcg acgtgactgt cgccccaagc   120
aacttcgcta acgggatcgc tgaatggatc agctctaact cgcgttcaca ggcttacaaa   180
gtaacctgta gcgttcgtca gagctctgcg cagaatcgca aatacaccat caaagtcgag   240
gtgcctaaag gcgcctggcg ttcgtactta aatatggaac taaccattcc aattttcgcc   300
acgaattccg actgcgagct tattgttaag gcaatgcaag gtctcctaaa agatggaaac   360
ccgattccct cagcaatcgc agcaaactcc ggcatctacg aggccagcgg ttccggacgg   420
gctgacgcat tggacgattt tgatctggat atgctgggaa gtgacgccct cgatgatttt   480
gaccttgaca tgcttggttc ggatgccctt gatgactttg acctcgacat gctcggcagt   540
gacgcccttg atgatttcga cctggacatg ctgattaact ctagagcggc cgcagatcca   600
aaaaagaaga gaaaggtaga tccaaaaaag aagagaaagg tagatccaaa aaagaagaga   660
aaggtagata cggccgcata g                                             681

SEQ ID NO: 7           moltype = DNA  length = 557
FEATURE                Location/Qualifiers
variation              320..339
                       note = wherein N is G, A, T or C
source                 1..557
                       mol_type = other DNA
                       organism = synthetic construct
SEQUENCE: 7
tgtacaaaaa agcaggcttt aaaggaacca attcagtcga ctggatccgg taccaaggtc    60
gggcaggaag agggcctatt tcccatgatt ccttcatatt tgcatatacg ataccaaggct   120
gttagagaga taattagaat taatttgact gtaaacacaa agatattagt acaaaatacg   180
tgacgtagaa agtaataatt tcttgggtag tttgcagttt taaaattatg ttttaaaatg   240
gactatcata tgcttaccgt aacttgaaag tatttcgatt tcttggcttt atatatcttg   300
tggaaaggac gaaacaccgn nnnnnnnnnn nnnnnnnnng ttttagagct agaaatagca   360
agttaaaata aggctagtcc gttatcaact tgaaaagtg gcaccgagtc ggtgctctgt   420
aggtcgactc tagaaaacat gaggatcacc catgtctgca gtattccgg gttcattaga   480
tcctaaggta cctaattgcc tagaaaacat gaggatcacc catgtctgca ggtcgactct   540
agaaattttt tctagac                                                  557

SEQ ID NO: 8           moltype = DNA  length = 882
FEATURE                Location/Qualifiers
misc_feature           1..882
                       note = Activation reporter construct
source                 1..882
                       mol_type = other DNA
                       organism = synthetic construct
SEQUENCE: 8
tagggataac agggtaatag tgtcccctcc accccacagt ggggcgaggt aggcgtgtac    60
ggtgggaggc ctatataagc agagctcgtt tagtgaaccg tcagatcgcc tggagaattc   120
gccaccatgg actacaagga tgacgacgat aaaaacttccg gtggcggact gggttccacc   180
gtgagcaagg gcgaggaggt catcaaagag ttcatgcgct tcaaggtgcg catggagggc   240
tccatgaacg gccacgagtt cgagatcgag ggcgagggcg agggccgccc ctacgagggc   300
acccagaccg ccaagctgaa ggtgaccaag ggcggccccc tgcccttcgc ctgggacatc   360
ctgtcccccc agttcatgta cggctccaag gcgtacgtga agcaccccgc cgacatcccc   420
gattacaaga agctgtcctt ccccgagggc ttcaagtggg agcgcgtgat gaacttcgag   480
gacggcggtc tggtgaccgt gacccaggac tcctccctgc aggacggcac gctgatctac   540
aaggtgaaga tgcgcggcac caacttcccc cccgacggcc ccgtaatgca gaagaagacc   600
atgggctggg aggcctccac cgagcgcctg taccccgcg acggcgtgct gaagggcgag   660
atccaccagg ccctgaagct gaaggacggg ggccactacc tggtggagtt caagaccatc   720
tacatggcca agaagcccgt gcaactgccc ggctactact acgtggacac caagctggac   780
atcacctccc acaacgagga ctacaccatc gtggaacagt acgagcgctc cgagggccgc   840
caccacctgt tcctgtacgg catggacgag ctgtacaagt aa                      882

SEQ ID NO: 9           moltype = DNA  length = 882
FEATURE                Location/Qualifiers
misc_feature           1..882
                       note = Activation reporter construct
source                 1..882
                       mol_type = other DNA
                       organism = synthetic construct
SEQUENCE: 9
tagggataac agggtaatag tggggccact agggacagga ttggcgaggt aggcgtgtac    60
ggtgggaggc ctatataagc agagctcgtt tagtgaaccg tcagatcgcc tggagaattc   120
gccaccatgg actacaagga tgacgacgat aaaaacttccg gtggcggact gggttccacc   180
gtgagcaagg gcgaggaggt catcaaagag ttcatgcgct tcaaggtgcg catggagggc   240
tccatgaacg gccacgagtt cgagatcgag ggcgagggcg agggccgccc ctacgagggc   300
acccagaccg ccaagctgaa ggtgaccaag ggcggccccc tgcccttcgc ctgggacatc   360
ctgtcccccc agttcatgta cggctccaag gcgtacgtga agcaccccgc cgacatcccc   420
gattacaaga agctgtcctt ccccgagggc ttcaagtggg agcgcgtgat gaacttcgag   480
gacggcggtc tggtgaccgt gacccaggac tcctccctgc aggacggcac gctgatctac   540
aaggtgaaga tgcgcggcac caacttcccc cccgacggcc ccgtaatgca gaagaagacc   600
atgggctggg aggcctccac cgagcgcctg taccccgcg acggcgtgct gaagggcgag   660
atccaccagg ccctgaagct gaaggacggg ggccactacc tggtggagtt caagaccatc   720
```

```
tacatggcca agaagcccgt gcaactgccc ggctactact acgtggacac caagctggac    780
atcacctccc acaacgagga ctacaccatc gtgaacagt acgagcgctc cgagggccgc    840
caccacctgt tcctgtacgg catggacgag ctgtacaagt aa                      882

SEQ ID NO: 10          moltype = DNA  length = 912
FEATURE                Location/Qualifiers
misc_feature           1..912
                       note = Specificity reporter library
variation              22..44
                       note = wherein N is G, A, T or C
variation              154..177
                       note = wherein N is G, A, T or C
source                 1..912
                       mol_type = other DNA
                       organism = synthetic construct
SEQUENCE: 10
tagggataac agggtaatag tnnnnnnnnn nnnnnnnnnn nnnncgaggt aggcgtgtac    60
ggtgggaggc ctatataagc agagctcgtt tagtgaaccg tcagatcgcc tggagaattc   120
gccaccatgg actacaagga tgacgacgat aaannnnnnn nnnnnnnnnn nnnnnnnact   180
tccggtggcg gactgggttc caccgtgagc aagggcgagg aggtcatcaa agagttcatg   240
cgcttcaagg tgcgcatgga gggctccatg aacggccacg agttcgagat cgagggcgag   300
ggcgagggcc gcccctacga gggcacccag accgccaagc tgaaggtgac caagggcgcc   360
ccctgccct tcgcctggga catcctgtcc ccccagttca tgtacggctc caaggcgtac    420
gtgaagcacc ccgccgacat ccccgattac aagaagctgt ccttccccga gggcttcaag   480
tgggagcgcg tgatgaactt cgaggacggc ggtctggtga ccgtgaccca ggactcctcc   540
ctgcaggacg gcacgctgat ctacaaggtg aagatgcgcg gcaccaactt cccccccgac   600
ggccccgtaa tgcagaagaa gaccatgggc tgggaggcct ccaccgagcg cctgtacccc   660
cgcgacggcg tgctgaaggg cgagatccac caggccctga gctgaagga cggcggccac    720
tacctggtgg agttcaagac catctacatg gccaagaagc ccgtcaact gcccggctac    780
tactacgtgg acaccaagct ggacatcacc tcccacaacg aggactacac catcgtggaa   840
cagtacgagc gctccgaggg ccgccaccac ctgttcctgt acggcatgga cgagctgtac   900
aagtaagaat tc                                                       912

SEQ ID NO: 11          moltype = DNA  length = 23
FEATURE                Location/Qualifiers
misc_feature           1..23
                       note = Target probe
source                 1..23
                       mol_type = other DNA
                       organism = synthetic construct
SEQUENCE: 11
ctggcggatc actcgcggtt agg                                            23

SEQ ID NO: 12          moltype = DNA  length = 23
FEATURE                Location/Qualifiers
misc_feature           1..23
                       note = Target probe
source                 1..23
                       mol_type = other DNA
                       organism = synthetic construct
SEQUENCE: 12
cctcggcctc caaaagtgct agg                                            23

SEQ ID NO: 13          moltype = DNA  length = 23
FEATURE                Location/Qualifiers
misc_feature           1..23
                       note = Target probe
source                 1..23
                       mol_type = other DNA
                       organism = synthetic construct
SEQUENCE: 13
acgctgattc ctgcagatca ggg                                            23

SEQ ID NO: 14          moltype = DNA  length = 23
FEATURE                Location/Qualifiers
misc_feature           1..23
                       note = Target probe
source                 1..23
                       mol_type = other DNA
                       organism = synthetic construct
SEQUENCE: 14
ccaggaatac gtatccacca ggg                                            23

SEQ ID NO: 15          moltype = DNA  length = 23
FEATURE                Location/Qualifiers
misc_feature           1..23
                       note = Target probe
source                 1..23
                       mol_type = other DNA
```

-continued

```
                            organism = synthetic construct
SEQUENCE: 15
gccacaccca agcgatcaaa tgg                                              23

SEQ ID NO: 16           moltype = DNA  length = 23
FEATURE                 Location/Qualifiers
misc_feature            1..23
                        note = Target probe
source                  1..23
                        mol_type = other DNA
                        organism = synthetic construct
SEQUENCE: 16
aaataataca ttctaaggta agg                                              23

SEQ ID NO: 17           moltype = DNA  length = 23
FEATURE                 Location/Qualifiers
misc_feature            1..23
                        note = Target probe
source                  1..23
                        mol_type = other DNA
                        organism = synthetic construct
SEQUENCE: 17
gctactgggg aggctgaggc agg                                              23

SEQ ID NO: 18           moltype = DNA  length = 23
FEATURE                 Location/Qualifiers
misc_feature            1..23
                        note = Target probe
source                  1..23
                        mol_type = other DNA
                        organism = synthetic construct
SEQUENCE: 18
tagcaataca gtcacattaa tgg                                              23

SEQ ID NO: 19           moltype = DNA  length = 23
FEATURE                 Location/Qualifiers
misc_feature            1..23
                        note = Target probe
source                  1..23
                        mol_type = other DNA
                        organism = synthetic construct
SEQUENCE: 19
ctcatgtgat cccccgtct cgg                                               23

SEQ ID NO: 20           moltype = DNA  length = 23
FEATURE                 Location/Qualifiers
misc_feature            1..23
                        note = Target probe
source                  1..23
                        mol_type = other DNA
                        organism = synthetic construct
SEQUENCE: 20
ccgggcagag agtgaacgcg cgg                                              23

SEQ ID NO: 21           moltype = DNA  length = 23
FEATURE                 Location/Qualifiers
misc_feature            1..23
                        note = Target probe
source                  1..23
                        mol_type = other DNA
                        organism = synthetic construct
SEQUENCE: 21
ttccttccct ctcccgtgct tgg                                              23

SEQ ID NO: 22           moltype = DNA  length = 23
FEATURE                 Location/Qualifiers
misc_feature            1..23
                        note = Target probe
source                  1..23
                        mol_type = other DNA
                        organism = synthetic construct
SEQUENCE: 22
tctctgcaaa gcccctggag agg                                              23

SEQ ID NO: 23           moltype = DNA  length = 23
FEATURE                 Location/Qualifiers
misc_feature            1..23
                        note = Target probe
source                  1..23
```

```
                        mol_type = other DNA
                        organism = synthetic construct
SEQUENCE: 23
aatgcagttg ccgagtgcag tgg                                         23

SEQ ID NO: 24           moltype = DNA   length = 23
FEATURE                 Location/Qualifiers
misc_feature            1..23
                        note = Target probe
source                  1..23
                        mol_type = other DNA
                        organism = synthetic construct
SEQUENCE: 24
cctcagcctc ctaaagtgct ggg                                         23

SEQ ID NO: 25           moltype = DNA   length = 23
FEATURE                 Location/Qualifiers
misc_feature            1..23
                        note = Target probe
source                  1..23
                        mol_type = other DNA
                        organism = synthetic construct
SEQUENCE: 25
gagtccaaat cctctttact agg                                         23

SEQ ID NO: 26           moltype = DNA   length = 23
FEATURE                 Location/Qualifiers
misc_feature            1..23
                        note = Target probe
source                  1..23
                        mol_type = other DNA
                        organism = synthetic construct
SEQUENCE: 26
gagtgtctgg atttgggata agg                                         23

SEQ ID NO: 27           moltype = DNA   length = 23
FEATURE                 Location/Qualifiers
misc_feature            1..23
                        note = Target probe
source                  1..23
                        mol_type = other DNA
                        organism = synthetic construct
SEQUENCE: 27
cagcacctca tctcccagtg agg                                         23

SEQ ID NO: 28           moltype = DNA   length = 23
FEATURE                 Location/Qualifiers
misc_feature            1..23
                        note = Target probe
source                  1..23
                        mol_type = other DNA
                        organism = synthetic construct
SEQUENCE: 28
tctaaaaccc agggaatcat ggg                                         23

SEQ ID NO: 29           moltype = DNA   length = 23
FEATURE                 Location/Qualifiers
misc_feature            1..23
                        note = Target probe
source                  1..23
                        mol_type = other DNA
                        organism = synthetic construct
SEQUENCE: 29
cacaaggcag ccagggatcc agg                                         23

SEQ ID NO: 30           moltype = DNA   length = 23
FEATURE                 Location/Qualifiers
misc_feature            1..23
                        note = Target probe
source                  1..23
                        mol_type = other DNA
                        organism = synthetic construct
SEQUENCE: 30
gatggcaagc tgagaaacac tgg                                         23

SEQ ID NO: 31           moltype = DNA   length = 23
FEATURE                 Location/Qualifiers
misc_feature            1..23
                        note = Target probe
```

```
                        source          1..23
                                        mol_type = other DNA
                                        organism = synthetic construct
SEQUENCE: 31
tgaaatgcac gcatacaatt agg                                               23

SEQ ID NO: 32           moltype = DNA   length = 23
FEATURE                 Location/Qualifiers
misc_feature            1..23
                        note = Target probe
source                  1..23
                        mol_type = other DNA
                        organism = synthetic construct
SEQUENCE: 32
ccagtccaga cctggccttc tgg                                               23

SEQ ID NO: 33           moltype = DNA   length = 23
FEATURE                 Location/Qualifiers
misc_feature            1..23
                        note = Target probe
source                  1..23
                        mol_type = other DNA
                        organism = synthetic construct
SEQUENCE: 33
cccagaaaaa cagaccctga agg                                               23

SEQ ID NO: 34           moltype = DNA   length = 23
FEATURE                 Location/Qualifiers
misc_feature            1..23
                        note = Target probe
source                  1..23
                        mol_type = other DNA
                        organism = synthetic construct
SEQUENCE: 34
aagggttgag cacttgttta ggg                                               23

SEQ ID NO: 35           moltype = DNA   length = 23
FEATURE                 Location/Qualifiers
misc_feature            1..23
                        note = Target probe
source                  1..23
                        mol_type = other DNA
                        organism = synthetic construct
SEQUENCE: 35
atgtctgagt tttggttgag agg                                               23

SEQ ID NO: 36           moltype = DNA   length = 23
FEATURE                 Location/Qualifiers
misc_feature            1..23
                        note = Target probe
source                  1..23
                        mol_type = other DNA
                        organism = synthetic construct
SEQUENCE: 36
ggtcccttga agggaagta ggg                                                23

SEQ ID NO: 37           moltype = DNA   length = 23
FEATURE                 Location/Qualifiers
misc_feature            1..23
                        note = Target probe
source                  1..23
                        mol_type = other DNA
                        organism = synthetic construct
SEQUENCE: 37
tggcagtcta ctcttgaaga tgg                                               23

SEQ ID NO: 38           moltype = DNA   length = 23
FEATURE                 Location/Qualifiers
misc_feature            1..23
                        note = Target probe
source                  1..23
                        mol_type = other DNA
                        organism = synthetic construct
SEQUENCE: 38
ggcacagtgc cagaggtctg tgg                                               23

SEQ ID NO: 39           moltype = DNA   length = 23
FEATURE                 Location/Qualifiers
misc_feature            1..23
```

```
                        note = Target probe
source                  1..23
                        mol_type = other DNA
                        organism = synthetic construct
SEQUENCE: 39
taaaaataaa aaaactaaca ggg                                          23

SEQ ID NO: 40           moltype = DNA   length = 23
FEATURE                 Location/Qualifiers
misc_feature            1..23
                        note = Target probe
source                  1..23
                        mol_type = other DNA
                        organism = synthetic construct
SEQUENCE: 40
tctgtgggg acctgcactg agg                                           23

SEQ ID NO: 41           moltype = DNA   length = 23
FEATURE                 Location/Qualifiers
misc_feature            1..23
                        note = Target probe
source                  1..23
                        mol_type = other DNA
                        organism = synthetic construct
SEQUENCE: 41
ggccagaggt caaggctagt ggg                                          23

SEQ ID NO: 42           moltype = DNA   length = 23
FEATURE                 Location/Qualifiers
misc_feature            1..23
                        note = Target probe
source                  1..23
                        mol_type = other DNA
                        organism = synthetic construct
SEQUENCE: 42
cacgaccgaa acccttctta cgg                                          23

SEQ ID NO: 43           moltype = DNA   length = 23
FEATURE                 Location/Qualifiers
misc_feature            1..23
                        note = Target probe
source                  1..23
                        mol_type = other DNA
                        organism = synthetic construct
SEQUENCE: 43
gttgaatgaa gacagtctag tgg                                          23

SEQ ID NO: 44           moltype = DNA   length = 23
FEATURE                 Location/Qualifiers
misc_feature            1..23
                        note = Target probe
source                  1..23
                        mol_type = other DNA
                        organism = synthetic construct
SEQUENCE: 44
taagaacaga gcaagttacg tgg                                          23

SEQ ID NO: 45           moltype = DNA   length = 23
FEATURE                 Location/Qualifiers
misc_feature            1..23
                        note = Target probe
source                  1..23
                        mol_type = other DNA
                        organism = synthetic construct
SEQUENCE: 45
tgtaaggtaa gagaggagag cgg                                          23

SEQ ID NO: 46           moltype = DNA   length = 23
FEATURE                 Location/Qualifiers
misc_feature            1..23
                        note = Target probe
source                  1..23
                        mol_type = other DNA
                        organism = synthetic construct
SEQUENCE: 46
tgacacacca actcctgcac tgg                                          23

SEQ ID NO: 47           moltype = DNA   length = 23
FEATURE                 Location/Qualifiers
```

-continued

```
                        1..23
misc_feature            note = Target probe
source                  1..23
                        mol_type = other DNA
                        organism = synthetic construct
SEQUENCE: 47
tttacccact tccttcgaaa agg                                               23

SEQ ID NO: 48           moltype = DNA  length = 23
FEATURE                 Location/Qualifiers
misc_feature            1..23
                        note = Target probe
source                  1..23
                        mol_type = other DNA
                        organism = synthetic construct
SEQUENCE: 48
gtggctggca ggctggctct ggg                                               23

SEQ ID NO: 49           moltype = DNA  length = 23
FEATURE                 Location/Qualifiers
misc_feature            1..23
                        note = Target probe
source                  1..23
                        mol_type = other DNA
                        organism = synthetic construct
SEQUENCE: 49
ctcccccggc ctcccccgcg cgg                                               23

SEQ ID NO: 50           moltype = DNA  length = 23
FEATURE                 Location/Qualifiers
misc_feature            1..23
                        note = Target probe
source                  1..23
                        mol_type = other DNA
                        organism = synthetic construct
SEQUENCE: 50
caaaacccgg cagcgaggct ggg                                               23

SEQ ID NO: 51           moltype = DNA  length = 23
FEATURE                 Location/Qualifiers
misc_feature            1..23
                        note = Target probe
source                  1..23
                        mol_type = other DNA
                        organism = synthetic construct
SEQUENCE: 51
aggagccgcc gcgcgctgat tgg                                               23

SEQ ID NO: 52           moltype = DNA  length = 23
FEATURE                 Location/Qualifiers
misc_feature            1..23
                        note = Target probe
source                  1..23
                        mol_type = other DNA
                        organism = synthetic construct
SEQUENCE: 52
cacacacacc cacacgagat ggg                                               23

SEQ ID NO: 53           moltype = DNA  length = 23
FEATURE                 Location/Qualifiers
misc_feature            1..23
                        note = Target probe
source                  1..23
                        mol_type = other DNA
                        organism = synthetic construct
SEQUENCE: 53
gaagaagcta aagagccaga ggg                                               23

SEQ ID NO: 54           moltype = DNA  length = 23
FEATURE                 Location/Qualifiers
misc_feature            1..23
                        note = Target probe
source                  1..23
                        mol_type = other DNA
                        organism = synthetic construct
SEQUENCE: 54
atgagaattt caataacctc agg                                               23

SEQ ID NO: 55           moltype = DNA  length = 23
```

```
FEATURE                 Location/Qualifiers
misc_feature            1..23
                        note = Target probe
source                  1..23
                        mol_type = other DNA
                        organism = synthetic construct
SEQUENCE: 55
tcccgctctg ttgcccaggc tgg                                              23

SEQ ID NO: 56           moltype = DNA  length = 23
FEATURE                 Location/Qualifiers
misc_feature            1..23
                        note = Target probe
source                  1..23
                        mol_type = other DNA
                        organism = synthetic construct
SEQUENCE: 56
cagacaccca ccaccatgcg tgg                                              23

SEQ ID NO: 57           moltype = DNA  length = 23
FEATURE                 Location/Qualifiers
misc_feature            1..23
                        note = Target probe
source                  1..23
                        mol_type = other DNA
                        organism = synthetic construct
SEQUENCE: 57
tcccaattta ctgggattac agg                                              23

SEQ ID NO: 58           moltype = DNA  length = 23
FEATURE                 Location/Qualifiers
misc_feature            1..23
                        note = Target probe
source                  1..23
                        mol_type = other DNA
                        organism = synthetic construct
SEQUENCE: 58
tgatttaaaa gttggaaacg tgg                                              23

SEQ ID NO: 59           moltype = DNA  length = 23
FEATURE                 Location/Qualifiers
misc_feature            1..23
                        note = Target probe
source                  1..23
                        mol_type = other DNA
                        organism = synthetic construct
SEQUENCE: 59
tctagttccc cacctagtct ggg                                              23

SEQ ID NO: 60           moltype = DNA  length = 23
FEATURE                 Location/Qualifiers
misc_feature            1..23
                        note = Target probe
source                  1..23
                        mol_type = other DNA
                        organism = synthetic construct
SEQUENCE: 60
gattaactga gaattcacaa ggg                                              23

SEQ ID NO: 61           moltype = DNA  length = 23
FEATURE                 Location/Qualifiers
misc_feature            1..23
                        note = Target probe
source                  1..23
                        mol_type = other DNA
                        organism = synthetic construct
SEQUENCE: 61
cgccaggagg ggtgggtcta agg                                              23

SEQ ID NO: 62           moltype = DNA  length = 23
FEATURE                 Location/Qualifiers
misc_feature            1..23
                        note = Reporter construct
source                  1..23
                        mol_type = other DNA
                        organism = synthetic construct
SEQUENCE: 62
gtcccctcca ccccacagtg ggg                                              23
```

```
SEQ ID NO: 63              moltype = DNA  length = 23
FEATURE                    Location/Qualifiers
misc_feature               1..23
                           note = Reporter construct
source                     1..23
                           mol_type = other DNA
                           organism = synthetic construct
SEQUENCE: 63
ggggccacta gggacaggat tgg                                              23

SEQ ID NO: 64              moltype = DNA  length = 71
FEATURE                    Location/Qualifiers
misc_feature               1..71
                           note = Target oligonucleotide sequence
source                     1..71
                           mol_type = other DNA
                           organism = synthetic construct
SEQUENCE: 64
taatactttt atctgtcccc tccaccccac agtggggcca ctagggacag gattggtgac      60
agaaaagccc c                                                          71

SEQ ID NO: 65              moltype = DNA  length = 20
FEATURE                    Location/Qualifiers
misc_feature               1..20
                           note = Target oligonucleotide sequence
source                     1..20
                           mol_type = other DNA
                           organism = synthetic construct
SEQUENCE: 65
ggggccacta gggacaggat                                                  20

SEQ ID NO: 66              moltype = RNA  length = 80
FEATURE                    Location/Qualifiers
misc_feature               1..80
                           note = Guide RNA
source                     1..80
                           mol_type = other RNA
                           organism = synthetic construct
SEQUENCE: 66
gttttagagc tagaaatagc aagttaaaat aaggctagtc cgttatcaac ttgaaaaagt      60
ggcaccgagt cggtgctttt                                                  80

SEQ ID NO: 67              moltype = DNA  length = 23
FEATURE                    Location/Qualifiers
misc_feature               1..23
                           note = Target oligonucleotide sequence
source                     1..23
                           mol_type = other DNA
                           organism = synthetic construct
SEQUENCE: 67
gtcccctcca ccccacagtg cag                                              23

SEQ ID NO: 68              moltype = DNA  length = 23
FEATURE                    Location/Qualifiers
misc_feature               1..23
                           note = Target oligonucleotide sequence
source                     1..23
                           mol_type = other DNA
                           organism = synthetic construct
SEQUENCE: 68
gtccctcca ccccacagtg caa                                               23

SEQ ID NO: 69              moltype = DNA  length = 23
FEATURE                    Location/Qualifiers
misc_feature               1..23
                           note = Target oligonucleotide sequence
source                     1..23
                           mol_type = other DNA
                           organism = synthetic construct
SEQUENCE: 69
gtcccctcca ccccacagtg cgg                                              23

SEQ ID NO: 70              moltype = DNA  length = 52
FEATURE                    Location/Qualifiers
misc_feature               1..52
                           note = Target oligonucleotide sequence
source                     1..52
                           mol_type = other DNA
                           organism = synthetic construct
```

```
SEQUENCE: 70
tgtcccctcc accccacagt ggggccacta gggacaggat tggtgacaga aa        52

SEQ ID NO: 71           moltype = DNA   length = 52
FEATURE                 Location/Qualifiers
misc_feature            1..52
                        note = Target oligonucleotide sequence
source                  1..52
                        mol_type = other DNA
                        organism = synthetic construct
SEQUENCE: 71
tgtccccccc accccacagt ggggccacta gggacaggat tggtgacaga aa        52

SEQ ID NO: 72           moltype = DNA   length = 52
FEATURE                 Location/Qualifiers
misc_feature            1..52
                        note = Target oligonucleotide sequence
source                  1..52
                        mol_type = other DNA
                        organism = synthetic construct
SEQUENCE: 72
aaaaccctcc accccacagt ggggccacta gggacaggat tggtgacaga aa        52

SEQ ID NO: 73           moltype = DNA   length = 52
FEATURE                 Location/Qualifiers
misc_feature            1..52
                        note = Target oligonucleotide sequence
source                  1..52
                        mol_type = other DNA
                        organism = synthetic construct
SEQUENCE: 73
tgtccctcc tttttcagt ggggccacta gggacaggat tggtgacaga aa          52

SEQ ID NO: 74           moltype = DNA   length = 23
FEATURE                 Location/Qualifiers
misc_feature            1..23
                        note = Target oligonucleotide sequence
source                  1..23
                        mol_type = other DNA
                        organism = synthetic construct
SEQUENCE: 74
caccggggtg gtgcccatcc tgg                                        23

SEQ ID NO: 75           moltype = DNA   length = 23
FEATURE                 Location/Qualifiers
misc_feature            1..23
                        note = Target oligonucleotide sequence
source                  1..23
                        mol_type = other DNA
                        organism = synthetic construct
SEQUENCE: 75
ggtgcccatc ctggtcgagc tgg                                        23

SEQ ID NO: 76           moltype = DNA   length = 23
FEATURE                 Location/Qualifiers
misc_feature            1..23
                        note = Target oligonucleotide sequence
source                  1..23
                        mol_type = other DNA
                        organism = synthetic construct
SEQUENCE: 76
cccatcctgg tcgagctgga cgg                                        23

SEQ ID NO: 77           moltype = DNA   length = 23
FEATURE                 Location/Qualifiers
misc_feature            1..23
                        note = Target oligonucleotide sequence
source                  1..23
                        mol_type = other DNA
                        organism = synthetic construct
SEQUENCE: 77
ggccacaagt tcagcgtgtc cgg                                        23

SEQ ID NO: 78           moltype = DNA   length = 23
FEATURE                 Location/Qualifiers
misc_feature            1..23
                        note = Target oligonucleotide sequence
source                  1..23
                        mol_type = other DNA
```

-continued

```
                            organism = synthetic construct
SEQUENCE: 78
cgcaaataag agctcaccta cgg                                          23

SEQ ID NO: 79               moltype = DNA  length = 23
FEATURE                     Location/Qualifiers
misc_feature                1..23
                            note = Target oligonucleotide sequence
source                      1..23
                            mol_type = other DNA
                            organism = synthetic construct
SEQUENCE: 79
ctgaagttca tctgcaccac cgg                                          23

SEQ ID NO: 80               moltype = DNA  length = 23
FEATURE                     Location/Qualifiers
misc_feature                1..23
                            note = Target oligonucleotide sequence
source                      1..23
                            mol_type = other DNA
                            organism = synthetic construct
SEQUENCE: 80
ccggcaagct gcccgtgccc tgg                                          23

SEQ ID NO: 81               moltype = DNA  length = 23
FEATURE                     Location/Qualifiers
misc_feature                1..23
                            note = Target oligonucleotide sequence
source                      1..23
                            mol_type = other DNA
                            organism = synthetic construct
SEQUENCE: 81
gaccaggatg ggcaccaccc cgg                                          23

SEQ ID NO: 82               moltype = DNA  length = 23
FEATURE                     Location/Qualifiers
misc_feature                1..23
                            note = Target oligonucleotide sequence
source                      1..23
                            mol_type = other DNA
                            organism = synthetic construct
SEQUENCE: 82
gccgtccagc tcgaccagga tgg                                          23

SEQ ID NO: 83               moltype = DNA  length = 23
FEATURE                     Location/Qualifiers
misc_feature                1..23
                            note = Target oligonucleotide sequence
source                      1..23
                            mol_type = other DNA
                            organism = synthetic construct
SEQUENCE: 83
ggccggacac gctgaacttg tgg                                          23

SEQ ID NO: 84               moltype = DNA  length = 23
FEATURE                     Location/Qualifiers
misc_feature                1..23
                            note = Target oligonucleotide sequence
source                      1..23
                            mol_type = other DNA
                            organism = synthetic construct
SEQUENCE: 84
taacagggta atgtcgaggc cgg                                          23

SEQ ID NO: 85               moltype = DNA  length = 23
FEATURE                     Location/Qualifiers
misc_feature                1..23
                            note = Target oligonucleotide sequence
source                      1..23
                            mol_type = other DNA
                            organism = synthetic construct
SEQUENCE: 85
aggtgagctc ttatttgcgt agg                                          23

SEQ ID NO: 86               moltype = DNA  length = 23
FEATURE                     Location/Qualifiers
misc_feature                1..23
                            note = Target oligonucleotide sequence
source                      1..23
```

```
                              mol_type = other DNA
                              organism = synthetic construct
SEQUENCE: 86
cttcagggtc agcttgccgt agg                                                 23

SEQ ID NO: 87            moltype = DNA  length = 23
FEATURE                  Location/Qualifiers
misc_feature             1..23
                         note = Target oligonucleotide sequence
source                   1..23
                         mol_type = other DNA
                         organism = synthetic construct
SEQUENCE: 87
gggcacgggc agcttgccgg tgg                                                 23

SEQ ID NO: 88            moltype = DNA  length = 23
FEATURE                  Location/Qualifiers
misc_feature             1..23
                         note = Target oligonucleotide sequence
source                   1..23
                         mol_type = other DNA
                         organism = synthetic construct
SEQUENCE: 88
gagatgatcg cccttcttc tgg                                                  23

SEQ ID NO: 89            moltype = DNA  length = 20
FEATURE                  Location/Qualifiers
misc_feature             1..20
                         note = Target oligonucleotide sequence
source                   1..20
                         mol_type = other DNA
                         organism = synthetic construct
SEQUENCE: 89
gagatgatcg cccttcttc                                                      20

SEQ ID NO: 90            moltype = DNA  length = 20
FEATURE                  Location/Qualifiers
misc_feature             1..20
                         note = Target oligonucleotide sequence
source                   1..20
                         mol_type = other DNA
                         organism = synthetic construct
SEQUENCE: 90
gtgatgaccg gccgttcttc                                                     20

SEQ ID NO: 91            moltype = DNA  length = 23
FEATURE                  Location/Qualifiers
misc_feature             1..23
                         note = Target oligonucleotide sequence
source                   1..23
                         mol_type = other DNA
                         organism = synthetic construct
SEQUENCE: 91
gtcccctcca ccccacagtg ggg                                                 23

SEQ ID NO: 92            moltype = DNA  length = 23
FEATURE                  Location/Qualifiers
misc_feature             1..23
                         note = Target oligonucleotide sequence
source                   1..23
                         mol_type = other DNA
                         organism = synthetic construct
SEQUENCE: 92
gagatgatcg cccgttcttc tgg                                                 23

SEQ ID NO: 93            moltype = RNA  length = 20
FEATURE                  Location/Qualifiers
misc_feature             1..20
                         note = RNA target sequence
source                   1..20
                         mol_type = other RNA
                         organism = synthetic construct
SEQUENCE: 93
gtcccctcca ccccacagtg                                                     20

SEQ ID NO: 94            moltype = RNA  length = 20
FEATURE                  Location/Qualifiers
misc_feature             1..20
                         note = RNA target sequence
```

```
source                      1..20
                            mol_type = other RNA
                            organism = synthetic construct
SEQUENCE: 94
gtcccctcca ccccacagtc                                                  20

SEQ ID NO: 95               moltype = RNA   length = 20
FEATURE                     Location/Qualifiers
misc_feature                1..20
                            note = RNA target sequence
source                      1..20
                            mol_type = other RNA
                            organism = synthetic construct
SEQUENCE: 95
gtcccctcca ccccacagag                                                  20

SEQ ID NO: 96               moltype = RNA   length = 20
FEATURE                     Location/Qualifiers
misc_feature                1..20
                            note = RNA target sequence
source                      1..20
                            mol_type = other RNA
                            organism = synthetic construct
SEQUENCE: 96
gtcccctcca ccccacactg                                                  20

SEQ ID NO: 97               moltype = RNA   length = 20
FEATURE                     Location/Qualifiers
misc_feature                1..20
                            note = RNA target sequence
source                      1..20
                            mol_type = other RNA
                            organism = synthetic construct
SEQUENCE: 97
gtcccctcca ccccactgtg                                                  20

SEQ ID NO: 98               moltype = RNA   length = 20
FEATURE                     Location/Qualifiers
misc_feature                1..20
                            note = RNA target sequence
source                      1..20
                            mol_type = other RNA
                            organism = synthetic construct
SEQUENCE: 98
gtcccctcca ccccagagtg                                                  20

SEQ ID NO: 99               moltype = RNA   length = 20
FEATURE                     Location/Qualifiers
misc_feature                1..20
                            note = RNA target sequence
source                      1..20
                            mol_type = other RNA
                            organism = synthetic construct
SEQUENCE: 99
gtcccctcca cccctcagtg                                                  20

SEQ ID NO: 100              moltype = RNA   length = 20
FEATURE                     Location/Qualifiers
misc_feature                1..20
                            note = RNA target sequence
source                      1..20
                            mol_type = other RNA
                            organism = synthetic construct
SEQUENCE: 100
gtcccctcca cccgacagtg                                                  20

SEQ ID NO: 101              moltype = RNA   length = 20
FEATURE                     Location/Qualifiers
misc_feature                1..20
                            note = RNA target sequence
source                      1..20
                            mol_type = other RNA
                            organism = synthetic construct
SEQUENCE: 101
gtcccctcca ccgacagtg                                                   20

SEQ ID NO: 102              moltype = RNA   length = 20
FEATURE                     Location/Qualifiers
misc_feature                1..20
```

```
                      note = RNA target sequence
source                1..20
                      mol_type = other RNA
                      organism = synthetic construct
SEQUENCE: 102
gtccctcca cgccacagtg                                                    20

SEQ ID NO: 103        moltype = RNA   length = 20
FEATURE               Location/Qualifiers
misc_feature          1..20
                      note = RNA target sequence
source                1..20
                      mol_type = other RNA
                      organism = synthetic construct
SEQUENCE: 103
gtccctcca gcccacagtg                                                    20

SEQ ID NO: 104        moltype = RNA   length = 20
FEATURE               Location/Qualifiers
misc_feature          1..20
                      note = RNA target sequence
source                1..20
                      mol_type = other RNA
                      organism = synthetic construct
SEQUENCE: 104
gtccctcct ccccacagtg                                                    20

SEQ ID NO: 105        moltype = RNA   length = 20
FEATURE               Location/Qualifiers
misc_feature          1..20
                      note = RNA target sequence
source                1..20
                      mol_type = other RNA
                      organism = synthetic construct
SEQUENCE: 105
gtccctcga ccccacagtg                                                    20

SEQ ID NO: 106        moltype = RNA   length = 20
FEATURE               Location/Qualifiers
misc_feature          1..20
                      note = RNA target sequence
source                1..20
                      mol_type = other RNA
                      organism = synthetic construct
SEQUENCE: 106
gtccctcca ccccacagac                                                    20

SEQ ID NO: 107        moltype = RNA   length = 20
FEATURE               Location/Qualifiers
misc_feature          1..20
                      note = RNA target sequence
source                1..20
                      mol_type = other RNA
                      organism = synthetic construct
SEQUENCE: 107
gtccctcca ccccactctg                                                    20

SEQ ID NO: 108        moltype = RNA   length = 20
FEATURE               Location/Qualifiers
misc_feature          1..20
                      note = RNA target sequence
source                1..20
                      mol_type = other RNA
                      organism = synthetic construct
SEQUENCE: 108
gtccctcca ccctgagtg                                                     20

SEQ ID NO: 109        moltype = RNA   length = 20
FEATURE               Location/Qualifiers
misc_feature          1..20
                      note = RNA target sequence
source                1..20
                      mol_type = other RNA
                      organism = synthetic construct
SEQUENCE: 109
gtccctcca ccggacagtg                                                    20

SEQ ID NO: 110        moltype = RNA   length = 20
FEATURE               Location/Qualifiers
```

```
misc_feature              1..20
                          note = RNA target sequence
source                    1..20
                          mol_type = other RNA
                          organism = synthetic construct
SEQUENCE: 110
gtccctcca ggccacagtg                                                    20

SEQ ID NO: 111            moltype = RNA  length = 20
FEATURE                   Location/Qualifiers
misc_feature              1..20
                          note = RNA target sequence
source                    1..20
                          mol_type = other RNA
                          organism = synthetic construct
SEQUENCE: 111
gtccctcgt ccccacagtg                                                    20

SEQ ID NO: 112            moltype = DNA  length = 23
FEATURE                   Location/Qualifiers
misc_feature              1..23
                          note = Target oligonucleotide sequence
source                    1..23
                          mol_type = other DNA
                          organism = synthetic construct
SEQUENCE: 112
ggggccacta gggacaggat ggg                                               23

SEQ ID NO: 113            moltype = RNA  length = 20
FEATURE                   Location/Qualifiers
misc_feature              1..20
                          note = RNA target sequence
source                    1..20
                          mol_type = other RNA
                          organism = synthetic construct
SEQUENCE: 113
gagatgatcg ccccttcttc                                                   20

SEQ ID NO: 114            moltype = RNA  length = 20
FEATURE                   Location/Qualifiers
misc_feature              1..20
                          note = RNA target sequence
source                    1..20
                          mol_type = other RNA
                          organism = synthetic construct
SEQUENCE: 114
gagatgatcg ccccttcttg                                                   20

SEQ ID NO: 115            moltype = RNA  length = 20
FEATURE                   Location/Qualifiers
misc_feature              1..20
                          note = RNA target sequence
source                    1..20
                          mol_type = other RNA
                          organism = synthetic construct
SEQUENCE: 115
gagatgatcg ccccttctac                                                   20

SEQ ID NO: 116            moltype = RNA  length = 20
FEATURE                   Location/Qualifiers
misc_feature              1..20
                          note = RNA target sequence
source                    1..20
                          mol_type = other RNA
                          organism = synthetic construct
SEQUENCE: 116
gagatgatcg ccccttcatc                                                   20

SEQ ID NO: 117            moltype = RNA  length = 20
FEATURE                   Location/Qualifiers
misc_feature              1..20
                          note = RNA target sequence
source                    1..20
                          mol_type = other RNA
                          organism = synthetic construct
SEQUENCE: 117
gagatgatcg ccccttgttc                                                   20

SEQ ID NO: 118            moltype = RNA  length = 20
```

```
FEATURE                 Location/Qualifiers
misc_feature            1..20
                        note = RNA target sequence
source                  1..20
                        mol_type = other RNA
                        organism = synthetic construct
SEQUENCE: 118
gagatgatcg ccctacttc                                                    20

SEQ ID NO: 119          moltype = RNA  length = 20
FEATURE                 Location/Qualifiers
misc_feature            1..20
                        note = RNA target sequence
source                  1..20
                        mol_type = other RNA
                        organism = synthetic construct
SEQUENCE: 119
gagatgatcg ccccatcttc                                                   20

SEQ ID NO: 120          moltype = RNA  length = 20
FEATURE                 Location/Qualifiers
misc_feature            1..20
                        note = RNA target sequence
source                  1..20
                        mol_type = other RNA
                        organism = synthetic construct
SEQUENCE: 120
gagatgatcg cccgttcttc                                                   20

SEQ ID NO: 121          moltype = RNA  length = 20
FEATURE                 Location/Qualifiers
misc_feature            1..20
                        note = RNA target sequence
source                  1..20
                        mol_type = other RNA
                        organism = synthetic construct
SEQUENCE: 121
gagatgatcg ccgcttcttc                                                   20

SEQ ID NO: 122          moltype = RNA  length = 20
FEATURE                 Location/Qualifiers
misc_feature            1..20
                        note = RNA target sequence
source                  1..20
                        mol_type = other RNA
                        organism = synthetic construct
SEQUENCE: 122
gagatgatcg cgccttcttc                                                   20

SEQ ID NO: 123          moltype = RNA  length = 20
FEATURE                 Location/Qualifiers
misc_feature            1..20
                        note = RNA target sequence
source                  1..20
                        mol_type = other RNA
                        organism = synthetic construct
SEQUENCE: 123
gagatgatcg gcccttcttc                                                   20

SEQ ID NO: 124          moltype = RNA  length = 20
FEATURE                 Location/Qualifiers
misc_feature            1..20
                        note = RNA target sequence
source                  1..20
                        mol_type = other RNA
                        organism = synthetic construct
SEQUENCE: 124
gagatgatcc cccttcttc                                                    20

SEQ ID NO: 125          moltype = RNA  length = 20
FEATURE                 Location/Qualifiers
misc_feature            1..20
                        note = RNA target sequence
source                  1..20
                        mol_type = other RNA
                        organism = synthetic construct
SEQUENCE: 125
gagatgatgg cccttcttc                                                    20
```

| | | |
|---|---|---|
| SEQ ID NO: 126<br>FEATURE<br>misc_feature<br>source | moltype = RNA length = 20<br>Location/Qualifiers<br>1..20<br>note = RNA target sequence<br>1..20<br>mol_type = other RNA<br>organism = synthetic construct | |
| SEQUENCE: 126<br>gagatgatcg cccottctag | | 20 |
| SEQ ID NO: 127<br>FEATURE<br>misc_feature<br>source | moltype = RNA length = 20<br>Location/Qualifiers<br>1..20<br>note = RNA target sequence<br>1..20<br>mol_type = other RNA<br>organism = synthetic construct | |
| SEQUENCE: 127<br>gagatgatcg cccottgatc | | 20 |
| SEQ ID NO: 128<br>FEATURE<br>misc_feature<br>source | moltype = RNA length = 20<br>Location/Qualifiers<br>1..20<br>note = RNA target sequence<br>1..20<br>mol_type = other RNA<br>organism = synthetic construct | |
| SEQUENCE: 128<br>gagatgatcg ccccaacttc | | 20 |
| SEQ ID NO: 129<br>FEATURE<br>misc_feature<br>source | moltype = RNA length = 20<br>Location/Qualifiers<br>1..20<br>note = RNA target sequence<br>1..20<br>mol_type = other RNA<br>organism = synthetic construct | |
| SEQUENCE: 129<br>gagatgatcg ccggttcttc | | 20 |
| SEQ ID NO: 130<br>FEATURE<br>misc_feature<br>source | moltype = RNA length = 20<br>Location/Qualifiers<br>1..20<br>note = RNA target sequence<br>1..20<br>mol_type = other RNA<br>organism = synthetic construct | |
| SEQUENCE: 130<br>gagatgatcg ggccttcttc | | 20 |
| SEQ ID NO: 131<br>FEATURE<br>misc_feature<br>source | moltype = RNA length = 20<br>Location/Qualifiers<br>1..20<br>note = RNA target sequence<br>1..20<br>mol_type = other RNA<br>organism = synthetic construct | |
| SEQUENCE: 131<br>gagatgatgc cccottcttc | | 20 |
| SEQ ID NO: 132<br>FEATURE<br>misc_feature<br>source | moltype = DNA length = 23<br>Location/Qualifiers<br>1..23<br>note = Target oligonucleotide sequence<br>1..23<br>mol_type = other DNA<br>organism = synthetic construct | |
| SEQUENCE: 132<br>gagatgatcg cccottcttc tgg | | 23 |
| SEQ ID NO: 133<br>FEATURE<br>misc_feature<br>source | moltype = RNA length = 20<br>Location/Qualifiers<br>1..20<br>note = RNA target sequence<br>1..20<br>mol_type = other RNA<br>organism = synthetic construct | |
| SEQUENCE: 133<br>ggggccacta gggacaggat | | 20 |

| | | |
|---|---|---|
| SEQ ID NO: 134<br>FEATURE<br>misc_feature<br><br>source | moltype = RNA  length = 19<br>Location/Qualifiers<br>1..19<br>note = RNA target sequence<br>1..19<br>mol_type = other RNA<br>organism = synthetic construct | |
| SEQUENCE: 134<br>gggccactag ggacaggat | | 19 |
| SEQ ID NO: 135<br>FEATURE<br>misc_feature<br><br>source | moltype = RNA  length = 18<br>Location/Qualifiers<br>1..18<br>note = RNA target sequence<br>1..18<br>mol_type = other RNA<br>organism = synthetic construct | |
| SEQUENCE: 135<br>ggccactagg gacaggat | | 18 |
| SEQ ID NO: 136<br>FEATURE<br>misc_feature<br><br>source | moltype = RNA  length = 17<br>Location/Qualifiers<br>1..17<br>note = RNA target sequence<br>1..17<br>mol_type = other RNA<br>organism = synthetic construct | |
| SEQUENCE: 136<br>gccactaggg acaggat | | 17 |
| SEQ ID NO: 137<br>FEATURE<br>misc_feature<br><br>source | moltype = RNA  length = 20<br>Location/Qualifiers<br>1..20<br>note = RNA target sequence<br>1..20<br>mol_type = other RNA<br>organism = synthetic construct | |
| SEQUENCE: 137<br>gagatgatcg ccccttcttc | | 20 |
| SEQ ID NO: 138<br>FEATURE<br>misc_feature<br><br>source | moltype = RNA  length = 18<br>Location/Qualifiers<br>1..18<br>note = RNA target sequence<br>1..18<br>mol_type = other RNA<br>organism = synthetic construct | |
| SEQUENCE: 138<br>gatgatcgcc ccttcttc | | 18 |
| SEQ ID NO: 139<br>FEATURE<br>misc_feature<br><br>source | moltype = RNA  length = 15<br>Location/Qualifiers<br>1..15<br>note = RNA target sequence<br>1..15<br>mol_type = other RNA<br>organism = synthetic construct | |
| SEQUENCE: 139<br>gatcgcccct tcttc | | 15 |
| SEQ ID NO: 140<br>FEATURE<br>misc_feature<br><br>source | moltype = RNA  length = 11<br>Location/Qualifiers<br>1..11<br>note = RNA target sequence<br>1..11<br>mol_type = other RNA<br>organism = synthetic construct | |
| SEQUENCE: 140<br>gccccttctt c | | 11 |
| SEQ ID NO: 141<br>FEATURE<br>misc_feature<br><br>source | moltype = DNA  length = 23<br>Location/Qualifiers<br>1..23<br>note = Target oligonucleotide sequence<br>1..23<br>mol_type = other DNA<br>organism = synthetic construct | |
| SEQUENCE: 141 | | |

```
gtcccctcca ccccacagtg crr                                                23

SEQ ID NO: 142          moltype =   length =
SEQUENCE: 142
000

SEQ ID NO: 143          moltype = DNA   length = 14
FEATURE                 Location/Qualifiers
misc_feature            1..14
                        note = Target oligonucleotide sequence
source                  1..14
                        mol_type = other DNA
                        organism = synthetic construct
SEQUENCE: 143
tgtcaaaaaa accc                                                          14

SEQ ID NO: 144          moltype = DNA   length = 14
FEATURE                 Location/Qualifiers
misc_feature            1..14
                        note = Target oligonucleotide sequence
source                  1..14
                        mol_type = other DNA
                        organism = synthetic construct
SEQUENCE: 144
tgtcgggggg accc                                                          14

SEQ ID NO: 145          moltype = DNA   length = 14
FEATURE                 Location/Qualifiers
misc_feature            1..14
                        note = Target oligonucleotide sequence
source                  1..14
                        mol_type = other DNA
                        organism = synthetic construct
SEQUENCE: 145
tgtcaaaaaa accc                                                          14

SEQ ID NO: 146          moltype = DNA   length = 14
FEATURE                 Location/Qualifiers
misc_feature            1..14
                        note = Target oligonucleotide sequence
source                  1..14
                        mol_type = other DNA
                        organism = synthetic construct
SEQUENCE: 146
tgtcgggggg accc                                                          14

SEQ ID NO: 147          moltype = DNA   length = 14
FEATURE                 Location/Qualifiers
misc_feature            1..14
                        note = Target oligonucleotide sequence
source                  1..14
                        mol_type = other DNA
                        organism = synthetic construct
SEQUENCE: 147
tgtcccccccc accc                                                         14

SEQ ID NO: 148          moltype = DNA   length = 14
FEATURE                 Location/Qualifiers
misc_feature            1..14
                        note = Target oligonucleotide sequence
source                  1..14
                        mol_type = other DNA
                        organism = synthetic construct
SEQUENCE: 148
tgtctttttt accc                                                          14

SEQ ID NO: 149          moltype = DNA   length = 14
FEATURE                 Location/Qualifiers
misc_feature            1..14
                        note = Target oligonucleotide sequence
source                  1..14
                        mol_type = other DNA
                        organism = synthetic construct
SEQUENCE: 149
tgtccccccc accc                                                          14

SEQ ID NO: 150          moltype = DNA   length = 14
FEATURE                 Location/Qualifiers
misc_feature            1..14
```

```
                    note = Target oligonucleotide sequence
source              1..14
                    mol_type = other DNA
                    organism = synthetic construct
SEQUENCE: 150
tgtctttttt accc                                                         14

SEQ ID NO: 151      moltype = DNA  length = 23
FEATURE             Location/Qualifiers
misc_feature        1..23
                    note = Target oligonucleotide sequence
source              1..23
                    mol_type = other DNA
                    organism = synthetic construct
SEQUENCE: 151
ggatcctgtg tccccgagct ggg                                               23

SEQ ID NO: 152      moltype = DNA  length = 23
FEATURE             Location/Qualifiers
misc_feature        1..23
                    note = Target oligonucleotide sequence
source              1..23
                    mol_type = other DNA
                    organism = synthetic construct
SEQUENCE: 152
gttaatgtgg ctctggttct ggg                                               23

SEQ ID NO: 153      moltype = DNA  length = 23
FEATURE             Location/Qualifiers
misc_feature        1..23
                    note = Target oligonucleotide sequence
source              1..23
                    mol_type = other DNA
                    organism = synthetic construct
SEQUENCE: 153
ggggccacta gggacaggat tgg                                               23

SEQ ID NO: 154      moltype = DNA  length = 23
FEATURE             Location/Qualifiers
misc_feature        1..23
                    note = Target oligonucleotide sequence
source              1..23
                    mol_type = other DNA
                    organism = synthetic construct
SEQUENCE: 154
cttcctagtc tcctgatatt ggg                                               23

SEQ ID NO: 155      moltype = DNA  length = 23
FEATURE             Location/Qualifiers
misc_feature        1..23
                    note = Target oligonucleotide sequence
source              1..23
                    mol_type = other DNA
                    organism = synthetic construct
SEQUENCE: 155
tggtcccagc tcggggacac agg                                               23

SEQ ID NO: 156      moltype = DNA  length = 23
FEATURE             Location/Qualifiers
misc_feature        1..23
                    note = Target oligonucleotide sequence
source              1..23
                    mol_type = other DNA
                    organism = synthetic construct
SEQUENCE: 156
agaaccagag ccacattaac cgg                                               23

SEQ ID NO: 157      moltype = DNA  length = 23
FEATURE             Location/Qualifiers
misc_feature        1..23
                    note = Target oligonucleotide sequence
source              1..23
                    mol_type = other DNA
                    organism = synthetic construct
SEQUENCE: 157
gtcaccaatc ctgtccctag tgg                                               23

SEQ ID NO: 158      moltype = DNA  length = 23
FEATURE             Location/Qualifiers
```

```
misc_feature            1..23
                        note = Target oligonucleotide sequence
source                  1..23
                        mol_type = other DNA
                        organism = synthetic construct
SEQUENCE: 158
agacccaata tcaggagact agg                                              23

SEQ ID NO: 159          moltype = DNA   length = 75
FEATURE                 Location/Qualifiers
misc_feature            1..75
                        note = Target oligonucleotide sequence
source                  1..75
                        mol_type = other DNA
                        organism = synthetic construct
SEQUENCE: 159
gggatcctgt gtccccgagc tgggaccacc ttatattccc agggccggtt aatgtggctc      60
tggttctggg tactt                                                       75

SEQ ID NO: 160          moltype = DNA   length = 69
FEATURE                 Location/Qualifiers
misc_feature            1..69
                        note = Target oligonucleotide sequence
source                  1..69
                        mol_type = other DNA
                        organism = synthetic construct
SEQUENCE: 160
gggatcctgt gtccccgagc tgggaccacc ttatattccc agggccggtt aatgtggttc      60
tgggtactt                                                              69

SEQ ID NO: 161          moltype = DNA   length = 113
FEATURE                 Location/Qualifiers
misc_feature            1..113
                        note = Target oligonucleotide sequence
source                  1..113
                        mol_type = other DNA
                        organism = synthetic construct
SEQUENCE: 161
gggatcctgt gtccccgagc tgggaccacc ttatattccc agggcagggc cggttggacc      60
accttatatt cccagggcag ggccggttaa tgtggctctg gttctgggta ctt             113

SEQ ID NO: 162          moltype = DNA   length = 34
FEATURE                 Location/Qualifiers
misc_feature            1..34
                        note = Target oligonucleotide sequence
source                  1..34
                        mol_type = other DNA
                        organism = synthetic construct
SEQUENCE: 162
gggatcctgt gtccccgtct ggttctgggt actt                                  34

SEQ ID NO: 163          moltype = DNA   length = 47
FEATURE                 Location/Qualifiers
misc_feature            1..47
                        note = Target oligoncleotide sequence
source                  1..47
                        mol_type = other DNA
                        organism = synthetic construct
SEQUENCE: 163
gggatcctgt gtccccgagc tgggaccacc ttatattctg gtactt                     47

SEQ ID NO: 164          moltype = DNA   length = 17
FEATURE                 Location/Qualifiers
misc_feature            1..17
                        note = Target oligonucleotide sequence
source                  1..17
                        mol_type = other DNA
                        organism = synthetic construct
SEQUENCE: 164
gggatcctgt ggtactt                                                     17

SEQ ID NO: 165          moltype = DNA   length = 93
FEATURE                 Location/Qualifiers
misc_feature            1..93
                        note = Target oligonucleotide sequence
source                  1..93
                        mol_type = other DNA
                        organism = synthetic construct
SEQUENCE: 165
```

```
agggccggtt aatgtggctc tggttctggg tactttatc tgtcccctcc accccacagt    60
ggggccacta gggacaggat tggtgacaga aaa                                 93
```

SEQ ID NO: 166           moltype = DNA   length = 83
FEATURE                  Location/Qualifiers
misc_feature             1..83
                         note = Target oligonucleotide sequence
source                   1..83
                         mol_type = other DNA
                         organism = synthetic construct
SEQUENCE: 166
```
agggccggtt aatgaatgtg gctctggttc tgggtacttt tatctgtccc ctccacccca    60
cagtggggcc actagacaga aaa                                            83
```

SEQ ID NO: 167           moltype = DNA   length = 76
FEATURE                  Location/Qualifiers
misc_feature             1..76
                         note = Target oligonucleotide sequence
source                   1..76
                         mol_type = other DNA
                         organism = synthetic construct
SEQUENCE: 167
```
agggccggtt aatgtggctc tggttctggg tactttatc tgtccccag tggggccact     60
gattggtgac agaaaa                                                    76
```

SEQ ID NO: 168           moltype = DNA   length = 29
FEATURE                  Location/Qualifiers
misc_feature             1..29
                         note = Target oligonucleotide sequence
source                   1..29
                         mol_type = other DNA
                         organism = synthetic construct
SEQUENCE: 168
```
agggccggtt caggattggt gacagaaaa                                      29
```

SEQ ID NO: 169           moltype = DNA   length = 34
FEATURE                  Location/Qualifiers
misc_feature             1..34
                         note = Target oligonucleotide sequence
source                   1..34
                         mol_type = other DNA
                         organism = synthetic construct
SEQUENCE: 169
```
agggccggtt aatgtggcga ttggtgacag aaaa                                34
```

SEQ ID NO: 170           moltype = DNA   length = 63
FEATURE                  Location/Qualifiers
misc_feature             1..63
                         note = Target oligonucleotide sequence
source                   1..63
                         mol_type = other DNA
                         organism = synthetic construct
SEQUENCE: 170
```
agggccggtt aatgtggctc tggttctggg tactttatc tgtccccgat tggtgacaga    60
aaa                                                                  63
```

SEQ ID NO: 171           moltype = DNA   length = 84
FEATURE                  Location/Qualifiers
misc_feature             1..84
                         note = Target oligonucleotide sequence
source                   1..84
                         mol_type = other DNA
                         organism = synthetic construct
SEQUENCE: 171
```
agggccggtt aatgtggctc tggttctggg tactttatc tgtcccctcc accccacagt    60
ggggacagga ttggtgacag aaaa                                           84
```

SEQ ID NO: 172           moltype = DNA   length = 27
FEATURE                  Location/Qualifiers
misc_feature             1..27
                         note = Target oligonucleotide sequence
source                   1..27
                         mol_type = other DNA
                         organism = synthetic construct
SEQUENCE: 172
```
agggccggtt aatgtggtga cagaaaa                                        27
```

SEQ ID NO: 173           moltype = DNA   length = 105
FEATURE                  Location/Qualifiers

```
misc_feature                    1..105
                                note = Target oligonucleotide sequence
source                          1..105
                                mol_type = other DNA
                                organism = synthetic construct
SEQUENCE: 173
agggccggtt aatgtggctc tggttctggg tacttttatc tgtcccctcc accccagggg        60
acagtctgtc ccctccaccc cagggacagg attggtgaca gaaaa                      105

SEQ ID NO: 174                  moltype = DNA  length = 80
FEATURE                         Location/Qualifiers
misc_feature                    1..80
                                note = Target oligonucleotide sequence
source                          1..80
                                mol_type = other DNA
                                organism = synthetic construct
SEQUENCE: 174
agggccggtt aatgtggctc tggttctggg tacttttatc tgtcccctcc accactaggg        60
acaggattgg tgacagaaaa                                                   80

SEQ ID NO: 175                  moltype = DNA  length = 53
FEATURE                         Location/Qualifiers
misc_feature                    1..53
                                note = Target oligonucleotide sequence
source                          1..53
                                mol_type = other DNA
                                organism = synthetic construct
SEQUENCE: 175
cccacagtgg ggccactagg gacaggattg gtgacagaaa agccccatac ccc               53

SEQ ID NO: 176                  moltype = DNA  length = 22
FEATURE                         Location/Qualifiers
misc_feature                    1..22
                                note = Target oligonucleotide sequence
source                          1..22
                                mol_type = other DNA
                                organism = synthetic construct
SEQUENCE: 176
cccacagtgg ggccactacc cc                                                22

SEQ ID NO: 177                  moltype = DNA  length = 96
FEATURE                         Location/Qualifiers
misc_feature                    1..96
                                note = Target oligonucleotide sequence
source                          1..96
                                mol_type = other DNA
                                organism = synthetic construct
SEQUENCE: 177
cccacagtgg ggccactagt agaaaagccc catccttagg cctcccccat ccttaggcct        60
cctcttcct agtctcctga tattgggtct aacccc                                  96

SEQ ID NO: 178                  moltype = DNA  length = 94
FEATURE                         Location/Qualifiers
misc_feature                    1..94
                                note = Target oligonucleotide sequence
source                          1..94
                                mol_type = other DNA
                                organism = synthetic construct
SEQUENCE: 178
cccacagtgg ggccactagg gacaggattg gtgacagaaa agccccatcc ttaggcctcc        60
tccttcctag tctcctgata ttgggtctaa cccc                                   94

SEQ ID NO: 179                  moltype = DNA  length = 62
FEATURE                         Location/Qualifiers
misc_feature                    1..62
                                note = Target oligonucleotide sequence
source                          1..62
                                mol_type = other DNA
                                organism = synthetic construct
SEQUENCE: 179
cccacagtgg ggccacccct taggcctcct cttcctagtc tcctgatatt gggtctaacc        60
cc                                                                      62

SEQ ID NO: 180                  moltype = DNA  length = 38
FEATURE                         Location/Qualifiers
misc_feature                    1..38
                                note = Target oligonucleotide sequence
source                          1..38
                                mol_type = other DNA
```

```
                            organism = synthetic construct
SEQUENCE: 180
cccacagtgg ggccactagt gatattgggt ctaacccc                             38

SEQ ID NO: 181          moltype = DNA   length = 94
FEATURE                 Location/Qualifiers
misc_feature            1..94
                        note = target oligonucleotide sequence
source                  1..94
                        mol_type = other DNA
                        organism = synthetic construct
SEQUENCE: 181
cccacagtgg ggccactagg gacaggattg gtgacaaaaa agccccatcc ttacgcctcc     60
tccttcctag tctcctgata ttgggtctaa cccc                                 94

SEQ ID NO: 182          moltype = DNA   length = 65
FEATURE                 Location/Qualifiers
misc_feature            1..65
                        note = Target oligonucleotide sequence
source                  1..65
                        mol_type = other DNA
                        organism = synthetic construct
SEQUENCE: 182
cccacagtgg ggccactagg gacaggcctc ctccttccta gtctcctgat attgggtcta     60
acccc                                                                 65

SEQ ID NO: 183          moltype = DNA   length = 102
FEATURE                 Location/Qualifiers
misc_feature            1..102
                        note = Target oligonucleotide sequence
source                  1..102
                        mol_type = other DNA
                        organism = synthetic construct
SEQUENCE: 183
cccacagtgg ggccactagg gacagggga caggattggt gacagaaaag ccccatcctt      60
aggcctcctc cttcctagtc tcctgatatt gggtctaacc cc                       102

SEQ ID NO: 184          moltype = DNA   length = 76
FEATURE                 Location/Qualifiers
misc_feature            1..76
                        note = Target oligonucleotide sequence
source                  1..76
                        mol_type = other DNA
                        organism = synthetic construct
SEQUENCE: 184
cccacaggat tggtgacaga aaagcccat ccttaggcct cctccttcct agtctcctga      60
tattgggtct aacccc                                                     76

SEQ ID NO: 185          moltype = DNA   length = 23
FEATURE                 Location/Qualifiers
misc_feature            1..23
                        note = Target oligonucleotide
source                  1..23
                        mol_type = other DNA
                        organism = synthetic construct
SEQUENCE: 185
ggggccacta gggacaggat ggg                                             23

SEQ ID NO: 186          moltype = DNA   length = 23
FEATURE                 Location/Qualifiers
misc_feature            1..23
                        note = Target oligonucleotide
source                  1..23
                        mol_type = other DNA
                        organism = synthetic construct
SEQUENCE: 186
gagatgatcg cccttcttc tgg                                              23

SEQ ID NO: 187          moltype = DNA   length = 75
FEATURE                 Location/Qualifiers
misc_feature            1..75
                        note = Target oligonucleotide sequence
source                  1..75
                        mol_type = other DNA
                        organism = synthetic construct
SEQUENCE: 187
gggatcctgt gtccccgagc tgggaccacc ttatattccc agggtcggtt aatgtggctc     60
tggttctggg tactt                                                      75
```

The invention claimed is:

1. A method of localizing an effector domain to a target nucleic acid sequence in a eukaryotic cell comprising
    providing to the cell a nucleic acid encoding a guide RNA complementary to the target nucleic acid sequence and an aptamer comprising a target of an RNA binding domain, wherein the aptamer is attached to the 3' end or the 5' end of the guide RNA, wherein the guide RNA is a tracrRNA-crRNA fusion,
    providing to the cell a nucleic acid encoding the effector domain and an RNA binding domain, wherein the RNA binding domain binds to the target of the RNA binding domain,
    providing to the cell a nucleic acid encoding a nuclease null or nickase Cas9 protein that interacts with the guide RNA, and
    wherein the cell expresses the guide RNA having the aptamer attached to the 3' end or the 5' end of the guide RNA, the effector domain fused to the RNA binding domain and the Cas9 protein, and
    wherein the guide RNA including the effector domain connected thereto and the Cas9 protein co-localize to the target nucleic acid sequence.

2. The method of claim 1 wherein the cell is a yeast cell, a plant cell or a mammalian cell.

3. The method or claim 1 wherein the cell is a human cell.

4. The method of claim 1 wherein the guide RNA is between about 10 to about 250 nucleotides.

5. The method of claim 1 wherein the guide RNA is between about 20 to about 100 nucleotides.

6. The method of claim 1 wherein the guide RNA is between about 100 to about 250 nucleotides.

7. The method of claim 1 wherein the target nucleic acid is genomic DNA, mitochondrial DNA, viral DNA or exogenous DNA.

8. The method of claim 1 wherein the aptamer comprises two copies of MS2 bacteriophage coat-protein binding RNA stem-loop.

9. The method of claim 1 wherein the RNA binding domain comprises MS2 bacteriophage coat-protein.

10. The method of claim 1 wherein multiple guide RNAs are introduced to the cell with each guide RNA being complementary to a different target nucleic acid sequence and having an aptamer comprising a target of an RNA binding domain, wherein the aptamer is attached to the 3' end or the 5' end of the guide RNA, wherein each guide RNA is a tracrRNA-crRNA fusion, and wherein multiple guide RNAs have the effector domain connected thereto.

11. A method of editing a target gene in a eukaryotic cell comprising
    providing to the cell a nucleic acid encoding a guide RNA complementary to a target DNA sequence within or adjacent to the target gene and an aptamer comprising a target of an RNA binding domain, wherein the aptamer is attached to the 3' end or the 5' end of the guide RNA, wherein the guide RNA is a tracrRNA-crRNA fusion,
    providing to the cell a nucleic acid encoding an effector domain and an RNA binding domain, wherein the RNA binding domain binds to the target of the RNA binding domain,
    providing to the cell a nucleic acid encoding a nickase Cas9 protein that interacts with the guide RNA, and
    wherein the cell expresses the guide RNA having the aptamer attached to the 3' end or the 5' end of the guide RNA, the effector domain fused to the RNA binding domain and the Cas9 protein, and
    wherein the guide RNA including the effector domain connected thereto and the Cas9 protein co-localize to the target DNA sequence and thereby edit the target gene.

12. The method of claim 11 wherein the cell is a yeast cell, a plant cell or a mammalian cell.

13. The method of claim 11 wherein the cell is a human cell.

14. The method of claim 11 wherein the guide RNA is between about 10 to about 250 nucleotides.

15. The method of claim 11 wherein the guide RNA is between about 20 to about 100 nucleotides.

16. The method of claim 11 wherein the guide RNA is between about 100 to about 250 nucleotides.

17. The method of claim 11 wherein the target nucleic acid is genomic DNA, mitochondrial DNA, viral DNA or exogenous DNA.

18. The method of claim 11 wherein the aptamer comprises two copies of MS2 bacteriophage coat-protein binding RNA stem-loop.

19. The method of claim 11 wherein the RNA binding domain comprises MS2 bacteriophage coat-protein.

20. The method of claim 11 wherein multiple guide RNAs are introduced to the cell with each guide RNA being complementary to a different target nucleic acid sequence and having an aptamer comprising a target of an RNA binding domain, wherein the aptamer is attached to the 3' end or the 5' end of the guide RNA, wherein each guide RNA is a tracrRNA-crRNA fusion, and wherein multiple guide RNAs have the effector domain connected thereto.

* * * * *